(12) United States Patent
Kasai et al.

(10) Patent No.: US 8,338,622 B2
(45) Date of Patent: Dec. 25, 2012

(54) HETEROCYCLIC COMPOUND

(75) Inventors: Shizuo Kasai, Osaka (JP); Masahiro Kamaura, Osaka (JP); Nobuo Cho, Tsukuba (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 0 days.

(21) Appl. No.: 12/994,329

(22) PCT Filed: May 29, 2009

(86) PCT No.: PCT/JP2009/059841
§ 371 (c)(1),
(2), (4) Date: Nov. 23, 2010

(87) PCT Pub. No.: WO2009/145286
PCT Pub. Date: Dec. 3, 2009

(65) Prior Publication Data
US 2011/0251187 A1 Oct. 13, 2011

Related U.S. Application Data

(60) Provisional application No. 61/129,032, filed on May 30, 2008.

(51) Int. Cl.
*C07D 207/04* (2006.01)
*A61K 31/40* (2006.01)
(52) U.S. Cl. .................. 548/556; 514/424
(58) Field of Classification Search .............. 548/556; 514/424
See application file for complete search history.

(56) References Cited

U.S. PATENT DOCUMENTS

| | | | |
|---|---|---|---|
| 4,664,694 A | 5/1987 | Brouwer et al. | |
| 5,411,981 A | 5/1995 | Gaillard-Kelly et al. | |
| 5,627,201 A | 5/1997 | Gaillard-Kelly et al. | |
| 6,414,002 B1 | 7/2002 | Cheng et al. | |
| 2003/0069275 A1 | 4/2003 | Cheng et al. | |
| 2003/0087935 A1 | 5/2003 | Cheng et al. | |
| 2003/0096846 A1 | 5/2003 | Cheng et al. | |
| 2004/0116417 A1 | 6/2004 | Boubia et al. | |
| 2004/0147560 A1 | 7/2004 | Cheng et al. | |
| 2004/0171644 A1 | 9/2004 | Cheng et al. | |
| 2005/0004114 A1 | 1/2005 | Whitehouse et al. | |
| 2005/0119311 A1 | 6/2005 | Cheng et al. | |
| 2005/0208535 A1 | 9/2005 | Kahn et al. | |
| 2007/0015797 A1 | 1/2007 | Cheng et al. | |
| 2008/0021043 A1 | 1/2008 | Hannam et al. | |
| 2008/0146574 A1 | 6/2008 | Whitehouse et al. | |
| 2010/0009363 A1 | 1/2010 | Kahn et al. | |
| 2010/0234365 A1 | 9/2010 | Liu et al. | |

FOREIGN PATENT DOCUMENTS

| | | |
|---|---|---|
| EP | 0 200 415 | 12/1986 |
| EP | 0 580 459 | 1/1994 |
| EP | 2 202 223 | 6/2010 |
| JP | 2-53780 | 2/1990 |
| WO | 95/33719 | 12/1995 |
| WO | 01/21602 | 3/2001 |
| WO | 03/031984 | 4/2003 |
| WO | 2004/099192 | 11/2004 |
| WO | 2005/059564 | 6/2005 |
| WO | 2006/043064 | 4/2006 |
| WO | 2008/076754 | 6/2008 |
| WO | 2008/112674 | 9/2008 |
| WO | 2010/119992 | 10/2010 |

OTHER PUBLICATIONS

Cannon, "Analog Design" in Burger's Medicinal Chemistry and Drug Discovery, 6th ed. 2003, Wiley, pp. 687-714.*
International Search Report issued Jul. 14, 2009 in International (PCT) Application No. PCT/JP2009/059841.
S. Stosic-Grujicic et al., "A Potent Immunomodulatory Compound, (S,R)-3-Phenyl-4,5-dihydro-5-isoxasole Acetic Acid, Prevents Spontaneous and Accelerated Forms of Autoimmune Diabetes in NOD Mice and Inhibits the Immunoinflammatory Diabetes Induced by Multiple Low Doses of Streptozotocin in CBA/H Mice", The Journal of Pharmacology and Experimental Therapeutics, vol. 320, No. 3, pp. 1038-1049, 2007.
K. Tachibana et al., "Discovery of an Orally-Active Nonsteroidal Androgen Receptor Pure Antagonist and the Structure-Activity Relationships of Its Derivatives", Chemical and Pharmaceutical Bulletin, vol. 56, No. 11, pp. 1555-1561, 2008.
D. Cousty-Berlin et al., "Preliminary Pharmacokinetics and Metabolism of Novel Non-Steroidal Antiandrogens in the Rat: Relation of their Systemic Activity to the Formation of a Common Metabolite", Journal of Steroid Biochemistry and Molecular Biology, vol. 51, No. 1/2, pp. 47-56, 1994.
Zhongguo Yaoke Daxue Xuebao, Journal of China Pharmaceutical University, 1991, vol. 22, No. 6, pp. 330-333, (with STN Search Result by the Applicants, p. 11, Answer 11 of 13).
STN Search Result by the Applicants, pp. 1-18, 2009.

* cited by examiner

*Primary Examiner* — Robert Havlin
(74) *Attorney, Agent, or Firm* — Wenderoth, Lind & Ponack, L.L.P.

(57) ABSTRACT

The present invention relates to a compound represented by

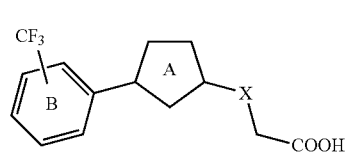
(I)

wherein each symbol is as defined in the specification, a salt thereof and the like.

13 Claims, No Drawings

HETEROCYCLIC COMPOUND

This application is a U.S. national stage of International Application No. PCT/JP2009/059841 filed May 29, 2009, which claims the benefit of U.S. provisional application Ser. No. 61/129,032 filed May 30, 2008.

TECHNICAL FIELD

The present invention relates to a novel heterocyclic compound, which is useful as an agent for the prophylaxis or treatment of diabetes, hyperlipidemia and the like; and the like.

BACKGROUND OF THE INVENTION

Retinol binding protein 4 (hereinafter sometimes to be abbreviated as "RBP4") is known to be a sole blood retinol transport protein mainly produced in the liver.

In recent years, moreover, RBP4 is suggested to be a factor inducing insulin resistance, as shown below.

(1) Since RBP4 expression increases in the adipocytes of GLUT4 knockout mouse showing insulin resistance, RBP4 is suggested to be a potential adipocytokine inducing insulin resistance (see Nature 436, 356-362 (2005) (non-patent document 1)).

(2) RBP4 overexpression mouse shows hyperglycemia and hyperinsulinemia, and RBP4 knockout mouse shows promotion of glucose tolerance and insulin sensitivity as phenotype (see Nature 436, 356-362 (2005) (non-patent document 1)).

(3) Mouse bred on a high-fat diet shows high blood RBP4 value, which is correlated with induction of insulin resistance (see Nature 436, 356-362 (2005) (non-patent document 1)).

(4) Disease model mouse showing diabetes and obesity pathology such as ob/ob mouse, 11β-HSD1 overexpression (adipose tissue specific) mouse, MC4R knockout mouse, GLUT4 knockout (adipose tissue and skeletal muscle specific) mouse and the like also shows high blood RBP4 value (see Nature 436, 356-362 (2005) (non-patent document 1)).

(5) It has been reported that blood RBP4 concentration and insulin sensitivity and sugar disposal rate are inversely correlated in human. The glucose infusion rate decreases as the blood RBP4 concentration increases in euglycemic hyperinsulinemic glucose clamp test (see Cell Metab., 6, 79-87 (2007) (non-patent document 2)).

(6) While exercise is known to improve insulin sensitivity, an extremely high correlation between such an improving effect and lowering of blood RBP4 concentration is shown (see N. Engl. J. Med., 354, 2552-2563 (2006) (non-patent document 3)).

(7) WO 2005/059564 (patent reference 1) describes that a compound that controls RBP4 activity is useful for the treatment of insulin resistance.

RBP4 is stably present in blood in the form of a complex resulting from the binding of retinol and TTR (transthyretin). When RBP4 is dissociated from TTR and becomes free, it is decomposed in and excreted from the kidney comparatively rapidly. Fenretinide, a retinol derivative, inhibits the binding of RBP4 and retinol, and consequently inhibits formation of a complex with TTR. It is known that administration of fenretinide to animal induces lowering of blood RBP4 (see Biochim. Biophys. Acta, 1294, 48-54 (1996) (non-patent document 4)).

From such foregoing findings, a compound that inhibits formation of a complex of RBP4 and TTR by inhibiting the binding of RBP4 and retinol is expected to lower blood RBP4 concentration and consequently induce correction of hyperglycemia and improvement of insulin resistance.

As mentioned above, a compound capable of lowering blood RBP4 concentration can be a therapeutic drug for diabetes.

In recent years, moreover, a report has documented that blood RBP4 value and blood TG (triglyceride) or LDL cholesterol value positively correlate in human, and blood RBP4 value negatively correlates with HDL cholesterol value (see J. Atheroscler. Thromb., 13, 209-215 (2006) (non-patent document 5), N. Engl. J. Med., 355, 1392-1395 (2006) (non-patent document 6), Diabetes, 56 (Supplement 1), A378 (1477-P) (2007) (non-patent document 7)), thus suggesting relationship between RBP4 and lipid metabolism.

In view of the above, a medicament having an action to lower blood RBP4 value (concentration) (also referred to as "RBP4 lowering action" in the present specification) (also referred to as "RBP4 lowering agent" in the present specification) can be an agent for the prophylaxis or treatment of hyperlipidemia.

As mentioned above, a medicament having an action to lower blood RBP4 value (concentration) (also referred to as "RBP4 lowering action" in the present specification) (also referred to as "RBP4 lowering agent" in the present specification) can be widely applicable to lifestyle-related diseases (diabetes, hyperlipidemia and the like).

As the compound having a structure similar to that of the compound of the present invention, the following compounds are known.

1) WO 03/031984 (patent document 2) discloses the following compound.

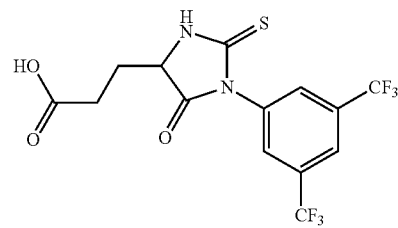

2) Zhongguo Yaoke Daxue Xuebao (1991), 22(6), 330-3 (non-patent document 8) discloses the following compound.

CAS registry No.: 143247-34-1

3) The following compounds are registered in the STN database.

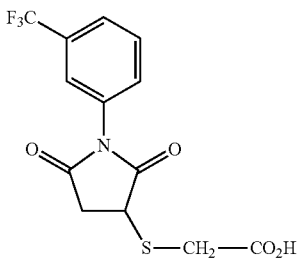

CAS registry No.: 736168-64-2

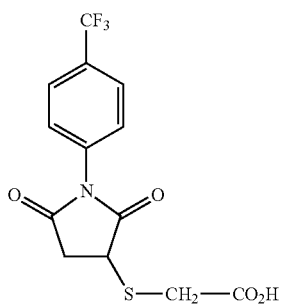

CAS registry No.: 452358-00-8

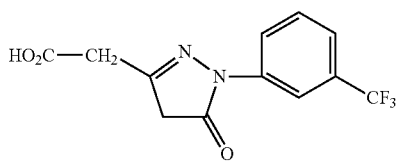

CAS registry No.: 1094556-59-8

4) US 2004/116417 (patent document 3) discloses the following compound.

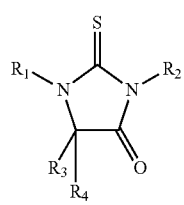

wherein $R_1$ is an aromatic ring group (the aromatic ring group is optionally substituted by halogen, $C_{1-4}$ alkoxy, $C_{1-4}$ alkyl (including cyclic alkyl), $C_{1-4}$ alkylthio, nitro, trifluoromethyl, trifluoromethoxy, methylenedioxy, an optionally substituted nitrogen-containing heterocyclic group and the like);

$R_2$ is hydrogen, $C_{1-3}$ alkyl (optionally substituted by an optionally esterified carboxylic acid) or the like; and $R_3$ and $R_4$ are independently hydrogen or $C_{1-4}$ alkyl.

5) WO 2006/043064 (patent document 4) discloses the following compounds.

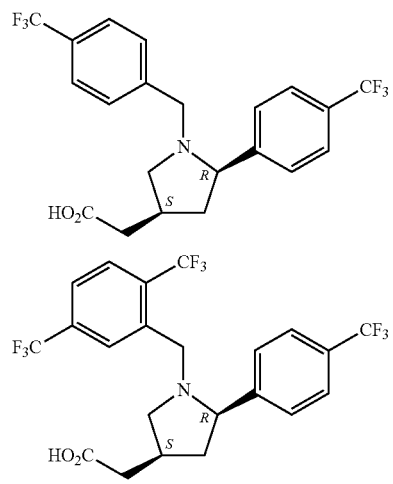

6) WO 95/33719 (patent document 5) discloses the following compounds.

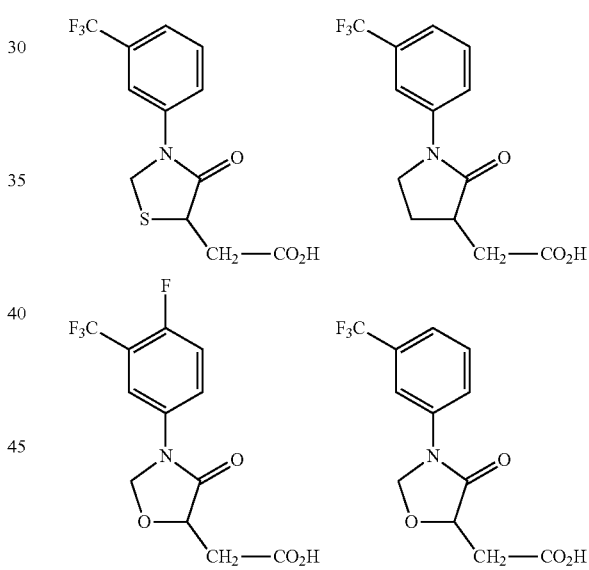

7) EP 200415 A (patent document 6) discloses the following compounds.

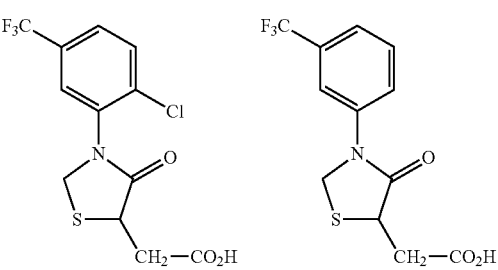

8) JP-A-02-053780 (patent document 7) discloses the following compound.

However, it has not been reported that the above-mentioned compound has a RBP4 lowering action.

CITATION LIST

Patent Documents

Patent document 1: WO 2005/059564
Patent document 2: WO 03/031984
Patent document 3: US 2004/116417
Patent document 4: WO 2006/043064
Patent document 5: WO 95/33719
Patent document 6: EP 200415 A
Patent document 7: JP-A-02-053780

Non-Patent Documents

Non-Patent document 1: Nature 436, 356-362 (2005)
Non-Patent document 2: Cell Metab., 6, 79-87 (2007)
Non-Patent document 3: N. Engl. J. Med., 354, 2552-2563 (2006)
Non-Patent document 4: Biochim. Biophys. Acta, 1294, 48-54 (1996)
Non-Patent document 5: J. Atheroscler. Thromb., 13, 209-215 (2006)
Non-Patent document 6: N. Engl. J. Med., 355, 1392-1395 (2006)
Non-Patent document 7: Diabetes, 56(Supplement 1), A378 (1477-P) (2007)
Non-Patent document 8: Zhongguo Yaoke Daxue Xuebao (1991), 22(6), 330-3

SUMMARY OF THE INVENTION

Problems to be Solved by the Invention

The present invention aims to provide a compound having a RBP4 lowering action and useful as a medicament for the prophylaxis or treatment of diabetes, hyperlipidemia and the like.

Means of Solving the Problems

As a result of the intensive studies of the compounds having a RBP4 lowering action, the present inventors have surprisingly found compounds represented by the following formula (I), a salt thereof or a prodrug thereof has a superior RBP4 lowering action, which resulted in the completion of the present invention.

Accordingly, the present invention relates to
[1] a compound represented by the formula wherein
ring A is a 5-membered non-aromatic heterocycle optionally further substituted by one substituent;
ring B is an optionally further substituted benzene ring; and
X is a bond, O, $CH_2O$, $OCH_2$, $CH_2$, $(CH_2)_2$, S, $CH_2S$, $SCH_2$, S(O), $CH_2S(O)$, $S(O)CH_2$, $S(O)_2$, $CH_2S(O)_2$ or $S(O)_2CH_2$,
provided that
{(3S,5R)-1-[4-(trifluoromethyl)benzyl]-5-[4-(trifluoromethyl)phenyl]pyrrolidin-3-yl}acetic acid,
{(3S,5R)-1-[2,5-bis(trifluoromethyl)benzyl]-5-[4-(trifluoromethyl)phenyl]pyrrolidin-3-yl}acetic acid,
{4-oxo-3-[(3-(trifluoromethyl)phenyl]-1,3-thiazolidin-5-yl}acetic acid,
{2-oxo-1-[3-(trifluoromethyl)phenyl]pyrrolidin-3-yl}acetic acid,
{3-[4-fluoro-3-(trifluoromethyl)phenyl]-4-oxo-1,3-oxazolidin-5-yl}acetic acid,
{4-oxo-3-[3-(trifluoromethyl)phenyl]-1,3-oxazolidin-5-yl}acetic acid,
{3-[2-chloro-5-(trifluoromethyl)phenyl]-4-oxo-1,3-thiazolidin-5-yl}acetic acid, and
{5-oxo-1-[3-(trifluoromethyl)phenyl]-4,5-dihydro-1H-pyrazol-3-yl}acetic acid
are excluded,
or a salt thereof;
[2] the compound of the above-mentioned [1], wherein X is O, $CH_2O$, $OCH_2$, $CH_2$, S, $CH_2S$, $SCH_2$, S(O) or $S(O)_2$;
[3] the compound of the above-mentioned [1], wherein ring B is a benzene ring optionally further substituted by 1 to 3 substituents selected from
  (a) a halogen atom,
  (b) a $C_{1-6}$ alkyl group optionally substituted by 1 to 3 halogen atoms, and
  (c) a $C_{1-6}$ alkoxy group optionally substituted by 1 to 3 halogen atoms;
[4] the compound of the above-mentioned [1], wherein
ring A is a 5-membered non-aromatic heterocycle optionally further substituted by one substituent selected from a $C_{1-6}$ alkyl group and an oxo group;
[5] the compound of the above-mentioned [1], wherein ring A is a pyrrolidine ring or a tetrahydrofuran ring, each of which is optionally further substituted by one oxo group;
[6] the compound of the above-mentioned [1], wherein
ring A is a 5-membered non-aromatic heterocycle optionally further substituted by one substituent selected from a $C_{1-6}$ alkyl group and an oxo group;
ring B is a benzene ring optionally further substituted by 1 to 3 substituents selected from
  (a) a halogen atom,
  (b) a $C_{1-4}$ alkyl group optionally substituted by 1 to 3 halogen atoms, and
  (c) a $C_{1-6}$ alkoxy group optionally substituted by 1 to 3 halogen atoms; and
X is O, $CH_2O$, $OCH_2$, $CH_2$, S, $CH_2S$, $SCH_2$, S(O) or $S(O)_2$;
[7] the compound of the above-mentioned [1], wherein
ring A is a pyrrolidine ring or a tetrahydrofuran ring, each of which is optionally further substituted by one oxo group;
ring B is a benzene ring further substituted by 1 to 3 substituents selected from (a) a halogen atom,
(b) a $C_{1-6}$ alkyl group optionally substituted by 1 to 3 halogen atoms, and
(c) a $C_{1-4}$ alkoxy group optionally substituted by 1 to 3 halogen atoms; and
X is bond;
[8] the compound of the above-mentioned [1], wherein
ring A is a 5-membered non-aromatic heterocycle optionally further substituted by one substituent selected from a $C_{1-6}$ alkyl group and an oxo group;
ring B is an optionally further substituted benzene ring; and X is O, S or $CH_2$;
[9] ({(3S)-1-[3,5-bis(trifluoromethyl)phenyl]pyrrolidin-3-yl}oxy)acetic acid or a salt thereof;
[10] ({1-[4-chloro-3-(trifluoromethyl)phenyl]pyrrolidin-3-yl}sulfanyl)acetic acid or a salt thereof;
[11] 3-{(2R,5S)-5-[3,5-bis(trifluoromethyl)phenyl]tetrahydrofuran-2-yl}propanoic acid or a salt thereof;
[12] a prodrug of the compound of the above-mentioned [1];
[13] a medicament comprising the compound of the above-mentioned [1] or a prodrug thereof;
[14] the medicament of the above-mentioned [13], which is a retinol binding protein 4 lowering agent;
[15] the medicament of the above-mentioned [13], which is an agent for the prophylaxis or treatment of a retinol binding protein 4-associated disease;
[16] the medicament of the above-mentioned [13], which is an agent for the prophylaxis or treatment of diabetes;
[17] a method of lowering retinol binding protein 4 in a mammal, which comprises administering an effective amount of the compound of the above-mentioned [1] or a prodrug thereof to the mammal;
[18] a method for the prophylaxis or treatment of diabetes in a mammal, which comprises administering an effective amount of the compound of the above-mentioned [1] or a prodrug thereof to the mammal;
[19] use of the compound of the above-mentioned [1] or a prodrug thereof for the production of a retinol binding protein 4 lowering agent;
[20] use of the compound of the above-mentioned [1] or a prodrug thereof for the production of an agent for the prophylaxis or treatment of diabetes;
and the like.

As another embodiment, the present invention relates to
[21] a compound represented by the formula

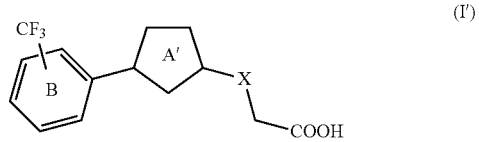

(I')

wherein
ring A' is an optionally further substituted 5-membered non-aromatic heterocycle;
ring B is an optionally further substituted benzene ring; and
X is a bond, O, $CH_2O$, $OCH_2$, $CH_2$, $(CH_2)_2$, S, $CH_2S$, $SCH_2$, $S(O)$, $CH_2S(O)$, $S(O)CH_2$, $S(O)_2$, $CH_2S(O)_2$ or $S(O)_2CH_2$, provided that
({1-[3,5-bis(trifluoromethyl)phenyl]-2,5-dioxoimidazolidin-4-yl}sulfanyl)acetic acid;
3-{5-oxo-2-thioxo-1-[3-(trifluoromethyl)phenyl]imidazolidin-4-yl}propanoic acid;
({2,5-dioxo-1-[3-(trifluoromethyl)phenyl]pyrrolidin-3-yl}sulfanyl)acetic acid; and
({2,5-dioxo-1-[4-(trifluoromethyl)phenyl]pyrrolidin-3-yl}sulfanyl)acetic acid
are excluded,
or a salt thereof;
[22] the compound of the above-mentioned [21], wherein ring A' is a 5-membered non-aromatic heterocycle optionally further substituted by one substituent selected from a $C_{1-6}$ alkyl group and an oxo group;
[23] a prodrug of the compound of the above-mentioned [21];
[24] a medicament comprising the compound of the above-mentioned [21] or a prodrug thereof;
[25] the medicament of the above-mentioned [24], which is a retinol binding protein 4 lowering agent;
[26] the medicament of the above-mentioned [24], which is an agent for the prophylaxis or treatment of diabetes;
and the like.

DETAILED DESCRIPTION OF THE INVENTION

The definition of each symbol in the formula (I) and the formula (I') is described in detail in the following.

The "halogen atom" in the present specification means, unless otherwise specified, a fluorine atom, a chlorine atom, a bromine atom or an iodine atom.

The "$C_{1-3}$ alkylenedioxy group" in the present specification means, unless otherwise specified, methylenedioxy, ethylenedioxy or the like.

The "$C_{1-5}$ alkyl group" in the present specification means, unless otherwise specified, methyl, ethyl, propyl, isopropyl, butyl, isobutyl, sec-butyl, tert-butyl, pentyl, isopentyl, neopentyl, 1-ethylpropyl, hexyl, isohexyl, 1,1-dimethylbutyl, 2,2-dimethylbutyl, 3,3-dimethylbutyl, 2-ethylbutyl or the like.

The "$C_{1-6}$ alkoxy group" in the present specification means, unless otherwise specified, methoxy, ethoxy, propoxy, isopropoxy, butoxy, isobutoxy, sec-butoxy, tert-butoxy or the like.

The "$C_{1-6}$ alkoxy-carbonyl group" in the present specification means, unless otherwise specified, methoxycarbonyl, ethoxycarbonyl, propoxycarbonyl, tert-butoxycarbonyl or the like.

The "$C_{1-6}$ alkyl-carbonyl group" in the present specification means, unless otherwise specified, acetyl, propanoyl, butanoyl, isobutanoyl, pentanoyl, isopentanoyl, hexanoyl or the like.

The "$C_{6-14}$ aryl-carbonyl group" in the present specification means, unless otherwise specified, benzoyl, naphthylcarbonyl, biphenylcarbonyl or the like.

The "$C_{1-6}$ alkylthio group" in the present specification means, unless otherwise specified, methylthio, ethylthio, propylthio, isopropylthio, butylthio, isobutylthio, sec-butylthio, tert-butylthio, pentylthio, isopentylthio, neopentylthio, 1-ethylpropylthio, hexylthio, isohexylthio, 1,1-dimethylbutylthio, 2,2-dimethylbutylthio, 3,3-dimethylbutylthio, 2-ethylbutylthio or the like.

The "$C_{1-6}$ alkylsulfinyl group" in the present specification means, unless otherwise specified, methylsulfinyl, ethylsulfinyl, propylsulfinyl, isopropylsulfinyl, butylsulfinyl, isobutylsulfinyl, sec-butylsulfinyl, tert-butylsulfinyl, pentylsulfinyl, isopentylsulfinyl, neopentylsulfinyl, 1-ethylpropylsulfinyl, hexylsulfinyl, isohexylsulfinyl, 1,1-dimethylbutylsulfinyl, 2,2-dimethylbutylsulfinyl, 3,3-dimethylbutylsulfinyl, 2-ethylbutylsulfinyl or the like.

The "$C_{1-6}$ alkylsulfonyl group" in the present specification means, unless otherwise specified, methylsulfonyl, ethylsulfonyl, propylsulfonyl, isopropylsulfonyl, butylsulfonyl, isobutylsulfonyl, sec-butylsulfonyl, tert-butylsulfonyl, pentylsulfonyl, isopentylsulfonyl, neopentylsulfonyl, 1-ethylpropylsulfonyl, hexylsulfonyl, isohexylsulfonyl, 1,1-dimethylbutylsulfonyl, 2,2-dimethylbutylsulfonyl, 3,3-dimethylbutylsulfonyl, 2-ethylbutylsulfonyl or the like.

Ring A is a 5-membered non-aromatic heterocycle optionally further substituted by one substituent.

Examples of the "5-membered non-aromatic heterocycle" of the "5-membered non-aromatic heterocycle optionally further substituted by one substituent" for ring A include pyrrolidine, pyrroline, imidazolidine, imidazoline, pyrazolidine, pyrazoline, oxazolidine, oxazoline, thiazolidine, thiazoline, 1,1-dioxidothiazolidine, 1,1-dioxidothiazoline, isoxazolidine, isoxazoline, isothiazolidine, isothiazoline, 1,1-dioxidoisothiazolidine, 1,1-dioxidoisothiazoline, tetrahydrofuran, dihydrofuran, tetrahydrothienyl, dihydrothienyl, 1,1-dioxidotetrahydrothienyl, 1,1-dioxidodihydrothienyl, dioxolyl, dioxolanyl and the like. Of these, pyrrolidine, imidazolidine, tetrahydrofuran and 1,1-dioxidoisothiazolidine are preferable, pyrrolidine and tetrahydrofuran are more preferable, and pyrrolidine is particularly preferable.

Ring A optionally has, besides ring B and X group, one substituent at substitutable position.

Examples of the substituent include (1) a $C_{3-10}$ cycloalkyl group (e.g., cyclopropyl, cyclohexyl);
(2) a $C_{6-14}$ aryl group (e.g., phenyl, naphthyl) optionally substituted by 1 to 3 substituents selected from
 (a) a $C_{1-6}$ alkyl group optionally substituted by 1 to 3 halogen atoms,
 (b) a hydroxy group,
 (c) a $C_{1-6}$ alkoxy group optionally substituted by 1 to 3 halogen atoms, and
 (d) a halogen atom,
(3) an aromatic heterocyclic group (e.g., thienyl, furyl, pyridyl, pyrazolyl, imidazolyl, tetrazolyl, oxazolyl, thiazolyl, oxadiazolyl, thiadiazolyl) optionally substituted by 1 to 3 substituents selected from
 (a) a $C_{1-6}$ alkyl group optionally substituted by 1 to 3 halogen atoms,
 (b) a hydroxy group,
 (c) a $C_{1-6}$ alkoxy group optionally substituted by 1 to 3 halogen atoms, and
 (d) a halogen atom;
(4) a non-aromatic heterocyclic group (e.g., tetrahydrofuryl, morpholinyl, thiomorpholinyl, piperidinyl, pyrrolidinyl, piperazinyl) optionally substituted by 1 to 3 substituents selected from
 (a) a $C_{1-6}$ alkyl group optionally substituted by 1 to 3 halogen atoms,
 (b) a hydroxy group,
 (c) a $C_{1-6}$ alkoxy group optionally substituted by 1 to 3 halogen atoms,
 (d) a halogen atom, and
 (e) an oxo group;
(5) an amino group optionally mono- or di-substituted by substituent(s) selected from
 (a) a $C_{1-6}$ alkyl group optionally substituted by 1 to 3 halogen atoms,
 (b) a $C_{1-6}$ alkyl-carbonyl group optionally substituted by 1 to 3 halogen atoms,
 (c) a $C_{6-14}$ aryl-carbonyl group optionally substituted by 1 to 3 halogen atoms,
 (d) a $C_{1-6}$ alkoxy-carbonyl group optionally substituted by 1 to 3 halogen atoms,
 (e) a $C_{1-6}$ alkylsulfonyl group (e.g., methylsulfonyl, ethylsulfonyl, isopropylsulfonyl, butylsulfonyl, pentylsulfonyl) optionally substituted by 1 to 3 halogen atoms,
 (f) a carbamoyl group optionally mono- or di-substituted by $C_{1-6}$ alkyl group(s) optionally substituted by 1 to 3 halogen atoms, and
 (g) an aromatic heterocyclic group (e.g., thienyl, furyl, pyridyl, pyrazolyl, imidazolyl, tetrazolyl, oxazolyl, thiazolyl, oxadiazolyl, thiadiazolyl);
(6) a $C_{1-6}$ alkyl-carbonyl group optionally substituted by 1 to 3 halogen atoms;
(7) a $C_{1-6}$ alkoxy-carbonyl group optionally substituted by 1 to 3 substituents selected from
 (a) a halogen atom,
 (b) a $C_{1-6}$ alkoxy group, and
 (c) a $C_{6-14}$ aryl group (e.g., phenyl);
(8) a $C_{1-6}$ alkylsulfonyl group (e.g., methylsulfonyl, ethylsulfonyl, isopropylsulfonyl) optionally substituted by 1 to 3 halogen atoms;
(9) a carbamoyl group optionally mono- or di-substituted by substituent(s) selected from
 (a) a $C_{1-6}$ alkyl group optionally substituted by 1 to 3 halogen atoms,
 (b) a $C_{1-6}$ alkylsulfonyl group (e.g., methylsulfonyl, ethylsulfonyl, isopropylsulfonyl, butylsulfonyl, pentylsulfonyl) optionally substituted by 1 to 3 halogen atoms,
 (c) a $C_{6-14}$ arylsulfonyl group (e.g., phenylsulfonyl) optionally substituted by an aromatic heterocyclic group (e.g., thienyl, furyl, pyridyl, pyrazolyl, imidazolyl, tetrazolyl, oxazolyl, thiazolyl, oxadiazolyl, thiadiazolyl), and
 (d) an aromatic heterocyclic group (e.g., thienyl, furyl, pyridyl, pyrazolyl, imidazolyl, tetrazolyl, oxazolyl, thiazolyl, oxadiazolyl, thiadiazolyl);
(10) a thiocarbamoyl group optionally mono- or di-substituted by $C_{1-6}$ alkyl group(s) optionally substituted by 1 to 3 halogen atoms;
(11) a sulfamoyl group optionally mono- or di-substituted by $C_{1-6}$ alkyl group(s) optionally substituted by 1 to 3 halogen atoms;
(12) a carboxy group;
(13) a hydroxy group;
(14) a $C_{1-6}$ alkoxy group optionally substituted by 1 to 3 substituents selected from
 (a) a halogen atom,
 (b) a carboxy group,
 (c) a $C_{1-6}$ alkoxy group,
 (d) a $C_{1-6}$ alkoxy-carbonyl group optionally substituted by 1 to 3 $C_{6-14}$ aryl group (e.g., phenyl), and
 (e) an amino group optionally mono- or di-substituted by substituent(s) selected from a $C_{1-6}$ alkyl group and a $C_{1-6}$ alkoxy-carbonyl group;
(15) a $C_{2-6}$ alkenyloxy group (e.g., ethenyloxy) optionally substituted by 1 to 3 halogen atoms;
(16) a $C_{7-13}$ aralkyloxy group (e.g., benzyloxy);
(17) a $C_{6-14}$ aryloxy group (e.g., phenyloxy, naphthyloxy);
(18) a $C_{1-6}$ alkyl-carbonyloxy group (e.g., acetyloxy, tart-butylcarbonyloxy);
(19) a $C_{6-14}$ aryl-carbonyl group optionally substituted by 1 to 3 substituents selected from
 (a) a halogen atom, and
 (b) a $C_{1-6}$ alkyl group optionally substituted by 1 to 3 halogen atoms;
(20) a non-aromatic heterocyclylcarbonyl group (e.g., pyrrolidinylcarbonyl, morpholinylcarbonyl, thiomorpholinylcarbonyl, 1-oxidothiomorpholinylcarbonyl) optionally substituted by 1 to 3 substituents selected from a $C_{1-6}$ alkyl group optionally substituted by 1 to 3 halogen atoms;

(21) a mercapto group;
(22) a $C_{1-6}$ alkylthio group (e.g., methylthio, ethylthio) optionally substituted by 1 to 3 substituents selected from
   (a) a halogen atom, and
   (b) a $C_{1-6}$ alkoxy-carbonyl group;
(23) a $C_{7-13}$ aralkylthio group (e.g., benzylthio);
(24) a $C_{6-14}$ arylthio group (e.g., phenylthio, naphthylthio);
(25) a cyano group;
(26) a nitro group;
(27) a halogen atom;
(28) a $C_{1-3}$ alkylenedioxy group;
(29) an aromatic heterocyclylcarbonyl group (e.g., pyrazolylcarbonyl, pyrazinylcarbonyl, isoxazolylcarbonyl, pyridylcarbonyl, thiazolylcarbonyl) optionally substituted by 1 to 3 substituents selected from a $C_{1-6}$ alkyl group optionally substituted by 1 to 3 halogen atoms;
(30) a formyl group;
(31) a $C_{1-6}$ alkyl group optionally substituted by 1 to 3 substituents selected from
   (a) a halogen atom,
   (b) a carboxy group,
   (c) a hydroxy group,
   (d) a $C_{1-6}$ alkoxy-carbonyl group,
   (e) a $C_{1-6}$ alkoxy group, and
   (f) an amino group optionally mono- or di-substituted by $C_{1-6}$ alkyl group(s);
(32) a $C_{2-10}$ alkenyl group (e.g., ethenyl, 1-propenyl) optionally substituted by 1 to 3 substituents selected from
   (a) a halogen atom,
   (b) a carboxy group,
   (c) a hydroxy group,
   (d) a $C_{1-6}$ alkoxy-carbonyl group,
   (e) a $C_{1-6}$ alkoxy group,
   (f) an amino group optionally mono- or di-substituted by $C_{1-6}$ alkyl group(s), and
   (g) a non-aromatic heterocyclic group (e.g., tetrahydrofuryl, morpholinyl, thiomorpholinyl, piperidinyl, pyrrolidinyl, piperazinyl, thiazolidinyl) optionally substituted by 1 to 3 substituents selected from
      (i) a $C_{1-6}$ alkyl group optionally substituted by 1 to 3 halogen atoms,
      (ii) a hydroxy group,
      (iii) a $C_{1-6}$ alkoxy group optionally substituted by 1 to 3 halogen atoms,
      (iv) a halogen atom, and
      (v) an oxo group;
(33) a $C_{7-13}$ aralkyl group (e.g., benzyl) optionally substituted by 1 to 3 substituents selected from
   (a) a $C_{1-6}$ alkyl group optionally substituted by 1 to 3 halogen atoms,
   (b) a hydroxy group,
   (c) a $C_{1-6}$ alkoxy group, and
   (d) a halogen atom,
(34) an oxo group,
and the like.

As the substituent, a $C_{1-6}$ alkyl group and an oxo group are preferable, and an oxo group is particularly preferable.

Ring A is preferably a 5-membered non-aromatic heterocycle (preferably pyrrolidine, imidazolidine, tetrahydrofuran, 1,1-dioxidoisothiazolidine) optionally further substituted by one substituent selected from a $C_{1-6}$ alkyl group and an oxo group, more preferably a 5-membered non-aromatic heterocycle (preferably pyrrolidine, imidazolidine, tetrahydrofuran, 1,1-dioxidoisothiazolidine) optionally further substituted by one oxo group, more preferably pyrrolidine or tetrahydrofuran, each of which is optionally further substituted by one oxo group, particularly preferably pyrrolidine not substituted by substituent other than ring B and X group.

Ring A' is an optionally further substituted 5-membered non-aromatic heterocycle.

Examples of the "5-membered non-aromatic heterocycle" of the "optionally further substituted 5-membered non-aromatic heterocycle" for ring A' include those similar to the "5-membered non-aromatic heterocycle" of the "5-membered non-aromatic heterocycle optionally further substituted by one substituent" for ring A. Of these, pyrrolidine, imidazolidine, tetrahydrofuran and 1,1-dioxidoisothiazolidine are preferable, pyrrolidine and tetrahydrofuran are more preferable, and pyrrolidine is particularly preferable.

Ring A' optionally has, besides ring B and X group, 1 to 3 substituents at substitutable position(s). Examples of the substituent include those exemplified as the "substituent" that the "5-membered non-aromatic heterocycle" of the "5-membered non-aromatic heterocycle optionally further substituted by one substituent" for ring A optionally has. When the number of the substituents is not less than 2, the respective substituents may be the same or different.

As the substituent, a $C_{1-6}$ alkyl group and an oxo group are preferable, and an oxo group is particularly preferable.

Ring A' is preferably a 5-membered non-aromatic heterocycle (preferably pyrrolidine, imidazolidine, tetrahydrofuran, 1,1-dioxidoisothiazolidine) optionally further substituted by one substituent selected from a $C_{1-6}$ alkyl group and an oxo group, more preferably a 5-membered non-aromatic heterocycle (preferably pyrrolidine, imidazolidine, tetrahydrofuran, 1,1-dioxidoisothiazolidine) optionally further substituted by one oxo group, more preferably pyrrolidine or tetrahydrofuran, each of which is optionally further substituted by one oxo group, particularly preferably pyrrolidine not substituted by substituent other than ring B and X group.

Ring B is an optionally further substituted benzene ring.

Ring B optionally has, besides ring A and a trifluoromethyl group, 1 to 4 substituents at substitutable position. Examples of the substituent include those exemplified as the "substituent" (excluding an oxo group) that the "5-membered non-aromatic heterocycle" of the "5-membered non-aromatic heterocycle optionally further substituted by one substituent" for ring A optionally has. When the number of the substituents is not less than 2, the respective substituents may be the same or different.

As the substituent,
(1) a halogen atom (preferably a fluorine atom, a chlorine atom, a bromine atom),
(2) a $C_{1-6}$ alkyl group optionally substituted by 1 to 3 halogen atoms (preferably a fluorine atom),
(3) a alkoxy group optionally substituted by 1 to 3 halogen atoms,
(4) a cyano group,
(5) an amino group optionally mono- or di-substituted by substituent(s) selected from
   (a) a $C_{1-6}$ alkyl group optionally substituted by 1 to 3 halogen atoms, and
   (b) alkylsulfonyl group optionally substituted by 1 to 3 halogen atoms,
(6) a non-aromatic heterocyclylcarbonyl group (e.g., thiomorpholinylcarbonyl, 1-oxidothiomorpholinylcarbonyl) optionally substituted by 1 to 3 substituents selected from a $C_{1-6}$ alkyl group optionally substituted by 1 to 3 halogen atoms
and the like are preferable.

Ring B is preferably a benzene ring optionally further substituted by 1 to 4 substituents selected from (1) a halogen atom (preferably a fluorine atom, a chlorine atom, a bromine atom), (2) a $C_{1-6}$ alkyl group optionally substituted by 1 to 3 halogen atoms (preferably a fluorine atom) (preferably trifluoromethyl), (3) a $C_{1-6}$ alkoxy group (preferably methoxy) optionally substituted by 1 to 3 halogen atoms, (4) a cyano group, (5) an amino group optionally mono- or di-substituted by substituent(s) selected from (a) a $C_{1-6}$ alkyl group (preferably methyl) optionally substituted by 1 to 3 halogen atoms, and (b) $C_{1-6}$ alkylsulfonyl group (preferably methylsulfonyl) optionally substituted by 1 to 3 halogen atoms, and (6) a non-aromatic heterocyclylcarbonyl group (e.g., thiomorpholinylcarbonyl, 1-oxidothiomorpholinylcarbonyl) optionally substituted by 1 to 3 substituents selected from a $C_{1-6}$ alkyl group optionally substituted by 1 to 3 halogen atoms.

Ring B is more preferably a benzene ring optionally further substituted by 1 to 4 substituents selected from a halogen atom (preferably a fluorine atom, a chlorine atom, a bromine atom) and a $C_{1-6}$ alkyl group optionally substituted by 1 to 3 halogen atoms (preferably a fluorine atom) (preferably trifluoromethyl).

As another embodiment, ring B is more preferably a benzene ring optionally further substituted by 1 to 3 substituents selected from (1) a halogen atom (preferably a fluorine atom, a chlorine atom, a bromine atom), (2) a $C_{1-6}$ alkyl group optionally substituted by 1 to 3 halogen atoms (preferably a fluorine atom) (preferably trifluoromethyl), and (3) a $C_{1-6}$ alkoxy group (preferably methoxy) optionally substituted by 1 to 3 halogen atoms.

In the embodiment, ring B is more preferably a benzene ring further substituted by 1 to 3 substituents selected from (1) a halogen atom (preferably a fluorine atom, a chlorine atom, a bromine atom), (2) a $C_{1-6}$ alkyl group optionally substituted by 1 to 3 halogen atoms (preferably a fluorine atom) (preferably trifluoromethyl), and (3) a $C_{1-6}$ alkoxy group (preferably methoxy) optionally substituted by 1 to 3 halogen atoms.

In the embodiment, ring B is further more preferably a benzene ring further substituted by one substituent selected from (1) a halogen atom (preferably a fluorine atom, a chlorine atom, a bromine atom), (2) a $C_{1-6}$ alkyl group optionally substituted by 1 to 3 halogen atoms (preferably a fluorine atom) (preferably trifluoromethyl), and (3) a $C_{3-6}$ alkoxy group (preferably methoxy) optionally substituted by 1 to 3 halogen atoms, wherein the substituent is bonded to the 3-position and the trifluoromethyl group bonded to ring B is bonded to the 5-position, with the bonding position of ring A as the 1-position.

That is, ring B is further more preferably a benzene ring represented by the formula:

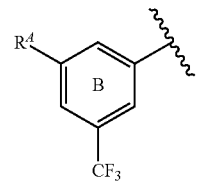

wherein
$R^A$ is
(1) a halogen atom (preferably a fluorine atom, a chlorine atom, a bromine atom),
(2) a $C_{1-6}$ alkyl group optionally substituted by 1 to 3 halogen atoms (preferably a fluorine atom) (preferably trifluoromethyl) or
(3) a $C_{1-6}$ alkoxy group (preferably methoxy) optionally substituted by 1 to 3 halogen atoms.

Ring B is particularly preferably a benzene ring represented by the formula:

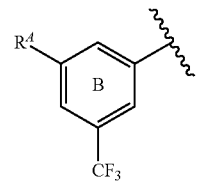

wherein
$R^A$ is
(1) a halogen atom (preferably a fluorine atom, a chlorine atom, a bromine atom) or
(2) a $C_{1-6}$ alkyl group optionally substituted by 1 to 3 halogen atoms (preferably a fluorine atom) (preferably trifluoromethyl).

X is a bond, O, $CH_2O$, $OCH_2$, $CH_2$, $(CH_2)_2$, S, $CH_2S$, $SCH_2$, $S(O)$, $CH_2S(O)$, $S(O)CH_2$, $S(O)_2$, $CH_2S(O)_2$ or $S(O)_2CH_2$.

X is preferably a bond, O, $CH_2$, S, $CH_2S$, $SCH_2$, $S(O)$ or $S(O)_2$, more preferably O, $CH_2$ or S, As another embodiment, X is preferably O, $CH_2O$, $OCH_2$, $CH_2$, S, $CH_2S$, $SCH_2$, $S(O)$ or $S(O)_2$, more preferably O, $CH_2O$, $CH_2$, S, $SCH_2$, $S(O)$ or $S(O)_2$.

As another embodiment, X is preferably a bond.

Preferable examples of compound (I) include the following compounds.

[Compound I-A]

A compound represented by the formula:

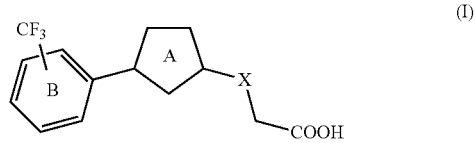

wherein
ring A is a 5-membered non-aromatic heterocycle (preferably pyrrolidine, imidazolidine, tetrahydrofuran, 1,1-dioxidoisothiazolidine) optionally further substituted by one substituent selected from a $C_{1-6}$ alkyl group and an oxo group;
ring B is a benzene ring optionally further substituted by 1 to 4 substituents selected from a halogen atom (preferably a fluorine atom, a chlorine atom) and a $C_{1-6}$ alkyl group optionally substituted by 1 to 3 halogen atoms (preferably a fluorine atom) (preferably trifluoromethyl); and X is O, S or $CH_2$ or a salt thereof.

[Compound I-B]

A compound represented by the formula:

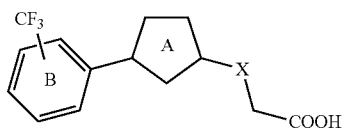
(I)

wherein ring A is a 5-membered non-aromatic heterocycle (preferably pyrrolidine, imidazolidine, tetrahydrofuran, 1,1-dioxido-isothiazolidine) optionally further substituted by one substituent selected from a $C_{1-6}$ alkyl group and an oxo group;

ring B is a benzene ring optionally further substituted by 1 to 4 substituents selected from (1) a halogen atom (preferably a fluorine atom, a chlorine atom, a bromine atom), (2) a $C_{1-6}$ alkyl group optionally substituted by 1 to 3 halogen atoms (preferably a fluorine atom) (preferably trifluoromethyl), (3) a $C_{1-4}$ alkoxy group (preferably methoxy) optionally substituted by 1 to 3 halogen atoms, (4) a cyano group, (5) an amino group optionally mono- or di-substituted by substituent(s) selected from (a) a $C_{1-6}$ alkyl group (preferably methyl) optionally substituted by 1 to 3 halogen atoms, and (b) a $C_{1-6}$ alkylsulfonyl group (preferably methylsulfonyl) optionally substituted by 1 to 3 halogen atoms, and (6) a non-aromatic heterocyclylcarbonyl group (e.g., thiomorpholinylcarbonyl, 1-oxidothiomorpholinylcarbonyl) optionally substituted by 1 to 3 substituents selected from a $C_{2-6}$ alkyl group optionally substituted by 1 to 3 halogen atoms; and X is bond, O, $CH_2O$, $OCH_2$, $CH_2$, $(CH_2)_2$, S, $CH_2S$, $SCH_2$, S(O), $CH_2S(O)$, $S(O)CH_2$, $S(O)_2$, $CH_2S(O)_2$ or $S(O)_2CH_2$, provided that {4-oxo-3-[3-(trifluoromethyl)phenyl]-1,3-thiazolidin-5-yl}acetic acid, {2-oxo-1-[3-(trifluoromethyl)phenyl]pyrrolidin-3-yl}acetic acid, {3-[4-fluoro-3-(trifluoromethyl)phenyl]-4-oxo-1,3-oxazolidin-5-yl}acetic acid, {4-oxo-3-[3-(trifluoromethyl)phenyl]-1,3-oxazolidin-5-yl}acetic acid, {3-[2-chloro-5-(trifluoromethyl)phenyl]-4-oxo-1,3-thiazolidin-5-yl}acetic acid, and {5-oxo-1-[3-(trifluoromethyl)phenyl]-4,5-dihydro-1H-pyrazol-3-yl}acetic acid are excluded, or a salt thereof.

[Compound I-C]

A compound represented by the formula:

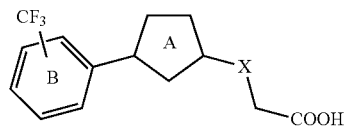
(I)

wherein ring A is a 5-membered non-aromatic heterocycle (preferably pyrrolidine, imidazolidine, tetrahydrofuran, 1,1-dioxido-isothiazolidine) optionally further substituted by one substituent selected from a $C_{1-6}$ alkyl group and an oxo group;

ring B is a benzene ring optionally further substituted by 1 to 3 substituents selected from (a) a halogen atom (preferably a fluorine atom, a chlorine atom, a bromine atom), (b) a $C_{1-6}$ alkyl group optionally substituted by 1 to 3 halogen atoms (preferably a fluorine atom) (preferably trifluoromethyl), and (c) a $C_{1-6}$ alkoxy group (preferably methoxy) optionally substituted by 1 to 3 halogen atoms; and X is O, $CH_2O$, $OCH_2$, $CH_2$, S, $CH_2S$, $SCH_2$, S(O) or $S(O)_2$, or a salt thereof.

[Compound I-D]

A compound represented by the formula:

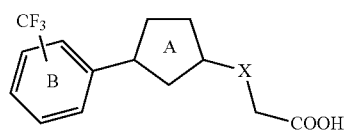
(I)

wherein ring A is a pyrrolidine ring or a tetrahydrofuran ring, each of which is optionally further substituted by one oxo group;

ring B is a benzene ring further substituted by 1 to 3 substituents selected from (a) a halogen atom (preferably a fluorine atom, a chlorine atom, a bromine atom), (b) a $C_{1-6}$ alkyl group optionally substituted by 1 to 3 halogen atoms (preferably a fluorine atom) (preferably trifluoromethyl), and (c) a $C_{1-6}$ alkoxy group (preferably methoxy) optionally substituted by 1 to 3 halogen atoms; and X is bond, or a salt thereof.

[Compound I-E]

A compound represented by the formula:

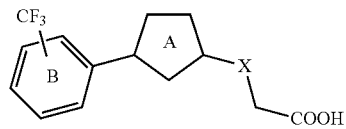
(I)

wherein ring A is a 5-membered non-aromatic heterocycle (preferably pyrrolidine, imidazolidine, tetrahydrofuran, 1,1-dioxidoisothiazolidine) optionally further substituted by one substituent selected from a $C_{1-6}$ alkyl group and an oxo group;
ring B is an optionally further substituted benzene ring; and
X is O, S or $CH_2$,
or a salt thereof.
[Compound I-F]
A compound represented by the formula:

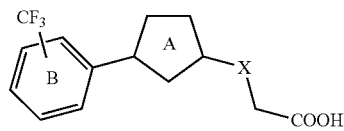 (I)

wherein
ring A is a pyrrolidine ring or a tetrahydrofuran ring, each of which is optionally further substituted by one oxo group;
ring B is a benzene ring represented by the formula:

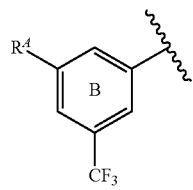

wherein
$R^A$ is
(1) a halogen atom (preferably a fluorine atom, a chlorine atom, a bromine atom),
(2) a $C_{1-6}$ alkyl group optionally substituted by 1 to 3 halogen atoms (preferably a fluorine atom) (preferably trifluoromethyl) or
(3) a alkoxy group (preferably methoxy) optionally substituted by 1 to 3 halogen atoms; and
X is bond, O, $CH_2O$, $OCH_2$, $CH_2$, $(CH_2)_2$, S, $CH_2S$, $SCH_2$, S(O), $CH_2S(O)$, $S(O)CH_2$, $S(O)_2$, $CH_2S(O)_2$ or $S(O)_2CH_2$,
or a salt thereof.
[Compound I-G]
({(3S)-1-[3,5-bis(trifluoromethyl)phenyl]pyrrolidin-3-yl}oxy)acetic acid or a salt thereof.
5-({1-[4-chloro-3-(trifluoromethyl)phenyl]pyrrolidin-3-yl}sulfanyl)acetic acid or a salt thereof.
3-{(2R,5S)-5-[3,5-bis(trifluoromethyl)phenyl]tetrahydrofuran-2-yl}propanoic acid or a salt thereof.

As a salt of the compound represented by the formula (I) or the formula (I'), a pharmacologically acceptable salt is preferable. Examples of such salt include salts with inorganic base, salts with organic base, salts with inorganic acid, salts with organic acid, salts with basic or acidic amino acid, and the like.

Preferable examples of the salt with inorganic base include alkali metal salts such as sodium salt, potassium salt and the like; alkaline earth metal salts such as calcium salt, magnesium salt and the like; aluminum salt: ammonium salt and the like.

Preferable examples of the salt with organic base include salts with trimethylamine, triethylamine, pyridine, picoline, ethanolamine, diethanolamine, triethanolamine, tromethamine[tris(hydroxymethyl)methylamine], tert-butylamine, cyclohexylamine, benzylamine, dicyclohexylamine, N,N-dibenzylethylenediamine and the like.

Preferable examples of the salt with inorganic acid include salts with hydrochloric acid, hydrobromic acid, nitric acid, sulfuric acid, phosphoric acid and the like.

Preferable examples of the salt with organic acid include salts with formic acid, acetic acid, trifluoroacetic acid, phthalic acid, fumaric acid, oxalic acid, tartaric acid, maleic acid, citric acid, succinic acid, malic acid, methanesulfonic acid, benzenesulfonic acid, p-toluenesulfonic acid and the like.

Preferable examples of the salt with basic amino acid include salts with arginine, lysine, ornithine and the like.

Preferable examples of the salt with acidic amino acid include salts with aspartic acid, glutamic acid and the like.

A prodrug of the compound represented by the formula (I) or the formula (I') (hereinafter, to be also referred to as compound (I) collectively) means a compound which is converted to compound (I) by a reaction due to an enzyme, an gastric acid, etc. under the physiological condition in the living body, that is, a compound which is converted to compound (I) by oxidation, reduction, hydrolysis, etc. according to an enzyme; a compound which is converted to compound (I) by hydrolysis etc. due to gastric acid, etc.

Examples of the prodrug of compound (I) include
a compound wherein an amino group of compound (I) is acylated, alkylated or phosphorylated (e.g., a compound wherein an amino group of compound (I) is eicosanoylated, alanylated, pentylaminocarbonylated, (5-methyl-2-oxo-1,3-dioxolen-4-yl)methoxycarbonylated, tetrahydrofuranylated, pyrrolidylmethylated, pivaloyloxymethylated or tert-butylated);
a compound wherein a hydroxy group of compound (I) is acylated, alkylated, phosphorylated or borated (e.g., a compound wherein a hydroxy group of compound (I) is acetylated, palmitoylated, propanoylated, pivaloylated, succinylated, fumarylated, alanylated or dimethylaminomethylcarbonylated);
a compound wherein a carboxyl group of compound (I) is esterified or amidated (e.g., a compound wherein a carboxyl group of compound (I) is ethyl esterified, phenyl esterified, carboxymethyl esterified, dimethylaminomethyl esterified, pivaloyloxymethyl esterified, ethoxycarbonyloxyethyl esterified, phthalidyl esterified, (5-methyl-2-oxo-1,3-dioxolen-4-yl)methyl esterified, cyclohexyloxycarbonylethyl esterified or methylamidated)
and the like. These compounds can be produced from compound (I) by a method known per se.

A prodrug for compound (I) may also be one which is converted to compound (I) under a physiological condition, such as those described in IYAKUHIN no KAIHATSU, Development of Pharmaceuticals, Vol. 7, Design of Molecules, p. 163-198, Published by HIROKAWA SHOTEN, 1990.

Compound (I) may be a solvate (e.g., hydrate) or a non-solvate (e.g., anhydride).

In addition, compound (I) may be labeled with an isotope (e.g., $^3H$, $^{14}C$, $^{35}S$, $^{125}I$) and the like.

Furthermore, a deuterium converter wherein $^1H$ is converted to $^2H(D)$ is also encompassed in compound (I).

Compound (I) or a prodrug thereof (hereinafter sometimes to be abbreviated simply as the compound of the present invention) has low toxicity, and can be used as an agent for the prophylaxis or treatment of various diseases mentioned below in a mammal (e.g., human, mouse, rat, rabbit, dog, cat, bovine, horse, swine, monkey) directly or in the form of a pharmaceutical composition by admixing with a pharmacologically acceptable carrier and the like.

Here, examples of the pharmacologically acceptable carrier include various organic or inorganic carrier substances conventionally used as preparation materials, which are added as excipient, lubricant, binder or disintegrant for solid dosage forms; as solvent, solubilizing agent, suspending agent, isotonicity agent, buffer or soothing agent for liquid preparation, and the like. Where necessary, preparation additives such as preservative, antioxidant, colorant, sweetener and the like can also be used.

Preferable examples of the excipient include lactose, sucrose, D-mannitol, D-sorbitol, starch, pregelatinized starch, dextrin, crystalline cellulose, low-substituted hydroxypropylcellulose, sodium carboxymethylcellulose, gum arabic, pullulan, light anhydrous silicic acid, synthetic aluminum silicate and magnesium aluminometasilicate.

Preferable examples of the lubricant include magnesium stearate, calcium stearate, talc and colloidal silica.

Preferable examples of the binder include pregelatinized starch, sucrose, gelatin, gum arabic, methylcellulose, carboxymethylcellulose, sodium carboxymethylcellulose, crystalline cellulose, sucrose, D-mannitol, trehalose, dextrin, pullulan, hydroxypropylcellulose, hydroxypropylmethylcellulose and polyvinylpyrrolidone.

Preferable examples of the disintegrant include lactose, sucrose, starch, carboxymethylcellulose, calcium carboxymethylcellulose, sodium croscarmellose, sodium carboxymethylstarch, light anhydrous silicic acid and low-substituted hydroxypropylcellulose.

Preferable examples of the solvent include water for injection, physiological brine, Ringer's solution, alcohol, propylene glycol, polyethylene glycol, sesame oil, corn oil, olive oil and cottonseed oil.

Preferable examples of the solubilizing agent include polyethylene glycol, propylene glycol, D-mannitol, trehalose, benzyl benzoate, ethanol, trisaminomethane, cholesterol, triethanolamine, sodium carbonate, sodium citrate, sodium salicylate and sodium acetate.

Preferable examples of the suspending agent include surfactants such as stearyltriethanolamine, sodium lauryl sulfate, lauryl aminopropionic acid, lecithin, benzalkonium chloride, benzethonium chloride, glyceryl monostearate and the like; hydrophilic polymers such as polyvinyl alcohol, polyvinylpyrrolidone, sodium carboxymethylcellulose, methylcellulose, hydroxymethylcellulose, hydroxyethylcellulose, hydroxypropylcellulose and the like; polysorbates and polyoxyethylene hydrogenated castor oil.

Preferable examples of the isotonicity agent include sodium chloride, glycerol, D-mannitol, D-sorbitol and glucose.

Preferable examples of the buffer include buffers such as phosphate, acetate, carbonate, citrate and the like.

Preferable examples of the soothing agent include benzyl alcohol.

Preferable examples of the preservative include paraoxybenzoates, chlorobutanol, benzyl alcohol, phenethyl alcohol, dehydroacetic acid and sorbic acid.

Preferable examples of the antioxidant include sulfite, ascorbate and the like.

Preferable examples of the colorant include aqueous food tar colors (e.g., food colors such as Food Red No. 2 and No. 3, Food Yellow No. 4 and No. 5, Food Blue No. 1 and No. 2, etc.), water insoluble lake dye (e.g., aluminum salt of the above-mentioned aqueous food tar color) and natural dye (e.g., β-carotene, chlorophyll, ferric oxide red).

Preferable examples of the sweetening agent include sodium saccharin, dipotassium glycyrrhizinate, aspartame and stevia.

Examples of the dosage form of the above-mentioned pharmaceutical composition include oral preparations such as tablets (inclusive of sugar-coated tablets, film-coated tablets, sublingual tablets, orally disintegrating tablets), capsules (inclusive of soft capsules, microcapsules), granules, powders, troches, syrups, emulsions, suspensions, films (e.g., orally disintegrable films) and the like; and parenteral agents such as injections (e.g., subcutaneous injections, intravenous injections, intramuscular injections, intraperitoneal injections, drip infusions), external preparations (e.g., dermal preparations, ointments), suppository (e.g., rectal suppositories, vaginal suppositories), pellets, nasal preparations, pulmonary preparations (inhalants), eye drops and the like. These may be safely administered orally or parenterally (e.g., topically, rectally, intravenously administered).

These preparations may be release control preparations (e.g., sustained-release microcapsule) such as immediate-release preparation, sustained-release preparation and the like.

A pharmaceutical composition can be produced by a method conventionally used in the technical field of pharmaceutical preparation, for example, the method described in the Japanese Pharmacopoeia and the like.

The content of the compound of the present invention in a pharmaceutical composition is about 0.01 to 100 wt %, preferably about 2 to 85 wt %, of the total composition.

While the dose of the compound of the present invention varies depending on the subject of administration, administration route, disease and the like, it is, for example, about 1 to 1000 mg, preferably about 3 to 300 mg, more preferably about 10 to 200 mg, in an amount of the compound of the present invention as an active ingredient of an oral preparation for administration to an adult (body weight about 60 kg) as a prophylactic or therapeutic drug for diabetes, and the dose can be administered in one to several portions a day.

During production of an oral preparation, coating may be applied as necessary for the purpose of masking of taste, enteric property or durability.

Examples of the coating base to be used for coating include sugar coating base, aqueous film coating base, enteric film coating base and sustained-release film coating base.

As the sugar coating base, sucrose is used. Moreover, one or more kinds selected from talc, precipitated calcium carbonate, gelatin, gum arabic, pullulan, carnauba wax and the like may be used in combination.

Examples of the aqueous film coating base include cellulose polymers such as hydroxypropyl cellulose, hydroxypropylmethyl cellulose, hydroxyethyl cellulose, methylhydroxyethyl cellulose etc.; synthetic polymers such as polyvinylacetal diethylaminoacetate, aminoalkyl methacrylate copolymer E [Eudragit E (trade name)], polyvinylpyrrolidone etc.; and polysaccharides such as pullulan etc.

Examples of the enteric film coating base include cellulose polymers such as hydroxypropylmethyl cellulose phthalate, hydroxypropylmethyl cellulose acetate succinate, carboxymethylethyl cellulose, cellulose acetate phthalate etc.; acrylic polymers such as methacrylic acid copolymer L [Eudragit L (trade name)], methacrylic acid copolymer LD [Eudragit L-30D55 (trade name)], methacrylic acid copolymer S [Eudragit S (trade name)] etc.; and naturally occurring substances such as shellac etc.

Examples of the sustained-release film coating base include cellulose polymers such as ethyl cellulose etc.; and acrylic polymers such as aminoalkyl methacrylate copolymer RS[Eudragit RS (trade name)], ethyl acrylate-methyl methacrylate copolymer suspension [Eudragit NE (trade name)] etc.

The above-mentioned coating bases may be used after mixing with two or more kinds thereof at appropriate ratios. For coating, for example, a light shielding agent such as titanium oxide, red ferric oxide and the like can be used.

The compound of the present invention shows low toxicity (e.g., acute toxicity, chronic toxicity, genetic toxicity, reproductive toxicity, cardiotoxicity, carcinogenicity and the like) and a few side effects. Therefore, it can be used as an agent for the prophylaxis or treatment or a diagnostic of various diseases in a mammal (e.g., human, bovine, horse, dog, cat, monkey, mouse, rat).

The compound of the present invention has a superior RBP4 (retinol-binding protein 4) lowering action. Accordingly, the compound of the present invention is useful as an agent for the prophylaxis or treatment of the diseases and conditions related to an increase in RBP4.

The compound of the present invention can be specifically used as an agent for the prophylaxis or treatment of obesity, diabetes (e.g., type 1 diabetes, type 2 diabetes, gestational diabetes, obese diabetes), hyperlipidemia (e.g., hypertriglyceridemia, hypercholesterolemia, high LDL-cholesterolemia, low HDL-cholesterolemia, postprandial hyperlipemia), hypertension, cardiac failure, diabetic complications [e.g., neuropathy, nephropathy, retinopathy, diabetic cardiomyopathy, cataract, macroangiopathy, osteopenia, hyperosmolar diabetic coma, infections (e.g., respiratory infection, urinary tract infection, gastrointestinal infection, dermal soft tissue infections, inferior limb infection), diabetic gangrene, xerostomia, hypacusis, cerebrovascular disorder, peripheral blood circulation disorder], metabolic syndrome (pathology having three or more selected from hypertriglyceridemia (TG), low HDL cholesterol (HDL-C), hypertension, abdomen obesity and impaired glucose tolerance), sarcopenia and the like.

For diagnostic criteria of diabetes, Japan Diabetes Society reported new diagnostic criteria in 1999.

According to this report, diabetes is a condition showing any of a fasting blood glucose level (glucose concentration of intravenous plasma) of not less than 126 mg/dl, a 75 g oral glucose tolerance test (75 g OGTT) 2 hr level (glucose concentration of intravenous plasma) of not less than 200 mg/dl, and a non-fasting blood glucose level (glucose concentration of intravenous plasma) of not less than 200 mg/dl. A condition not falling under the above-mentioned diabetes and different from "a condition showing a fasting blood glucose level (glucose concentration of intravenous plasma) of less than 110 mg/dl or a 75 g oral glucose tolerance test (75 g OGTT) 2 hr level (glucose concentration of intravenous plasma) of less than 140 mg/dl" (normal type) is called a "borderline type".

In addition, ADA (American Diabetes Association) in 1997 and WHO in 1998 reported new diagnostic criteria of diabetes.

According to these reports, diabetes is a condition showing a fasting blood glucose level (glucose concentration of intravenous plasma) of not less than 126 mg/dl and a 75 g oral glucose tolerance test 2 hr level (glucose concentration of intravenous plasma) of not less than 200 mg/dl.

According to the above-mentioned reports, impaired glucose tolerance is a condition showing fasting blood sugar level (glucose concentration of intravenous plasma) of less than 126 mg/dl and a 75 g oral glucose tolerance test 2 hr level (glucose concentration of intravenous plasma) of not less than 140 mg/dl and less than 200 mg/dl. According to the report of ADA, a condition showing a fasting blood glucose level (glucose concentration of intravenous plasma) of not less than 110 mg/dl and less than 126 mg/dl is called IFG (Impaired Fasting Glucose). According to the report of WHO, among the IFG (Impaired Fasting Glucose), a condition showing a 75 g oral glucose tolerance test 2 hr level (glucose concentration of intravenous plasma) of less than 140 mg/dl is called IFG (Impaired Fasting Glycemia).

The compound of the present invention can also be used as an agent for the prophylaxis or treatment of diabetes, borderline type, impaired glucose tolerance, IFG (Impaired Fasting Glucose) and IFG (Impaired Fasting Glycemia), as determined according to the above-mentioned new diagnostic criteria. Moreover, the compound of the present invention can prevent progress of borderline type, impaired glucose tolerance, IFG (Impaired Fasting Glucose) or IFG (Impaired Fasting Glycemia) into diabetes.

The compound of the present invention can also be used as an agent for the prophylaxis or treatment of osteoporosis, cachexia (e.g., carcinomatous cachexia, tuberculous cachexia, diabetic cachexia, hemopathic cachexia, endocrinopathic cachexia, infectious cachexia or cachexia induced by acquired immunodeficiency syndrome), fatty liver, polycystic ovary syndrome, renal disease (e.g., diabetic nephropathy, glomerulonephritis, glomerulosclerosis, nephrosis syndrome, hypertensive nephrosclerosis, terminal renal disorder), muscular dystrophy, myocardial infarction, angina pectoris, cerebrovascular disorder (e.g., cerebral infarction, cerebral apoplexy), Alzheimer's disease, Parkinson's disease, anxiety, dementia, insulin resistance syndrome, syndrome X, hyperinsulinemia, sensory abnormality in hyperinsulinemia, tumor (e.g., leukemia, breast cancer, prostate cancer, skin cancer), irritable bowel syndrome, acute or chronic diarrhea, inflammatory disease (e.g., rheumatoid arthritis, spondylitis deformans, osteoarthritis, lumbago, gout, postoperative or posttraumatic inflammation, swelling, neuralgia, pharyngolaryngitis, cystitis, hepatitis (including nonalcoholic steatohepatitis), pneumonia, pancreatitis, enteritis, inflammatory intestine disease (including inflammatory colitis), ulcerative colitis, stomach mucosainjury (including stomach mucosainjury caused by aspirin)), small intestine mucosainjury, malabsorption, testis dysfunction, visceral obesity syndrome, sarcopenia or age-related macular degeneration.

The compound of the present invention can further be used for secondary prevention or suppression of progression of the above-mentioned various diseases (e.g., cardiovascular events such as myocardial infarction and the like).

With the aim of enhancing the action of the compound of the present invention or decreasing the dose of the compound and the like, the compound can be used in combination with other medicaments such as therapeutic agents for diabetes, therapeutic agents for diabetic complications, therapeutic agents for hyperlipidemia, antihypertensive agents, antiobesity agents, diuretics, antithrombotic agents and the like (hereinafter to be abbreviated as concomitant drug). The time of administration of the compound of the present invention and that of the concomitant drug are not limited, and they may be administered simultaneously or in a staggered manner to the administration subject. In addition, the compound of the present invention and the concomitant drug may be administered as two kinds of preparations containing respective active ingredients or a single preparation containing both active ingredients.

The dose of the concomitant drug can be appropriately determined based on the dose employed clinically. In addition, the mixing ratio of the compound of the present invention and the concomitant drug can be appropriately determined according to the administration subject, administration route, target disease, condition, combination, and the like. For example, when the administration subject is a human, the concomitant drug may be used in an amount of 0.01 to 100 parts by weight per 1 part by weight of the compound of the present invention.

Examples of the therapeutic agents for diabetes include insulin preparations (e.g., animal insulin preparations extracted from pancreas of bovine or swine; human insulin preparations genetically synthesized using *Escherichia coli* or yeast; zinc insulin; protamine zinc insulin; fragment or derivative of insulin (e.g., INS-1), oral insulin preparation), insulin sensitizers (e.g., pioglitazone or a salt thereof (preferably hydrochloride), rosiglitazone or a salt thereof (preferably maleate), Tesaglitazar, Ragaglitazar, Muraglitazar, Edaglitazone, Metaglidasen, Naveglitazar, AMG-131, THR-0921, TAK-379), α-glucosidase inhibitors (e.g., voglibose, acarbose, miglitol, emiglitate), biguanides (e.g., metformin, buformin or a salt thereof (e.g., hydrochloride, fumarate, succinate)), insulin secretagogues [e.g., sulfonylurea (e.g., tolbutamide, glibenclamide, gliclazide, chlorpropamide, tolazamide, acetohexamide, glyclopyramide, glimepiride, glipizide, glybuzole), repaglinide, nateglinide, mitiglinide or a calcium salt hydrate thereof], dipeptidyl peptidase IV inhibitors (e.g., Alogliptin, Vildagliptin, Sitagliptin, Saxagliptin, T-6666, TS-021), β3 agonists (e.g., AJ-9677), GPR40 agonists, GLP-1 receptor agonists [e.g., GLP-1, GLP-1MR agent, N,N-2211, AC-2993 (exendin-4), BIM-51077, Aib(8, 35)hGLP-1(7,37)$NH_2$, CJC-1131], amylin agonists (e.g., pramlintide), phosphotyrosine phosphatase inhibitors (e.g., sodium vanadate), gluconeogenesis inhibitors (e.g., glycogen phosphorylase inhibitors, glucose-6-phosphatase inhibitors, glucagon antagonists), SGLUT (sodium-glucose cotransporter) inhibitors (e.g., T-1095), 11β-hydroxysteroid dehydrogenase inhibitors (e.g., BVT-3498), adiponectin or agonist thereof, IKK inhibitors (e.g., AS-2868), leptin resistance improving drugs, somatostatin receptor agonists, glucokinase activators (e.g., Ro-28-1675), GIP (Glucose-dependent insulinotropic peptide) and the like.

Examples of the therapeutic agent for diabetic complications include aldose reductase inhibitors (e.g., tolrestat, epalrestat, zenarestat, zopolrestat, minalrestat, fidarestat, CT-112), neurotrophic factors and increasing drugs thereof (e.g., NGF, NT-3, BDNF, neurotrophin production/secretion promoting agents (e.g., 4-(4-chlorophenyl)-2-(2-methyl-1-imidazolyl)-5-[3-(2-methylphenoxy)propyl]oxazole) described in WO01/14372, TAK-583), nerve regeneration promoters (e.g., Y-128), PKC inhibitors (e.g., ruboxistaurin mesylate), AGE inhibitors (e.g., ALT946, pimagedine, pyratoxanthine, N-phenacylthiazolium bromide (ALT766), ALT-711, EXO-226, pyridorin, pyridoxamine), active oxygen scavengers (e.g., thioctic acid), cerebral vasodilators (e.g., tiapuride, mexiletine), somatostatin receptor agonists (e.g., BIM23190), apoptosis signal regulating kinase-1 (ASK-1) inhibitor and the like.

Examples of the therapeutic agent for hyperlipidemia include statin compounds (e.g., cerivastatin, pravastatin, simvastatin, lovastatin, atorvastatin, fluvastatin, itavastatin, rosuvastatin, pitavastatin or a salt thereof (e.g., sodium salt, calcium salt)), squalene synthase inhibitors (e.g., lapaquistat acetate), fibrate compounds (e.g., bezafibrate, clofibrate, simfibrate, clinofibrate), ACAT inhibitors (e.g., Avasimibe, Eflucimibe), anion exchange resins (e.g., colestyramine), probucol, nicotinic acid drugs (e.g., nicomol, niceritrol), ethyl icosapentate, phytosterols (e.g., soysterol, γ-oryzanol) and the like.

Examples of the antihypertensive agent include angiotensin converting enzyme inhibitors (e.g., captopril, enalapril, delapril), angiotensin II antagonists (e.g., candesartan cilexetil, losartan, eprosartan, valsartan, telmisartan, irbesartan, tasosartan, 1-[[2'-(2,5-dihydro-5-oxo-4H-1,2,4-oxadiazol-3-yl)biphenyl-4-yl]methyl]-2-ethoxy-1H-benzimidazole-7-carboxylic acid, TAK-491), calcium antagonists (e.g., manidipine, nifedipine, amlodipine, efonidipine, nicardipine), potassium channel openers (e.g., levcromakalim, L-27152, AL 0671, NIP-121), clonidine and the like.

Examples of the antiobesity agent include central nervous system antiobesity drugs (e.g., dexfenfluramine, fenfluramine, phentermine, sibutramine, amfepramone, dexamphetamine, mazindol, phenylpropanolamine, clobenzorex; MCH receptor antagonists (e.g., SB-568849; SNAP-7941; compound described in WO01/82925 and WO01/87834); neuropeptide Y antagonists (e.g., CP-422935); cannabinoid receptor antagonists (e.g., SR-141716, SR-147778); ghrelin antagonist; 11β-hydroxysteroid dehydrogenase inhibitors (e.g., BVT-3498)), pancreatic lipase inhibitors (e.g., orlistat, cetilistat), β3 agonists (e.g., AJ-9677, A240140), anorectic peptides (e.g., leptin, CNTF (ciliary neurotrophic factor)), cholecystokinin agonists (e.g., lintitript, FPL-15849), anorexigenic agents (e.g., P-57) and the like.

Examples of the diuretics include xanthine derivatives (e.g., theobromine sodium salicylate, theobromine calcium salicylate), thiazide preparations (e.g., ethiazide, cyclopenthiazide, trichloromethiazide, hydrochlorothiazide, hydroflumethiazide, benzylhydrochlorothiazide, penflutizide, polythiazide, methyclothiazide), antialdosterone preparations (e.g., spironolactone, triamterene), carbonic anhydrase inhibitors (e.g., acetazolamide), chlorobenzenesulfonamide agents (e.g., chlortalidone, mefruside, indapamide), azosemide, isosorbide, ethacrynic acid, piretanide, bumetanide, furosemide and the like.

Examples of the antithrombotic agent include heparin (e.g., heparin sodium, heparin calcium, dalteparin sodium), warfarin (e.g., warfarin potassium), anti-thrombin drugs (e.g., aragatroban, dabigatran), thrombolytic agents (e.g., urokinase, tisokinase, alteplase, nateplase, monteplase, pamiteplase), platelet aggregation inhibitors (e.g., ticlopidine hydrochloride, cilostazol, ethyl icosapentate, beraprost sodium, sarpogrelate hydrochloride), prasugrel, E5555, SHC530348), FXa inhibitors (e.g., TAK-442, rivaroxaban, apixaban, DU-156, YM150) and the like.

In the following, the production methods of compound (I) of the present invention are explained.

Compound (I) can be produced according to a method known per se, for example, a method described in detail below, or a method analogous thereto.

Each symbol in the reaction schemes, $R^1$, $R^2$, $X^1$, $X^2$, $L^1$, $L^2$, $L^3$ and ring C are as defined above below. Unless otherwise specified, the other symbols are as defined above.

$R^1$ is a hydrogen atom or a carboxyl-protecting group. Specific examples of the carboxyl-protecting group include those mentioned below. Of these, a $C_{1-6}$ alkyl group optionally substituted by 1 to 3 halogen atoms; a $C_{7-20}$ aralkyl group (e.g., benzyl, trityl) optionally substituted by 1 to 5 substituents selected from a halogen atom, a $C_{1-6}$ alkoxy group, a nitro group and the like; and the like are preferable.

$R^2$ is a protecting group for amine. Specific examples of the protecting group for amine include those similar to the amino-protecting group mentioned below.

$X^1$ is O or S.

$X^2$ is $CH_2$, O or S.

$L^1$, $L^2$ and $L^3$ are independently a leaving group.

Preferable specific examples of $L^1$ include a halogen atom (preferably chlorine, bromine, iodine), a $C_{1-6}$ alkylsulfonyloxy group optionally substituted by 1 to 3 halogen atoms (e.g., methanesulfonyloxy, ethanesulfonyloxy, trifluoromethanesulfonyloxy), an arylsulfonyloxy group optionally having substituent(s) (e.g., benzenesulfonyloxy, p-toluenesulfonyloxy) and the like.

Preferable specific examples of $L^2$ include a dialkylphosphono group (preferably a dimethylphosphono group, a diethylphosphono group), a triphenylphosphonium group and the like.

Preferable specific examples of $L^3$ include a dihydroxyboranyl group, a dialkoxyboranyl group (preferably 4,4,5,5-tetramethyl-1,3,2-dioxaboran-2-yl), trialkylstannyl group (preferably trimethylstannyl group, n-tributylstannyl group) and the like.

Ring C is a 5-membered aromatic heterocycle or unsaturated heterocycle. Examples of the 5-membered aromatic heterocycle include thiophene, furan, pyrrole, imidazole, pyrazole, triazole, tetrazole, thiazole, isothiazole, thiadiazole, oxazole, isoxazole, oxadiazole and the like. Examples of the 5-membered unsaturated heterocycle include a ring having at least one double bond, from among those exemplified as the "5-membered non-aromatic heterocycle" of the "optionally further substituted 5-membered non-aromatic heterocycle" for ring A.

Specific examples of ring C include furan, pyrrole and the like.

In the following production methods, the "ether solvents", "halogenated hydrocarbon solvents", "aromatic solvents", "nitrile solvents", "ester solvents", "amide solvents", "ketone solvents", "sulfoxide solvents", "alcohol solvents", "organic acid solvents" means the followings.

Examples of the "ether solvents" include diethyl ether, tetrahydrofuran (THF), 1,4-dioxane, 1,2-dimethoxyethane and the like.

Examples of the "halogenated hydrocarbon solvents" include dichloromethane, chloroform, 1,2-dichloroethane, carbon tetrachloride, 1,1,2,2-tetrachloroethane and the like.

Examples of the "aromatic solvents" include benzene, toluene, xylene, pyridine, mesitylene and the like.

Examples of the "nitrile solvents" include acetonitrile, propionitrile and the like.

Examples of the "ester solvents" include ethyl acetate, methyl acetate and the like.

Examples of the "amide solvents" include N,N-dimethylformamide (DMF), N,N-dimethylacetamide, N-methylpyrrolidone and the like.

Examples of the "ketone solvents" include acetone, methylethyl ketone and the like.

Examples of the "sulfoxide solvents" include dimethyl sulfoxide (DMSO) and the like.

Examples of the "alcohol solvents" include methanol, ethanol, isopropanol, tert-butanol and the like.

Examples of the "organic acid solvents" include formic acid, acetic acid, trifluoroacetic acid, methanesulfonic acid and the like.

Unless otherwise specified, the starting material compound in the following production methods is commercially available, or can be produced according to a method known per se or a method analogous thereto.

The compound as a starting material may be used in a form of a salt. Examples of the salt include those similar to the above-mentioned salt of the compound represented by the formula (I).

(Production Method A)

Of compound (I) of the present invention, a compound represented by the following formula (Ia) or (Ib) (compound (Ia) or compound (Ib)) can be produced, for example, according to the following Reaction Scheme 1.

(Reaction Scheme 1)

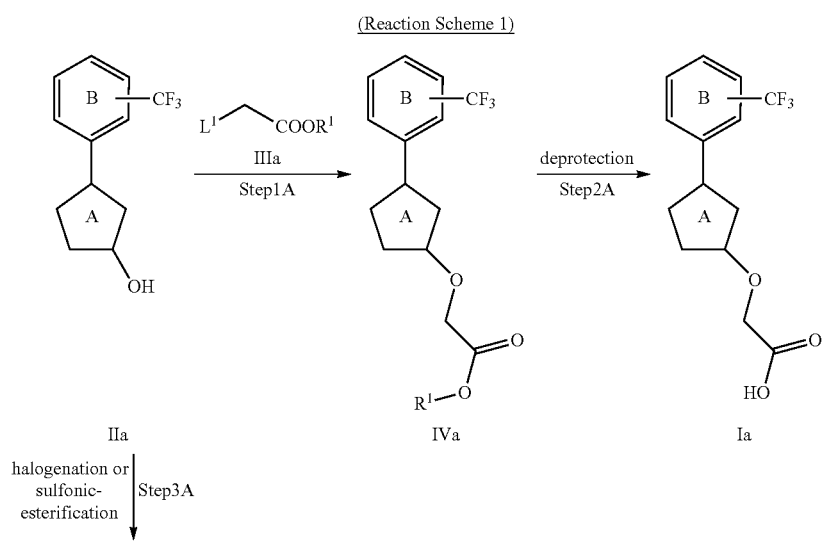

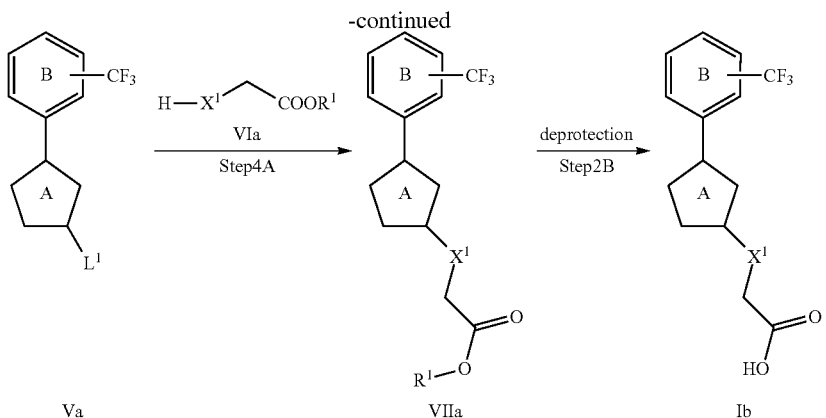

In this production method, compound (Ia) or compound (Ib) can be produced from compound (IIa) by the following steps.

Step 1A: a step of obtaining compound (IVa) by subjecting compound (IIa) to an alkylation reaction with compound (IIIa);

Step 2A: a step of obtaining compound (Ia) by removing $R^1$ which is the carboxyl-protecting group of compound (IVa);

Step 3A: a step of obtaining compound (Va) by subjecting the hydroxy group of compound (IIa) to a halogenation or sulfonic-esterification reaction;

Step 4A: a step of obtaining compound (VIIa) by subjecting compound (Va) to an alkylation reaction with compound (VIa);

Step 2B: a step of obtaining compound (Ib) by removing $R^1$ which is the carboxyl-protecting group of compound (VIIa).

Each step is explained in detail in the following.

(Step 1A)

Compound (IVa) can be produced by reacting compound (IIa) with compound (IIIa) in the presence of a base.

Examples of the base include amines (e.g., triethylamine, N,N-diisopropylethylamine, pyridine, 4-dimethylaminopyridine, 1,8-diazabicyclo[5.4.0]-7-undecene); alkali metal carbonates (e.g., potassium carbonate, sodium carbonate, cesium carbonate, sodium hydrogencarbonate, potassium hydrogencarbonate); alkali metal phosphates (e.g., tripotassium phosphate, trisodium phosphate); alkali metal acetates (sodium acetate, potassium acetate); alkali metal hydrides (e.g., sodium hydride, potassium hydride); alkali metal hydroxides (e.g., sodium hydroxide, potassium hydroxide); alkali metal $C_{1-6}$ alkoxides (e.g., sodium methoxide, sodium tert-butoxide, potassium tert-butoxide) and the like. Of these, sodium hydride, sodium carbonate, potassium tert-butoxide and the like are preferable.

The amount of the base to be used is generally 0.1 to 100 equivalents, preferably 1 to 10 equivalents, per 1 equivalent of compound (IIa)

Specific examples of compound (IIIa) include methyl bromoacetate, tert-butyl bromoacetate, sodium chloroacetate and the like.

Compound (IIIa) may be commercially available product, or can be produced according to a method known per se or a method analogous thereto.

The amount of compound (IIIa) to be used is generally 1 to 100 equivalents, preferably 1 to 5 equivalents, per 1 equivalent of compound (IIa).

This reaction is carried out without solvent or in an inert solvent. Examples of the inert solvent include ether solvents, halogenated hydrocarbon solvents, nitrile solvents, aromatic solvents, ester solvents, amide solvents, water and the like. These solvents may be used in a mixture of two or more kinds thereof at an appropriate ratio. Of these, tetrahydrofuran, acetonitrile, N,N-dimethylformamide, N,N-dimethylacetamide, dimethyl sulfoxide and the like are preferable.

Where necessary, a phase-transfer catalyst (e.g., tetrabutylammonium bromide, tetrabutylammonium hydrogensulfate etc.) may be used for this reaction.

The amount of the phase-transfer catalyst to be used is generally 0.01 to 0.5 equivalents, preferably 0.01 equivalents to 0.1 equivalents, per 1 equivalent of compound (IIa).

The reaction temperature of this reaction is generally about 30° C. to 200° C., preferably 50° C. to 120° C.

The reaction time of this reaction is generally 0.5 hr to 24 hr.

Compound (IIa) can be produced according to a method known per se (e.g., U.S. Pat. No. 5,670,656; WO 2006/21401; WO 2004/110994) or a method analogous thereto.

(Step 2A)

The removal of the protecting group $R^1$ of compound (IVa) is carried out according to a method known per se, for example, the method described in Protective Groups in Organic Synthesis, John Wiley and Sons (1980) and the like. Examples of the removal of the protecting group include a method using a acid, a base and the like, and the like.

(Step 3A)

Compound (Va) can be produced by converting the hydroxy group of compound (IIa) into a halogen atom using a halogenating reagent.

Examples of the halogenating reagent include thionyl chloride, thionyl bromide, phosphorus trichloride, phosphorus pentachloride, phosphorus oxychloride, carbon tetrabromide and the like.

The amount of the halogenating reagent to be used is generally 1 to 100 equivalents, preferably 1 to 10 equivalents, per 1 equivalent of compound (IIa).

This reaction is generally carried out in an inert solvent (e.g., ether solvents, halogenated hydrocarbon solvents, aromatic solvents etc.) or without solvent. These solvents may be used in a mixture of two or more kinds thereof at an appropriate ratio. Of these, tetrahydrofuran, toluene, carbon tetrachloride and the like are preferable.

The reaction temperature of this reaction is generally −20° C. to 200° C., preferably 0° C. to 100° C.

The reaction time of this reaction is generally 0.5 hr to 24 hr.

Compound (Va) can also be produced by converting the hydroxy group of compound (IIa) into an optionally halogenated $C_{1-6}$ alkylsulfonyloxy group, an arylsulfonyloxy group optionally having substituent(s) (e.g., benzenesulfonyloxy, p-toluenesulfonyloxy) and the like, using an optionally halogenated $C_{1-6}$ alkylsulfonyl chloride (e.g., methanesulfonyl chloride, ethanesulfonyl chloride, trifluoromethanesulfonyl chloride), an arylsulfonyl chloride optionally having substituent(s) (e.g., benzenesulfonyl chloride, p-toluenesulfonyl chloride) and the like.

The amount of the optionally halogenated $C_{1-6}$ alkylsulfonyl chloride or arylsulfonyl chloride optionally having substituent(s) to be used is generally 1 to 10 equivalents, preferably 1 to 5 equivalents, per 1 equivalent of compound (IIa).

This reaction is generally carried out in an inert solvent (e.g., ether solvents, halogenated hydrocarbon solvents, aromatic solvents, amide solvents etc.) or without solvent. These solvents may be used in a mixture of two or more kinds thereof at an appropriate ratio. Of these, tetrahydrofuran, toluene, carbon tetrachloride, N,N-dimethylformamide and the like are preferable.

Where necessary, a base may be used for this reaction.

Examples of the base include amines (e.g., triethylamine, N,N-diisopropylethylamine, pyridine, 4-dimethylaminopyridine); alkali metal carbonates (e.g., potassium carbonate, sodium carbonate, cesium carbonate); alkali metal phosphates (e.g., tripotassium phosphate, trisodium phosphate); alkali metal hydrides (e.g., sodium hydride, potassium hydride); alkali metal hydroxides (e.g., sodium hydroxide, potassium hydroxide) and the like. Of these, pyridine, triethylamine, potassium carbonate, tripotassium phosphate, sodium hydride and the like are preferable.

The amount of the base to be used is generally 1 to 100 equivalents, preferably 1 to 10 equivalents, per 1 equivalent of compound (IIa).

The reaction temperature of this reaction is generally −20° C. to 200° C., preferably 0° C. to 100° C.

The reaction time of this reaction is, for example, 0.5 hr to 48 hr.

(Step 4A)

Compound (VIIa) can be produced by reacting compound (Va) with compound (VIa) in the presence of a base.

Examples of the base include amines (e.g., triethylamine, N,N-diisopropylethylamine, pyridine, 4-dimethylaminopyridine, 1,8-diazabicyclo[5.4.0]-7-undecene); alkali metal carbonates (e.g., potassium carbonate, sodium carbonate, cesium carbonate, sodium hydrogencarbonate, potassium hydrogencarbonate); alkali metal phosphates (e.g., tripotassium phosphate, trisodium phosphate); alkali metal acetates (sodium acetate, potassium acetate); alkali metal hydrides (e.g., sodium hydride, potassium hydride); alkali metal hydroxides (e.g., sodium hydroxide, potassium hydroxide); alkali metal $C_{1-6}$ alkoxides (e.g., sodium methoxide, sodium tert-butoxide, potassium tert-butoxide) and the like. Of these, sodium hydride, sodium carbonate, potassium tert-butoxide and the like are preferable.

The amount of the base to be used is generally 1 to 100 equivalents, preferably 1 to 10 equivalents, per 1 equivalent of compound (Va).

Specific examples of compound (VIa) include ethyl thioglycolate, ethyl glycolate and the like.

Compound (VIa) may be commercially available product, or can be produced according to a method known per se or a method analogous thereto.

The amount of compound (VIa) to be used is generally 1 to 10 equivalents, preferably 1 to 5 equivalents, per 1 equivalent of compound (Va).

This reaction is carried out without solvent or in an inert solvent. Examples of the inert solvent include ether solvents, halogenated hydrocarbon solvents, nitrile solvents, aromatic solvents, ester solvents, amide solvents, water and the like. These solvents may be used in a mixture of two or more kinds thereof at an appropriate ratio. Of these, tetrahydrofuran, acetonitrile, N,N-dimethylformamide, N,N-dimethylacetamide, dimethyl sulfoxide and the like are preferable.

Where necessary, a phase-transfer catalyst (e.g., tetrabutylammonium bromide, tetrabutylammonium hydrogensulfate etc.) may be used for this reaction.

The amount of the phase-transfer catalyst to be used is generally 0.01 to 0.5 equivalents, preferably 0.01 equivalents to 0.1 equivalents, per 1 equivalent of compound (Va).

The reaction temperature of this reaction is generally about 30° C. to 200° C., preferably 50° C. to 120° C.

The reaction time of this reaction is generally 0.5 hr to 24 hr.

(Step 2B)

Compound (Ib) can be produced from compound (VIIa) under the conditions and method similar to those exemplified in Step 2A.

(Production Method B)

Of compound (I) of the present invention, a compound represented by the following formula (Ic) (compound (Ic)) can be produced, for example, according to the following Reaction Scheme 2.

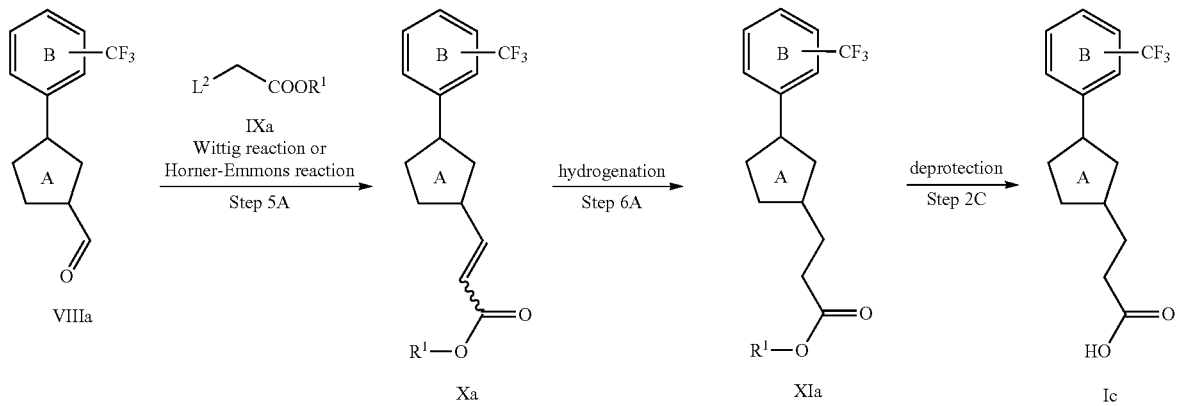

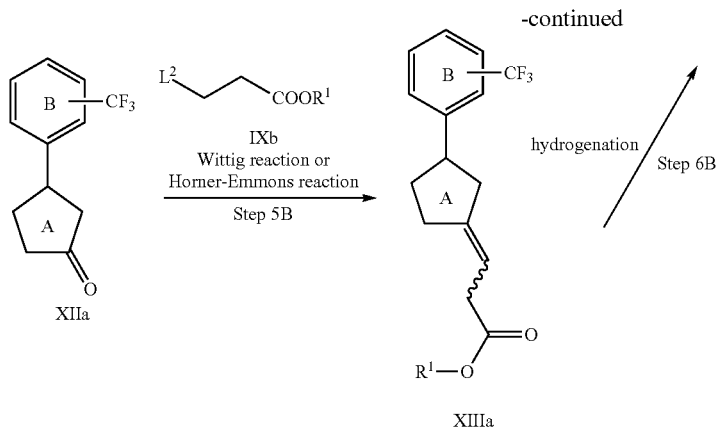

In this production method, compound (Ic) can be produced from compound (VIIIa) or compound (XIIa) by the following steps.
Step 5A: a step of obtaining compound (Xa) by subjecting compound (VIIIa) to the Wittig reaction or Horner-Emmons reaction with compound (IXa);
Step 6A: a step of obtaining compound (XIa) by subjecting compound (Xa) to a hydrogenation reaction;
Step 5B: a step of obtaining compound (XIIIa) by subjecting compound (XIIa) to the Wittig reaction or Horner-Emmons reaction with compound (IXb);
Step 6B: a step of obtaining compound (XIa) by subjecting compound (XIIIa) to a hydrogenation reaction;
Step 2C: a step of obtaining compound (Ic) by removing $R^1$ which is the carboxyl-protecting group of compound (XIa).

Each step is explained in detail in the following.
(Step 5A)
Compound (Xa) can be produced as E form, Z form or a mixture of E form and Z form by subjecting compound (VIIIa) to the Wittig reaction or Horner-Emmons reaction with compound (IXa).

The Wittig reaction or Horner-Emmons reaction is generally carried out using a base according to a method known per se (e.g., J. Chem. Soc. Perkin Trans. 1, 2895 (1996), 5th edition, Jikken Kagaku Koza, 13 vol., 118-139 pages (2005), Maruzen).

Specific examples of compound (IXa) include alkylphosphonic acid diester (e.g., ethyl diethylphosphonoacetate, tert-butyl diethylphosphonoacetate) or triphenylphosphine ylides (e.g., (ethoxycarbonylmethyl)triphenylphosphonium bromide, (tert-butoxycarbonylmethyl)triphenylphosphonium chloride) and the like.

Compound (IXa) may be commercially available product, or can be produced according to a method known per se or a method analogous thereto.

The amount of compound (IXa) to be used is generally 0.8 to 10 equivalents, preferably 0.8 to 3 equivalents, per 1 equivalent of compound (VIIIa).

Examples of the base include amines (e.g., triethylamine, N,N-diisopropylethylamine, pyridine, 4-dimethylaminopyridine, 1,8-diazabicyclo[5.4.0]-7-undecene); alkali metal carbonates (e.g., potassium carbonate, sodium carbonate, cesium carbonate, sodium hydrogencarbonate, potassium hydrogencarbonate); alkali metal phosphates (e.g., tripotassium phosphate, trisodium phosphate); alkali metal acetates (sodium acetate, potassium acetate); alkali metal hydrides (e.g., sodium hydride, potassium hydride); alkali metal hydroxides (e.g., sodium hydroxide, potassium hydroxide); alkali metal $C_{1-6}$ alkoxides (e.g., sodium methoxide, sodium tert-butoxide, potassium tert-butoxide); organic lithiums (e.g., n-butyllithium, sec-butyllithium, tert-butyllithium); metal amides (e.g., lithiumdiisopropylamide, potassium hexamethyl disilazide) and the like. Of these, sodium hydride, sodium carbonate, potassium tert-butoxide, n-butyllithium and the like are preferable.

The amount of the base to be used is 1 to 5 equivalents, more preferably 1 to 2 equivalents, per 1 equivalent of compound (VIIIa).

This reaction is carried out in an inert solvent (e.g., those exemplified in Step 1A). These solvents may be used in a mixture of two or more kinds thereof at an appropriate ratio. Of these, diethyl ether, tetrahydrofuran, acetonitrile, N,N-dimethylformamide, ethanol and the like are preferable.

This reaction is preferably carried out in an inert gas such as dry argon, dry nitrogen and the like.

The reaction temperature of this reaction is generally about −78° C. to 150° C., preferably −78° C. to 100° C.

The reaction time of this reaction is generally 0.5 to 24 hr.

Compound (VIIIa) can be produced according to a method known per se (e.g., Synth. Commun. 16, 1343 (1986); J. Am. Chem. Soc. 99, 7020 (1977); WO 2005/92099) or a method analogous thereto.

(Step 6A)
Compound (XIa) can be produced by subjecting compound (Xa) to a hydrogenation reaction.

The hydrogenation reaction is generally carried out using a catalyst according to a method known per se (e.g., Jikken Kagaku Koza (Courses in Experimental Chemistry), 15 vol., oxidation and reduction (II), 333-448 pages (1977), Maruzen).

Examples of the catalyst include palladium carbon, palladium carbon-ethylene diamine complex, palladium black, platinum dioxide, Raney-nickel, Raneycobalt and the like. Of these, palladium carbon, palladium carbon-ethylene diamine complex, platinum dioxide and the like are preferable.

The amount of the catalyst to be used is generally 5 to 1000 wt %, preferably 5 to 300 wt %, relative to compound (Xa).

In the hydrogenation reaction, instead of hydrogen gas, various hydrogen source (e.g., formic acid, ammonium formate, triethylammonium formate, sodium phosphinate, hydrazine) may be used.

The amount of the hydrogen source to be used is generally 1 to 10 equivalents, preferably 1 to 5 equivalents, per 1 equivalent of compound (Xa).

This reaction is carried out in an inert solvent (e.g., those exemplified in Step 1A), organic acid solvents and the like.

These solvents may be used in a mixture of two or more kinds thereof at an appropriate ratio. Of these, methanol, ethanol, acetic acid, tetrahydrofuran, ethyl acetate and the like are preferable.

Where necessary, this reaction may be carried out under pressurization. When pressurized, the pressure is generally 2 to 10 atm, preferably 2 to 5 atm.

The reaction temperature of this reaction is generally about −20° C. to 100° C., preferably 0° C. to 80° C.

The reaction time of this reaction is generally 0.5 to 100 hr, preferably 0.5 to 50 hr.
(Step 5B)

Compound (XIIIa) can be produced from compound (XIIa) and compound (IXb) under the conditions and method similar to those exemplified in Step 5A.

known per se (e.g., 4th edition, Jikken Kagaku Koza, 19 vol., 57-61 pages (1992), Maruzen) or a method analogous thereto.
(Step 6B)

Compound (XIa) can also be produced from compound (XIIIa) under the conditions and method similar to those exemplified in Step 6A.
(Step 2C)

Compound (Ic) can be produced from compound (XIa) under the conditions and method similar to those exemplified in Step 2A.
(Production Method C)

Of compound (I) of the present invention, a compound represented by the following formula (Ic) (compound (Ic)) can also be produced, for example, according to the following Reaction Scheme 3.

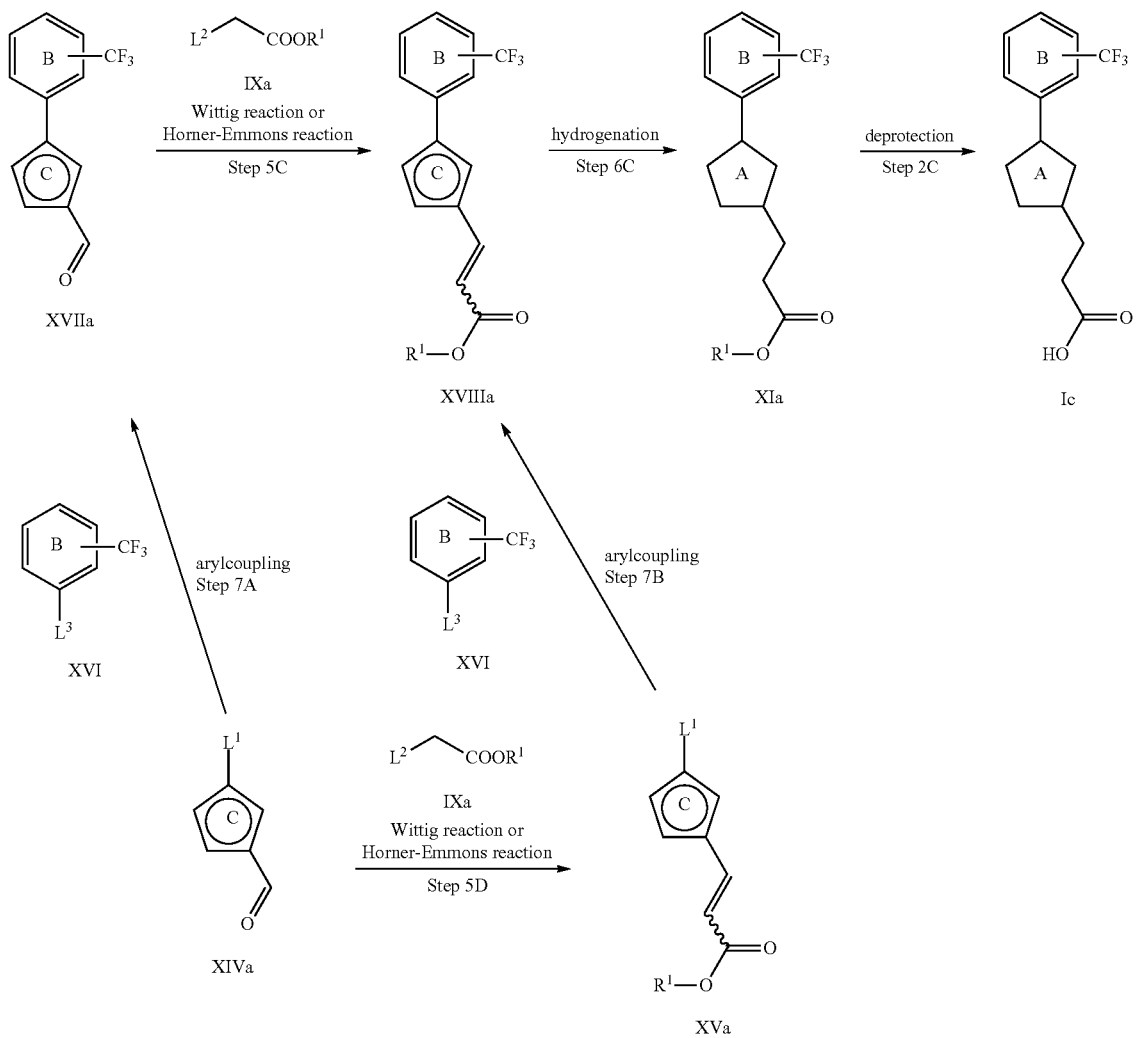

(Reaction Scheme 3)

Compound (XIIa) can be produced according to a method known per se (e.g., Bioorg. Med. Chem. 11, 145 (2003); J. Org. Chem. 54, 220 (1989); J. Org. Chem. 49, 2500 (1984)) or a method analogous thereto.

Compound (IXb) may be commercially available product (e.g., 2-(ethoxycarbonyl)ethyltriphenylphosphonium bromide), or can also be synthesized according to a method In this production method, compound (Ic) can be produced from compound (XIVa) by the following steps.

Step 7A: a step of obtaining compound (XVIIa) by subjecting compound (XIVa) to an aryl coupling reaction with arylboronic acid derivative (XVI);

Step 5C: a step of obtaining compound (XVIIIa) by subjecting compound (XVIIa) to the Wittig reaction or Horner-Emmons reaction with compound (IXa);
Step 5D: a step of obtaining compound (XVa) by subjecting compound (XIVa) to the Wittig reaction or Horner-Emmons reaction with compound (IXa);
Step 7B: a step of obtaining compound (XVIIIa) by subjecting compound (XVa) to an aryl coupling reaction with arylboronic acid derivative (XVI);
Step 6C: a step of obtaining compound (XIa) by subjecting compound (XVIIIa) to a hydrogenation reaction;
Step 2C: a step of obtaining compound (Ic) by removing $R^1$ which is the carboxyl-protecting group of compound (XIa).

Each step is explained in detail in the following.
(Step 7A)

Compound (XVIIa) can be produced by subjecting compound (XIVa) to an aryl coupling reaction with compound (XVI).

The amount of compound (XVI) to be used is generally 1 to 10 equivalents, preferably 1 to 5 equivalents, per 1 equivalent of compound (XIVa).

The aryl coupling reaction is generally carried out using a transition metal catalyst in the presence of a base according to a method known per se (e.g., 5th edition, Jikken Kagaku Koza, 18 vol., 327-351 pages (2005), Maruzen; Chem. Rev., 102, 1359 (2002)).

Examples of the transition metal catalyst include palladium complexes (e.g., tetrakis(triphenylphosphine)palladium(0), dichlorobis(triphenylphosphine)palladium(II), bis(dibenzylideneacetone)palladium(0), palladium(II) acetate, palladium(II) chloride), nickel complexes (e.g., dichloro[1,2-bis(diphenylphosphino)ethane]nickel(II), bis(1,5-cyclooctadiene)nickel (0)) and the like. Of these, tetrakis(triphenylphosphine)palladium(0) is preferable.

The amount of the transition metal catalyst to be used is generally 0.00001 to 5 equivalents, preferably 0.0001 to 1 equivalent, per 1 equivalent of compound (XIVa).

For advantageous progression of this reaction, a phosphine ligand to the transition metal catalyst may be co-used.

Examples of the phosphine ligand include triphenylphosphine, tris(2-methylphenyl)phosphine, 1,2-bis(diphenylphosphino)ethane, 1,3-bis(diphenylphosphino)propane, 1,1'-bis(diphenylphosphino)ferrocene and the like.

The amount of the phosphine ligand to be used is generally 1 to 50 equivalents, preferably 2 to 20 equivalents, per 1 equivalent of the transition metal catalyst.

Examples of the base include those exemplified in Step 5A. Of these, sodium carbonate, cesium carbonate, potassium tert-butoxide and the like are preferable.

The amount of the base to be used is generally 1 to 20 equivalents, preferably 1 to 10 equivalents, per 1 equivalent of compound (XIVa).

This reaction is carried out in an inert solvent (e.g., those exemplified in Step 1A). These solvents may be used in a mixture of two or more kinds thereof at an appropriate ratio. Of these, dimethoxyethane, tetrahydrofuran, benzene, toluene, N,N-dimethylformamide, water and the like are preferable.

This reaction is preferably carried out in an inert gas such as argon, nitrogen and the like.

The reaction temperature of this reaction is generally about 10° C. to 200° C., preferably 50° C. to 150° C.

The reaction time of this reaction is generally 0.5 to 100 hr, preferably 5 to 80 hr.

Compound (XIVa) may be commercially available product, or can be produced according to a method known per se (e.g., Can. J. Chem. 6B, 1305 (1990)) or a method analogous thereto.

Compound (XVI) may be commercially available product, or can be produced according to a method known per se (e.g., 5th edition, Jikken Kagaku Koza, 18 vol., 95-102, 183-188 pages (2005), Maruzen; US 2003/0225106) or a method analogous thereto.
(Step 5C)

Compound (XVIIIa) can be produced from compound (XVIIa) and compound (IXa) under the conditions and method similar to those exemplified in Step 5A.
(Step 5D)

Compound (XVa) can be produced from compound (XIVa) and compound (IXa) under the conditions and method similar to those exemplified in Step 5A.
(Step 7B)

Compound (XVIIIa) can also be produced from compound (XVa) and compound (XVI) under the conditions and method similar to those exemplified in Step 7A.
(Step 6C)

Compound (XIa) can be produced from compound (XVIIIa) under the conditions and method similar to those exemplified in Step 6A.
(Production Method D)

Of compound (I) of the present invention, a compound represented by the following formula (Id) (compound (Id)) can be produced, for example, according to the following Reaction Scheme 4.

(Reaction Scheme 4)

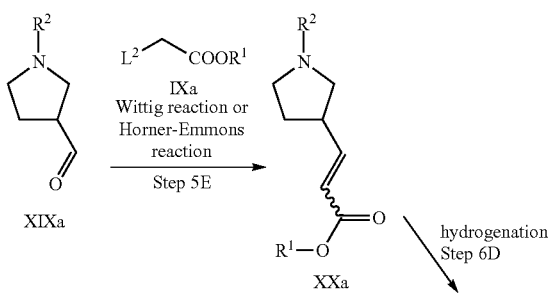

-continued

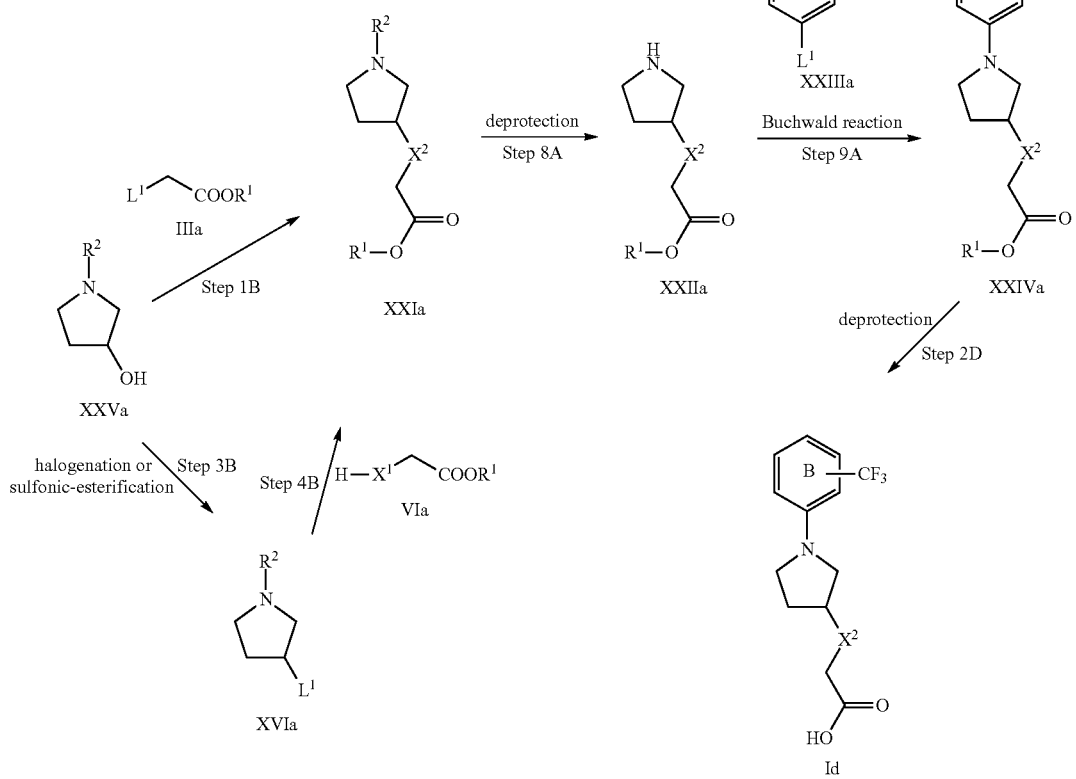

In this production method, compound (Id) can be produced from compound (XIXa) or compound (XXVa) by the following steps.

Step 5E: a step of obtaining compound (XXa) by subjecting compound (XIXa) to the Wittig reaction or Horner-Emmons reaction with compound (IXa);

Step 6D: a step of obtaining compound (XXIa) by subjecting compound (XXa) to a hydrogenation reaction;

Step 1B: a step of obtaining compound (XXIa) by subjecting compound (XXVa) to an alkylation reaction with compound (IIIa);

Step 3B: a step of obtaining compound (XVIa) by subjecting the hydroxy group of compound (XXVa) to a halogenation or sulfonic-esterification reaction;

Step 4B: a step of obtaining compound (XXIa) by subjecting compound (XVIa) to an alkylation reaction with compound (VIa);

Step 8A: a step of obtaining compound (XXIIa) by removing $R^2$ which is the protecting group for amine of compound (XXIa);

Step 9A: a step of obtaining compound (XXIVa) by subjecting compound (XXIIa) to the Buchwald reaction with compound (XXIIIa);

Step 2D: a step of obtaining compound (Id) by removing $R^1$ which is the carboxyl-protecting group of compound (XXIVa).

Each step is explained in detail in the following.
(Step 5E)

Compound (XXa) can be produced from compound (XIXa) and compound (IXa) under the conditions and method similar to those exemplified in Step 5A.

Compound (XIXa) may be commercially available product. Alternatively, compound (XIXa) can also be produced according to a method known per se (e.g., WO 2004/5255; WO 2005/49602) or a method analogous thereto.
(Step 6D)

Compound (XXIa) can be produced from compound (XXa) under the conditions and method similar to those exemplified in Step 6A.
(Step 1B)

Compound (XXIa) can also be produced from compound (XXVa) and compound (IIIa) under the conditions and method similar to those exemplified in Step 1A.
(Step 3B)

Compound (XVIa) can be produced from compound (XXVa) under the conditions and method similar to those exemplified in Step 3A.

Compound (XXVa) may be commercially available product. Alternatively, compound (XXVa) can also be produced according to a method known per se or a method analogous thereto.
(Step 4B)

Compound (XXIa) can also be produced from compound (XVIa) and compound (VIa) under the conditions and method similar to those exemplified in Step 4A.
(Step 8A)

The removal of the protecting group $R^2$ of compound (XXIa) can be carried out according to a method known per se, for example, the method described in Protective Groups in Organic Synthesis, John Wiley and Sons (1980) and the like. Examples of the removal of the protecting group $R^2$ include a method using a acid, a base and the like, hydrogenation and the like.

(Step 9A)

Compound (XXIVa) can be produced by subjecting compound (XXIIa) to the Buchwald reaction with compound (XXIIIa).

The amount of compound (XXIIIa) to be used is generally 1 to 10 equivalents, preferably 1 to 5 equivalents, per 1 equivalent of compound (XXIIa).

The Buchwald reaction is generally carried out using a transition metal catalyst in the presence of a base according to a method known per se (e.g., Org. Synth. 78, 23 (2000); Org. Lett. 5, 2413 (2003)).

Examples of the transition metal catalyst include palladium complexes (e.g., tris(dibenzylideneacetone)dipalladium(0), palladium(II) acetate, 1,1'-bis(diphenylphosphino)ferrocenedichloropalladium(II), bis(dibenzylideneacetone)palladium(0)) and the like. Of these, tris(dibenzylideneacetone)dipalladium(0) and palladium(II) acetate are preferable.

The amount of the transition metal catalyst to be used is generally 0.00001 to 5 equivalents, preferably 0.0001 to 1 equivalent, per 1 equivalent of compound (XXIIa).

For advantageous progression of this reaction, a phosphine ligand to the transition metal catalyst may be co-used.

Examples of the phosphine ligand include 2,2'-bis(diphenylphosphino)-1,1'-binaphthyl, 9,9-dimethyl-4,5-bis(diphenylphosphino)xanthene and the like.

The amount of the phosphine ligand to be used is generally 1 to 50 equivalents, preferably 2 to 20 equivalents, per 1 equivalent of the transition metal catalyst.

Examples of the base include amines (e.g., triethylamine, N,N-diisopropylethylamine, pyridine, 4-dimethylaminopyridine, 1,8-diazabicyclo[5.4.0]-7-undecene, 1,3,4,6,7,8-hexahydro-1-methyl-2H-primido[1,2-a]pyrimidine); alkali metal carbonates (e.g., potassium carbonate, sodium carbonate, cesium carbonate, sodium hydrogencarbonate, potassium hydrogencarbonate); alkali metal phosphates (e.g., tripotassium phosphate, trisodium phosphate); alkali metal acetates (sodium acetate, potassium acetate); alkali metal hydrides (e.g., sodium hydride, potassium hydride); alkali metal hydroxides (e.g., sodium hydroxide, potassium hydroxide); alkali metal $C_{1-6}$ alkoxides (e.g., sodium methoxide, sodium tert-butoxide, potassium tert-butoxide); organic lithiums (e.g., n-butyllithium, sec-butyllithium, tert-butyllithium); metal amides (e.g., lithiumdiisopropylamide, potassium hexamethyl disilazide) and the like. Of these, cesium carbonate, sodium methoxide, sodium tert-butoxide, potassium tert-butoxide, tripotassium phosphate, 1,3,4,6,7,8-hexahydro-1-methyl-2H-primido[1,2-a]pyrimidine and the like are preferable.

The amount of the base to be used is generally 1 to 20 equivalents, preferably 1 to 10 equivalents, per 1 equivalent of compound (XXIIa).

This reaction is carried out in an inert solvent (e.g., those exemplified in Step 1A). These solvents may be used in a mixture of two or more kinds thereof at an appropriate ratio. Of these, dimethoxyethane, dioxane, tetrahydrofuran, benzene, toluene, N,N-dimethylformamide and the like are preferable.

This reaction is preferably carried out in an inert gas such as argon, nitrogen and the like inert gas.

The reaction temperature of this reaction is generally about 30° C. to 200° C., preferably 50° C. to 150° C.

The reaction time of this reaction is generally 0.5 to 100 hr, preferably 5 to 80 hr.

Compound (XXIIIa) may be commercially available product, or can be produced according to a method known per se or a method analogous thereto.

(Step 2D)

Compound (Id) can be produced from compound (XXIVa) under the conditions and method similar to those exemplified in Step 2A.

(Production Method E)

Of compound (I) of the present invention, a compound represented by the following formula (Ie) (compound (Ie) can be produced, for example, according to the following Reaction Scheme 5.

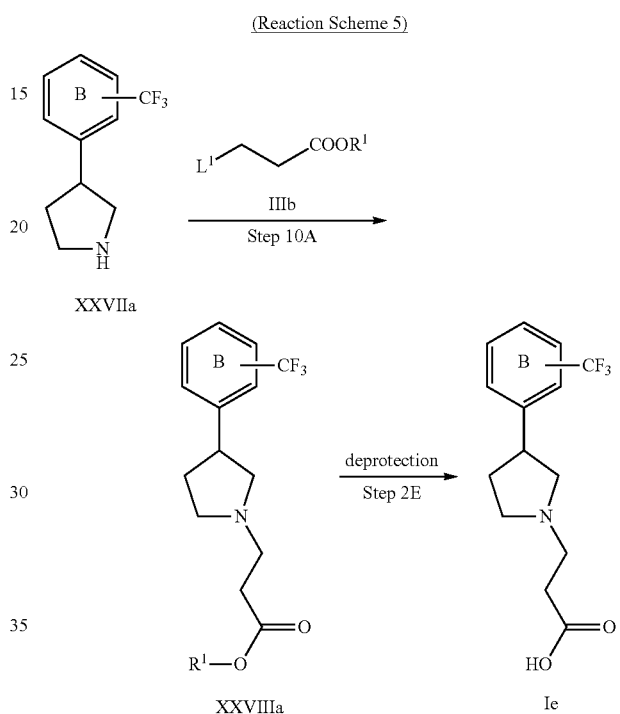

(Reaction Scheme 5)

In this production method, compound (Ie) can be produced from compound (XXVIIa) by the following steps.

Step 10A: a step of obtaining compound (XXVIIIa) by subjecting compound (XXVIIa) to an alkylation reaction with compound (IIIb);

Step 2E: a step of obtaining compound (Ie) by removing $R^1$ which is the carboxyl-protecting group of compound (XXVIIIa).

Each step is explained in detail in the following.

(Step 10A)

Compound (XXVIIIa) can be produced reacting compound (XXVIIa) with compound (IIIb).

Where necessary, a base may be used for this reaction.

Examples of the base include those exemplified in Step 1A. Of these, sodium hydride, sodium carbonate, potassium carbonate, potassium tert-butoxide, potassium hexamethyl disilazide and the like are preferable.

The amount of the base to be used is generally 0.1 to 100 equivalents, preferably 1 to 10 equivalents, relative to compound (XXVIIa).

Specific examples of compound (IIIb) include methyl 3-bromopropionate, tert-butyl 3-chloropropionate, methyl 3-chloropropionate and the like.

Compound (IIIb) may be commercially available product, or can be produced according to a method known per se or a method analogous thereto.

The amount of compound (IIIb) to be used is generally 1 to 100 equivalents, preferably 1 to 5 equivalents, per 1 equivalent of compound (XXVIIa).

This reaction is carried out without solvent or in an inert solvent. Examples of the inert solvent include those exemplified in Step 1A. Of these, tetrahydrofuran, acetonitrile, N,N-dimethylformamide, N,N-dimethylacetamide, dimethyl sulfoxide and the like are preferable.

Where necessary, a phase-transfer catalyst (e.g., tetrabutylammonium bromide, tetrabutylammonium hydrogensulfate etc.) may be used for this reaction.

The amount of the phase-transfer catalyst to be used is generally 0.01 to 0.5 equivalents, preferably 0.01 equivalents to 0.1 equivalents, per 1 equivalent of compound (XXVIIa).

The reaction temperature of this reaction is generally −78° C. to 200° C., preferably −78° C. to 120° C.

The reaction time of this reaction is generally 0.5 hr to 24 hr.

Compound (XXVIIa) can be produced according to a method known per se (e.g., Tetrahedron Lett. 29, 2525 (1988); U.S. Pat. No. 6,211,199; Synthesis 11, 1023 (1991)) or a method analogous thereto.

(Step 2E)

Compound (Ie) can be produced from compound (XXVIIIa) under the conditions and method similar to those exemplified in Step 2A.

(Production Method F)

Of compound (I) of the present invention, a compound represented by the following formula (If) (compound (If)) and a compound represented by the following formula (Ig) (compound (Ig)) can be produced, for example, according to the following Reaction Scheme 6.

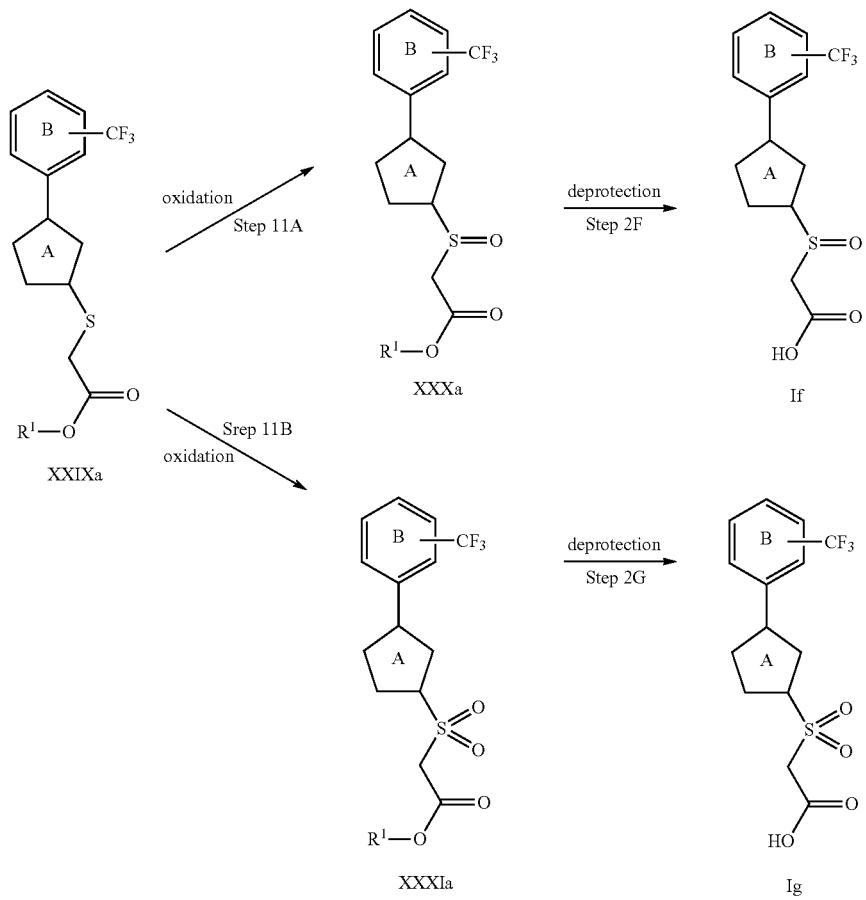

(Reaction Scheme 6)

In this production method, compound (If) or compound (Ig) can be produced from compound (XXIXa) by the following steps.

Step 11A: a step of obtaining compound (XXXa) by subjecting compound (XXIXa) to an oxidation reaction;

Step 11B: a step of obtaining compound (XXXIa) by subjecting compound (XXIXa) to an oxidation reaction;

Step 2F: a step of obtaining compound (If) by removing $R^1$ which is the carboxyl-protecting group of compound (XXXa);

Step 2G: a step of obtaining compound (Ig) by removing $R^1$ which is the carboxyl-protecting group of compound (XXXIa).

Each step is explained in detail in the following.

(Step 11A)

Compound (XXXa) can be produced by subjecting compound (XXIXa) to an oxidation reaction.

The oxidation reaction can be generally carried out using an oxidant according to a method known per se (e.g., 5th edition, Jikken Kagaku Koza, vol. 17, page 205 (2005), Maruzen) or a method analogous thereto.

Examples of the oxidant include m-chloroperbenzoic acid, oxone-persulfate compound, benzoyl peroxide, bis(trimethylsilyl)peroxide, dimethyldioxirane, hydrogen peroxide and the like.

The amount of the oxidant to be used is generally about 1 to about 10 equivalents, preferably about 1 to 1.2 equivalents, per 1 equivalent of compound (XXIXa).

This reaction can be carried out, for example, in the presence of a catalytic amount of titanium tetraisopropoxide, sodium tartrate, sodium tungstate, phenylphosphonic acid, a quaternary ammonia salt and the like.

The amount of the catalyst to be used is generally 0.001 to 0.1 equivalents, per 1 equivalent of compound (XXIXa).

This reaction is generally carried out in an inert solvent (e.g., halogenated hydrocarbon solvents, ester solvents, nitrile solvents, ether solvents etc.) or without solvent. These solvents may be used in a mixture of two or more kinds thereof at an appropriate ratio. Of these, dichloromethane, ethyl acetate, acetonitrile and the like are preferable.

The reaction temperature of this reaction is generally about 0° C. to 100° C., preferably 0° C. to 80° C.

The reaction time of this reaction is, for example, 0.5 hr to 1 day.

Compound (XXIXa) can be produced according to the aforementioned Step 4A, Step 9A and the like.

(Step 11B)

Compound (XXXIa) can be produced by subjecting compound (XXIXa) to an oxidation reaction in the same manner as in Step 11A.

(Step 2F)

Compound (If) can be produced from compound (XXXa) under the conditions and method similar to those exemplified in Step 2A.

(Step 2G)

Compound (Ig) can be produced from compound (XXXIa) under the conditions and method similar to those exemplified in Step 2A.

(Production Method G)

Of compound (I) of the present invention, a compound represented by the following formula (Ih) (compound (Ih)) can be produced, for example, according to the following Reaction Scheme 7.

(Reaction Scheme 7)

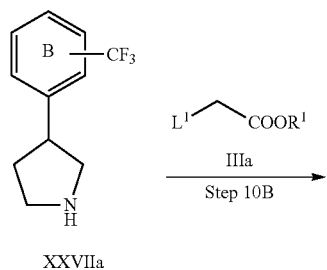

XXVIIa

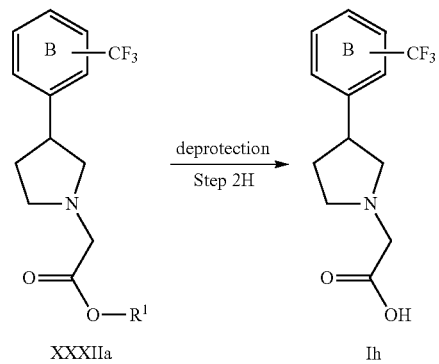

In this production method, compound (Ih) can be produced from compound (XXVIIa) by the following steps.

Step 10B: a step of obtaining compound (XXXIIa) by subjecting compound (XXVIIa) to an alkylation reaction with compound (IIIa);

Step 2H: a step of obtaining compound (Ih) by removing $R^1$ which is the carboxyl-protecting group of compound (XXXIIa).

Each step is explained in detail in the following.

(Step 10B)

Compound (XXXIIa) can be produced from compound (XXVIIa) under the conditions and method similar to those exemplified in Step 10A.

(Step 2H)

Compound (Ih) can be produced from compound (XXXIIa) under the conditions and method similar to those exemplified in Step 2A.

(Production Method H)

Of compound (I) of the present invention, a compound represented by the following formula (Ii) (compound (Ii)) can be produced, for example, according to the following Reaction Scheme 8.

(Reaction Scheme 8)

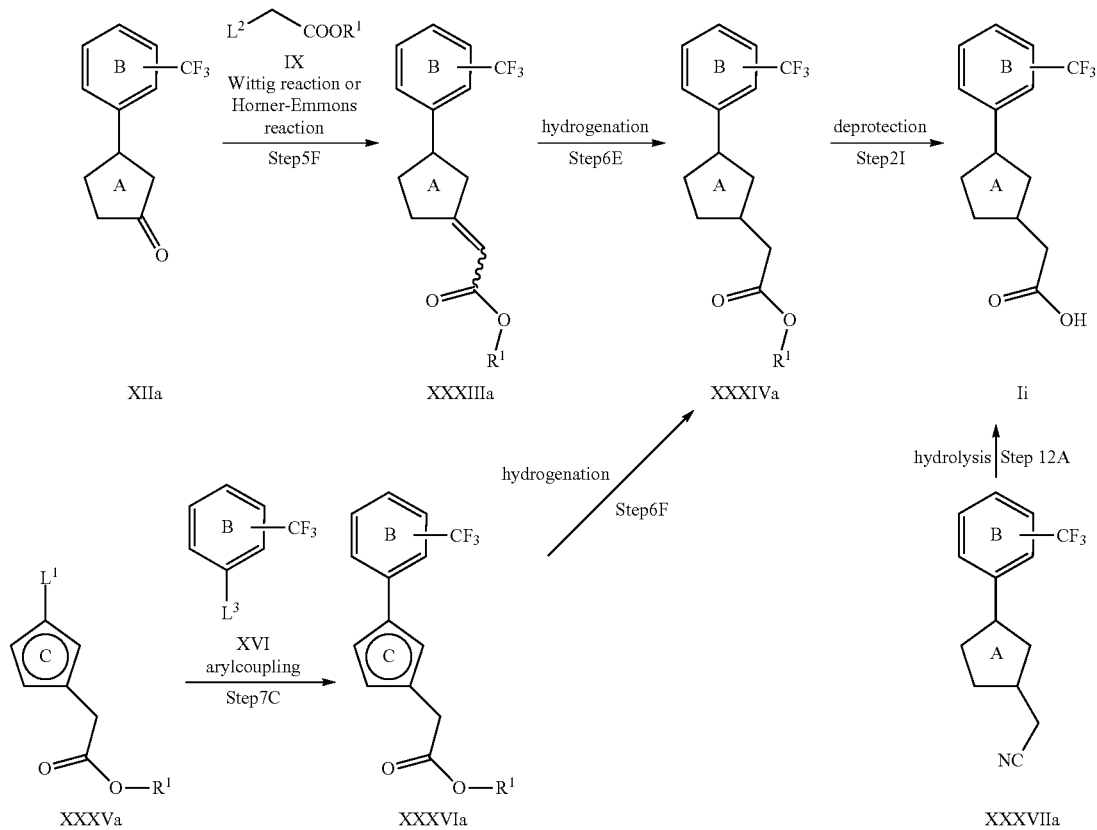

In this production method, compound (Ii) can be produced from compound (XIIa), compound (XXXVa) or compound (XXXVIIa) by the following steps.

Step 5F: a step of obtaining compound (XXXIIIa) by subjecting compound (XIIa) to the Wittig reaction or Horner-Emmons reaction with compound (IXa);

Step 6E: a step of obtaining compound (XXXIVa) by subjecting compound (XXXIIIa) to a hydrogenation reaction;

Step 7C: a step of obtaining compound (XXXVIa) by subjecting compound (XXXVa) to an aryl coupling reaction with compound (XVI);

Step 6F: a step of obtaining compound (XXXIVa) by subjecting compound (XXXVIa) to a hydrogenation reaction;

Step 2I: a step of obtaining compound (Ii) by removing $R^1$ which is the carboxyl-protecting group of compound (XXXIVa);

Step 12A: a step of obtaining compound (Ii) by subjecting the cyano group of compound (XXXVIIa) to hydrolysis.

Each step is explained in detail in the following.
(Step 5F)
Compound (XXXIIIa) can be produced from compound (XIIa) under the conditions and method similar to those exemplified in Step 5B.
(Step 6E)
Compound (XXXIVa) can be produced from compound (XXXIIIa) under the conditions and method similar to those exemplified in Step 6A.
(Step 7C)
Compound (XXXVIa) can be produced from compound (XXXVa) under the conditions and method similar to those exemplified in Step 7A.

Compound (XXXVa) may be commercially available product. Alternatively, compound (XXXVa) can also be produced according to a method known per se (e.g., US 2007/244094) or a method analogous thereto.
(Step 6F)
Compound (XXXIVa) can also be produced from compound (XXXVIa) under the conditions and method similar to those exemplified in Step 6A.
(Step 2I)
Compound (Ii) can be produced from compound (XXXIVa) under the conditions and method similar to those exemplified in Step 2A.
(Step 12A)
The hydrolysis of the cyano group of compound (XXX-VIIa) can be carried out according to a method known per se (e.g., 4th edition, Jikken Kagaku Koza, 22 vol., 12-13 pages, 5th edition, Jikken Kagaku Koza, 16 vol., 15-16 pages) and the like. Examples of the hydrolysis of the cyano group include a method using an acid, a base and the like.

Compound (XXXVIIa) can be produced according to a method known per se (e.g., J. Heterocycl. Chem. 22, 129 (1985); U.S. Pat. No. 5,145,865) or a method analogous thereto.

(Production Method I)

Of compound (I) of the present invention, a compound represented by the following formula (Ij) (compound (Ij)) can be produced, for example, according to the following Reaction Scheme 9.

(Reaction Scheme 9)

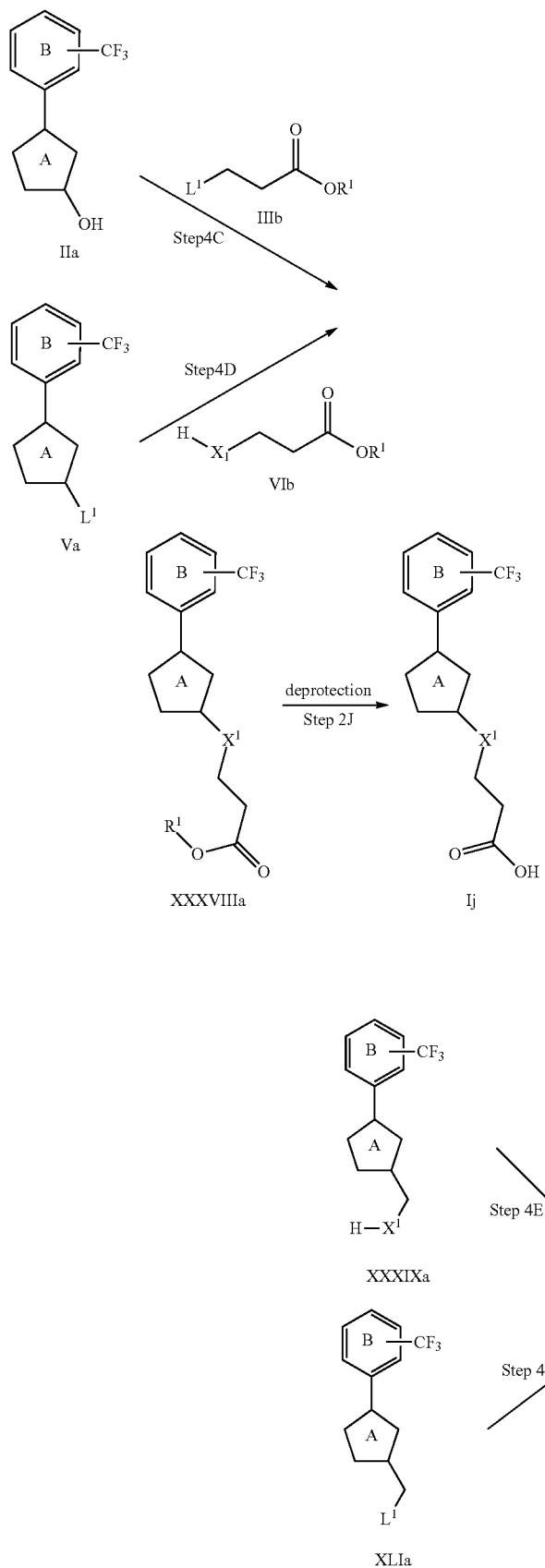

In this production method, compound (Ij) can be produced from compound (IIa) or compound (Va) by the following steps.

Step 4C: a step of obtaining compound (XXXVIIIa) by subjecting compound (IIa) to an alkylation reaction with compound (IIIb);

Step 4D: a step of obtaining compound (XXXVIIIa) by subjecting compound (Va) to an alkylation reaction with compound (VIb);

Step 2J: a step of obtaining compound (Ij) by removing $R^1$ which is the carboxyl-protecting group of compound (XXXVIIIa).

Each step is explained in detail in the following.

(Step 4C)

Compound (XXXVIIIa) can be produced from compound (IIa) and compound (IIIb) under the conditions and method similar to those exemplified in Step 1A.

(Step 4D)

Compound (XXXVIIIa) can also be produced from compound (Va) and compound (VIb) under the conditions and method similar to those exemplified in Step 4A.

Specific examples of compound (VIb) include ethyl 3-mercaptopropionate, tert-butyl 3-hydroxypropionate and the like.

Compound (VIb) may be commercially available product, or can be produced according to a method known per se or a method analogous thereto.

(Step 2J)

Compound (Ij) can be produced from compound (XXXVIIIa) under the conditions and method similar to those exemplified in Step 2A.

(Production Method J)

Of compound (I) of the present invention, a compound represented by the following formula (Ik) (compound (Ik)) can be produced, for example, according to the following Reaction Scheme 10.

(Reaction Scheme 10)

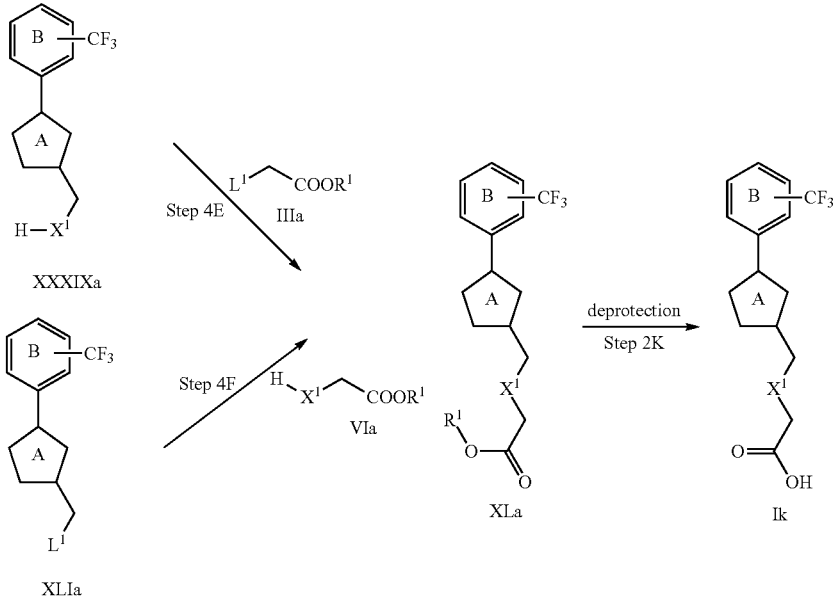

In this production method, compound (Ik) can be produced from compound (XXXIXa) or compound (XLIa) by the following steps.

Step 4E: a step of obtaining compound (XLa) by subjecting compound (XXXIXa) to an alkylation reaction with compound (IIIa);

Step 4F: a step of obtaining compound (XLa) by subjecting compound (XLIa) to an alkylation reaction with compound (VIa);

Step 2K: a step of obtaining compound (Ik) by removing $R^1$ which is the carboxyl-protecting group of compound (XLa).

Each step is explained in detail in the following.

(Step 4E)

Compound (XLa) can be produced from compound (XXXIXa) and compound (IIIa) under the conditions and method similar to those exemplified in Step 1A.

Compound (XXXIXa) can be produced according to a method known per se (e.g., Tetrahedron 63, 3049 (2007); Chem. Pharm. Bull. 47, 1549 (1999)) or a method analogous thereto.

(Step 4F)

Compound (XLa) can also be produced from compound (XLIa) and compound (VIa) under the conditions and method similar to those exemplified in Step 4A.

Compound (XLIa) can be produced according to a method known per se (e.g., WO 2005/61470) or a method analogous thereto.

(Step 2K)

Compound (Ik) can be produced from compound (XLa) under the conditions and method similar to those exemplified in Step 2A.

(Production Method K)

Of compound (I) of the present invention, a compound represented by the following formula (II) (compound (II)) can be produced, for example, according to the following Reaction Scheme 11.

(Reaction Scheme 11)

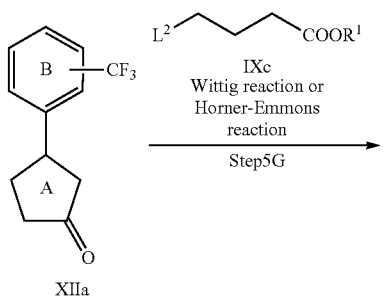

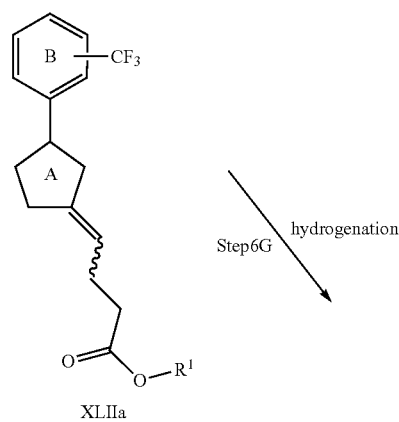

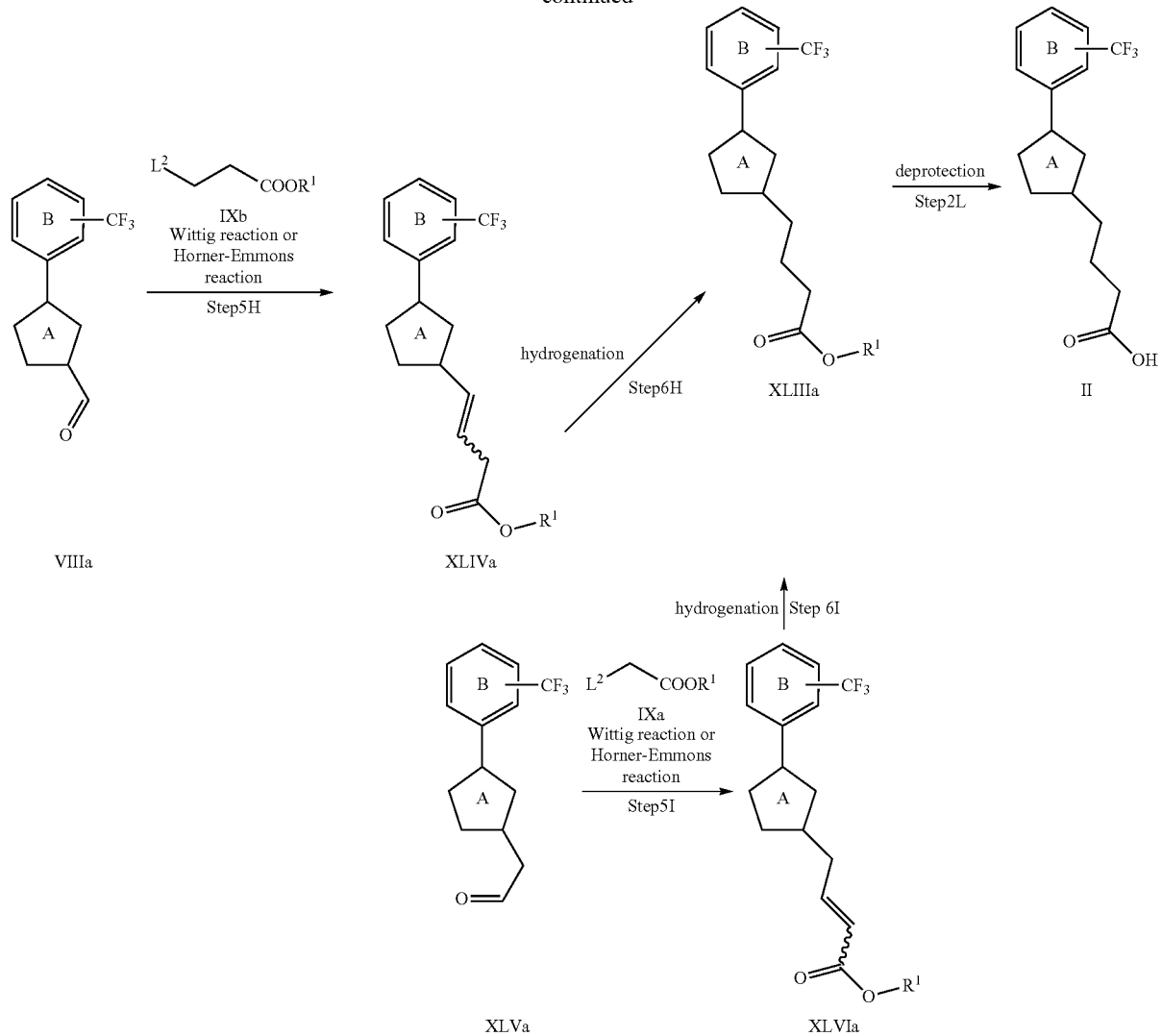

In this production method, compound (II) can be produced from compound (XIIa), compound (VIIIa) or compound (XLVa) by the following steps.

Step 5G: a step of obtaining compound (XLIIa) by subjecting compound (XIIa) to the Wittig reaction or Horner-Emmons reaction with compound (IXc);

Step 6G: a step of obtaining compound (XLIIIa) by subjecting compound (XLIIa) to a hydrogenation reaction;

Step 5H: a step of obtaining compound (XLIVa) by subjecting compound (VIIIa) to the Wittig reaction or Horner-Emmons reaction with compound (IXb);

Step 6H: a step of obtaining compound (XLIIIa) by subjecting compound (XLIVa) to a hydrogenation reaction;

Step 5I: a step of obtaining compound (XLVIa) by subjecting compound (XLVa) to the Wittig reaction or Horner-Emmons reaction with compound (IXa);

Step 6I: a step of obtaining compound (XLIIIa) by subjecting compound (XLVIa) to a hydrogenation reaction;

Step 2L: a step of obtaining compound (II) by removing $R^1$ which is the carboxyl-protecting group of compound (XLIIIa).

Each step is explained in detail in the following.
(Step 5G)

Compound (XLIIa) can be produced from compound (XIIa) and compound (IXc) under the conditions and method similar to those exemplified in Step 5B.

Specific examples of compound (IXc) include commercially available [3-(ethoxycarbonyl)propyl]triphenylphosphonium bromide and the like.

Compound (IXc) may be commercially available product, or can be produced according to a method known per se or a method analogous thereto.
(Step 6G)

Compound (XLIIIa) can be produced from compound (XLIIa) under the conditions and method similar to those exemplified in Step 6B.
(Step 5H)

Compound (XLIVa) can be produced from compound (VIIIa) and compound (IXb) under the conditions and method similar to those exemplified in Step 5A.
(Step 6H)

Compound (XLIIIa) can also be produced from compound (XLIVa) under the conditions and method similar to those exemplified in Step 6A.

(Step 5I)

Compound (XLVIa) can be produced from compound (XLVa) and compound (IXa) under the conditions and method similar to those exemplified in Step 5A.

Compound (XLVa) can be produced according to a method known per se (e.g., Tetrahedron Lett. 38, 603 (1997); WO 2003/76424; WO 2005/85232) or a method analogous thereto.

(Step 6I)

Compound (XLIIIa) can also be produced from compound (XLVIa) under the conditions and method similar to those exemplified in Step 6A.

(Step 2L)

Compound (Il) can be produced from compound (XLIIIa) under the conditions and method similar to those exemplified in Step 2A.

(Production Method L)

Of compound (I) of the present invention, a compound represented by the following formula (Im) (compound (Im)) can be produced, for example, according to the following Reaction Scheme 12.

(Reaction Scheme 12)

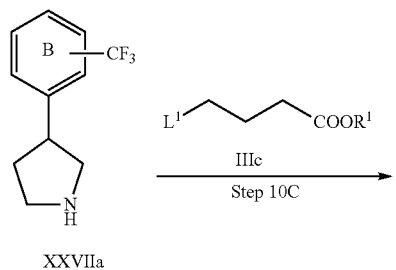

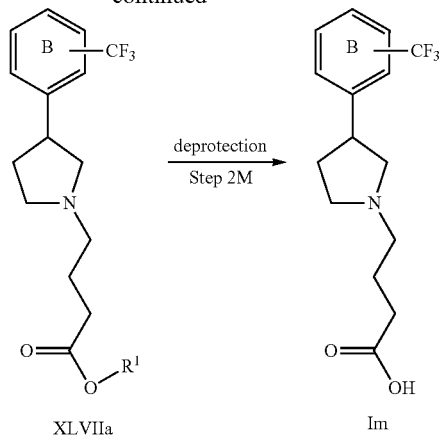

In this production method, compound (Im) can be produced from compound (XXVIIa) by the following steps.
Step 10C: a step of obtaining compound (XLVIIa) by subjecting compound (XXVIIa) to an alkylation reaction with compound (IIIc);
Step 2M: a step of obtaining compound (Im) by removing $R^1$ which is the carboxyl-protecting group of compound (XLVIIa).

Each step is explained in detail in the following.
(Step 10C)

Compound (XLVIIa) can be produced from compound (XXVIIa) and compound (IIIc) under the conditions and method similar to those exemplified in Step 10A.
(Step 2M)

Compound (Im) can be produced from compound (XLVIIa) under the conditions and method similar to those exemplified in Step 2A.

(Production Method M)

Of compound (I) of the present invention, a compound represented by the following formula (In) (compound (In)) and a compound represented by the following formula (Io) (compound (Io)) can be produced, for example, according to the following Reaction Scheme 13.

(Reaction Scheme 13)

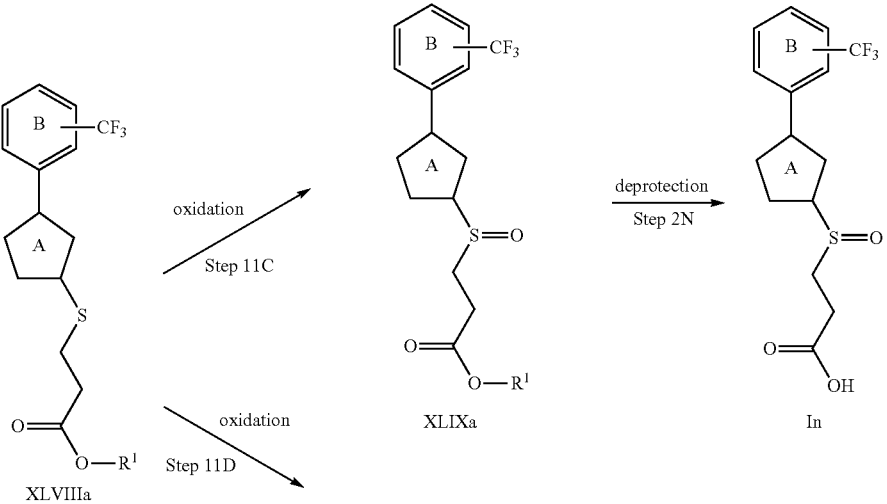

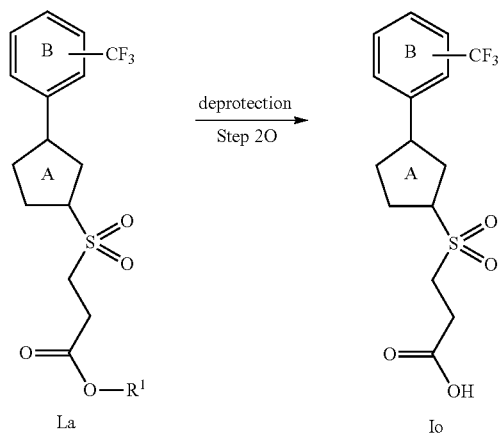

In this production method, compound (In) or compound (Io) can be produced from compound (XLVIIIa) by the following steps.
Step 11C: a step of obtaining compound (XLIXa) by subjecting compound (XLVIIIa) to an oxidation reaction;
Step 11D: a step of obtaining compound (La) by subjecting compound (XLVIIIa) to an oxidation reaction;
Step 2N: a step of obtaining compound (In) by removing $R^1$ which is the carboxyl-protecting group of compound (XLIXa);
Step 2O: a step of obtaining compound (Io) by removing $R^1$ which is the carboxyl-protecting group of compound (La).
Each step is explained in detail in the following.
(Step 11C)
Compound (XLIXa) can be produced by subjecting compound (XLVIIIa) to an oxidation reaction in the same manner as in Step 11A.
Compound (XLVIIIa) can be produced according to Step 4C, Step 4D and the like.

(Step 11D)
Compound (La) can be produced by subjecting compound (XLVIIIa) to an oxidation reaction in the same manner as in Step 11A.
(Step 2N)
Compound (In) can be produced from compound (XLIXa) under the conditions and method similar to those exemplified in Step 2A.
(Step 2O)
Compound (Io) can be produced from compound (La) under the conditions and method similar to those exemplified in Step 2A.
(Production Method N)
Of compound (I) of the present invention, a compound represented by the following formula (Ip) (compound (Ip)) and a compound represented by the following formula (Iq) (compound (Iq)) can be produced, for example, according to the following Reaction Scheme 14.

(Reaction Scheme 14)

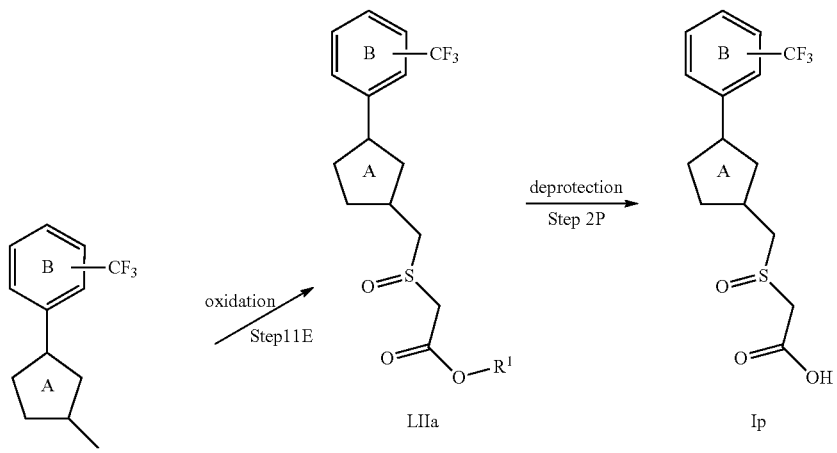

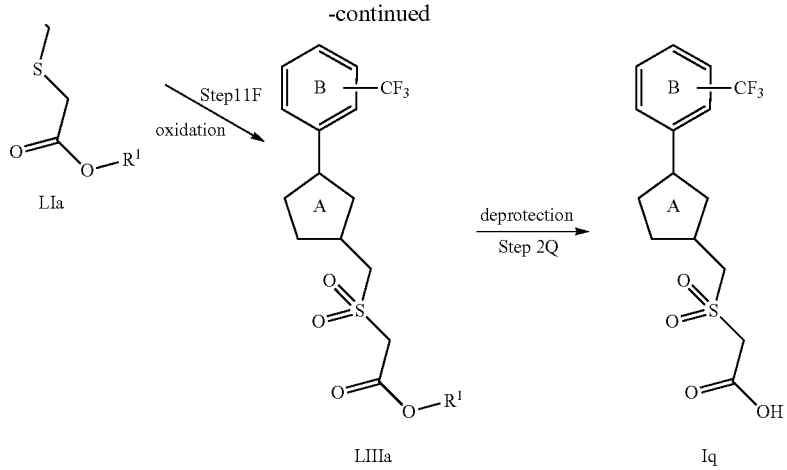

In this production method, compound (Ip) or compound (Iq) can be produced from compound (LIa) by the following steps.
Step 11E: a step of obtaining compound (LIIa) by subjecting compound (LIa) to an oxidation reaction;
Step 11F: a step of obtaining compound (LIIIa) by subjecting compound (LIa) to an oxidation reaction;
Step 2P: a step of obtaining compound (Ip) by removing $R^1$ which is the carboxyl-protecting group of compound (LIIa);
Step 2Q: a step of obtaining compound (Iq) by removing $R^1$ which is the carboxyl-protecting group of compound (LIIIa).

Each step is explained in detail in the following.
(Step 11E)
Compound (LIIa) can be produced by subjecting compound (LIa) to an oxidation reaction in the same manner as in Step 11A.
Compound (LIa) can be produced according to Step 4E, Step 4F and the like.

(Step 11F)
Compound (LIIIa) can be produced by subjecting compound (LIa) to an oxidation reaction in the same manner as in Step 11A.
(Step 2P)
Compound (Ip) can be produced from compound (LIIa) under the conditions and method similar to those exemplified in Step 2A.
(Step 2Q)
Compound (Iq) can be produced from compound (LIIIa) under the conditions and method similar to those exemplified in Step 2A.

(Production Method O)
Of compound (I) of the present invention, a compound represented by the following formula (Ir) (compound (Ir)) and a compound represented by the following formula (Is) (compound (Is)) can be produced, for example, according to the following Reaction Scheme 15.

(Reaction Scheme 15)

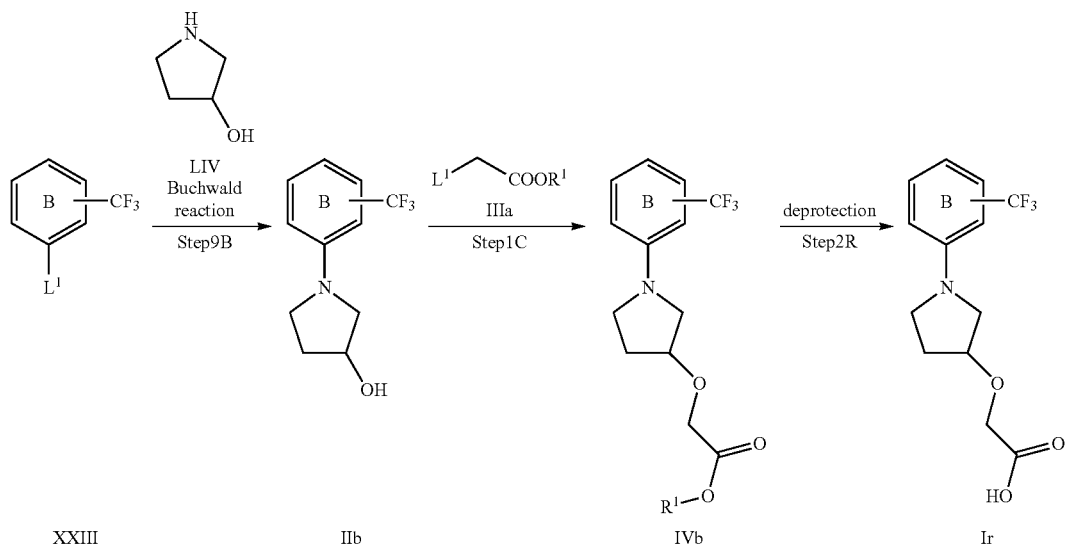

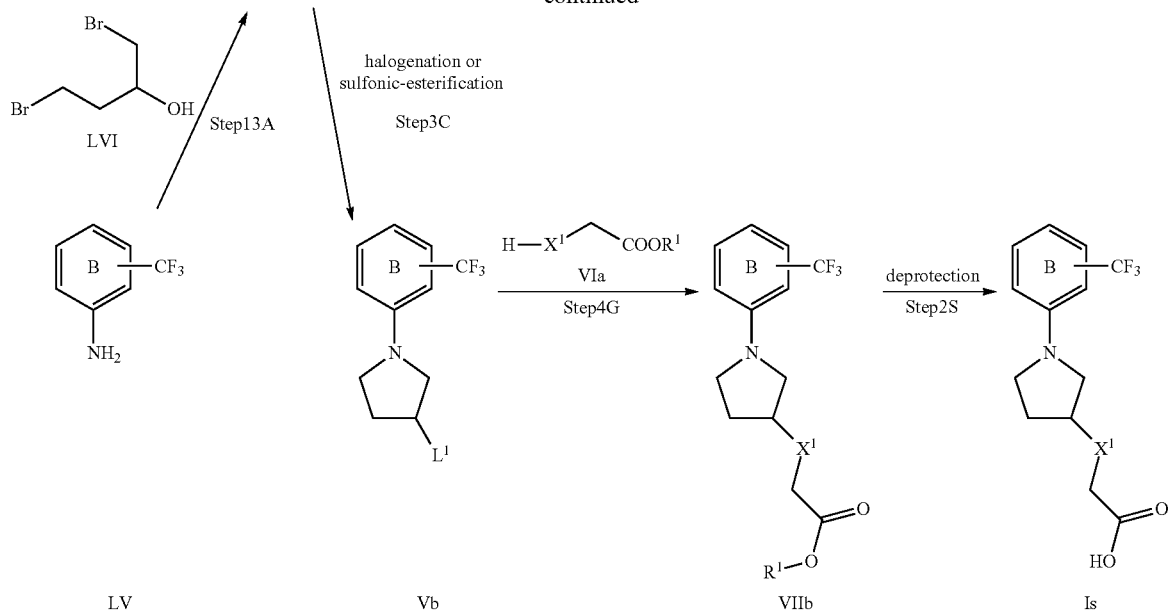

In this production method, compound (IIb) can be produced from compound (XXIII) or compound (LV), and compound (Ir) or compound (Is) can be produced from compound (IIb), by the following steps.
Step 9B: a step of obtaining compound (IIb) by subjecting compound (XXIII) to the Buchwald reaction with compound (LIV);
Step 13A: a step of obtaining compound (IIb) by reacting compound (LV) with compound (LVI);
Step 1C: a step of obtaining compound (IVb) by subjecting compound (IIb) to an alkylation reaction with compound (IIIa);
Step 2R: a step of obtaining compound (Ir) by removing $R^1$ which is the carboxyl-protecting group of compound (IVb);
Step 3C: a step of obtaining compound (Vb) by subjecting the hydroxy group of compound (IIb) to a halogenation or sulfonic-esterification;
Step 4G: a step of obtaining compound (VIIb) by subjecting compound (Vb) to an alkylation reaction with compound (VIa);
Step 2S: a step of obtaining compound (Is) by removing $R^1$ which is the carboxyl-protecting group of compound (VIIb).

Each step is explained in detail in the following.
(Step 9B)
Compound (IIb) can be produced from compound (XXIII) and compound (LIV) under the conditions and method similar to those exemplified in Step 9A.

Compound (XXIII) may be commercially available product, or can be synthesized according to a method known per se or a method analogous thereto.

The racemate or optically active form of compound (LIV) may be commercially available product, or can be produced according to a method known per se or a method analogous thereto.
(Step 13A)
Compound (IIb) can also be produced from compound (LV) and compound (LVI) according to a method known per se (e.g., EP 757051; Org. Lett. 7, 2409 (2005)).

Compound (LV) and compound (LVI) may be commercially available product, or can be synthesized according to a method known per se or a method analogous thereto.

(Step 1C)
Compound (IVb) can be produced from compound (IIb) and compound (IIIa) under the conditions and method similar to those exemplified in Step 1A.
(Step 2R)
Compound (Ir) can be produced from compound (IVb) under the conditions and method similar to those exemplified in Step 2A.
(Step 3C)
Compound (Vb) can be produced from compound (IIb) under the conditions and method similar to those exemplified in Step 3A.
(Step 4G)
Compound (VIIb) can be produced from compound (Vb) and compound (VIa) under the conditions and method similar to those exemplified in Step 4A.
(Step 2S)
Compound (Is) can be produced from compound (VIIb) under the conditions and method similar to those exemplified in Step 2A.
(Production Method P)
Of compound (I) of the present invention, a compound represented by the following formula (It) (compound (It)) can be produced, for example, according to the following Reaction Scheme 16.

(Reaction Scheme 16)

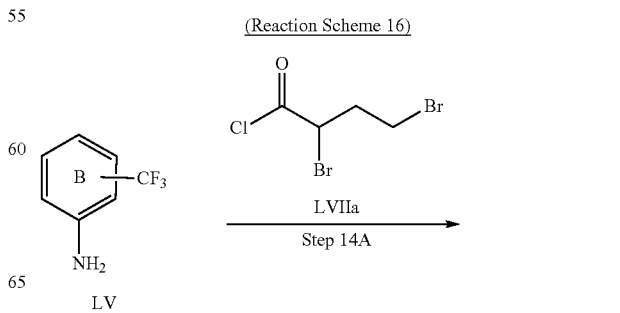

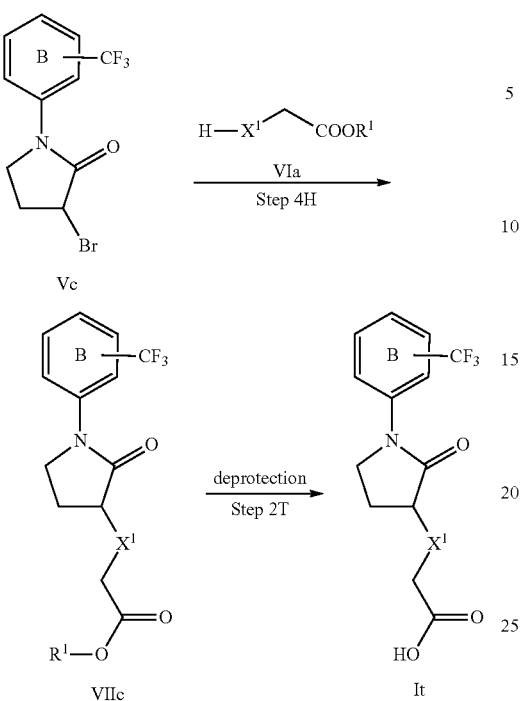

In this production method, compound (It) can be produced from compound (LV) by the following steps.

Step 14A: a step of obtaining compound (Vc) by subjecting compound (LV) to amidation with compound (LVIIa), and then subjecting the resulting compound to an intramolecular ring closure reaction;

Step 4H: a step of obtaining compound (VIIc) by subjecting compound (Vc) to an alkylation reaction with compound (VIa);

Step 2T: a step of obtaining compound (It) by removing $R^1$ which is the carboxyl-protecting group of compound (VIIc).

Each step is explained in detail in the following.

(Step 14A)

Compound (Vc) can be produced from compound (LV) and compound (LVIIa) according to a method known per se (e.g., US 2003/87909).

Compound (LVIIa) may be commercially available product, or can be produced according to a method known per se or a method analogous thereto.

(Step 4H)

Compound (VIIc) can be produced from compound (Vc) and compound (VIa) under the conditions and method similar to those exemplified in Step 4A.

(Step 2T)

Compound (It) can be produced from compound (VIII) under the conditions and method similar to those exemplified in Step 2A.

(Production Method Q)

Of compound (I) of the present invention, a compound represented by the following formula (Iu) (compound (Iu)) can be produced, for example, according to the following Reaction Scheme 17.

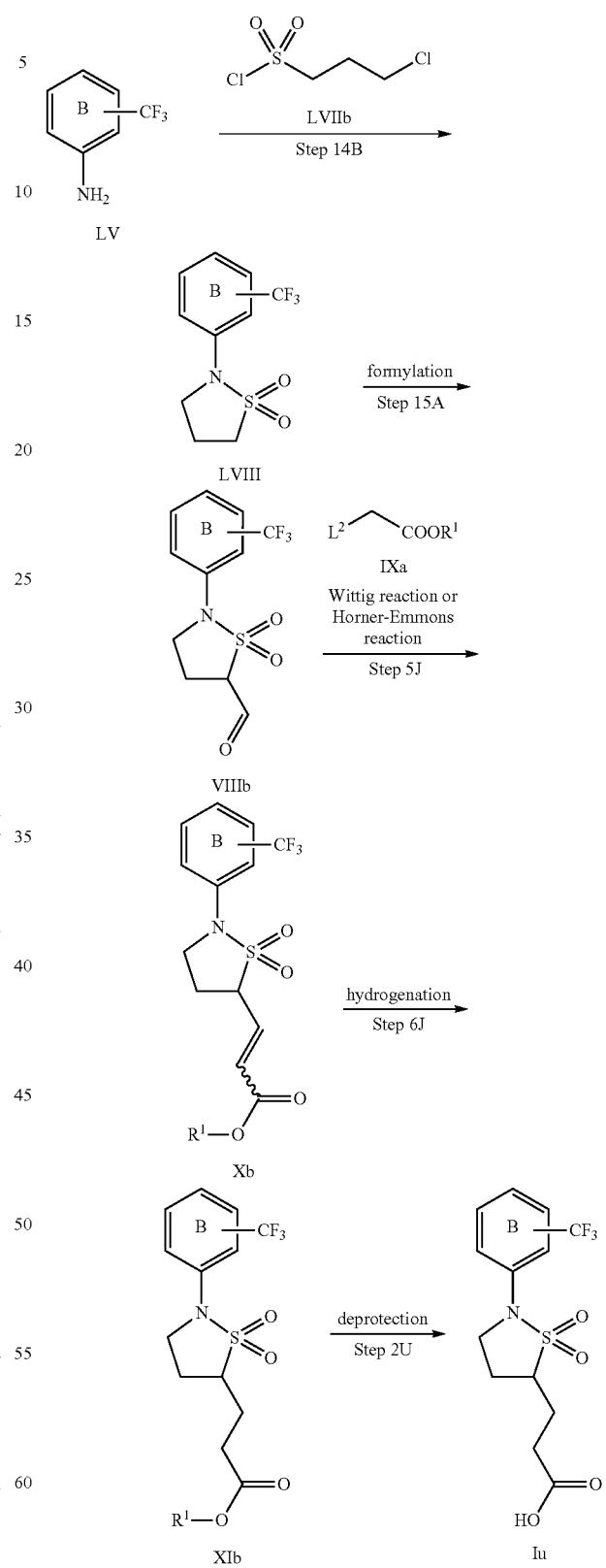

In this production method, compound (Iu) can be produced from compound (LV) by the following steps.

Step 14B: a step of obtaining compound (LVIII) by subjecting compound (LV) to sulfonamidation with compound (LVIIb), and then subjecting the resulting compound to an intramolecular ring closure reaction;
Step 15A: a step of obtaining compound (VIIIb) by subjecting compound (LVIII) to formylation;
Step 5J: a step of obtaining compound (Xb) by subjecting compound (VIIIb) to the Wittig reaction or Horner-Emmons reaction with compound (IXa);
Step 6J: a step of obtaining compound (XIb) by subjecting compound (Xb) to a hydrogenation reaction.
Step 2U: a step of obtaining compound (Iu) by removing $R^1$ which is the carboxyl-protecting group of compound (XIb).

Each step is explained in detail in the following.
(Step 14B)

Compound (LVIII) can be produced from compound (LV) and compound (LVIIb) according to a method known per se (e.g., WO 2003/106405).

Compound (LVIIb) may be commercially available product, or can be produced according to a method known per se or a method analogous thereto.
(Step 15A)

Compound (VIIIb) can be produced by subjecting compound (LVIII) to formylation.

The formylation is carried out by reacting compound (LVIII) with a formylating agent which is a electrophile in the presence of a organic metal reagent which is a base, according to a method known per se (e.g., Tetrahedron Lett. 24, 1647 (1983); 5th edition, Jikken Kagaku Koza, vol. 15, pages 78-87 (2003), Maruzen), or a method analogous thereto.

Preferable examples of the organic metal reagent include organic lithium reagents (n-butyl lithium, sec-butyl lithium, tert-butyl lithium, lithium diisopropylamide, lithium hexamethyl disilazide).

The amount of the organic metal reagent to be used is generally 1 to 10 equivalents, preferably 1 to 5 equivalents, per 1 equivalent of compound (LVIII).

Specific examples of the formylating agent include formaldehyde, formate (ethyl formate and the like), N,N-dimethylformamide, N-formylpiperidine and the like. These may be commercially available product, or can be produced according to a method known per se or a method analogous thereto.

The amount of the formylating agent to be used is generally 1 to 10 equivalents, preferably 1 to 3 equivalents, per 1 equivalent of compound (LVIII).

This reaction is carried out in an inert solvent (e.g., those exemplified in Step 1A). These solvents may be used in a mixture of two or more kinds thereof at an appropriate ratio. Of these, diethyl ether, tetrahydrofuran and the like are preferable.

This reaction is preferably carried out in an inert gas such as dry argon, dry nitrogen and the like.

The reaction temperature of this reaction is generally about −78° C. to 80° C., preferably −78° C. to 40° C.

The reaction time of this reaction is generally 0.5 to 16 hr.
(Step 5J)

Compound (Xb) can be produced from compound (VIIIb) and compound (IXa) under the conditions and method similar to those exemplified in Step 5A.
(Step 6J)

Compound (XIb) can be produced from compound (Xb) under the conditions and method similar to those exemplified in Step 6A.
(Step 2U)

Compound (Iu) can be produced from compound (XIb) under the conditions and method similar to those exemplified in Step 2A.

(Production Method R)

Of compound (I) of the present invention, a compound represented by the following formula (Iv) (compound (Iv)) can be produced, for example, according to the following Reaction Scheme 18.

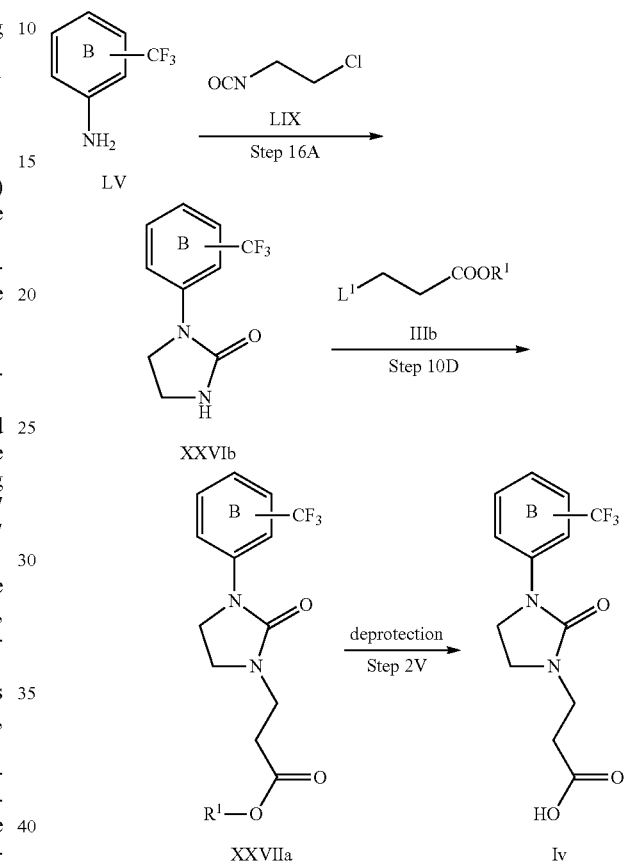

(Reaction Scheme 18)

In this production method, compound (Iv) can be produced from compound (LV) by the following steps.
Step 16A: a step of obtaining compound (XXVIb) by subjecting compound (LV) to ureation with compound (LIX), and then subjecting the resulting compound to an intramolecular ring closure reaction;
Step 10D: a step of obtaining compound (XXVIIa) by subjecting compound (XXVIb) to an alkylation reaction with compound (IIIb);
Step 2V: a step of obtaining compound (Iv) by removing $R^1$ which is the carboxyl-protecting group of compound (XXVIIa).

Each step is explained in detail in the following.
(Step 16A)

Compound (XXVIb) can be produced from compound (LV) and compound (LIX) according to a method known per se (e.g., WO 2004/9558).

Compound (LIX) may be commercially available product, or can be produced according to a method known per se or a method analogous thereto.
(Step 10D)

Compound (XXVIIa) can be produced from compound (XXVIb) and compound (IIIb) under the conditions and method similar to those exemplified in Step 10A.

(Step 2V)

Compound (Iv) can be produced from compound (XXVIIa) under the conditions and method similar to those exemplified in Step 2A.

(Production Method S)

Of compound (I) of the present invention, a compound represented by the following formula (Iw) (compound (Iw)) can be produced, for example, according to the following Reaction Scheme 19.

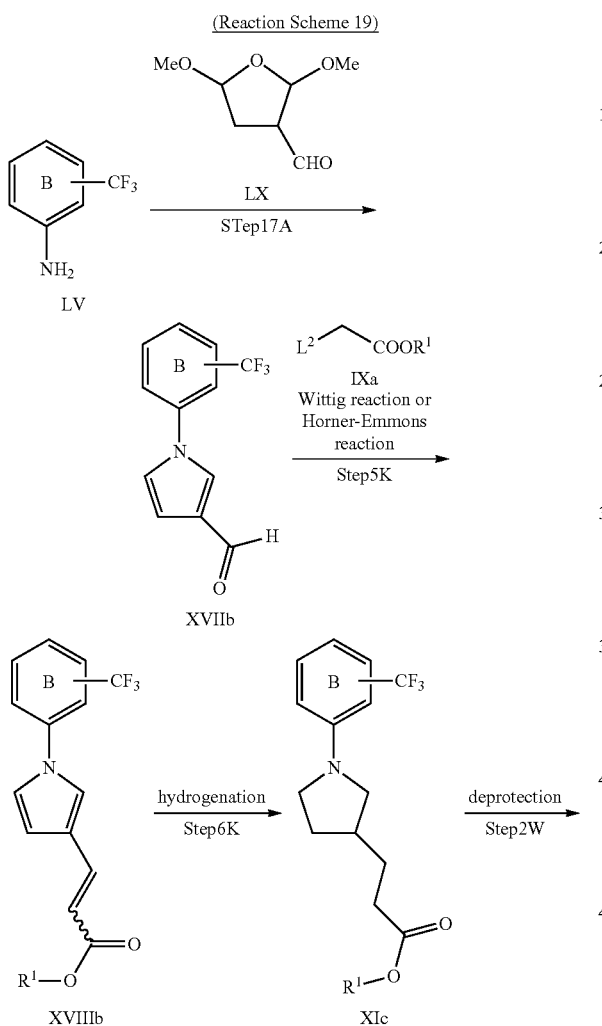

In this production method, compound (Iw) can be produced from compound (LV) by the following steps.

Step 17A: a step of obtaining compound (XVIIb) by reacting compound (LV) with compound (LX);

Step 5K: a step of obtaining compound (XVIIIb) by subjecting compound (XVIIb) to the Wittig reaction or Horner-Emmons reaction with compound (IXa);

Step 6K: a step of obtaining compound (XIc) by subjecting compound (XVIIIb) to a hydrogenation reaction;

Step 2W: a step of obtaining compound (Iw) by removing $R^1$ which is the carboxyl-protecting group of compound (XIc).

Each step is explained in detail in the following.

(Step 17A)

Compound (XVIIb) can be produced from compound (LV) and compound (LX) according to a method known per se (e.g., J. Med. Chem. 38, 4950 (1995)).

Compound (LX) may be commercially available product, or can be produced according to a method known per se or a method analogous thereto.

(Step 5K)

Compound (XVIIIb) can be produced from compound (XVIIb) and compound (IXa) under the conditions and method similar to those exemplified in Step 5A.

(Step 6K)

Compound (XIc) can be produced from compound (XVIIIb) under the conditions and method similar to those exemplified in Step 6A.

(Step 2W)

Compound (Iw) can be produced from compound (XIc) under the conditions and method similar to those exemplified in Step 2A.

(Production Method T)

Of compound (I) of the present invention, a compound represented by the following formula (Ix) (compound (Ix)) can be produced, for example, according to the following Reaction Scheme 20.

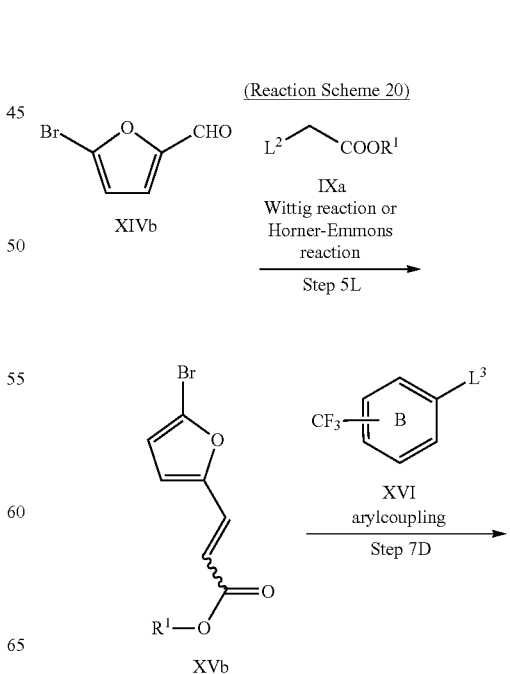

67

-continued

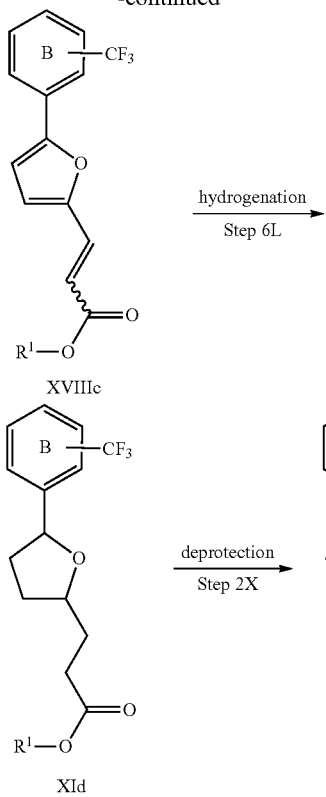

In this production method, compound (Ix) can be produced from compound (XIVb) by the following steps.

Step 5L: a step of obtaining compound (XVb) by subjecting compound (XIVb) to the Wittig reaction or Horner-Emmons reaction with compound (IXa);

Step 7D: a step of obtaining compound (XVIIIc) by subjecting compound (XVb) to an aryl coupling reaction with compound (XVI);

Step 6L: a step of obtaining compound (XId) by subjecting compound (XVIIIc) to a hydrogenation reaction;

Step 2X: a step of obtaining compound (Ix) by removing $R^1$ which is the carboxyl-protecting group of compound (XId).

Each step is explained in detail in the following.

(Step 5L)

Compound (XVb) can be produced from compound (XIVb) and compound (IXa) under the conditions and method similar to those exemplified in Step 5A.

Compound (XIVb) may be commercially available product, or can be produced according to a method known per se or a method analogous thereto.

(Step 7D)

Compound (XVIIIc) can be produced from compound (XVb) and compound (XVI) under the conditions and method similar to those exemplified in Step 7A.

(Step 6L)

Compound (XId) can be produced from compound (XVIIIc) under the conditions and method similar to those exemplified in Step 6A.

(Step 2X)

Compound (Ix) can be produced from compound (XId) under the conditions and method similar to those exemplified in Step 2A.

68

(Production Method U)

Of compound (I) of the present invention, a compound represented by the following formula (Iy) (compound (Iy)) can be produced, for example, according to the following Reaction Scheme 21.

(Reaction Scheme 21)

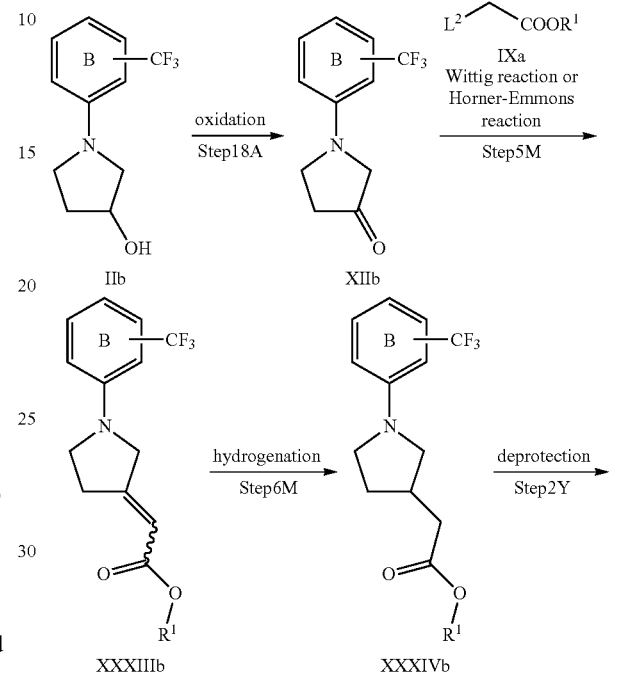

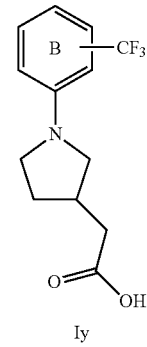

In this production method, compound (Iy) can be produced from compound (IIb) by the following steps.

Step 18A: a step of obtaining ketone form (XIIb) by subjecting the hydroxy group of compound (IIb) to an oxidation reaction;

Step 5M: a step of obtaining compound (XXXIIIb) by subjecting compound (XIIb) to the Wittig reaction or Horner-Emmons reaction with compound (IXa);

Step 6M: a step of obtaining compound (XXXIVb) by subjecting compound (XXXIIIb) to a hydrogenation reaction;

Step 2Y: a step of obtaining compound (Iy) by removing $R^1$ which is the carboxyl-protecting group of compound (XXXIVb).

Each step is explained in detail in the following.

(Step 18A)

Compound (XIIb) can be produced by subjecting compound (IIb) to an oxidation reaction according to a method known per se (e.g., Bioorg. Med. Chem. 11, 145 (2003)).

(Step 5M)

Compound (XXXIIIb) can be produced from compound (XIIb) and compound (IXa) under the conditions and method similar to those exemplified in Step 5A.

(Step 6M)

Compound (XXXIVb) can be produced from compound (XXXIIIb) under the conditions and method similar to those exemplified in Step 6A.

(Step 2Y)

Compound (Iy) can be produced from compound (XXXIVb) under the conditions and method similar to those exemplified in Step 2A.

(Production Method V)

Of compound (I) of the present invention, a compound represented by the following formula (Iz) (compound (Iz)) can be produced, for example, according to the following Reaction Scheme 22.

(Reaction Scheme 22)

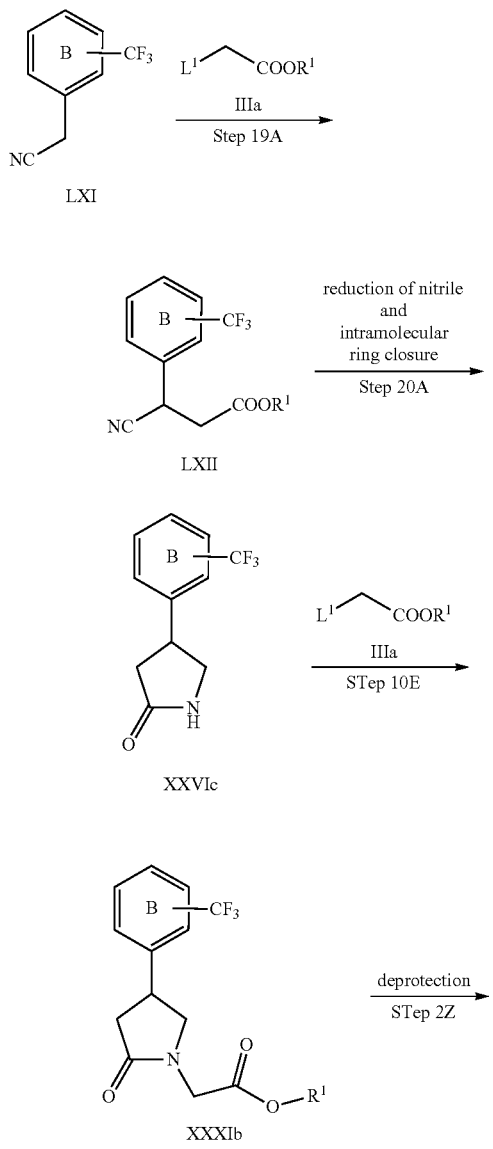

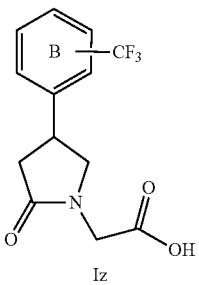

In this production method, compound (Iz) can be produced from compound (LXI) by the following steps.

Step 19A: a step of obtaining compound (LXII) by reacting compound (LXI) with compound (IIIa);

Step 20A: a step of obtaining compound (XXVIc) by subjecting the cyano group of compound (LXII) to an intramolecular ring closure reaction due to a reduction reaction;

Step 10E: a step of obtaining compound (XXXIb) by subjecting compound (XXVIc) to an alkylation reaction with compound (IIIc);

Step 2Z: a step of obtaining compound (Iz) by removing $R^1$ which is the carboxyl-protecting group of compound (XXXIb).

Each step is explained in detail in the following.

(Step 19A)

Compound (LXII) can be produced by subjecting compound (LXI) to an alkylation reaction with compound (IIIa) according to a method known per se (e.g., Tetrahedron 53, 5501 (1997); WO 2004/55016).

Compound (LXI) may be commercially available product, or can be produced according to a method known per se or a method analogous thereto.

(Step 20A)

Compound (XXVIc) can be produced by subjecting compound (LXII) to an intramolecular ring closure reaction due to a reduction reaction according to a method known per se (e.g., U.S. Pat. No. 6,211,199).

(Step 10E)

Compound (XXXIb) can be produced from compound (XXVIc) and compound (IIIa) under the conditions and method similar to those exemplified in Step 10A.

(Step 2Z)

Compound (Iz) can be produced from compound (XXXIb) under the conditions and method similar to those exemplified in Step 2A.

In the compounds obtained by each reaction mentioned above, a functional group in the molecule can also be converted to an object functional group by combining chemical reactions known per se. Here, examples of the chemical reaction include oxidation reaction, reduction reaction, alkylation reaction, acylation reaction, ureation reaction, hydrolysis, amination reaction, esterification reaction, aryl coupling reaction, deprotection reaction and the like.

In the above-mentioned production methods, when the starting compound has an amino group, a carboxyl group, a hydroxy group or a carbonyl group as a substituent, a protecting group generally used in peptide chemistry and the like may be introduced into these groups. By removing the protecting group as necessary after the reaction, the object compound can be obtained.

Examples of the amino-protecting group include a formyl group, a $C_{1-6}$ alkyl-carbonyl group (e.g., acetyl, propanoyl), a $C_{1-6}$ alkoxy-carbonyl group (e.g., methoxycarbonyl, ethoxycarbonyl), a benzoyl group, a $C_{7-13}$ aralkyl-carbonyl group (e.g., benzylcarbonyl), a $C_{7-13}$-aralkyloxy-carbonyl group (e.g., benzyloxycarbonyl, 9-fluorenylmethoxycarbonyl), a $C_{7-13}$ aralkyl group (e.g., benzyl, benzhydryl), a trityl group, a phthaloyl group, a N,N-dimethylaminomethylene group, a trisubstituted silyl group (e.g., trimethylsilyl, triethylsilyl, dimethylphenylsilyl, tert-butyldimethylsilyl, tert-butyldiethylsilyl), a $C_{2-6}$ alkenyl group (e.g., 1-allyl) and the like. These groups are optionally substituted by 1 to 3 substituents selected from a halogen atom, a $C_{1-6}$ alkoxy group, a nitro group and the like.

Examples of the carboxyl-protecting group include a $C_{1-6}$ alkyl group, a $C_{7-20}$ aralkyl group (e.g., benzyl, trityl), a phenyl group, a trisubstituted silyl group (e.g., trimethylsilyl, triethylsilyl, dimethylphenylsilyl, tert-butyldimethylsilyl, tert-butyldiethylsilyl), a $C_{2-6}$ alkenyl group (e.g., 1-allyl) and the like. These groups are optionally substituted by 1 to 5 substituents selected from a halogen atom, a $C_{1-6}$ alkoxy group, a nitro group and the like.

Examples of the hydroxyl-protecting group include a $C_{1-6}$ alkyl group, a phenyl group, a trityl group, a $C_{7-13}$ aralkyl group (e.g., benzyl), a formyl group, a $C_{1-6}$ alkyl-carbonyl group (e.g., acetyl, propanoyl), a benzoyl group, a $C_{7-13}$ aralkyl-carbonyl group (e.g., benzylcarbonyl), a 2-tetrahydropyranyl group, a 2-tetrahydrofuranyl group, a trisubstituted silyl group (e.g., trimethylsilyl, triethylsilyl, dimethylphenylsilyl, tert-butyldimethylsilyl, tert-butyldiethylsilyl), a $C_{2-6}$ alkenyl group (e.g., 1-allyl) and the like. These groups are optionally substituted by 1 to 3 substituents selected from a halogen atom, a $C_{1-6}$ alkyl group, a $C_{1-6}$ alkoxy group, a nitro group and the like.

Examples of the carbonyl-protecting group include a cyclic acetal (e.g., 1,3-dioxane), a non-cyclic acetal (e.g., di-$C_{1-6}$ alkyl acetal) and the like.

In addition, these protecting groups may be introduced or removed according to a method known per se, for example, the method described in Protective Groups in Organic Synthesis, John Wiley and Sons (1980) and the like. Examples of the method include a method using acid, base, ultraviolet rays, hydrazine, phenylhydrazine, sodium N-methyldithiocarbamate, tetrabutylammonium fluoride, palladium acetate, trialkylsilyl halide (e.g., trimethylsilyl iodide, trimethylsilyl bromide etc.) and the like, a reduction method and the like.

The compound of the present invention obtained by each of the above-mentioned production methods can be isolated and purified according to a means known per se, such as solvent extraction, liquid conversion, solvent transfer, crystallization, recrystallization, chromatography and the like. On the other hand, the starting compound may be directly used as a starting material of the next step in the form of a reaction mixture without isolation.

When the compound of the present invention contains an optical isomer, a stereoisomer, a regioisomer or a rotamer, these are also encompassed in the compound of the present invention, and can be obtained as a single product according to synthesis and separation methods known per se. For example, when the compound of the present invention contains an optical isomer, an optical isomer resolved from this compound is also encompassed in the compound of the present invention.

The optical isomer can be produced by a method known per se.

The compound of the present invention may be a crystal.

Crystals of the compound of the present invention (hereinafter sometimes to be abbreviated as the crystals of the present invention) can be produced by crystallization according to crystallization methods known per se.

In the present specification, the melting point means that measured using, for example, a micromelting point apparatus (Yanako, MP-500D or Buchi, B-545), a DSC (differential scanning calorimetry) device (SEIKO, EXSTAR6000) or the like.

In general, the melting points vary depending on the measurement apparatuses, the measurement conditions and the like. The crystal in the present specification may show different values from the melting point described in the present specification, as long as they are within each of a general error range.

The crystal of the present invention is superior in physicochemical properties (e.g., melting point, solubility, stability) and biological properties (e.g., pharmacokinetics (absorption, distribution, metabolism, excretion), efficacy expression), and thus it is extremely useful as a medicament.

The present invention is explained in more detail in the following by referring to Reference Examples, Examples, Experimental Examples and Formulation Examples, which are not to be construed as limitative.

The LC-MS analysis in the Reference Examples and Examples were performed under the following conditions.
  measurement device: Waters LC-MS system
  HPLC part: Agilent HP 1100
  MS part: Micromass ZMD
  column: CAPCELL PAK C18 UG120, S-3 µm, 1.5×35 mm (Shiseido Co., Ltd.)
  solvent: SOLUTION A; 0.05% trifluoroacetic acid-containing water, SOLUTION B; 0.04% trifluoroacetic acid-containing acetonitrile
  gradient cycle: 0.00 min (SOLUTION A/SOLUTION B=90/10), 2.00 min (SOLUTION A/SOLUTION B=5/95), 2.75 min (SOLUTION A/SOLUTION B=5/95), 2.76 min (SOLUTION A/SOLUTION B=90/10), 3.60 min (SOLUTION A/SOLUTION B=90/10)
  injection volume: 2 µL, flow rate: 0.5 mL/min, detection method: UV220 nm
  MS conditions ionization method: ESI Reference Example 1

1-[3,5-bis(trifluoromethyl)phenyl]pyrrolidin-3-ol

A solution of 3,5-bis(trifluoromethyl)phenyl bromide (21.1 g), 3-hydroxypyrrolidine (6.53 g), tris(dibenzylideneacetone)dipalladium(0) (1.47 g), (±)-2,2'-bis(diphenylphosphino)-1,1'-binaphthyl (1.99 g) and sodium tert-butoxide (10.6 g) in toluene (140 ml) was stirred under an argon gas atmosphere at 100° C. for 18 hr. After cooling to room temperature, water was added to the reaction mixture, and the mixture was extracted with ethyl acetate. The organic layer was washed with saturated brine, dried over anhydrous magnesium sulfate, and filtered. The filtrate was concentrated, and the residue was purified by silica gel column chromatography (hexane/ethyl acetate 95:5-70:30) to give the title compound (13.2 g, yield 61%) as colorless crystals.
$^1$H-NMR (300 MHz, CDCl$_3$) δ: 1.82 (br, 1H), 2.08-2.25 (m, 2H), 3.30-3.34 (m, 1H), 3.39-3.46 (m, 1H), 3.52-3.60 (m, 2H), 4.64-4.68 (m, 1H), 6.85 (s, 2H), 7.11 (s, 1H).

Reference Example 2 ethyl ({1-[3,5-bis(trifluoromethyl)phenyl]pyrrolidin-3-yl}sulfanyl)acetate

To a solution of 1-[3,5-bis(trifluoromethyl)phenyl]pyrrolidin-3-ol (13.2 g) obtained in Reference Example 1 in pyridine (70 mL) was added p-toluenesulfonyl chloride (9.7 g), and the mixture was stirred at room temperature for 18 hr. Water was added to the reaction mixture, and the mixture was extracted with ethyl acetate. The organic layer was washed with saturated brine, dried over anhydrous magnesium sulfate, and filtered. The filtrate was concentrated. To the obtained residue were added ethyl thioglycolate (6.13 g), potassium carbonate (13.0 g) and N,N-dimethylformamide (180 mL), and the mixture was stirred at 120° C. for 3 hr. After cooling to room temperature, water was added to the reaction mixture, and the mixture was extracted with ethyl acetate. The organic layer was washed with saturated brine, dried over anhydrous magnesium sulfate, and filtered. The filtrate was concentrated, and the residue was purified by silica gel column chromatography (hexane/ethyl acetate 100:0-80:20) to give the title compound (6.83 g, yield 39%) as a colorless oil.

$^1$H-NMR (300 MHz, CDCl$_3$) δ: 1.31 (t, J=7.2 Hz, 3H), 2.09-2.13 (m, 1H), 2.44-2.50 (m, 1H), 3.29-3.34 (m, 1H), 3.32 (s, 2H), 3.37-3.45 (m, 1H), 3.51-3.56 (m, 1H), 3.69-3.80 (m, 2H), 4.21 (q, J=7.2 Hz, 2H), 6.84 (s, 2H), 7.12 (s, 1H).

Reference Example 3 methyl ({1-[3,5-bis(trifluoromethyl)phenyl]pyrrolidin-3-yl}sulfonyl)acetate

A solution of ({1-[3,5-bis(trifluoromethyl)phenyl]pyrrolidin-3-yl}sulfanyl)acetic acid (500 mg) obtained in Example 1, methyl iodide (93 μL) and potassium carbonate (500 mg) in N,N-dimethylformamide (5 ml) was stirred at room temperature for 18 hr. Water was added to the reaction mixture, and the mixture was extracted with ethyl acetate. The organic layer was washed with saturated brine, dried over anhydrous magnesium sulfate, and filtered. The filtrate was concentrated. To a solution of the obtained residue in dichloromethane (25 ml) was added m-chloroperbenzoic acid (642 mg), and the mixture was stirred at room temperature for 3 hr. To the reaction mixture was added aqueous potassium carbonate solution, and the mixture was extracted with ethyl acetate. The organic layer was washed with saturated brine, dried over anhydrous magnesium sulfate, and filtered. The filtrate was concentrated, and the residue was purified by NH-silica gel column chromatography (hexane:ethyl acetate 90:10-80:20) to give the title compound (400 mg, yield 71%) as colorless crystals.

$^1$H-NMR (300 MHz, CDCl$_3$) δ: 2.52-2.61 (m, 1H), 2.64-2.71 (m, 1H), 3.48-3.56 (m, 1H), 3.62-3.69 (m, 1H), 3.85 (s, 3H), 3.77-3.90 (m, 2H), 4.07-4.08 (m, 2H), 4.35-4.39 (m, 1H), 6.90 (s, 2H), 7.20 (s, 1H).

Reference Example 4 ethyl ({1-[3,5-bis(trifluoromethyl)phenyl]-2-oxopyrrolidin-3-yl}sulfanyl)acetate To a solution of 3,5-bis(trifluoromethyl)aniline (17.0 g) and triethylamine (13.9 mL) in tetrahydrofuran (500 mL) was added 2,4-dibromobutanoyl chloride (10.0 mL), and the mixture was stirred at room temperature for 3 hr. Water was added to the reaction mixture, and the mixture was extracted with ethyl acetate. The organic layer was washed with saturated brine, dried over anhydrous magnesium sulfate, and filtered. The filtrate was concentrated. The obtained residue was dissolved in N,N-dimethylformamide (400 ml), sodium hydride (3.2 g) was added to the solution at 0° C., and the mixture was stirred at room temperature for 3 hr. Water was added to the reaction mixture, and the mixture was extracted with ethyl acetate. The organic layer was washed with saturated brine, dried over anhydrous magnesium sulfate, and filtered. The filtrate was concentrated. To the obtained residue were added ethyl thioglycolate (9.13 g), potassium carbonate (13.8 g) and N,N-dimethylformamide (500 mL), and the mixture was stirred at 60° C. for 3 hr. After cooling to room temperature, water was added to the reaction mixture, and the mixture was extracted with ethyl acetate. The organic layer was washed with saturated brine, dried over anhydrous magnesium sulfate, and filtered. The filtrate was concentrated, and the residue was purified by silica gel column chromatography (hexane/ethyl acetate 95:5-80:20) to give the title compound (19.5 g, yield 64%) as a colorless oil.

$^1$H-NMR (300 MHz, CDCl$_3$) δ: 1.29 (t, J=7.2 Hz, 3H), 2.04-2.16 (m, 1H), 2.63-2.70 (m, 1H), 3.36-3.41 (m, 1H), 3.84-4.08 (m, 4H), 4.21 (q, J=7.2 Hz, 2H), 7.65 (s, 1H), 8.14 (s, 2H).

Reference Example 5 ethyl ({1-[3,5-bis(trifluoromethyl)phenyl]-2-oxopyrrolidin-3-yl}sulfinyl)acetate A solution of ethyl ({1-[3,5-bis(trifluoromethyl)phenyl]-2-5 oxopyrrolidin-3-yl}sulfanyl)acetate (3.0 g) obtained in Reference Example 4 and m-chloroperbenzoic acid (1.7 g) in dichloromethane (25 ml) was stirred at room temperature for 18 hr. To the reaction mixture was added aqueous sodium hydrogensulfite solution, and the mixture was extracted with ethyl acetate. The organic layer was washed with saturated brine, dried over anhydrous magnesium sulfate, and filtered. The filtrate was concentrated, and the residue was purified by silica gel column chromatography (hexane/ethyl acetate 90:10-70:30) to give the title compound (1.8 g, yield 58%) as a colorless oil.

$^1$H-NMR (300 MHz, CDCl$_3$) δ: 1.26-1.35 (m, 3H), 2.58-2.94 (m, 2H), 3.88-4.79 (m, 7H), 7.64-7.69 (m, 1H), 8.13-8.15 (m, 2H).

Reference Example 6 ethyl ({1-[3,5-bis(trifluoromethyl)phenyl]-2-oxopyrrolidin-3-yl}sulfonyl)acetate A solution of ethyl ({1-[3,5-bis(trifluoromethyl)phenyl]-2-oxopyrrolidin-3-yl}sulfanyl)acetate (3.0 g) obtained in Reference Example 4 and m-chloroperbenzoic acid (3.48 g) in dichloromethane (50 ml) was stirred at room temperature for 18 hr. To the reaction mixture was added aqueous sodium hydrogensulfite solution, and the mixture was extracted with ethyl acetate. The organic layer was washed with saturated brine, dried over anhydrous magnesium sulfate, and filtered. The filtrate was concentrated, and the residue was purified by silica gel column chromatography (hexane/ethyl acetate 90:10-80:20) to give the title compound (1.6 g, yield 50%) as a colorless oil.

$^1$H-NMR (300 MHz, CDCl$_3$) δ: 1.34 (t, J=7.2 Hz, 3H), 2.61-2.75 (m, 1 H), 2.88-2.99 (m, 1H), 3.95-4.19 (m, 3H), 4.31 (q, J=7.2 Hz, 2H), 4.89-5.01 (s, 2H), 7.71 (s, 1H), 8.12 (s, 2H).

Reference Example 7

1-[3-fluoro-2-(trifluoromethyl)phenyl]pyrrolidin-3-ol

The title compound (6.2 g, yield 24%) was obtained from 1-bromo-3-fluoro-2-(trifluoromethyl)benzene and 3-hydroxypyrrolidine by a method similar to that in Reference Example 1.

¹H-NMR (300 MHz, CDCl₃) δ: 1.83 (br, 1H), 1.93-2.01 (m, 1H), 2.10-2.21 (m, 1H), 3.15-3.23 (m, 2H), 3.51-3.63 (m, 2H), 4.50 (br, 1H), 6.60-6.66 (m, 1H), 6.76-6.79 (m, 1H), 7.25-7.32 (m, 1H).

Reference Example 8 ethyl ({1-[3-fluoro-2-(trifluoromethyl)phenyl]pyrrolidin-3-yl}sulfanyl)acetate

The title compound (1.43 g, yield 16%) was obtained from 1-[3-fluoro-2-(trifluoromethyl)phenyl]pyrrolidin-3-ol obtained in Reference Example 7 by a method similar to that in Reference Example 2.

¹H-NMR (300 MHz, CDCl₃) δ: 1.28 (t, J=7.2 Hz, 3H), 1.90-1.97 (m, 1H), 2.33-2.39 (m, 1H), 3.19-3.25 (m, 1H), 3.28 (s, 2H), 3.35-3.43 (m, 2H), 3.54-3.59 (m, 1H), 3.65-3.70 (m, 1H), 4.21 (q, J=7.2 Hz, 2H), 6.61-6.67 (m, 1H), 6.74-6.77 (m, 1H), 7.26-7.32 (m, 1H).

Reference Example 9

1-[2,4-bis(trifluoromethyl)phenyl]pyrrolidin-3-ol

The title compound (6.84 g, yield 45%) was obtained from 1-bromo-2,4-bis(trifluoromethyl)benzene and 3-hydroxypyrrolidine by a method similar to that in Reference Example 1.

¹H-NMR (300 MHz, CDCl₃) δ: 1.78 (br, 1H), 2.05-2.17 (m, 2H), 3.32-3.45 (m, 2H), 3.69-3.77 (m, 2H), 4.58-4.59 (m, 1H), 6.93 (d, J=8.7 Hz, 1H), 7.55 (d, J=8.7 Hz, 1H), 7.81 (s, 1H).

Reference Example 10 ethyl ({1-[2,4-bis(trifluoromethyl)phenyl]pyrrolidin-3-yl}sulfanyl)acetate

The title compound (5.81 g, yield 64%) was obtained from 1-[2,4-bis(trifluoromethyl)phenyl]pyrrolidin-3-ol obtained in Reference Example 9 by a method similar to that in Reference Example 2.

¹H-NMR (300 MHz, CDCl₃) δ: 1.29 (t, J=7.2 Hz, 3H), 1.98-2.04 (m, 1H), 2.35-2.42 (m, 1H), 3.30 (s, 2H), 3.37-3.43 (m, 1H), 3.50-3.65 (m, 3H), 3.80-3.86 (m, 1H), 4.20 (q, J=7.2 Hz, 2H), 6.91 (d, J=9.0 Hz, 1H), 7.56 (dd, J=9.0, 1.5 Hz, 1H), 7.80 (d, J=1.5 Hz, 1H).

Reference Example 11 ethyl ({1-[2,4-bis(trifluoromethyl)phenyl]pyrrolidin-3-yl}sulfonyl)acetate

The title compound (1.2 g, yield 74%) was obtained from ethyl ({1-[2,4-bis(trifluoromethyl)phenyl]pyrrolidin-3-yl}sulfanyl)acetate obtained in Reference Example 10 by a method similar to that in Reference Example 6.

¹H-NMR (300 MHz, CDCl₃) δ: 1.34 (t, J=7.2 Hz, 3H), 2.42-2.61 (m, 2H), 3.47-3.62 (m, 2H), 3.82 (d, J=7.2 Hz, 2H), 4.02 (d, J=7.2 Hz, 2H), 4.19-4.32 (m, 3H), 7.10-7.13 (m, 1H), 7.63-7.66 (m, 1H), 7.84 (s, 1H).

Reference Example 12 ethyl 3-(pyrrolidin-3-yl)propanoate

To a solution of ethyl diethylphosphonoacetate (15.9 g) in tetrahydrofuran (200 mL) was added sodium hydride (60% in oil, 2.88 g) at room temperature, and the mixture was stirred for 30 min. To the reaction mixture was added benzyl 3-formylpyrrolidine-1-carboxylate (15.0 g) and the mixture was stirred for 4 hr. Water was added to the reaction mixture, and the mixture was extracted with ethyl acetate. The organic layer was washed with water and saturated brine, dried over anhydrous magnesium sulfate, and filtered. The filtrate was concentrated and the residue was dissolved in methanol (500 ml), palladium hydroxide/carbon (2.0 g) was added, and the mixture was stirred under a hydrogen atmosphere (3 atm) at 40° C. for 4 hr. The reaction solution was allowed to cool to room temperature, the reaction system was substituted by nitrogen, filtered, and the solvent was evaporated to give the title compound (8.0 g, yield 73%) as a colorless oil.

¹H-NMR (300 MHz, CDCl₃) δ: 1.26 (t, J=7.2 Hz, 3H), 1.45-1.57 (m, 1H), 1.69-1.82 (m, 2H), 2.04-2.26 (m, 2H), 2.31-2.36 (m, 2H), 2.65-2.72 (m, 1H), 3.06-3.73 (m, 3H), 4.12 (d, J=7.2 Hz, 2H), 6.57 (br, 1H).

Reference Example 13 ethyl 3-{1-[4-chloro-3-(trifluoromethyl)phenyl]pyrrolidin-3-yl}propanoate

The title compound (5.0 g, yield 61%) was obtained from 4-bromo-1-chloro-2-(trifluoromethyl)benzene and ethyl 3-(pyrrolidin-3-yl)propanoate obtained in Reference Example 12 by a method similar to that in Reference Example 1.

¹H-NMR (300 MHz, CDCl₃) δ: 1.53 (t, J=7.2 Hz, 3H), 1.65-1.75 (m, 1H), 1.77-1.85 (m, 2H), 2.14-2.24 (m, 1H), 2.27-2.42 (m, 3H), 2.91 (t, J=8.4 Hz, 1H), 3.23-3.46 (m, 3H), 4.14 (q, J=7.2 Hz, 2H), 6.51-6.55 (m, 1H), 6.73-6.74 (m, 1H), 7.23-7.25 (m, 1H).

Reference Example 14 ethyl 3-{1-[2-chloro-3-(trifluoromethyl)phenyl]pyrrolidin-3-yl}propanoate

The title compound (895 mg, yield 13%) was obtained from 1-bromo-2-chloro-3-(trifluoromethyl)benzene and ethyl 3-(pyrrolidin-3-yl)propanoate obtained in Reference Example 12 by a method similar to that in Reference Example 1.

¹H-NMR (300 MHz, CDCl₃) δ: 1.26 (t, J=7.2 Hz, 3H), 1.57-1.64 (m, 1H), 1.78-1.85 (m, 2H), 2.10-2.27 (m, 2H), 2.35-2.40 (m, 2H), 3.18-3.23 (m, 1H), 3.27-3.34 (m, 1H), 3.37-3.43 (m, 1H), 3.53-3.61 (m, 1H), 4.14 (q, J=7.2 Hz, 2H), 7.02-7.06 (m, 1H), 7.17-7.20 (m, 2H).

Reference Example 15 tert-butyl ({1-[3,5-bis(trifluoromethyl)phenyl]pyrrolidin-3-yl}oxy)acetate

A suspension of sodium hydride (oil 60%, 1.34 g) in tetrahydrofuran (50 ml) was ice-cooled. A solution of 1-[3,5-bis(trifluoromethyl)phenyl]pyrrolidin-3-ol (5.0 g) obtained in Reference Example 1 in tetrahydrofuran (100 ml) was added dropwise, and the mixture was stirred for 30 min. To the mixture was added tert-butyl bromoacetate (0.59 g), and the mixture was stirred at 55° C. for 16 hr. The reaction mixture was allowed to cool to room temperature, saturated aqueous ammonium chloride (10 mL) was added and the mixture was partitioned between ethyl acetate (200 mL)-water (200 ml). The organic layer was washed with saturated brine, dried over anhydrous magnesium sulfate, and filtered. The filtrate was concentrated under reduced pressure. The obtained residue was purified by silica gel column chromatography (hexane/ethyl acetate 100:0-70:30) to give the title compound (3.35 g, yield 49%) as a pale-yellow oil.

$^1$H-NMR (300 MHz, CDCl$_3$) δ: 1.48 (s, 9H), 2.02-2.37 (m, 2H), 3.35-3.61 (m, 4H), 4.03 (s, 2H), 4.28-4.40 (m, 1H), 6.85 (s, 2H), 7.11 (s, 1H).

Reference Example 16

1-[3,5-bis(trifluoromethyl)phenyl]imidazolidin-2-one

To a solution of 3,5-bis(trifluoromethyl)aniline (21.1 g) and triethylamine (13.9 mL) in toluene (200 ml) was slowly added 2-chloroethyl isocyanate (10.0 g) at 0° C., and the mixture was stirred at 60° C. for 4 hr. To the reaction solution was added ethyl acetate, and the mixture was washed with water and saturated brine, dried over anhydrous sodium sulfate, and concentrated under reduced pressure. The residue was dissolved in N,N-dimethylformamide (250 ml), sodium hydride (4.0 g) was slowly added at 0° C., and the mixture was stirred at room temperature for 3 hr. To the reaction solution was added ethyl acetate, and the mixture was washed with water and saturated brine, and dried over sodium sulfate. The solvent was concentrated under reduced pressure to give the title compound as a white solid (7.0 g, yield 26%).

$^1$H-NMR (300 MHz, CDCl$_3$) δ: 3.46 (t, J=7.8 Hz, 2H), 3.99 (t, J=7.8 Hz, 2H), 7.45 (s, 1H), 7.61 (s, 1H), 8.19 (s, 2H).

Reference Example 17 ethyl 3-{3-[3,5-bis(trifluoromethyl)phenyl]-2-oxoimidazolidin-1-yl}propanoate

To a solution of 1-[3,5-bis(trifluoromethyl)phenyl]imidazolidin-2-one (0.30 g) obtained in Reference Example 16 and ethyl 3-bromopropionate (214 mg) in N,N-dimethylformamide (5 ml) was added sodium hydride (60% in oil, 48 mg) at room temperature, and the mixture was stirred at 100° C. for 16 hr. To the reaction mixture were added ethyl 3-bromopropionate (100 mg) and sodium hydride (60% in oil, 15 mg), and the mixture was stirred at 100° C. for 4 hr. The reaction mixture was allowed to cool to room temperature, saturated aqueous ammonium chloride (10 ml) was added, and the reaction mixture was concentrated under reduced pressure. To the obtained residue was added water, and the mixture was extracted with ethyl acetate. The organic layer was washed with saturated brine, dried over anhydrous magnesium sulfate, and filtered. The filtrate was concentrated under reduced pressure. The obtained residue was purified by silica gel column chromatography (hexane:ethyl acetate 60:40-20:80) to give the title compound (181 mg, yield 45%) as a colorless oil.

$^1$H-NMR (300 MHz, CDCl$_3$) δ: 1.27 (t, J=7.19 Hz, 3H), 2.64 (t, J=6.63 Hz, 2H), 3.52-3.72 (m, 4H), 3.80-4.02 (m, 2H), 4.17 (q, J=7.19 Hz, 2H), 7.51 (s, 1H), 8.04 (s, 2H).

Reference Example 18

(3S)-1-[3,5-bis(trifluoromethyl)phenyl]pyrrolidin-3-ol

A solution of 3,5-bis(trifluoromethyl)phenyl bromide (44.0 g), (S)-3-hydroxypyrrolidine hydrochloride (17.8 g), tris(dibenzylideneacetone)dipalladium(0) (5.88 g), (±)-2,2'-bis(diphenylphosphino)-1,1'-binaphthyl (8.00 g) and sodium tert-butoxide (36.0 g) in toluene (280 ml) was refluxed with stirring under an argon gas atmosphere for 16 hr. After cooling to room temperature, water was added to the reaction mixture, and the mixture was extracted with ethyl acetate. The organic layer was washed with saturated brine, dried over anhydrous sodium sulfate, and filtered. The filtrate was concentrated, and the residue was purified by silica gel column chromatography (petroleum ether:ethyl acetate 20:1-2:1) to give the title compound (12.0 g, yield 28%) as a white solid.

$^1$H-NMR (300 MHz, CDCl$_3$) δ: 1.67 (br, 1H), 2.08-2.36 (m, 2H), 3.28-3.38 (m, 1H), 3.38-3.50 (m, 1H), 3.50-3.65 (m, 2H), 4.55-4.81 (m, 1H), 6.87 (s, 2H), 7.13 (s, 1H).

Reference Example 19

(3R)-1-[3,5-bis(trifluoromethyl)phenyl]pyrrolidin-3-ol

A mixed solution of 3,5-bis(trifluoromethyl)phenyl bromide (22.0 g), (R)-3-hydroxypyrrolidine hydrochloride (9.23 g), palladium(II) acetate (0.84 g), (±)-2,2'-bis(diphenylphosphino)-1,1'-binaphthyl (4.68 g) and cesium carbonate (73.4 g) in toluene (300 mL)-1,4-dioxane (100 mL) was stirred under an argon gas atmosphere at 80° C. for 16 hr. The solid was filtered off, and the filtrate was washed with saturated brine and water, dried over anhydrous sodium sulfate, and filtered. The filtrate was concentrated, and the residue was purified by silica gel column chromatography (petroleum ether:ethyl acetate 10:1-3:1) to give the title compound (13.7 g, yield 61%) as a white solid.

$^1$H-NMR (300 MHz, CDCl$_3$) δ: 1.74 (br, 1H), 2.06-2.31 (m, 2H), 3.28-3.38 (m, 1H), 3.39-3.50 (m, 1H), 3.50-3.66 (m, 2H), 4.61-4.73 (m, 1H), 6.87 (s, 2H), 7.12 (s, 1H).

Reference Example 20

4-[3,5-bis(trifluoromethyl)phenyl]furan-2-carbaldehyde

A solution of 3,5-bis(trifluoromethyl)phenylboronic acid (8.84 g), 4-bromo-2-furaldehyde (5.0 g), 2M aqueous sodium carbonate solution (71.4 mL), tetrakis(triphenylphosphine)palladium(0) (1.65 g) in 1,2-dimethoxyethane (300 ml) was stirred under an argon gas atmosphere at 90° C. for 16 hr. After cooling to room temperature, the reaction mixture was concentrated, water was added, and the mixture was extracted with ethyl acetate. The organic layer was washed with saturated brine, dried over anhydrous magnesium sulfate, and filtered. The filtrate was concentrated, and the residue was purified by silica gel column chromatography (hexane:ethyl acetate 98:2-90:10) to give the title compound (7.26 g, yield 82%) as a white solid.

$^1$H-NMR (300 MHz, CDCl$_3$) δ: 7.58 (s, 1H), 7.86 (s, 1H), 7.93 (s, 2H), 8.09 (s, 1H), 9.76 (s, 1H).

Reference Example 21 ethyl (2E)-3-{4-[3,5-bis(trifluoromethyl)phenyl]furan-2-yl}prop-2-enoate

To a solution of 4-[3,5-bis(trifluoromethyl)phenyl]furan-2-carbaldehyde (2.70 g) obtained in Reference Example 20 and ethyl diethylphosphonoacetate (2.16 g) in tetrahydrofuran (50 ml) was added sodium hydride (60% in oil, 456 mg) at room temperature, and the mixture was stirred for 1 hr. To the reaction mixture was added saturated aqueous ammonium chloride (10 ml), and the mixture was concentrated under reduced pressure. To the obtained residue was added water, and the mixture was extracted with ethyl acetate. The organic layer was washed with saturated brine, dried over anhydrous magnesium sulfate, and filtered. The filtrate was concentrated to give a pale-yellow solid. This was recrystallized from hexane-ethyl acetate to give the title compound (2.51 g, yield 76%) as a white solid.

$^1$H-NMR (300 MHz, CDCl$_3$) δ: 1.34 (t, J=7.16 Hz, 3H), 4.27 (q, J=7.10 Hz, 2H), 6.42 (d, J=15.8 Hz, 1H), 6.93 (s, 1H), 7.46 (d, J=15.8 Hz, 1H), 7.80 (s, 1H), 7.88 (s, 3H).

Reference Example 22 ethyl 3-{4-[3,5-bis(trifluoromethyl)phenyl]tetrahydrofuran-2-yl}propanoate

To a solution of ethyl. (2E)-3-{4-[3,5-bis(trifluoromethyl)phenyl]furan-2-yl}prop-2-enoate (500 mg) obtained in Reference Example 21 in a mixed solvent of ethanol (5 mL) and ethyl acetate (10 mL) was added 10% palladium/carbon (containing water (50%), 50 mg), and the mixture was stirred under a hydrogen atmosphere (1 atm) at room temperature for 3 hr. The reaction system was substituted with nitrogen and filtered. The solvent was evaporated to give a stereoisomer mixture of the title compound (510 mg, yield >99%) as a colorless oil.

LC-MS ESI(+) m/z: 385 (M+H)$^+$, retention time 2.68 min.

Reference Example 23

1-[4-chloro-3-(trifluoromethyl)phenyl]pyrrolidin-3-ol

The title compound (8.56 g, yield 90%) was obtained from bromo-4-chloro-3-(trifluoromethyl)benzene and 3-hydroxypyrrolidine by a method similar to that in Reference Example 1.

$^1$H-NMR (300 MHz, CDCl$_3$) δ: 1.67 (br, 1H), 2.02-2.29 (m, 2H), 3.21-3.30 (m, 1H), 3.31-3.42 (m, 1H), 3.44-3.58 (m, 2H), 4.58-4.70 (m, 1H), 6.51-6.63 (m, 1H), 6.77-6.82 (m, 1H), 7.26-7.31 (m, 1H).

Reference Example 24

1-[4-chloro-3-(trifluoromethyl)phenyl]pyrrolidin-3-yl 4-methylbenzenesulfonate

To a solution of 1-[4-chloro-3-(trifluoromethyl)phenyl] pyrrolidin-3-ol (3.0 g) obtained in Reference Example 23 in pyridine (20 mL) was added p-toluenesulfonyl chloride (2.8 g), and the mixture was stirred at room temperature for 16 hr. The reaction mixture was concentrated, water was added to the residue, and the mixture was extracted with ethyl acetate. The organic layer was washed with saturated brine, dried over anhydrous magnesium sulfate, and filtered. The filtrate was concentrated, and the residue was purified by silica gel column chromatography (hexane:ethyl acetate 90:10-75:25) to give the title compound (3.66 g, yield 77%) as white crystals.

$^1$H-NMR (300 MHz, CDCl$_3$) δ: 2.10-2.38 (m, 2H), 2.45 (s, 3H), 3.28-3.61 (m, 4H), 5.13-5.34 (m, 1H), 6.47-6.56 (m, 1H), 6.66-6.71 (m, 1H), 7.23-7.30 (m, 1H), 7.35 (m, 2H), 7.79 (m, 2H).

Reference Example 25 ethyl ({1-[4-chloro-3-(trifluoromethyl)phenyl]pyrrolidin-3-yl}sulfanyl)acetate

To a solution of 1-[4-chloro-3-(trifluoromethyl)phenyl] pyrrolidin-3-yl 4-methylbenzenesulfonate (3.65 g) obtained in Reference Example 24 in N,N-dimethylformamide (20 mL) were added ethyl thioglycolate (1.26 g) and potassium carbonate (5.92 g), and the mixture was stirred at 120° C. for 3 hr. After cooling to room temperature, the reaction mixture was concentrated, water was added, and the mixture was extracted with ethyl acetate. The organic layer was washed with saturated brine, dried over anhydrous magnesium sulfate, and filtered. The filtrate was concentrated, and the residue was purified by silica gel column chromatography (hexane:ethyl acetate 95:5-80:20) to give the title compound (2.95 g, yield 92%) as a yellow oil.

$^1$H-NMR (300 MHz, CDCl$_3$) δ: 1.31 (t, J=7.1 Hz, 3H), 1.97-2.16 (m, 1 H), 2.35-2.51 (m, 1H), 3.16-3.41 (m, 4H), 3.41-3.54 (m, 1H), 3.62-3.76 (m, 2H), 4.22 (q, J=7.1 Hz, 2H), 6.53-6.61 (m, 1H), 6.74-6.80 (m, 1H), 7.23-7.34 (m, 1H).

Reference Example 26

1-[2-chloro-3-(trifluoromethyl)phenyl]pyrrolidin-3-ol and 1-[3-(trifluoromethyl)phenyl]pyrrolidin-3-ol A mixture of 1-[2-chloro-3-(trifluoromethyl)phenyl]pyrrolidin-3-ol and 1-[3-(trifluoromethyl)phenyl]pyrrolidin-3-ol was obtained as a brown oil (8.08 g, yield 90%) from 1-bromo-2-chloro-3-(trifluoromethyl)benzene and 3-hydroxypyrrolidine by a method similar to that in Reference Example 1. This was used for the next reaction without performing further purification.

Reference Example 27

1-[2-chloro-3-(trifluoromethyl)phenyl]pyrrolidin-3-yl 4-methylbenzenesulfonate and 1-[3-(trifluoromethyl)phenyl]pyrrolidin-3-yl 4-methylbenzenesulfonate A mixture of 1-[2-chloro-3-(trifluoromethyl)phenyl]pyrrolidin 3-yl 4-methylbenzenesulfonate and 1-[3-(trifluoromethyl)phenyl]pyrrolidin-3-yl 4-methylbenzenesulfonate was obtained as white crystals (3.35 g, yield 69%) from a mixture of 1-[2-chloro-3-(trifluoromethyl)phenyl]pyrrolidin-3-ol and 1-[3-(trifluoromethyl)phenyl]pyrrolidin-3-ol obtained in Reference Example 26 by a method similar to that in Reference Example 24. This was used for the next reaction without performing further purification.

LC-MS ESI(+) m/z: 386 (M+H)$^+$, retention time 2.74 min; 420 (M+H)$^+$, retention time 2.74 min.

Reference Example 28 ethyl ({1-[2-chloro-3-(trifluoromethyl)phenyl]pyrrolidin-3-yl}sulfanyl)acetate

The title compound (1.08 g, yield 61%) was obtained as a yellow oil from a mixture of 1-[2-chloro-3-(trifluoromethyl) phenyl]pyrrolidin-3-yl 4-methylbenzenesulfonate and 1-[3-(trifluoromethyl)phenyl]pyrrolidin-3-yl 4-methylbenzenesulfonate obtained in Reference Example 27 by a method similar to that in Reference Example 25.

$^1$H-NMR (300 MHz, CDCl$_3$) δ: 1.24-1.34 (m, 3H), 1.89-2.04 (m, 1H), 2.33-2.47 (m, 1H), 3.27-3.41 (m, 3H), 3.42-3.55 (m, 2H), 3.55-3.68 (m, 1H), 3.76-3.86 (m, 1H), 4.15-4.25 (m, 2H), 7.04-7.13 (m, 1H), 7.19-7.29 (m, 2H).

Reference Example 29 ethyl ({1-[3-(trifluoromethyl)phenyl]pyrrolidin-3-yl}sulfanyl)acetate

The title compound (267 mg, yield 17%) was obtained as a yellow oil from a mixture of 1-[2-chloro-3-(trifluoromethyl) phenyl]pyrrolidin-3-yl 4-methylbenzenesulfonate and 1-[3-(trifluoromethyl)phenyl]pyrrolidin-3-yl 4-methylbenzenesulfonate obtained in Reference Example 27 by a method similar to that in Reference Example 25.

$^1$H-NMR (300 MHz, CDCl$_3$) δ: 1.31 (t, J=7.2 Hz, 3H), 1.99-2.14 (m, 1 H), 2.36-2.52 (m, 1H), 3.21-3.44 (m, 4H), 3.44-3.57 (m, 1H), 3.61-3.79 (m, 2H), 4.22 (q, J=7.2 Hz, 2H), 6.60-6.74 (m, 2H), 6.87-6.97 (m, 1H), 7.26-7.35 (m, 1H).

Reference Example 30

1-[2,5-bis(trifluoromethyl)phenyl]pyrrolidin-3-ol

A solution of 2,5-bis(trifluoromethyl)phenyl bromide (4.45 g), 3-hydroxypyrrolidine (1.2 g), palladium(II) acetate (0.16 g), (±)-2,2'-bis(diphenylphosphino)-1,1'-binaphthyl (0.87 g) and cesium carbonate (13.6 g) in toluene (74 mL) was stirred under an argon gas atmosphere at 80° C. for 16 hr. The reaction mixture was allowed to cool to room temperature, water was added, and the mixture was extracted with ethyl acetate. The extract was washed with saturated brine, dried over anhydrous magnesium sulfate, and filtered. The filtrate was concentrated, and the residue was purified by silica gel column chromatography (hexane:ethyl acetate 90:10-75:25) to give the title compound (3.79 g, yield 91%) as an orange oil.

$^1$H-NMR (300 MHz, CDCl$_3$) δ: 1.72 (d, J=4.9 Hz, 1H), 1.95-2.10 (m, 1 H), 2.10-2.24 (m, 1H), 3.21-3.43 (m, 2H), 3.60-3.78 (m, 2H), 4.48-4.65 (m, 1H), 7.01-7.16 (m, 1H), 7.16-7.23. (m, 1H), 7.63-7.74 (m, 1H).

Reference Example 31 ethyl (2E)-3-(5-bromofuran-2-yl)prop-2-enoate

To a solution (200 ml) of ethyl diethylphosphonoacetate (10.5 g) in N,N-dimethylformamide was added sodium hydride (60% in oil, 1.87 g), and the mixture was stirred under a nitrogen atmosphere at room temperature for 15 min. To this solution was added a solution of 5-bromo-2-furaldehyde (7.45 g) in N,N-dimethylformamide (40 ml), and the mixture was stirred under a nitrogen atmosphere at room temperature for 1 hr. The reaction was quenched with saturated ammonium chloride solution (50 ml) and the reaction solution was partitioned between ethyl acetate (900 mL) and water (900 mL). The organic layer was washed with water and saturated brine, dried over anhydrous magnesium sulfate, and filtered. The filtrate was concentrated under reduced pressure and the obtained residue was purified by silica gel column chromatography (hexane:ethyl acetate 90:10-85:15) to give the title compound (10.0 g, yield 96%) as a pale-yellow solid.

$^1$H-NMR (300 MHz, CDCl$_3$) δ: 1.32 (t, J=7.2 Hz, 3H), 4.24 (q, J=7.2 Hz, 2H), 6.31 (d, J=15.6 Hz, 1H), 6.40 (d, J=3.4 Hz, 1H), 6.54 (d, J=3.6 Hz, 1H), 7.31 (d, J=15.8 Hz, 1H).

Reference Example 32 ethyl (2E)-3-{5-[3,5-bis(trifluoromethyl)phenyl]furan-2-yl}prop-2-enoate

To a mixture of ethyl (2E)-3-(5-bromofuran-2-yl)prop-2-enoate (10.0 g) obtained in Reference Example 31, 3,5-bis(trifluoromethyl)phenylboronic acid (11.0 g) and 2M sodium carbonate (102 mL) in dimethoxyethane (500 ml) was added tetrakis(triphenylphosphine)palladium(0) (2.00 g) under an argon gas atmosphere, and the mixture was stirred at 110° C. for 9 hr, and then at 95° C. for 15 hr. The reaction solution was allowed to cool to room temperature, concentrated, and partitioned between ethyl acetate (500 ml) and water (500 mL). The ethyl acetate layer was washed with water and saturated brine, dried over anhydrous magnesium sulfate, and filtered. The filtrate was concentrated under reduced pressure and the obtained residue was purified by silica gel column chromatography (hexane:ethyl acetate 90:10-85:15) to give the title compound (13.2 g, yield 85%) as a pale-yellow solid.

$^1$H-NMR (300 MHz, CDCl$_3$) δ: 1.35 (t, J=7.0 Hz, 3H), 4.29 (q, J=7.2 Hz, 2H), 6.49 (d, J=15.9 Hz, 1H), 6.74 (d, J=3.8 Hz, 1H), 6.92 (d, J=3.4 Hz, 1H), 7.46 (d, J=15.9 Hz, 1H), 7.79 (s, 1H), 8.10 (s, 2H).

Reference Example 33 ethyl 3-{5-[3,5-bis(trifluoromethyl)phenyl]tetrahydrofuran-2-yl}propanoate

A solution of ethyl (2E)-3-{5-[3,5-bis(trifluoromethyl)phenyl]furan-2-yl}prop-2-enoate (13.1 g) obtained in Reference Example 32 and 10% palladium/carbon (containing water (50%), 3.48 g) in ethanol-tetrahydrofuran (3:1, 320 ml) was stirred under a hydrogen atmosphere (1 atm) at room temperature for 2 days. The reaction solution was diluted with ethyl acetate and filtered through silica gel. The silica gel was washed with ethyl acetate (500 ml), the filtrate and washing were combined, and the solvent was removed under reduced pressure to give the title compound (13.2 g, yield 99%) as a colorless oil.

$^1$H-NMR (300 MHz, CDCl$_3$) δ: 7.78 (s, 3H), 4.96 (t, J=7.3 Hz, 1H), 4.15 (q, J=7.2 Hz, 2H), 4.07 (t, J=7.3 Hz, 1H), 2.63-2.32 (m, 3H), 2.20-2.09 (m, 1H), 2.05-1.96 (m, 2H), 1.88-1.60 (m, 2H), 1.26 (t, J=7.1 Hz, 3H).

Reference Example 34

1-[3,5-bis(trifluoromethyl)phenyl]-1H-pyrrole-3-carbaldehyde

A solution of 3,5-bis(trifluoromethyl)aniline (3.58 g) and 2,5-dimethoxy-3-tetrahydrofurancarbaldehyde (2.50 g) in acetic acid (16 mL) was stirred at 90° C. for 30 min. After cooling to room temperature, the reaction solution was concentrated under reduced pressure, and the residue was partitioned between ethyl acetate and saturated sodium hydrogencarbonate solution. The ethyl acetate layer was washed with water and saturated brine, dried over anhydrous magnesium sulfate, and filtered. The filtrate was concentrated under reduced pressure and the obtained residue was purified by silica gel column chromatography (hexane:ethyl acetate 70:30) to give the title compound (2.44 g, yield 51%) as a pale-yellow solid.

$^1$H-NMR (300 MHz, CDCl$_3$) δ: 6.90 (dd, J=3.1, 1.6 Hz, 1H), 7.18 (t, J=2.4 Hz, 1H), 7.75 (d, J=2.3 Hz, 1H), 7.88 (s, 3H), 9.91 (s, 1 H).

Reference Example 35 ethyl (2E)-3-[(1-[3,5-bis(trifluoromethyl)phenyl]-1H-pyrrol-3-yl]prop-2-enoate

To a solution (35 ml) of ethyl diethylphosphonoacetate (1.77 g) in N,N-dimethylformamide was added sodium hydride (60% in oil, 0.32 g), and the mixture was stirred under a nitrogen atmosphere at room temperature for 15 min. To the solution was added a solution of 1-[3,5-bis(trifluoromethyl)phenyl]-1H-pyrrole-3-carbaldehyde (2.20 g) obtained in Reference Example 34 in N,N-dimethylformamide (10 ml) and the mixture was stirred under a nitrogen atmosphere at room temperature for 1 hr. The reaction was quenched with saturated ammonium chloride solution (10 mL) and the reaction solution was partitioned between ethyl acetate (120 ml) and water (120 ml). The organic layer was washed with water and saturated brine, dried over anhydrous magnesium sulfate, and filtered. The filtrate was concentrated under reduced pressure. The obtained solid was triturated with hexane to give the title compound (2.37 g, yield 88%) as a white solid.

$^1$H-NMR (300 MHz, CDCl$_3$) δ: 1.33 (t, J=7.2 Hz, 3H), 4.25 (q, J=7.2 Hz, 2H), 6.22 (d, J=15.8 Hz, 1H), 6.65 (dd, J=2.9, 1.4 Hz, 1 H), 7.14 (t, J=2.4 Hz, 1H), 7.34 (t, J=1.9 Hz, 1H), 7.64 (d, J=15.8 Hz, 1H), 7.75-7.85 (m, 3H).

Reference Example 36 ethyl 3-{1-[3,5-bis(trifluoromethyl)phenyl]pyrrolidin-3-yl}propanoate

A solution of ethyl (2E)-3-{1-[3,5-bis(trifluoromethyl)phenyl]-1H-pyrrol-3-yl}prop-2-enoate (0.60 g) obtained in Reference Example 35 and 10% palladium/carbon (containing water (50%), 0.17 g) in ethanol-tetrahydrofuran (4:1, 20 ml) was stirred under a hydrogen atmosphere (1 atm) at room temperature for 16 hr. The reaction solution was filtered through celite, and the filtrate was concentrated. The residue was purified by silica gel column chromatography (hexane: ethyl acetate 90:10) to give the title compound (0.47 g, yield 77%) as a white solid.

$^1$H-NMR (300 MHz, CDCl$_3$) δ: 1.28 (t, J=7.2 Hz, 3H), 1.68-1.75 (m, 1 H), 1.78-1.87 (m, 2H), 2.20-2.27 (m, 1H), 2.30-2.50 (m, 3H), 2.98 (t, J=8.6 Hz, 1H), 3.23-3.63 (m, 3H), 4.16 (q, J=7.2 Hz, 2H), 6.83 (s, 2H), 7.09 (s, 1H).

Reference Example 37

N-[3,5-bis(trifluoromethyl)phenyl]-3-chloropropanesulfonamide

A solution of 3-chloropropanesulfonyl chloride (5.0 g) and 3,5-bis(trifluoromethyl)aniline (6.47 g) in pyridine (50 ml) was stirred at room temperature for 16 hr. The reaction solution was concentrated under reduced pressure, and the residue was partitioned between ethyl acetate and 1N hydrochloric acid. The organic layer was washed with water and saturated brine, dried over anhydrous magnesium sulfate, and filtered. The filtrate was concentrated under reduced pressure and the obtained residue was purified by silica gel column chromatography (hexane:ethyl acetate 95:5-60:40) to give the title compound (7.20 g, yield 69%) as a pale-brown solid.

$^1$H-NMR (300 MHz, CDCl$_3$) δ: 2.29-2.42 (m, 2H), 3.37 (t, J=6.1 Hz, 2H), 3.68 (t, J=7.5 Hz, 2H), 7.66 (s, 2H), 7.69 (s, 1H).

Reference Example 38

2-[3,5-bis(trifluoromethyl)phenyl]isothiazolidine 1,1-dioxide

To a solution of N-[3,5-bis(trifluoromethyl)phenyl]-3-chloropropanesulfonamide (7.10) obtained in Reference Example 37 in N,N-dimethylformamide (100 mL) was added sodium hydride (60% in oil, 0.84 g), and the mixture was stirred at room temperature for 3 hr. To the reaction mixture was added saturated ammonium chloride and the solution was partitioned between ethyl acetate and water. The organic layer was washed with water and saturated brine, dried over anhydrous magnesium sulfate, and filtered. The filtrate was concentrated under reduced pressure and the obtained residue was purified by silica gel column chromatography (hexane: ethyl acetate 90:10-40:60) to give the title compound (2.44 g, yield 38%) as a pale-brown solid.

$^1$H-NMR (300 MHz, CDCl$_3$) δ: 2.62 (t, J=7.3 Hz, 2H), 3.45 (t, J=7.3 Hz, 2H), 3.86 (t, J=6.6 Hz, 2H), 7.62 (s, 1H), 7.64 (s, 2H).

Reference Example 39

2-[3,5-bis(trifluoromethyl)phenyl]isothiazolidine-5-carbaldehyde 1,1-dioxide

A solution of 2-[3,5-bis(trifluoromethyl)phenyl]isothiazolidine 1,1-dioxide (1.77 g) obtained in Reference Example 38 in tetrahydrofuran (60 mL) was cooled to −78° C. under an argon atmosphere, and a solution (1.1 mol/L, 14.5 mL) of lithium hexamethyldisilazide in tetrahydrofuran was added dropwise. This was stirred for 30 min, ethyl formate (0.59 g) was added and the mixture was stirred at −78° C. for 1 hr, and at room temperature for 16 hr. To the reaction mixture was added saturated ammonium chloride solution, the mixture was concentrated under reduced pressure and the residue was partitioned between ethyl acetate and water. The ethyl acetate layer was washed with water and saturated brine, dried over anhydrous magnesium sulfate, and filtered. The filtrate was concentrated under reduced pressure and the obtained residue was purified by silica gel column chromatography (hexane: ethyl acetate 90:10-30:70) to give the title compound (1.63 g, yield 85%) as a pale-yellow amorphous form. This was used for the next reaction without performing further purification and identification.

Reference Example 40 ethyl (2E)-3-{2-[3,5-bis(trifluoromethyl)phenyl]-1,1-dioxidoisothiazolidin-5-yl}prop-2-enoate To a solution (10 mL) of ethyl diethylphosphonoacetate (1.01 g) in N,N-dimethylformamide was added sodium hydride (60% in oil, 0.18 g) and the mixture was stirred under a nitrogen atmosphere at room temperature for 15 min. To the solution was added a solution of 2-[3,5-bis(trifluororaethyl)phenyl]isothiazolidine-5-carbaldehyde 1,1-dioxide (1.63 g) obtained in Reference Example 39 in N,N-dimethylformamide (6 ml), and the mixture was stirred under a nitrogen atmosphere at room temperature for 1 hr. The reaction was quenched with saturated ammonium chloride solution and the reaction solution was partitioned between ethyl acetate and water. The organic layer was washed with water and saturated brine, dried over anhydrous magnesium sulfate, and filtered. The filtrate was concentrated under reduced pressure, the obtained residue was purified by silica gel column chromatography (hexane:ethyl acetate 90:10-40:60) and the obtained yellow solid was recrystallized from hexane-ethyl acetate to give the title compound (0.43 g, yield 22%) as a pale-yellow solid.

$^1$H-NMR (300 MHz, CDCl$_3$) δ: 1.32 (t, J=7.2 Hz, 3H), 2.48-2.68 (m, 1 H), 2.67-2.85 (m, 1H), 3.79-3.92 (m, 2H), 4.06-4.22 (m, 1H), 4.26 (q, J=7.2 Hz, 2H), 6.23 (d, J=15.5 Hz, 1H), 6.90 (dd, J=15.5, 8.5 Hz, 1H), 7.65 (s, 3H).

Reference Example 41 ethyl 3-{2-[3,5-bis(trifluoromethyl)phenyl]-1,1-dioxidoisothiazolidin-5-yl}propanoate A solution of ethyl (2E)-3-{2-[3,5-bis(trifluoromethyl)phenyl]-1,1-dioxidoisothiazolidin-5-yl}prop-2-enoate (0.32 g) obtained in Reference Example 40 and 20% palladium hydroxide carbon (containing water (50%), 0.10 g) in ethanol-tetrahydrofuran (3:1, 20 mL) was stirred under a hydrogen atmosphere (4 atm) at 50° C. for B hr. The reaction solution was filtered with a membrane filter (Advantec, 0.5 μm), and the filtrate was concentrated to give the title compound (0.29 g, yield 91%) as a white solid.
$^{1}$H-NMR (300 MHz, CDCl$_{3}$) δ: 1.28 (t, J=7.2 Hz, 3H), 2.08-2.43 (m, 3 H), 2.58-2.75 (m, 3H), 3.44-3.65 (m, 1H), 3.72-3.85 (m, 2H), 4.17 (q, J=7.2 Hz, 2H), 7.61 (s, 1H), 7.63 (s, 2H).

Reference Example 42

1-[2-(trifluoromethyl)phenyl]pyrrolidin-3-ol

The title compound (3.72 g, yield 67%) was obtained from 2-(trifluoromethyl)phenyl bromide and 3-hydroxypyrrolidine by a method similar to that in Reference Example 1.
$^{1}$H-NMR (300 MHz, CDCl$_{3}$) δ: 1.87 (d, J=6.1 Hz, 1H), 1.92-2.07 (m, 1H), 2.10-2.28 (m, 1H), 3.04-3.31 (m, 2H), 3.39-3.67 (m, 2H), 4.41-4.59 (m, 1H), 6.96 (t, J=7.6 Hz, 1H), 7.08 (d, J=8.3 Hz, 1H), 7.35-7.46 (m, 1H), 7.59 (m, 1H).

Reference Example 43

1-[3-(trifluoromethyl)phenyl]pyrrolidin-3-ol

The title compound (2.67 g, yield 54%) was obtained from 3-(trifluoromethyl)phenyl bromide and 3-hydroxypyrrolidine by a method similar to that in Reference Example 1.
$^{1}$H-NMR (300 MHz, CDCl$_{3}$) δ: 1.67 (br. s, 1H), 2.06-2.32 (m, 2H), 3.24-3.33 (m, 1H), 3.33-3.46 (m, 1H), 3.47-3.65 (m, 2H), 4.52-4.70 (m, 1H), 6.61-6.81 (m, 2H), 6.91 (d, J=7.6 Hz, 1 H), 7.30 (t, J=8.0 Hz, 1H).

Reference Example 44

1-[4-(trifluoromethyl)phenyl]pyrrolidin-3-ol

The title compound (2.71 g, yield 55%) was obtained from 4-(trifluoromethyl)phenyl bromide and 3-hydroxypyrrolidine by a method similar to that in Reference Example 1.
$^{1}$H-NMR (300 MHz, CDCl$_{3}$) δ: 1.67 (d, J=3.8 Hz, 1H), 2.02-2.30 (m, 2H), 3.25-3.34 (m, 1H), 3.36-3.45 (m, 1H), 3.47-3.63 (m, 2H), 4.64 (br. s, 1H), 6.55 (d, J=8.7 Hz, 2H), 7.44 (d, J=8.7 Hz, 2H).

Reference Example 45 ethyl 3-[3,5-bis(trifluoromethyl)phenyl]-3-cyanopropanoate

A solution of 3,5-bis(trifluoromethyl)phenylacetonitrile (8.30 g) in tetrahydrofuran (80 ml) was cooled to −78° C. under an argon gas atmosphere, and a solution (1.9 M, 17.3 ml) of sodium hexamethyldisilazane in tetrahydrofuran was added dropwise. After the completion of the dropwise addition, the solution was stirred at 10° C. for 15 min, and cooled to −78° C. again. To the solution was added ethyl bromoacetate (5.48 g), and the mixture was stirred at room temperature for 16 hr. The reaction solution was partitioned between ethyl acetate and water, and the ethyl acetate layer was washed with water and saturated brine, dried over anhydrous magnesium sulfate, and filtered. The filtrate was concentrated under reduced pressure and the obtained residue was purified by silica gel column chromatography (hexane:ethyl acetate 100:0-70:30) to give the title compound (7.50 g, yield 67%) as a brown oil.
$^{1}$H-NMR (300 MHz, CDCl$_{3}$) δ: 1.25 (t, J=7.2 Hz, 3H), 2.81-2.99 (m, 1 H), 3.01-3.19 (m, 1H), 4.19 (q, 2H), 4.47 (t, J=7.2 Hz, 1H), 7.87 (s, 2H), 7.90 (s, 1H).

Reference Example 46

4-[3,5-bis(trifluoromethyl)phenyl]pyrrolidin-2-one

To a solution of ethyl 3-[3,5-bis(trifluoromethyl)phenyl]-3-cyanopropanoate (7.40 g) obtained in Reference Example 45 and dichloro cobalt hexahydrate (10.4 g) in methanol (300 mL) was added sodium borohydride (12.4 g) while the reaction solution was maintained at not more than 30° C., and the mixture was stirred at room temperature for 18 hr. The reaction solution was concentrated under reduced pressure, and the residue was partitioned between ethyl acetate and water. The ethyl acetate layer was washed with water and saturated brine, dried over anhydrous magnesium sulfate, and filtered. The filtrate was concentrated under reduced pressure and the obtained residue was purified by silica gel column chromatography (hexane:ethyl acetate 50:50-0:100) to give the title compound (2.67 g, yield 41%) as a white solid.
$^{1}$H-NMR (300 MHz, CDCl$_{3}$) δ: 2.43-2.56 (m, 1H), 2.75-2.89 (m, 1H), 3.38-3.54 (m, 1H), 3.74-3.96 (m, 2H), 6.23 (br. s, 1H), 7.71 (s, 2H), 7.81 (s, 1H).

Reference Example 47 methyl {4-[3,5-bis(trifluoromethyl)phenyl]-2-oxopyrrolidin-1-yl}acetate

To a solution of 4-[3,5-bis(trifluoromethyl)phenyl]pyrrolidin-2-one (0.70 g) obtained in Reference Example 46 in N,N-dimethylformamide (10 mL) was added sodium hydride (60% in oil, 0.10 g) under ice-cooling, and the mixture was stirred for 30 min. To the solution was added a solution of methyl bromoacetate (0.54 g) in N,N-dimethylformamide (5 ml), and the mixture was stirred at room temperature for 4 hr. The reaction was quenched with saturated ammonium chloride solution and the solution was partitioned between ethyl acetate and water. The organic layer was washed with saturated brine, dried over anhydrous magnesium sulfate, and filtered. The filtrate was concentrated under reduced pressure and the obtained residue was purified by silica gel column chromatography (hexane:ethyl acetate 90:10-50:50) to give the title compound (0.65 g, yield 75%) as a as a pale-brown oil.
$^{1}$H-NMR (300 MHz, CDCl$_{3}$) δ: 2.48-2.67 (m, 1H), 2.84-3.04 (m, 1H), 3.56-3.66 (m, 1H), 3.72-3.83 (m, 1H), 3.77 (s, 3H), 3.86-3.97 (m, 1H), 3.99-4.10 (m, 1H), 4.21-4.37 (m, 1H), 7.76 (s, 2H), 7.81 (s, 1H).

Reference Example 48

1-[3,5-bis(trifluoromethyl)phenyl]pyrrolidin-3-one

To a solution of 1-[3,5-bis(trifluoromethyl)phenyl]pyrrolidin-3-ol (5.0 g) obtained in Reference Example 1 and triethylamine (16.9 g) in dimethyl sulfoxide (50 ml) was added pyridine-sulfur trioxide complex (7.98 g) under ice-cooling, and the mixture was stirred at 0° C. for 30 min, and then at room temperature for 20 hr. The reaction solution was partitioned between ethyl acetate and water, and the organic layer was washed with water and saturated brine, dried over anhydrous magnesium sulfate, and filtered. The filtrate was concentrated under reduced pressure and the obtained residue was purified by silica gel column chromatography (hexane:ethyl acetate 90:10-40:60) to give the title compound (3.51 g, yield 71%) as a brown oil.

$^1$H-NMR (300 MHz, CDCl$_3$) δ: 2.82 (t, J=7.6 Hz, 2H), 3.80 (t, J=7.5 Hz, 4H), 6.98 (s, 2H), 7.28 (s, 1H).

Reference Example 49 ethyl (2E/Z) (2E/Z)-{1-[3,5-bis(trifluoromethyl)phenyl]pyrrolidin-3-ylidene}ethanoate To a solution (15 mL) of ethyl diethylphosphonoacetate (1.24 g) in N,N-dimethylformamide was added sodium hydride (60% in oil, 0.22 g), and the mixture was stirred at room temperature under a nitrogen atmosphere for 15 min. To the solution was added 1-[3,5-bis(trifluoromethyl)phenyl]pyrrolidin-3-one (1.50 g) obtained in Reference Example 48 in N,N-dimethylformamide (10 mL) and the mixture was stirred at room temperature under a nitrogen atmosphere for 1 hr. The reaction was quenched with saturated ammonium chloride solution (10 mL) and the reaction solution was partitioned between ethyl acetate and water. The organic layer was washed with water and saturated brine, dried over anhydrous magnesium sulfate, and filtered. The filtrate was concentrated under reduced pressure and the obtained residue was purified by silica gel column chromatography (hexane:ethyl acetate 90:10-60:40) to give the title compound (1.13 g, yield 61%, E form, Z form mixture) as a pale-yellow oil. LC/MS ESI(+) m/z: 386 (M+H)$^+$, retention time 2.11 min; 386 (M+H)$^+$, retention time 2.29 min.

Reference Example 50 ethyl {1-[3,5-bis(trifluoromethyl)phenyl]pyrrolidin-3-yl}acetate

A solution of ethyl (2E/Z)-{1-[3,5-bis(trifluoromethyl)phenyl]pyrrolidin-3-ylidene}ethanoate (0.70 g) obtained in Reference Example 49 and 10% palladium/carbon (containing water (50%), 0.20 g) in ethanol-tetrahydrofuran (3:1, 320 ml) was stirred under a hydrogen atmosphere (1 atm) at room temperature for 16 hr. The reaction solution was diluted with ethyl acetate, and filtered through silica gel. Silica gel was washed with ethyl acetate (500 ml), and the filtrate and washing were combined. The solvent was evaporated under reduced pressure to give the title compound (13.2 g, yield 99%) as a colorless oil.

$^1$H-NMR (300 MHz, CDCl$_3$) δ: 1.29 (t, J=7.2 Hz, 3H), 1.67-1.90 (m, 1 H), 2.19-2.38 (m, 1H), 2.41-2.59 (m, 2H), 2.68-2.88 (m, 1H), 2.97-3.09 (m, 1H), 3.29-3.50 (m, 2H), 3.55-3.68 (m, 1H), 4.18 (q, J=7.2 Hz, 2H), 6.84 (s, 2H), 7.10 (s, 1H).

Reference Example 51 methyl 3-({1-[3,5-bis(trifluoromethyl)phenyl]pyrrolidin-3-yl}sulfanyl)propanoate The title compound (0.46 g, yield 18%) was obtained from 1-[3,5-bis(trifluoromethyl)phenyl]pyrrolidin-3-ol obtained in Reference Example 1 and methyl 3-mercaptopropionate by a method similar to that in Reference Example 2.

$^1$H-NMR (300 MHz, CDCl$_3$) δ: 1.98-2.17 (m, 1H), 2.34-2.53 (m, 1H), 2.60-2.71 (m, 2H), 2.84-2.95 (m, 2H), 3.23-3.35 (m, 1H), 3.36-3.46 (m, 1H), 3.47-3.64 (m, 2H), 3.68-3.80 (m, 4H), 6.84 (s, 2H), 7.13 (s, 1H).

Reference Example 52

1-[4-fluoro-2-(trifluoromethyl)phenyl]pyrrolidin-3-ol

A solution of 1-bromo-4-fluoro-2-(trifluoromethyl)benzene (4.6 g), 3-hydroxypyrrolidine (1.5 g), palladium(II) acetate (193 mg), (±)-2,2'-bis(diphenylphosphino)-1,1'-binaphthyl (1.07 g) and cesium carbonate (16.8 g) in toluene (90 mL) was stirred under an argon gas atmosphere at 85° C. for 16 hr. After cooling to room temperature, water was added to the reaction mixture, and the mixture was extracted with ethyl acetate. The organic layer was washed with saturated brine, dried over anhydrous magnesium sulfate, and filtered. The filtrate was concentrated, and the residue was purified by silica gel column chromatography (hexane/ethyl acetate 90:10-65:35) to give the title compound (3.58 g, yield 84%) as a yellow oil.

$^1$H-NMR (300 MHz, CDCl$_3$) δ: 1.88-2.03 (m, 2H), 2.14-2.30 (m, 1H), 3.00-3.17 (m, 2H), 3.33-3.41 (m, 1H), 3.41-3.52 (m, 1H), 4.48 (br. s, 1H), 7.08-7.23 (m, 2H), 7.28-7.37 (m, 1H).

Reference Example 53

1-[4-fluoro-3-(trifluoromethyl)phenyl]pyrrolidin-3-ol

A solution of 4-bromo-1-fluoro-2-(trifluoromethyl)benzene (10 g), 3-hydroxypyrrolidine (3.56 g), palladium(II) acetate (462 mg), (±)-2,2'-bis(diphenylphosphino)-1,1'-binaphthyl (2.57 g) and cesium carbonate (26.8 g) in toluene (220 ml) was stirred under an argon gas atmosphere at 90° C. for 16 hr. After cooling to room temperature, the reaction mixture was filtered through celite, and the celite was washed with ethyl acetate. The filtrate and washing were combined and the solution was washed with water and saturated brine, dried over anhydrous magnesium sulfate, and filtered. The filtrate was concentrated, and the residue was purified by silica gel column chromatography (hexane/ethyl acetate 80:20-25:75) to give the title compound (5.91 g, yield 58%) as a pale-yellow oil.

$^1$H-NMR (300 MHz, CDCl$_3$) δ: 1.72 (d, J=3.4 Hz, 1H), 2.00-2.29 (m, 2 H), 3.25 (d, J=10.2 Hz, 1H), 3.33 (td, J=8.8, 3.6 Hz, 1H), 3.40-3.59 (m, 2H), 4.63 (br. s, 1H), 6.54-6.70 (m, 2H), 7.05 (t, J=9.4 Hz, 1H).

Reference Example 54

1-[2-fluoro-4-(trifluoromethyl)phenyl]pyrrolidin-3-ol

A solution of 1-bromo-2-fluoro-4-(trifluoromethyl)benzene (4.6 g), 3-hydroxypyrrolidine (1.5 g), palladium(II) acetate (137 mg), (±)-2,2'-bis(diphenylphosphino)-1,1'-binaphthyl (1.07 g) and cesium carbonate (16.8 g) in toluene (90 ml) was stirred under an argon gas atmosphere at 85° C. for 16 hr. After cooling to room temperature, water was added to the reaction mixture, and the mixture was extracted with ethyl acetate. The organic layer was washed with saturated brine, dried over anhydrous magnesium sulfate, and filtered. The filtrate was concentrated, and the residue was purified by silica gel column chromatography (hexane/ethyl acetate 90:10-65:35) to give the title compound (2.82 g, yield 66%) as a gray solid.

$^1$H-NMR (300 MHz, CDCl$_3$) δ: 1.63 (d, J=4.5 Hz, 1H), 1.96-2.22 (m, 2H), 3.40-3.57 (m, 2H), 3.61-3.81 (m, 2H), 4.51-4.66 (m, 1H), 6.64 (t, J=9.1 Hz, 1H), 7.15-7.25 (m, 2H).

Reference Example 55

1-[2-fluoro-5-(trifluoromethyl)phenyl]pyrrolidin-3-ol

A solution of 2-bromo-1-fluoro-4-(trifluoromethyl)benzene (4.6 g), 3-hydroxypyrrolidine (1.5 g), palladium(II) acetate (193 mg), (±)-2,2'-bis(diphenylphosphino)-1,1'-binaphthyl (1.07 g) and cesium carbonate (16.8 g) in toluene (90 ml) was stirred under an argon gas atmosphere at 85° C. for 16 hr. After cooling to room temperature, water was added to the reaction mixture, and the mixture was extracted with ethyl acetate. The organic layer was washed with saturated brine, dried over anhydrous magnesium sulfate, and filtered. The filtrate was concentrated, and the residue was purified by silica gel column chromatography (hexane/ethyl acetate 90:10-65:35) to give the title compound (2.12 g, yield 49%) as a brown oil.

$^1$H-NMR (300 MHz, CDCl$_3$) δ: 1.67 (d, J=4.3 Hz, 1H), 1.96-2.23 (m, 2H), 3.35-3.49 (m, 2H), 3.56-3.76 (m, 2H), 4.49-4.65 (m, 1H), 6.79-6.88 (m, 1H), 6.88-6.96 (m, 1H), 6.97-7.10 (m, 1H).

Reference Example 56

1-[2-fluoro-3-(trifluoromethyl)phenyl]pyrrolidin-3-ol

2-Fluoro-3-(trifluoromethyl)aniline (5.0 g) and 1,4-dibromobutan-2-ol (6.7 g) were stirred at 100° C. for 3 hr. After cooling to room temperature, to the reaction mixture was added saturated aqueous sodium carbonate solution, and the mixture was extracted with ethyl acetate. The organic layer was washed with saturated brine, dried over anhydrous magnesium sulfate, and filtered. The filtrate was concentrated, and the residue was purified by silica gel column chromatography (hexane/ethyl acetate 90:10-50:50) to give the title compound (1.9 g, yield 27%) as a pale-yellow solid.

$^1$H-NMR (300 MHz, CDCl$_3$) δ: 1.70 (d, J=3.8 Hz, 1H), 1.94-2.24 (m, 2H), 3.34-3.52 (m, 2H), 3.60-3.77 (m, 2H), 4.58 (br. s, 1H), 6.83 (m, J=8.3, 8.3 Hz, 1H), 6.90 (m, J=7.6, 6.1 Hz, 1H), 7.04 (t, J=8.0 Hz, 1H).

Reference Example 57

1-[2,4-bis(trifluoromethyl)phenyl]pyrrolidin-3-ol

A solution of 1-bromo-2,4-bis(trifluoromethyl)benzene (4.45 g), 3-hydroxypyrrolidine (1.2 g), palladium(II) acetate (156 mg), (±)-2,2'-bis(diphenylphosphino)-1,1'-binaphthyl (846 mg) and cesium carbonate (13.6 g) in toluene (74 ml) was stirred under an argon gas atmosphere at 85° C. for 16 hr. After cooling to room temperature, water was added to the reaction mixture, and the mixture was extracted with ethyl acetate. The organic layer was washed with saturated brine, dried over anhydrous magnesium sulfate, and filtered. The filtrate was concentrated, and the residue was purified by silica gel column chromatography (hexane/ethyl acetate 90:10-65:35) to give the title compound (3.28 g, yield 79%) as a brown oil.

$^1$H-NMR (300 MHz, CDCl$_3$) δ: 1.66 (d, J=4.2 Hz, 1H), 1.97-2.25 (m, 2H), 3.24-3.54 (m, 2H), 3.64-3.88 (m, 2H), 4.49-4.70 (m, 1H), 6.94 (d, J=9.1 Hz, 1H), 7.56 (dd, J=8.7, 1.9 Hz, 1H), 7.82 (s, 1H).

Reference Example 58

N-[3-bromo-5-(trifluoromethyl)phenyl]acetamide

To a solution of 3-bromo-5-(trifluoromethyl)aniline (10 g) in pyridine (50 mL) was added acetic anhydride (5.6 g) at 0° C., and the mixture was stirred at room temperature for 16 hr. The reaction mixture was concentrated, 1M hydrochloric acid was added, and the mixture was extracted with ethyl acetate. The organic layer was washed with 1M hydrochloric acid, saturated aqueous sodium hydrogencarbonate solution, and saturated brine, dried over anhydrous magnesium sulfate, and filtered. The filtrate was concentrated to give the title compound (12.9 g, yield quant.) as a white solid.

$^1$H-NMR (300 MHz, CDCl$_3$) δ: 2.21 (s, 3H), 7.36 (br. s, 1H), 7.49 (s, 1 H), 7.68 (s, 1H), 7.99 (s, 1H).

Reference Example 59

N-[3-bromo-5-(trifluoromethyl)phenyl]-N-methylacetamide

To a solution of N-[3-bromo-5-(trifluoromethyl)phenyl]acetamide (6.6 g) obtained in Reference Example 58 in DMF (71 mL) was added sodium hydride (60% in oil, 1.22 g) at 0° C. The reaction mixture was stirred at room temperature for min, methyl iodide (4.98 g) was added, and the mixture was stirred at room temperature for 16 hr. To the reaction mixture was added saturated aqueous ammonium chloride solution, and the mixture was concentrated, and partitioned between water and ethyl acetate. The organic layer was washed with saturated brine, dried over anhydrous magnesium sulfate, and filtered. The filtrate was concentrated to give the title compound (6.37 g, yield 92%) as a yellow oil.

$^1$H-NMR (300 MHz, CDCl$_3$) δ: 1.96 (br. s, 3H), 3.30 (s, 3H), 7.43 (s, 1H), 7.58 (s, 1H), 7.74 (s, 1H).

Reference Example 60

N-[3-(3-hydroxypyrrolidin-1-yl)-5-(trifluoromethyl)phenyl]-N-methylacetamide

A solution of N-[3-bromo-5-(trifluoromethyl)phenyl]-N-methylacetamide (6.37 g) obtained in Reference Example 59, 3-hydroxypyrrolidine (1.7 g), palladium(II) acetate (219 mg), (±)-2,2'-bis(diphenylphosphino)-1,1'-binaphthyl (1.2 g) and cesium carbonate (19 g) in toluene (100 ml) was stirred under an argon gas atmosphere at 85° C. for 16 hr. After cooling to room temperature, water was added to the reaction mixture, and the mixture was extracted with ethyl acetate. The organic layer was washed with saturated brine, dried over anhydrous magnesium sulfate, and filtered. The filtrate was concentrated, and the residue was purified by silica gel column chromatography (hexane/ethyl acetate 34:66-0:100) to give the title compound (5.02 g, yield 85%) as a pale-yellow solid.

$^1$H-NMR (300 MHz, CDCl$_3$) δ: 1.92 (s, 3H), 2.01-2.31 (m, 3H), 3.25 (s, 3H), 3.27-3.34 (m, 1H), 3.34-3.46 (m, 1H), 3.46-3.61 (m, 2 H), 4.66 (br. s, 1H), 6.46 (s, 1H), 6.70-6.74 (m, 2H).

Reference Example 61

4-{[3-bromo-5-(trifluoromethyl)phenyl]carbonyl}thiomorpholine

A solution of 3-bromo-5-(trifluoromethyl)benzoic acid (10 g), thiomorpholine (5.0 g), HOBt (7.4 g) and EDCI (9.26 g) in acetonitrile (113 ml) was stirred at room temperature for 16 hr. To the reaction mixture was added saturated aqueous sodium hydrogencarbonate solution, and the mixture was extracted with ethyl acetate. The organic layer was washed with saturated brine, dried over anhydrous magnesium sulfate, and filtered. The filtrate was concentrated to give the title compound (12.3 g, yield 94%) a yellow oil.

$^1$H-NMR (300 MHz, CDCl$_3$) δ: 2.61 (br. s, 2H), 2.73 (br. s, 2H), 3.66 (br. s, 2H), 4.11 (br. s, 2H), 7.55-7.59 (m, 1H), 7.69-7.72 (m, 1H), 7.81-7.84 (m, 1H).

Reference Example 62

1-[3-(thiomorpholin-4-ylcarbonyl)-5-(trifluoromethyl)phenyl]pyrrolidin-3-ol

A solution of 4-{[3-bromo-5-(trifluoromethyl)phenyl]carbonyl}thiomorpholine (5.0 g) obtained in Reference Example 61, 3-hydroxypyrrolidine (1.35 g), palladium(II) acetate (158.5 mg), (±)-2,2'-bis(diphenylphosphino)-1,1'-binaphthyl (884 mg) and cesium carbonate (13.8 g) in toluene (71 mL) was stirred under an argon gas atmosphere at 90° C. for 16 hr. After cooling to room temperature, water was added to the reaction mixture, and the mixture was extracted with ethyl acetate. The organic layer was washed with saturated brine, dried over anhydrous magnesium sulfate, and filtered. The filtrate was concentrated, and the residue was purified by silica gel column chromatography (hexane/ethyl acetate 50:50-0:100) to give the title compound (5.56 g, yield quant.) as a pale-yellow solid.

$^1$H-NMR (300 MHz, CDCl$_3$) δ: 1.94 (d, J=4.2 Hz, 1H), 2.01-2.27 (m, 2 H), 2.57 (br. s, 2H), 2.73 (br. s, 2H), 3.22-3.33 (m, 1H), 3.33-3.46 (m, 1H), 3.46-3.58 (m, 2H), 3.66 (br. s, 2H), 4.01 (br. s, 2H), 4.57-4.72 (m, 1H), 6.65 (s, 1H), 6.75 (s, 1H), 6.84 (s, 1H).

Reference Example 63

4-{[3-bromo-5-(trifluoromethyl)phenyl]carbonyl}thiomorpholine 1-oxide

To a solution of 4-{[3-bromo-5-(trifluoromethyl)phenyl]carbonyl}thiomorpholine (4.5 g) obtained in Reference Example 61 in acetone (170 mL) was added aqueous solution (170 ml) of Oxone (registered trade mark, 7.8 g) at 0° C., and the mixture was directly stirred at 0° C. for 1 hr. The reaction mixture was extracted with ethyl acetate. The organic layer was washed with saturated brine, dried over anhydrous magnesium sulfate, and filtered. The filtrate was concentrated, and the residue was purified by silica gel column chromatography (hexane/ethyl acetate 60:40-0:100) to give the title compound (2.99 g, yield 84%) as a pale-yellow amorphous form.

$^1$H-NMR (300 MHz, CDCl$_3$) δ: 2.88 (br. s, 4H), 3.70 (br. s, 1H), 4.12 (br. s, 2H), 4.59 (br. s, 1H), 7.60-7.64 (m, 1H), 7.73-7.77 (m, 1H), 7.85-7.89 (m, 1H).

Reference Example 64

1-{3-[(1-oxidothiomorpholin-4-yl)carbonyl]-5-(trifluoromethyl)phenyl}pyrrolidin-3-ol A solution of 4-{[3-bromo-5-(trifluoromethyl)phenyl]carbonyl}thiomorpholine 1-oxide (2.99 g) obtained in Reference Example 63, 3-hydroxypyrrolidine (774 mg), palladium (II) acetate (91 mg), (±)-2,2'-bis(diphenylphosphino)-1,1'-binaphthyl (504 mg) and cesium carbonate (7.9 g) in a mixed solvent of toluene (40 ml) and DMF (15 ml) was stirred under an argon gas atmosphere at 80° C. for 16 hr. After cooling to room temperature, the reaction mixture was concentrated, water was added to the residue, and the mixture was extracted with ethyl acetate. The organic layer was washed with saturated brine, dried over anhydrous magnesium sulfate, and filtered. The filtrate was concentrated, and the residue was purified by silica gel column chromatography (ethyl acetate/methanol 100:0-80:20) to give the title compound (2.10 g, yield 69%) as a white solid.

$^1$H-NMR (300 MHz, CDCl$_3$) δ: 1.87 (d, 1H), 2.06-2.27 (m, 2H), 2.96 (br. s, 4H), 3.30 (d, J=10.6 Hz, 1H), 3.41 (td, J=8.7, 3.4 Hz, 1H), 3.47-3.62 (m, 2H), 3.77 (br. s, 1H), 4.12 (br. s, 2H), 4.57 (br. s, 1H), 4.62-4.74 (m, 1H), 6.68 (s, 1H), 6.79 (s, 1H), 6.86 (s, 1H).

Reference Example 65

N-[3-bromo-5-(trifluoromethyl)phenyl]methanesulfonamide

To a solution of 3-bromo-5-(trifluoromethyl)aniline (10 g) in pyridine (50 ml) was added methanesulfonyl chloride (5.73 g) at 0° C., and the mixture was stirred at room temperature for 16 hr. The reaction mixture was concentrated, saturated aqueous sodium hydrogencarbonate solution was added, and the mixture was extracted with ethyl acetate. The organic layer was washed with 1M hydrochloric acid and saturated brine, dried over anhydrous magnesium sulfate, and filtered. The filtrate was concentrated to give the title compound (13.4 g, yield quant.) as a pale-yellow solid.

$^1$H-NMR (300 MHz, CDCl$_3$) δ: 3.10 (s, 3H), 6.71-7.05 (m, 1H), 7.39 (s, 1H), 7.53-7.62 (m, 2H).

Reference Example 66

N-[3-bromo-5-(trifluoromethyl)phenyl]-N-methyl-methanesulfonamide

To a solution of N-[3-bromo-5-(trifluoromethyl)phenyl]methanesulfonamide (6.77 g) obtained in Reference Example 65 in DMF (65 ml) was added sodium hydride (60% in oil, 1.1 g) at 0° C. The reaction mixture was stirred at room temperature for 10 min, methyl iodide (4.53 g) was added, and the mixture was stirred at room temperature for 16 hr. To the reaction mixture was added saturated aqueous ammonium chloride solution, and the mixture was concentrated, and partitioned between water and ethyl acetate. The organic layer was washed with saturated brine, dried over anhydrous magnesium sulfate, and filtered. The filtrate was concentrated to give the title compound (7.19 g, yield quant.) as a yellow oil.

$^1$H-NMR (300 MHz, CDCl$_3$) δ: 2.90 (s, 3H), 3.36 (s, 3H), 7.58 (s, 1H), 7.68 (s, 1H), 7.74 (s, 1H).

Reference Example 67

N-[3-(3-hydroxypyrrolidin-1-yl)-5-(trifluoromethyl)phenyl]-N-methylmethanesulfonamide A solution of N-[3-bromo-5-(trifluoromethyl)phenyl]-N-methylmethanesulfonamide (7.19 g) obtained in Reference Example 66, 3-hydroxypyrrolidine (1.71 g), palladium(II) acetate (221 mg), (±)-2,2'-bis(diphenylphosphino)-1,1'-binaphthyl (1.23 g) and cesium carbonate (19.3 g) in toluene (100 ml) was stirred under an argon gas atmosphere at 85° C. for 16 hr. After cooling to room temperature, water was added to the reaction mixture, and the mixture was extracted with ethyl acetate. The organic layer was washed with saturated brine, dried over anhydrous magnesium sulfate, and filtered. The filtrate was concentrated, and the residue was purified by silica gel column chromatography (hexane/ethyl acetate 33:67-0:100) to give the title compound (5.45 g, yield 82%) as a brown amorphous form.

$^1$H-NMR (300 MHz, CDCl$_3$) δ: 1.91 (br. s, 1H), 2.06-2.30 (m, 2H), 2.86 (s, 3H), 3.26-3.34 (m, 1H), 3.32 (s, 3H), 3.34-3.62 (m, 3H), 4.59-4.70 (m, 1H), 6.66 (s, 1H), 6.75 (s, 1H), 6.80 (s, 1H).

Reference Example 68

1-[3-bromo-5-(trifluoromethyl)phenyl]pyrrolidin-3-ol

3-Bromo-5-(trifluoromethyl)aniline (5.0 g) and 1,4-dibromobutan-2-ol (4.83 g) were stirred at 100° C. for 3 hr. After cooling to room temperature, to the reaction mixture was added saturated aqueous sodium carbonate solution, and the mixture was extracted with ethyl acetate. The organic layer was washed with saturated brine, dried over anhydrous magnesium sulfate, and filtered. The filtrate was concentrated, and the residue was purified by silica gel column chromatography (hexane/ethyl acetate 90:10-50:50) to give the title compound (5.6 g, yield 22%) as a brown oil.

$^1$H-NMR (300 MHz, CDCl$_3$) δ: 1.66 (br. s, 1H), 2.08-2.27 (m, 2H), 3.23-3.32 (m, 1H), 3.38 (td, J=8.8, 3.4 Hz, 1H), 3.44-3.59 (m, 2H), 4.65 (br. s, 1H), 6.65 (s, 1H), 6.80 (t, J=1.9 Hz, 1H), 7.02 (s, 1H).

Reference Example 69

1-[3-methoxy-5-(trifluoromethyl)phenyl]pyrrolidin-3-ol

3-Methoxy-5-(trifluoromethyl)aniline (15.0 g) and 1,4-dibromobutan-2-ol (18.3 g) were stirred at 100° C. for 3 hr. After cooling to room temperature, to the reaction mixture was added saturated aqueous sodium carbonate solution, and the mixture was extracted with ethyl acetate. The organic layer was washed with saturated brine, dried over anhydrous magnesium sulfate, and filtered. The filtrate was concentrated, and the residue was purified by silica gel column chromatography (hexane/ethyl acetate 90:10-50:50) to give the title compound (9.57 g, yield 47%) as an orange oil.

$^1$H-NMR (300 MHz, CDCl$_3$) δ: 1.64 (d, J=4.7 Hz, 1H), 2.06-2.27 (m, 2H), 3.23-3.32 (m, 1H), 3.32-3.43 (m, 1H), 3.46-3.59 (m, 2H), 3.82 (s, 3H), 4.55-4.69 (m, 1H), 6.20 (t, J=2.3 Hz, 1H), 6.40 (s, 1H), 6.47 (s, 1H).

Reference Example 70

1-[3-chloro-5-(trifluoromethyl)phenyl]pyrrolidin-3-ol

A solution of 1-bromo-3-chloro-5-(trifluoromethyl)benzene (5.0 g), 3-hydroxypyrrolidine (1.85 g), palladium(II) acetate (217 mg), (±)-2,2'-bis(diphenylphosphino)-1,1'-binaphthyl (1.2 g) and cesium carbonate (18.8 g) in toluene (96 mL) was stirred under an argon gas atmosphere at 85° C. for 16 hr. After cooling to room temperature, water was added, and the mixture was extracted with ethyl acetate. The organic layer was washed with saturated brine, dried over anhydrous magnesium sulfate, and filtered. The filtrate was concentrated, and the residue was purified by silica gel column chromatography (hexane/ethyl acetate 80:20-10:90) to give the title compound (4.11 g, yield 80%) as a brown oil.

$^1$H-NMR (300 MHz, CDCl$_3$) δ: 1.65 (d, J=3.8 Hz, 1H), 2.00-2.29 (m, 2 H), 3.19-3.32 (m, 1H), 3.38 (td, J=8.7, 3.4 Hz, 1H), 3.45-3.60 (m, 2H), 4.58-4.72 (m, 1H), 6.61 (s, 1H), 6.63-6.68 (m, 1H), 6.88 (s, 1H).

Reference Example 71

1-[3-fluoro-5-(trifluoromethyl)phenyl]pyrrolidin-3-ol

A solution of 1-bromo-3-fluoro-5-(trifluoromethyl)benzene (10.0 g), 3-hydroxypyrrolidine (3.58 g), palladium(II) acetate (461 mg), (±)-2,2'-bis(diphenylphosphino)-1,1'-binaphthyl (2.56 g) and cesium carbonate (26.7 g) in toluene (222 ml) was stirred under an argon gas atmosphere at 90° C. for 16 hr. After cooling to room temperature, the reaction mixture was filtered through celite, and the celite was washed with ethyl acetate. The filtrate and washing were combined and the solution was washed with water and saturated brine. This was dried over anhydrous magnesium sulfate, and filtered. The filtrate was concentrated, and the residue was purified by silica gel column chromatography (hexane/ethyl acetate 98:2-20:80) to give the title compound (10.65 g, yield quant.) as a brown oil.

$^1$H-NMR (300 MHz, CDCl$_3$) δ: 1.73 (br. s, 1H), 2.05-2.28 (m, 2H), 3.27 (d, J=10.6 Hz, 1H), 3.38 (td, J=8.9, 3.4 Hz, 1H), 3.45-3.59 (m, 2H), 4.55-4.70 (m, 1H), 6.35 (dt, J=11.7, 2.3 Hz, 1 H), 6.52 (s, 1H), 6.60 (d, J=8.7 Hz, 1H).

Reference Example 72

(3S)-1-[4-chloro-2-(trifluoromethyl)phenyl]pyrrolidin-3-ol

A solution of 1-bromo-4-chloro-2-(trifluoromethyl)benzene (15.0 g), (3S)-pyrrolidin-3-ol (5.0 g), palladium(II) acetate (561 mg), (±)-2,2'-bis(diphenylphosphino)-1,1'-binaphthyl (3.11 g) and cesium carbonate (37.8 g) in toluene (280 ml) was stirred under an argon gas atmosphere at 100° C. for 18 hr. After cooling to room temperature, water was added to the reaction mixture, and the mixture was extracted with ethyl acetate. The organic layer was washed with saturated brine, dried over anhydrous magnesium sulfate, and filtered. The filtrate was concentrated, and the residue was purified by silica gel column chromatography (hexane/ethyl acetate 95:5-80:20) to give the title compound (12.4 g, yield 81%) as a colorless oil.

$^1$H-NMR (300 MHz, CDCl$_3$) δ: 1.92-2.04 (m, 2H), 2.10-2.22 (m, 1H), 3.17-3.24 (m, 2H), 3.50-3.61 (m, 2H), 4.51 (br. s, 1H), 6.96 (d, J=9.0 Hz, 1H), 7.31-7.35 (m, 1H), 7.54-7.55 (m, 1H).

Reference Example 73

[2-methoxy-3-(trifluoromethyl)phenyl]boronic acid and [3-methoxy-2-(trifluoromethyl)phenyl]boronic acid To a solution of 1-methoxy-2-(trifluoromethyl)benzene (6.30 g, 35.8 mmol) in THF (150 mL) was added n-BuLi (21.0 ml, 2.50 M hexane solution, 53.7 mmol), and the mixture was stirred at room temperature for 1 hr. The solution was cooled to −78° C., tris(1-methylethyl)borate (8.08 g, 43.0 mmol) was added, and the mixture was stirred at −78° C. for 0.5 hr. The reaction solution was allowed to cool to room temperature and stirred for 16 hr. The mixture was acidified with 1M hydrochloric acid and extracted with ethyl acetate (300 mL). The extract was dried over anhydrous sodium sulfate, filtered, and concentrated under reduced pressure to give a mixture (6.52 g, yield 83%) of [2-methoxy-3-(trifluoromethyl)phenyl]boronic acid and [3-methoxy-2-(trifluoromethyl)phenyl]boronic acid.

Reference Example 75

[2-cyano-3-(trifluoromethyl)phenyl]boronic acid

To a solution of 2,2,6,6-tetramethylpiperidine (0.99 g, 7.02 mmol) in THF (25 ml) was added n-BuLi (2.80 ml, 2.5 M hexane solution, 7.02 mmol) at −10° C. After stirring for 10 min, this solution was cooled to −78° C., tris(1-methylethyl)borate (1.58 g, 8.4 mmol) was added, and the mixture was stirred for 5 min. To this solution was added a solution of 2-(trifluoromethyl)benzonitrile (1.00 g, 5.85 mmol) in THF (10 ml), and the mixture was stirred at −78° C. for 2 hr. The reaction solution was allowed to warm to room temperature, the reaction was quenched with acetic acid, and the solvent was evaporated under reduced pressure. Ethyl acetate was added to the residue, the precipitated solid was filtered off, and the filtrate was concentrated to give the title compound (3.14 g) as a mixture. This was used for the next reaction without performing further purification and identification.

Reference Example 76 ethyl (2E)-3-{5-[3-fluoro-5-(trifluoromethyl)phenyl]furan-2-yl}prop-2-enoate

A solution of ethyl (2E)-3-(5-bromofuran-2-yl)prop-2-enoate (0.64 g, 2.62 mmol) obtained in Reference Example 31, [3-fluoro-5-(trifluoromethyl)phenyl]boronic acid (0.60 g, 2.88 mmol), tetrakis(triphenylphosphine)palladium (0.15 g, 0.13 mmol) and 2M sodium carbonate solution (6.56 ml, 13.1 mmol) in N,N-dimethylacetamide (30 mL) was stirred under an argon atmosphere for 16 hr. After cooling the reaction solution to room temperature, the solid was filtered off, and the filtrate was concentrated under reduced pressure. The obtained residue was purified by silica gel column chromatography (petroleum ether/ethyl acetate 100:0-95:5) to give the title compound (0.62 g, yield 72%) as a yellow solid.

$^1$H-NMR (300 MHz, CDCl$_3$) δ: 1.35 (t, J=6.9 Hz, 3H), 1.27 (q, J=7.2 Hz, 2H), 6.45 (d, J=15.6 Hz, 1H), 6.71 (d, J=3.9 Hz, 1H), 6.84 (d, J=3.6 Hz, 1H), 7.26 (m, 1H), 7.45 (d, J=15.9 Hz, 1H), 7.58 (m, 1H), 7.72 (s, 1H).

Reference Example 77 ethyl 3-{(5-[3-fluoro-5-(trifluoromethyl)phenyl]tetrahydrofuran-2-yl}propanoate

A solution of ethyl (2E)-3-{5-[3-fluoro-5-(trifluoromethyl)phenyl]furan-2-yl}prop-2-enoate (0.62 g, 1.89 mmol) obtained in Reference Example 76, and palladium hydroxide (10% on carbon, 30 mg) in methanol (100 ml) was stirred under a hydrogen atmosphere at room temperature for 16 hr. After confirmation of the completion of the reaction by TLC, the reaction solution was filtered and concentrated under reduced pressure. The residue was purified by silica gel column chromatography (petroleum ether/ethyl acetate 95:5) to give the title compound (0.55 g, yield 88%) as a yellow oil.

$^1$H-NMR (300 MHz, CDCl$_3$) δ: 1.26 (t, J=7.2 Hz, 3H), 1.61-1.85 (m, 2H), 1.97-2.04 (m, 2H), 2.12-2.20 (m, 1H), 2.36-2.47 (m, 1H), 2.50-2.60 (m, 2H), 4.05-4.19 (m, 3H), 4.96 (t, J=7.4 Hz, 1H), 7.78 (s, 3H).

Reference Example 78 ethyl (2E)-3-{5-[3-methoxy-5-(trifluoromethyl)phenyl]furan-2-yl}prop-2-enoate

A solution of ethyl (2E)-3-(5-bromofuran-2-yl)prop-2-enoate (0.61 g, 2.50 mmol) obtained in Reference Example 31, [3-methoxy-5-(trifluoromethyl)phenyl]boronic acid (0.50 g, 2.27 mmol), tetrakis(triphenylphosphine)palladium (0.26 g, 0.23 mmol) and 2 M sodium carbonate solution (5.68 ml, 11.4 mmol) in N,N-dimethylacetamide (25 ml) was stirred under an argon atmosphere for 16 hr. After cooling the reaction solution to room temperature, the solid was filtered off, and the filtrate was concentrated under reduced pressure. The obtained residue was purified by silica gel column chromatography (petroleum ether/ethyl acetate 98:2-95:5) to give the title compound (0.53 g, yield 68%) as a yellow solid.

$^1$H-NMR (300 MHz, CDCl$_3$) δ: 1.34 (t, J=7.2 Hz, 3H), 3.91 (s, 3H), 4.27 (q, J=7.2 Hz, 2H), 6.44 (d, J=15.6 Hz, 1H), 6.70 (d, J=3.6 Hz, 1H), 6.80 (d, J=3.6 Hz, 1H), 7.06 (s, 1H), 7.38 (s, 1H), 7.45 (d, J=15.6 Hz, 1H), 7.52 (s, 1H).

Reference Example 79 ethyl 3-{5-[3-methoxy-5-(trifluoromethyl)phenyl]tetrahydrofuran-2-yl}propanoate

A solution of ethyl (2E)-3-{5-[3-methoxy-5-(trifluoromethyl)phenyl]furan-2-yl}prop-2-enoate (0.48 g, 1.41 mmol) obtained in Reference Example 78 and palladium (10% on carbon, 50 mg) in methanol (50 ml) was stirred under a hydrogen atmosphere at room temperature for 16 hr. After confirmation of the completion of the reaction by TLC, the reaction solution was filtered and concentrated under reduced pressure to give the title compound (0.49 g, yield>99%) as a colorless oil.

$^1$H-NMR (300 MHz, CDCl$_3$) δ: 1.26 (t, J=7.2 Hz, 3H), 1.64-1.84 (m, 2H), 1.94-2.01 (q, J=7.5 Hz, 2H), 2.06-2.13 (m, 1H), 2.27-2.35 (m, 1H), 2.42-2.56 (m, 2H), 3.84 (s, 3H), 4.03-4.07 (m, 1H), 4.13 (q, J=7.2 Hz, 2H), 4.87 (t, J=7.5 Hz, 1H), 6.70 (s, 1H), 7.07 (s, 1H), 7.15 (s, 1H).

Reference Example 80 ethyl (2E)-3-{5-[4-methoxy-3-(trifluoromethyl)phenyl]furan-2-yl}prop-2-enoate

A solution of ethyl (2E)-3-(5-bromofuran-2-yl)prop-2-enoate (0.61 g, 2.50 mmol) obtained in Reference Example 31, [4-methoxy-3-(trifluoromethyl)phenyl]boronic acid (0.50 g, 2.27 mmol), tetrakis(triphenylphosphine)palladium (0.26 g, 0.23 mmol) and 2M sodium carbonate solution (5.68 mL, 11.4 mmol) in N,N-dimethylacetamide (25 ml) was stirred under an argon atmosphere for 16 hr. After cooling the reaction solution to room temperature, the solid was filtered off, and the filtrate was concentrated under reduced pressure. The obtained residue was purified by silica gel column chromatography (petroleum ether/ethyl acetate 98:2-95:5) to give the title compound (0.46 g, yield 60%) as a yellow solid.

$^1$H-NMR (300 MHz, CDCl$_3$) δ: 1.34 (t, J=7.2 Hz, 3H), 3.95 (s, 3H), 4.27 (q, J=7.2 Hz, 2H), 6.39 (d, J=15.6 Hz, 1H), 6.65-6.68 (m, 2H), 7.04 (d, J=8.7 Hz, 1H), 7.43 (d, J=15.6 Hz, 1H), 7.84 (dd, J=8.7, 2.1 Hz, 1H), 7.89 (d, J=2.1 Hz, 1H).

Reference Example 81 ethyl 3-{5-[4-methoxy-3-(trifluoromethyl)phenyl]tetrahydrofuran-2-yl}propanoate

A solution of ethyl (2E)-3-{5-[4-methoxy-3-(trifluoromethyl)phenyl]furan-2-yl}prop-2-enoate (0.39 g, 1.15 mmol) obtained in Reference Example 80 and palladium (10% on carbon, 40 mg) in methanol (25 mL) was stirred under a hydrogen atmosphere at room temperature for 16 hr. After confirmation of the completion of the reaction by TLC, the reaction solution was filtered and concentrated under reduced pressure to give the title compound (0.40 g, yield>99%) as a colorless oil.

$^1$H-NMR (300 MHz, CDCl$_3$) δ: 1.25 (t, J=7.2 Hz, 3H), 1.59-1.78 (m, 2H), 1.93-2.00 (m, 2H), 2.06-2.14 (m, 1H), 2.23-2.33 (m, 1H), 2.44-2.52 (m, 2H), 3.88 (s, 3H), 4.01-4.05 (m, 1H), 4.14 (q, J=7.2 Hz, 2H), 4.80 (t, J=7.2 Hz, 1H), 6.96 (d, J=8.4 Hz, 1H), 7.46 (dd, J=8.4, 1.8 Hz, 1H), 7.51 (d, J=1.8 Hz, 1H).

Reference Example 82 ethyl (2E)-3-{5-[2-fluoro-3-(trifluoromethyl)phenyl]furan-2-yl}prop-2-enoate

A solution of ethyl (2E)-3-(5-bromofuran-2-yl)prop-2-enoate (0.65 g, 2.64 mmol) obtained in Reference Example 31, [2-fluoro-3-(trifluoromethyl)phenyl]boronic acid (0.50 g, 2.40 mmol), tetrakis(triphenylphosphine)palladium (0.28 g, 0.24 mmol) and 2M sodium carbonate solution (6.00 mL, 12.0 mmol) in N,N-dimethylacetamide (25 ml) was stirred under an argon atmosphere for 16 hr. After cooling the reaction solution to room temperature, the solid was filtered off, and the filtrate was concentrated under reduced pressure. The obtained residue was purified by silica gel column chromatography (petroleum ether/ethyl acetate 98:2-95:5) to give the title compound (0.36 g, yield 46%) as a yellow solid.

$^1$H-NMR (300 MHz, CDCl$_3$) δ: 1.34 (t, J=7.2 Hz, 3H), 4.27 (q, J=7.2 Hz, 2H), 6.44 (d, J=15.9 Hz, 1H), 6.74 (d, J=3.6 Hz, 1H), 6.99 (t, J=3.6 Hz, 1H), 7.32 (t, J=7.8 Hz, 1H), 7.45 (d, J=15.9 Hz, 1H), 7.54 (t, J=6.9 Hz, 1H), 8.08 (t, J=6.9 Hz, 1H).

Reference Example 83 ethyl 3-{5-[2-fluoro-3-(trifluoromethyl)phenyl]tetrahydrofuran-2-yl}propanoate

A solution of ethyl (2E)-3-{5-[2-fluoro-3-(trifluoromethyl)phenyl]furan-2-yl}prop-2-enoate (0.36 g, 1.10 mmol) obtained in Reference Example 82 and palladium (10% on carbon, 40 mg) in methanol (25 ml) was stirred under a hydrogen atmosphere at room temperature for 26 hr. After confirmation of the completion of the reaction by TLC, the reaction solution was filtered and concentrated under reduced pressure to give the title compound (0.28 g, yield 76%) as a colorless oil.

$^1$H-NMR (300 MHz, CDCl$_3$) δ: 1.25 (t, J=7.2 Hz, 3H), 1.59-1.68 (m, 1H), 1.71-1.81 (m, 1H), 1.96-2.03 (m, 2H), 2.05-2.15 (m, 1H), 2.42-2.60 (m, 3H), 4.02-4.11 (m, 1H), 4.14 (q, J=7.2 Hz, 2H), 5.14 (t, J=6.9 Hz, 1H), 7.22 (t, J=7.8 Hz, 1H), 7.48 (t, J=6.6 Hz, 1H), 7.72 (t, J=7.8 Hz, 1H).

Reference Example 84 ethyl (2E)-3-{5-[3-(trifluoromethyl)phenyl]furan-2-yl}prop-2-enoate

A solution of ethyl (2E)-3-(5-bromofuran-2-yl)prop-2-enoate (1.42 g, 5.79 mmol) obtained in Reference Example 31, [3-(trifluoromethyl)phenyl]boronic acid (1.00 g, 5.26 mmol), tetrakis(triphenylphosphine)palladium (0.61 g, 0.53 mmol) and 2M sodium carbonate solution (13.2 mL, 26.4 mmol) in N,N-dimethylacetamide (50 mL) was stirred under an argon atmosphere for 16 hr. After cooling the reaction solution to room temperature, the solid was filtered off, and the filtrate was concentrated under reduced pressure. The obtained residue was purified by silica gel column chromatography (petroleum ether/ethyl acetate 98:2-95:5) to give the title compound (0.96 g, yield 59%) as a yellow solid.

Reference Example 85 ethyl 3-{5-[3-(trifluoromethyl)phenyl]tetrahydrofuran-2-yl}propanoate

A solution of ethyl (2E)-3-{5-[3-(trifluoromethyl)phenyl]furan-2-yl}prop-2-enoate (0.36 g, 1.10 mmol) obtained in Reference Example 84 and palladium (10% on carbon, 40 mg) in methanol (25 mL) was stirred under a hydrogen atmosphere at room temperature for 2 hr. After confirmation of the completion of the reaction by TLC, the reaction solution was filtered and concentrated under reduced pressure to give the title compound (0.73 g, yield 75%) as a colorless oil.

$^1$H-NMR (300 MHz, CDCl$_3$) δ: 1.25 (t, J=7.2 Hz, 3H), 1.65-1.82 (m, 2H), 1.95-2.08 (m, 2H), 2.16-2.30 (m, 1H), 2.40-2.46 (m, 1H), 2.48-2.54 (m, 2H), 4.04-4.09 (m, 1H), 4.14 (q, J=7.2 Hz, 2H), 4.90 (t, J=6.9 Hz, 1H), 7.43-7.58 (m, 4H).

Reference Example 86 ethyl (2E)-3-{5-[2-cyano-3-(trifluoromethyl)phenyl]furan-2-yl}prop-2-enoate

A solution of ethyl (2E)-3-(5-bromofuran-2-yl)prop-2-enoate (1.30 g, 5.32 mmol) obtained in Reference Example 31, [2-cyano-3-(trifluoromethyl)phenyl]boronic acid (3.14 g, 5.85 mmol) obtained in Reference Example 75, tetrakis(triphenylphosphine)palladium (0.62 g, 0.53 mmol) and 2M sodium carbonate solution (13.3 ml, 26.6 mmol) in N,N-dimethylacetamide (50 mL) was stirred under an argon atmosphere for 16 hr. After cooling the reaction solution to room temperature, the solid was filtered off, and the filtrate was concentrated under reduced pressure. The obtained residue was purified by silica gel column chromatography (petroleum ether/ethyl acetate 98:2) to give the title compound (0.70 g, yield 39%) as a yellow solid.

Reference Example 87 ethyl 3-{(5-[2-cyano-3-(trifluoromethyl)phenyl]tetrahydrofuran-2-yl}propanoate

A solution of ethyl (2E)-3-{5-[2-cyano-3-(trifluoromethyl)phenyl]furan-2-yl}prop-2-enoate (0.70 g, 2.08 mmol)

obtained in Reference Example 86 and palladium (10% on carbon, 70 mg) in methanol (50 mL) was stirred under a hydrogen atmosphere at room temperature for 16 hr. After confirmation of the completion of the reaction by TLC, the reaction solution was filtered and concentrated under reduced pressure to give the title compound (0.34 g, yield 48%) as a colorless oil.

Reference Example 88 ethyl (2E)-3-{5-[4-fluoro-3-(trifluoromethyl)phenyl]furan-2-yl}prop-2-enoate

A solution of ethyl (2E)-3-(5-bromofuran-2-yl)prop-2-enoate (0.65 g, 2.64 mmol) obtained in Reference Example 31, [4-fluoro-3-(trifluoromethyl)phenyl]boronic acid (0.50 g, 2.40 mmol), tetrakis(triphenylphosphine)palladium (0.28 g, 0.24 mmol) and 2M sodium carbonate solution (6.56 ml, 13.1 mmol) in N,N-dimethylacetamide (25 ml) was stirred under an argon atmosphere for 16 hr. After cooling the reaction solution to room temperature, the solid was filtered off, and the filtrate was concentrated under reduced pressure. The obtained residue was purified by silica gel column chromatography (petroleum ether/ethyl acetate 98:2-95:5) to give the title compound (0.60 g, yield 76%) as a yellow solid.
$^1$H-NMR (300 MHz, CDCl$_3$) δ: 1.34 (t, J=7.2 Hz, 3H), 4.27 (q, J=7.2 Hz, 2H), 6.42 (d, J=15.9 Hz, 1H), 6.69 (d, J=3.6 Hz, 1H), 6.74 (d, J=3.6 Hz, 1H), 7.24 (t, J=9.3 Hz, 1H), 7.43 (d, J=15.9 Hz, 1H), 7.83-7.92 (m, 2H).

Reference Example 89 ethyl 3-{5-[4-fluoro-3-(trifluoromethyl)phenyl]tetrahydrofuran-2-yl}propanoate

A solution of ethyl (2E)-3-{5-[4-fluoro-3-(trifluoromethyl)phenyl]furan-2-yl}prop-2-enoate (0.60 g, 1.83 mmol) obtained in Reference Example 88 and palladium (10% on carbon, 60 mg) in methanol (25 ml) was stirred under a hydrogen atmosphere at room temperature for 20 hr. After confirmation of the completion of the reaction by TLC, the reaction solution was filtered and concentrated under reduced pressure to give the title compound (0.54 g, yield 88%) as a colorless solid.
$^1$H-NMR (300 MHz, CDCl$_3$) δ: δ 1.27 (t, J=7.2 Hz, 3H), 1.62-1.71 (m, 3H), 1.97 (q, J=12.9 Hz, 2H), 2.08-2.17 (m, 1H), 2.29-2.36 (m, 2H), 4.04-4.08 (m, 1H), 4.15 (q, J=7.2 Hz, 2H), 4.87 (t, J=6.9 Hz, 1H), 7.16 (t, J=9.6 Hz, 1H), 7.51-7.57 (m, 2H).

Reference Example 90 ethyl (2E)-3-{5-[2-methoxy-3-(trifluoromethyl)phenyl]furan-2-yl}prop-2-enoate

Reference Example 91 ethyl (2E)-3-{5-[3-methoxy-2-(trifluoromethyl)phenyl]furan-2-yl}prop-2-enoate

A solution of ethyl (2E)-3-(5-bromofuran-2-yl)prop-2-enoate (4.20 g, 17.1 mmol) obtained in Reference Example 31, a mixture (6.52 g, 29.6 mmol) of [2-methoxy-3-(trifluoromethyl)phenyl]boronic acid and [3-methoxy-2-(trifluoromethyl)phenyl]boronic acid obtained in Reference Example 73, tetrakis(triphenylphosphine)palladium (0.60 g, 0.52 mmol) and 2M sodium carbonate solution (35 mL, 70 mmol) in N,N-dimethylacetamide (100 ml) was stirred under an argon atmosphere for 16 hr. After cooling the reaction solutions to room temperature, the solid was filtered off, and the filtrates were concentrated under reduced pressure. The obtained residues were purified by silica gel column chromatography (petroleum ether/ethyl acetate 98:2-95:5) to give the title compounds both as yellow solids. ethyl (2E)-3-{5-[2-methoxy-3-(trifluoromethyl)phenyl]furan-2-yl}prop-2-enoate (3.08 g, yield 53%):
$^1$H-NMR (300 MHz, CDCl$_3$) δ: 1.35 (t, J=7.2 Hz, 3H), 3.81 (s, 3H), 4.27 (q, J=7.2 Hz, 2H), 6.43 (d, J=15.6 Hz, 1H), 6.75 (d, J=3.6 Hz, 1H), 7.07 (d, J=3.6 Hz, 1H), 7.29 (t, J=7.8 Hz, 1H), 7.47 (d, J=15.6 Hz, 1H), 7.57 (dd, J=7.8, 1.2 Hz, 1H), 8.04 (dd, J=7.8, 1.2 Hz, 1H).

ethyl (2E)-3-{5-[3-methoxy-2-(trifluoromethyl)phenyl]furan-2-yl}prop-2-enoate (0.32 g, yield 5.5%)

$^1$H-NMR (300 MHz, CDCl$_3$) δ: 1.32 (t, J=7.2 Hz, 3H), 3.94 (s, 3H), 4.25 (q, J=7.2 Hz, 2H), 6.33 (d, J=15.2 Hz, 1H), 6.53 (d, J=3.2 Hz, 1H), 6.66 (d, J=3.2 Hz, 1H), 7.10 (t, J=8.8 Hz, 2H), 7.44 (d, J=15.2 Hz, 1H), 7.50 (t, J=8.0 Hz, 1H).

Reference Example 92 ethyl 3-{5-[2-methoxy-3-(trifluoromethyl)phenyl]tetrahydrofuran-2-yl}propanoate

A solution of ethyl (2E)-3-{5-[2-methoxy-3-(trifluoromethyl)phenyl]furan-2-yl}prop-2-enoate (0.80 g, 2.35 mmol) obtained in Reference Example 90 and palladium (10% on carbon, 80 mg) in methanol (50 mL) was stirred under a hydrogen atmosphere at room temperature for 5.5 hr. After confirmation of the completion of the reaction by TLC, the reaction solution was filtered and concentrated under reduced pressure. The residue was purified by silica gel column chromatography (petroleum ether/ethyl acetate 30:1-10:1) to give the title compound (0.34 g, yield 42%) as a colorless oil.
$^1$H-NMR (300 MHz, CDCl$_3$) δ: 1.26 (t, J=7.2 Hz, 3H), 1.64-1.79 (m, 2H), 1.96-2.04 (m, 2H), 2.07-2.17 (m, 1H), 2.35-2.42 (m, 1H), 2.45-2.54 (m, 2H), 3.85 (s, 3H), 4.01-4.05 (m, 1H), 4.14 (q, J=7.2 Hz, 2H), 5.17 (t, J=6.9 Hz, 1H), 7.24 (t, J=7.2 Hz, 1H), 7.50 (dd, J=7.8, 1.5 Hz, 1H), 7.70 (dd, J=7.8, 1.5 Hz, 1H).

Reference Example 93 ethyl 3-{5-[3-methoxy-2-(trifluoromethyl)phenyl]tetrahydrofuran-2-yl}propanoate

A solution of ethyl (2E)-3-{5-[3-methoxy-2-(trifluoromethyl)phenyl]furan-2-yl}prop-2-enoate (0.30 g, 0.88 mmol) obtained in Reference Example 91 and palladium (10% on carbon, 120 mg) in methanol (30 ml) was stirred under a hydrogen atmosphere at room temperature for 16 hr. After confirmation of the completion of the reaction by TLC, the reaction solution was filtered and concentrated under reduced pressure. The residue was purified by silica gel column chromatography (petroleum ether/ethyl acetate 30:1-10:1) to give the title compound (0.17 g, yield 56%) as a colorless oil.
$^1$H-NMR (300 MHz, CDCl$_3$) δ: 1.27 (t, J=7.2 Hz, 3H), 1.51-1.58 (m, 1H), 1.67-1.72 (m, 1H), 1.99-2.08 (m, 3H), 2.40-2.59 (m, 3H), 3.88 (s, 3H), 3.98-4.02 (m, 1H), 4.15 (q, J=7.2 Hz, 2H), 5.29-5.33 (m, 1H), 6.92 (d, J=7.6 Hz, 1H), 7.40-7.47 (m, 2H).

Reference Example 94

5-[3,5-bis(trifluoromethyl)phenyl]furan-2-carbaldehyde

A solution of 5-bromofuran-2-carbaldehyde (2.54 g, 14.5 mmol), [3,5-bis(trifluoromethyl)phenyl]boronic acid (3.93 g, 15.2 mmol), tetrakis(triphenylphosphine)palladium (0.59 g, 0.51 mmol) and 2M sodium carbonate solution (36 mL, 72 mmol) in THF (150 ml) was stirred under an argon atmosphere for 16 hr. The reaction solution was allowed to cool to room temperature and concentrated under reduced pressure, and the residue was partitioned between ethyl acetate and water. The organic layer was washed with water and saturated brine, dried over anhydrous magnesium sulfate filtration, and concentrated. The residue was purified by silica gel column chromatography (ethyl acetate), and the obtained solid was disrupted in hexane to give the title compound (4.46 g, yield>99%) as a pale-yellow solid. LC/MS (ESI+) m/z: 309 (M+H)+.

Reference Example 95

{5-[3,5-bis(trifluoromethyl)phenyl]furan-2-yl}methanol

To a solution of 5-[3,5-bis(trifluoromethyl)phenyl]furan-2-carbaldehyde (5.69 g, 18.5 mmol) obtained in Reference Example 94 in ethanol (170 ml) was added sodium borohydride (1.40 g, 36.9 mmol), and the mixture was stirred at room temperature for 1 hr. The reaction solution was concentrated under reduced pressure, and the obtained residue was partitioned between ethyl acetate and water. The organic layer was washed with water and saturated brine, dried over anhydrous magnesium sulfate filtration, and concentrated. The obtained residue was purified by silica gel column chromatography (hexane/ethyl acetate 90:10-50:50) to give the title compound (5.02 g, yield 87%) as a white solid.
$^1$H-NMR (300 MHz, CDCl$_3$) δ: 1.81 (t, J=6.1 Hz, 1H), 4.72 (d, J=6.1 Hz, 2H), 6.46 (d, J=3.4 Hz, 1H), 6.80 (d, J=3.4 Hz, 1H), 7.74 (s, 1H), 8.07 (s, 2H).

Reference Example 96 ethyl ({5-[3,5-bis(trifluormethyl)phenyl]furan-2-yl}methoxy)acetate

To a solution of {5-[3,5-bis(trifluoromethyl)phenyl]furan-2-yl}methanol (1.00 g, 3.22 mmol) obtained in Reference Example 95 in N,N-dimethylformamide (30 mL) was added sodium hydride (60% in oil, 0.14 g, 3.55 mmol), and the mixture was stirred at room temperature for 15 min. To the solution was added a solution of ethyl bromoacetate (0.59 g, 3.55 mmol) in N,N-dimethylformamide (5 ml), and the mixture was stirred at room temperature for 30 min and at 80° C. for 5 hr. The reaction solution was allowed to cool to room temperature, poured into saturated ammonium chloride solution (100 ml), and the mixture was extracted with ethyl acetate (100 mL). The ethyl acetate layer was washed with water and saturated brine, dried over anhydrous magnesium sulfate, filtered, and concentrated under reduced pressure. The residue was purified by silica gel column chromatography (hexane/ethyl acetate 90:10-30:70) to give the title compound (0.42 g, yield 33%) as a yellow oil.
$^1$H-NMR (300 MHz, CDCl$_3$) δ: 1.29 (t, J=7.2 Hz, 3H), 4.16 (s, 2H), 4.24 (q, J=7.1 Hz, 2H), 4.68 (s, 2H), 6.52 (d, J=3.4 Hz, 1H), 6.81 (d, J=3.0 Hz, 1H), 7.74 (s, 1H), 8.07 (s, 2H).

Reference Example 97 ethyl ({5-[3,5-bis(trifluoromethyl)phenyl]tetrahydrofuran-2-yl}methoxy)acetate

A solution of ethyl ({5-[3,5-bis(trifluoromethyl)phenyl]furan-2-yl}methoxy)acetate (0.40 g, 1.01 mmol) obtained in Reference Example 96 and palladium (10% on carbon, containing water (50%), 100 mg) in ethanol (20 ml) was stirred under a hydrogen atmosphere at room temperature for 16 hr. After confirmation of the completion of the reaction by TLC, the reaction solution was filtered and concentrated under reduced pressure. The residue was purified by silica gel column chromatography (hexane/ethyl acetate 90:10-40:60) to give the title compound (0.29 g, yield 72%) as a colorless oil.
$^1$H-NMR (300 MHz, CDCl$_3$) δ: 1.28 (t, J=7.2 Hz, 3H), 1.75-2.21 (m, 3H), 2.29-2.55 (m, 1H), 3.65-3.85 (m, 2H), 4.19 (s, 2H), 4.20-4.28 (m, 2H), 4.29-4.43 (m, 1H), 5.03 (t, J=7.3 Hz, 1H), 7.76 (s, 1H), 7.86 (s, 2H).

Reference Example 98

2-[3,5-bis(trifluoromethyl)phenyl]-5-(chloromethyl)furan

To a solution of {5-[3,5-bis(trifluoromethyl)phenyl]furan-2-yl}methanol (8.26 g, 26.6 mmol) obtained in Reference Example 95 in THF (130 mL) was added thionyl chloride (4.76 g, 39.9 mmol) at 0° C., and the mixture was stirred for 30 min. The reaction mixture was further stirred at room temperature for 3 hr and concentrated under reduced pressure, and the residue was partitioned between ethyl acetate and water. The organic layer was washed with saturated sodium hydrogencarbonate solution and saturated brine, dried over anhydrous magnesium sulfate, filtered, and concentrated to give the title compound (8.43 g, yield 96%) as a white solid.
$^1$H-NMR (300 MHz, CDCl$_3$) δ: 4.67 (s, 2H), 6.53 (d, J=3.4 Hz, 1H), 6.80 (d, J=3.4 Hz, 1H), 7.76 (s, 1H), 8.07 (s, 2H).

Reference Example 99

{5-[3,5-bis(trifluoromethyl)phenyl]furan-2-yl}acetonitrile

A solution of 2-[3,5-bis(trifluoromethyl)phenyl]-5-(chloromethyl)furan (8.40 g, 25.6 mmol) obtained in Reference Example 98, potassium cyanide (3.33 g, 51.1 mmol) and 18-crown-6 (6.76 g, 25.6 mmol) in acetonitrile (250 mL) was stirred at 0° C. for 1 hr and at room temperature for 8 hr. The reaction solution was concentrated under reduced pressure, and the residue was partitioned between ethyl acetate and water. The organic layer was washed with saturated brine, dried over anhydrous magnesium sulfate, and filtered, and the filtrate was concentrated under reduced pressure. The residue was purified by silica gel column chromatography (hexane/ethyl acetate 90:10-30:70), and the obtained yellow solid was washed with hexane to give the title compound (3.92 g, 48%) as a yellow solid.
$^1$H-NMR (300 MHz, CDCl$_3$) δ: 3.89 (s, 2H), 6.51 (d, J=3.8 Hz, 1H), 6.82 (d, J=3.8 Hz, 1H), 7.76 (s, 1H), 8.04 (s, 2H).

Reference Example 100

{5-[3,5-bis(trifluoromethyl)phenyl]furan-2-yl}acetic acid

A solution of {5-[3,5-bis(trifluoromethyl)phenyl]furan-2-yl}acetonitrile (1.90 g, 5.95 mmol) obtained in Reference Example 99 and 8M sodium hydroxide solution (5 mL, 40 mmol) in ethanol (20 mL) was heated under reflux for 40 min. The reaction solution was allowed to cool to room temperature, and concentrated under reduced pressure. The residue was adjusted to pH 2 with 6M hydrochloric acid under ice-cooling, and partitioned between ethyl acetate and water. The organic layer was washed with saturated brine and dried over anhydrous magnesium sulfate filtration, and the filtrate was concentrated under reduced pressure. The obtained dark-brown solid was recrystallized from toluene-hexane to give the title compound (1.43 g, 71%) as pale-brown crystals.

$^1$H-NMR (300 MHz, DMSO-d$_6$) δ: 3.82 (s, 2H), 6.49 (d, J=3.4 Hz, 1H), 7.37 (d, J=3.4 Hz, 1H), 7.96 (s, 1H), 8.25 (s, 2H), 12.67 (br. s, 1H).

Example 1

({1-[3,5-bis(trifluoromethyl)phenyl]pyrrolidin-3-yl}sulfanyl)acetic acid

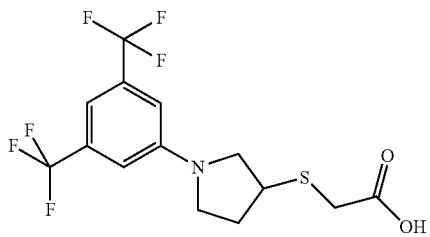

A solution of ethyl ({1-[3,5-bis(trifluoromethyl)phenyl]pyrrolidin-3-yl}sulfanyl)acetate (6.80 g) obtained in Reference Example 2 and lithium hydroxide monohydrate (1.38 g) in tetrahydrofuran (100 ml)-water (100 ml) was stirred at room temperature for 3 hr. The reaction mixture was adjusted to pH 5 with aqueous 6N hydrochloric acid solution, and extracted with ethyl acetate. The organic layer was washed with saturated brine, dried over anhydrous magnesium sulfate, and filtered. The filtrate was concentrated to give the title compound (4.27 g, yield 68%) as colorless crystals.

$^1$H-NMR (300 MHz, CDCl$_3$) δ: 2.05-2.17 (m, 1H), 2.43-2.54 (m, 1H), 3.30-3.35 (m, 1H), 3.37 (s, 2H), 3.41-3.46 (m, 1H), 3.52-3.59 (m, 1H), 3.70-3.81 (m, 2H), 6.84 (s, 2H), 7.13 (s, 1H), 11.82 (br, 1H).

Example 2

({1-[3,5-bis(trifluoromethyl)phenyl]pyrrolidin-3-yl}sulfinyl)acetic acid

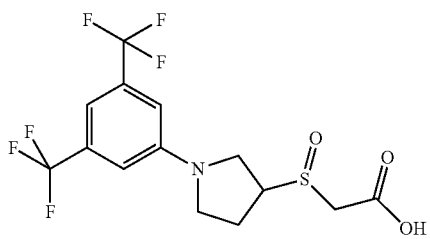

A solution of ({1-[3,5-bis(trifluoromethyl)phenyl]pyrrolidin-3-yl}sulfanyl)acetic acid (500 mg) obtained in Example 1 and m-chloroperbenzoic acid (321 mg) in dichloromethane (25 mL) was stirred at room temperature for 2 hr. The solvent was evaporated, and the residue was purified by preparative HPLC (instrument: Gilson Inc., High throughput purification system; column: YMC Combiprep ODS-A, S-5 µm, 50×20 mm; solvent: SOLUTION A; 0.1% trifluoroacetic acid-containing water, SOLUTION B; 0.1% trifluoroacetic acid-containing acetonitrile; gradient cycle: 0.00 min (SOLUTION A/SOLUTION B=90/10), 1.00 min (SOLUTION A/SOLUTION B=90/10), 4.20 min (SOLUTION A/SOLUTION B=10/90), 5.40 min (SOLUTION A/SOLUTION B=10/90), 5.50 min (SOLUTION A/SOLUTION B=90/10), and 5.60 min (SOLUTION A/SOLUTION B=90/10); flow rate: 25 mL/min; detection method: UV 220 nm) to give the title compound (471 mg, yield 90%).

$^1$H-NMR (300 MHz, DMSO-d$_6$) δ: 2.25-2.19 (m, 1H), 2.40-2.48 (m, 1H), 3.36-3.52 (m, 3H), 3.66-3.72 (m, 1H), 3.78-3.82 (m, 2H), 4.02-4.09 (m, 1H), 7.08-7.17 (m, 3H), 13.24 (br, 1H).

Example 3

({1-[3,5-bis(trifluoromethyl)phenyl]pyrrolidin-3-yl}sulfonyl)acetic acid

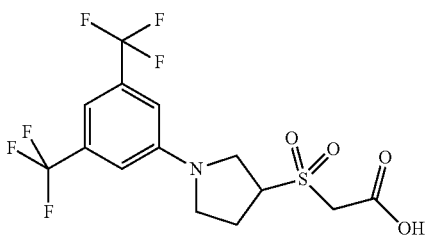

The title compound (245 mg, yield 66%) was obtained from methyl ({1-[3,5-bis(trifluoromethyl)phenyl]pyrrolidin-3-yl}sulfonyl)acetate obtained in Reference Example 3 by a method similar to that in Example 1.

$^1$H-NMR (300 MHz, DMSO-d$_6$) δ: 2.44-2.47 (m, 2H), 3.46-3.56 (s, 2H), 3.72-3.81 (m, 2H), 4.37-4.53 (m, 3H), 7.10 (s, 2H), 7.19 (S, 1H), 13.56 (br, 1H).

Example 4

({1-[3,5-bis(trifluoromethyl)phenyl]-2-oxopyrrolidin-3-yl}sulfanyl)acetic acid

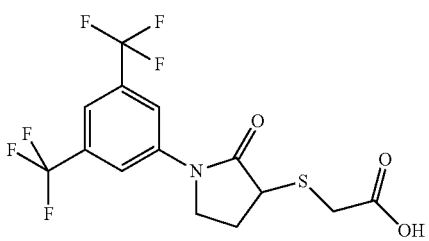

The title compound (1.0 g, yield 77%) was obtained from ethyl ({1-[3,5-bis(trifluoromethyl)phenyl]-2-oxopyrrolidin-3-yl}sulfanyl)acetate obtained in Reference Example 4 by a method similar to that in Example 1.

¹H-NMR (300 MHz, DMSO-d₆) δ: 1.97-2.06 (m, 1H), 2.54-2.66 (s, 1H), 3.45-3.68 (m, 2H), 3.95-4.05 (m, 3H), 7.88 (s, 1H), 8.32 (s, 2H), 12.69 (br, 1H).

Example 5

({1-[3,5-bis(trifluoromethyl)phenyl]-2-oxopyrrolidin-3-yl}sulfinyl)acetic acid

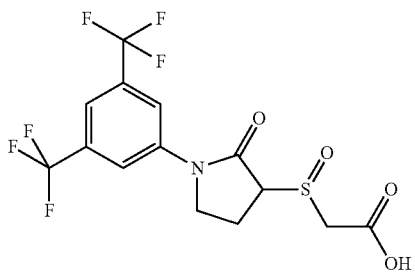

The title compound (120 mg, yield 41%) was obtained from ethyl ({1-[3,5-bis(trifluoromethyl)phenyl]-2-oxopyrrolidin-3-yl}sulfinyl)acetate obtained in Reference Example 5 by a method similar to that in Example 1.
¹H-NMR (300 MHz, DMSO-d₆) δ: 2.43-2.68 (m, 2H), 3.67-3.72 (m, 1H), 4.00-4.34 (m, 4H), 7.92 (s, 1H), 8.34 (s, 2H), 13.35 (br, 1 H).

Example 6

({1-[3,5-bis(trifluoromethyl)phenyl]-2-oxopyrrolidin-3-yl}sulfonyl)acetic acid

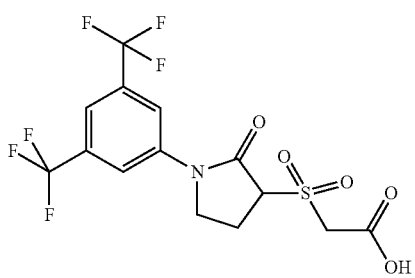

The title compound (520 mg, yield 69%) was obtained from ethyl ({1-[3,5-bis(trifluoromethyl)phenyl]-2-oxopyrrolidin-3-yl}sulfonyl)acetate obtained in Reference Example 6 by a method similar to that in Example 1.
¹H-NMR (300 MHz, DMSO-d₆) δ: 2.54-2.62 (m, 2H), 4.04-4.14 (m, 2H), 4.44-4.49 (m, 1H), 4.69-4.74 (m, 1H), 4.94 (t, J=7.8 Hz, 1H), 7.96 (s, 1H), 8.33 (s, 2H), 13.63 (br, 1H).

Example 7

({1-[3-fluoro-2-(trifluoromethyl)phenyl]pyrrolidin-3-yl}sulfanyl)acetic acid

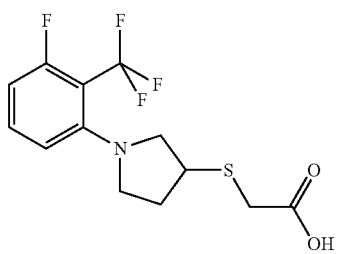

The title compound (101 mg, yield 31%) was obtained from ethyl ({1-[3-fluoro-2-(trifluoromethyl)phenyl]pyrrolidin-3-yl}sulfanyl)acetate obtained in Reference Example 8 by a method similar to that in Example 1.
¹H-NMR (300 MHz, CDCl₃) δ: 1.89-2.05 (m, 1H), 2.35-2.43 (m, 1H), 3.17-3.27 (m, 1H), 3.33 (s, 2H), 3.38-3.44 (m, 2H), 3.52-3.71 (m, 1H), 6.61-6.68 (m, 1H), 6.74-6.77 (m, 1H), 7.19-7.33 (m, 1H), 9.15 (br, 1H).

Example 8

({1-[2,4-bis(trifluoromethyl)phenyl]pyrrolidin-3-yl}sulfonyl)acetic acid

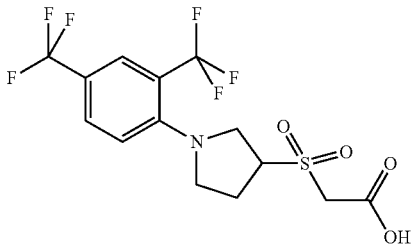

The title compound (535 mg, yield 81%) was obtained from ethyl({1-[2,4-bis(trifluoromethyl)phenyl]pyrrolidin-3-yl}sulfonyl)acetate obtained in Reference Example 11 by a method similar to that in Example 1.
¹H-NMR (300 MHz, CDCl₃) δ: 2.45-2.62 (m, 2H), 3.45-3.64 (m, 2H), 3.82 (d, J=7.2 Hz, 2H), 4.15-4.03 (m, 2H), 4.17-4.26 (m, 1 H), 7.14 (d, J=8.7 Hz, 1H), 7.28 (br, 1H), 7.66 (d, J=8.7 Hz, 1H), 7.86 (s, 1H).

Example 9

({1-[3,5-bis(trifluoromethyl)phenyl]pyrrolidin-3-yl}oxy)acetic acid

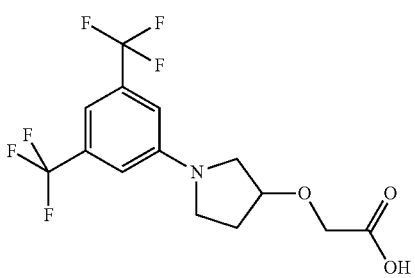

tert-Butyl ({1-[3,5-bis(trifluoromethyl)phenyl]pyrrolidin-3-yl}oxy)acetate (3.35 g) obtained in Reference Example 15 was dissolved in trifluoroacetic acid (6.5 mL), and the solution was stirred at room temperature for 5 hr. To the reaction mixture was added toluene (10 mL), and the mixture was concentrated under reduced pressure. Water (30 mL) was added to the obtained residue, and the mixture was adjusted to pH 4 with saturated sodium hydrogencarbonate solution and extracted with ethyl acetate (30 mL×2). The extract was washed with saturated brine, dried over anhydrous magnesium sulfate, and filtered. The filtrate was concentrated under reduced pressure to give a brown solid, which was recrystallized from hexane-ethyl acetate to give the title compound (1.85 g, yield 64%) as a white solid.

¹H-NMR (300 MHz, CDCl₃) δ: 2.09-2.42 (m, 2H), 3.38-3.65 (m, 4H), 4.21 (s, 2H), 4.33-4.45 (m, 1H), 6.86 (s, 2H), 7.14 (s, 1H).

Example 10

({1-[3,5-bis(trifluoromethyl)phenyl]pyrrolidin-3-yl}sulfanyl)acetic acid

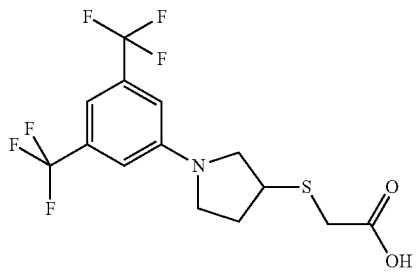

({1-[3,5-Bis(trifluoromethyl)phenyl]pyrrolidin-3-yl}sulfanyl)acetic acid (210 mg, two kinds of racemates) obtained in Example 1 was subjected to chiral preparative HPLC (column: CHIRALPAK AS(BF001) 50 mm ID×500 mmL; solvent: hexane/2-propanol/formic acid=970/30/1 (v/v/v); flow rate: 80 ml/min; detection method: UV 220 nm; temperature: 25° C.) to give a compound (tR1) having a shorter retention time, which was recrystallized from ethyl acetate-hexane to give the title compound (68.5 mg, yield 33%).

¹H-NMR (300 MHz, DMSO-d₆) δ: 1.94-2.03 (m, 1H), 2.35-2.51 (m, 1 H), 3.30-3.53 (m, 5H), 3.65-3.80 (m, 2H), 7.01 (s, 2H), 7.12 (s, 1H), 12.67 (br, 1H).

Example 11

({1-[3,5-bis(trifluoromethyl)phenyl]pyrrolidin-3-yl}sulfanyl)acetic acid

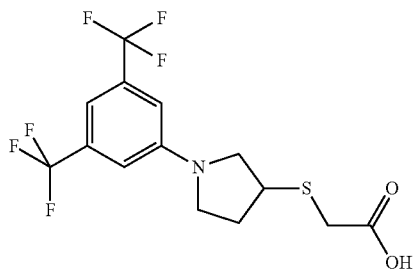

({1-[3,5-Bis(trifluoromethyl)phenyl]pyrrolidin-3-yl}sulfanyl)acetic acid (210 mg, two kinds of racemate) obtained in Example 1 was subjected to chiral preparative HPLC (column CHIRALPAK AS(BF001) 50 mm ID×500 mL; solvent: hexane/2-propanol/formic acid=970/30/1 (v/v/v); flow rate: 80 ml/min; detection method: UV 220 nm; temperature: 25° C.) to give a compound (tR2) having a longer retention time, which was recrystallized from ethyl acetate-hexane to give the title compound (65.6 mg, yield 31%).

¹H-NMR (300 MHz, DMSO-d₆) δ: 1.94-2.03 (m, 1H), 2.35-2.51 (m, 1 H), 3.30-3.53 (m, 5H), 3.65-3.80 (m, 2H), 7.01 (s, 2H), 7.12 (s, 1H), 12.67 (br, 1H).

Example 12 calcium ({1-[2,4-bis(trifluoromethyl)phenyl]pyrrolidin-3-yl}sulfanyl)acetate

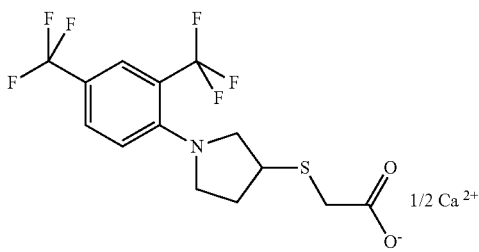

A solution of ethyl ({1-[2,4-bis(trifluoromethyl)phenyl]pyrrolidin-3-yl}sulfanyl)acetate (1.30 g) obtained in Reference Example 10 and lithium hydroxide monohydrate (419 mg) in tetrahydrofuran-water (1:1, 400 mL) was stirred at room temperature for 1 hr. The reaction mixture was adjusted to pH 5 with 1N aqueous hydrochloric acid solution, and the mixture was extracted with ethyl acetate. The organic layer was washed with saturated brine, dried over anhydrous magnesium sulfate, and filtered, and the filtrate was concentrated to give a colorless oil (1.11 g). The colorless oil (1.11 g) was dissolved in methanol (50 ml), aqueous solution (10 mL) of potassium hydrogencarbonate (297 mg) was added, and the mixture was stirred at room temperature for 1 hr. The solvent was evaporated and the residue was dissolved in methanol (50 mL). Aqueous solution (10 ml) of calcium chloride (161 mg) was added, and the mixture was stirred at room temperature for 1 hr. The solvent was evaporated and the residue was dissolved in tetrahydrofuran (20 ml). The insoluble material was filtered off, and the filtrate was concentrated to give the title compound (1.00 g, yield 86%) as colorless crystals.

¹H-NMR (300 MHz, DMSO-d₆) δ: 1.03-1.05 (m, 1H), 1.88-1.94 (m, 1H), 3.17-3.80 (m, 6H), 7.10 (d, J=9.0 Hz, 1H), 7.69 (d, J=9.0 Hz, 1H), 7.75 (s, 1H).

Example 13

3-{1-[4-chloro-3-(trifluoromethyl)phenyl]pyrrolidin-3-yl}propanoic acid

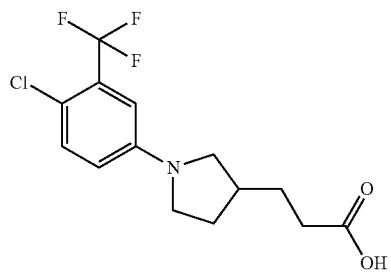

The title compound (2.66 g, yield 60%) was obtained from ethyl 3-{1-[4-chloro-3-(trifluoromethyl)phenyl]pyrrolidin- 3-yl}propanoate obtained in Reference Example 13 by a method similar to that in Example 1.

$^1$H-NMR (300 MHz, CDCl$_3$) δ: 1.58-1.67 (m, 3H), 2.10-2.12 (m, 1H), 2.23-2.34 (m, 3H), 2.89 (t, J=8.4 Hz, 1H), 3.19-3.46 (m, 3 H), 6.72-6.77 (m, 2H), 7.37-7.40 (m, 1H), 12.08 (s, 1H).

Example 14

3-{1-[2-chloro-3-(trifluoromethyl)phenyl]pyrrolidin-3-yl}propanoic acid

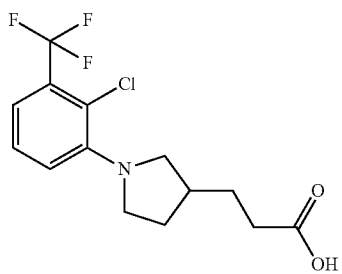

The title compound (532 mg, yield 66%) was obtained from ethyl 3-{1-[2-chloro-3-(trifluoromethyl)phenyl]pyrrolidin-3-yl}propanoate obtained in Reference Example 14 by a method similar to that in Example 1.

$^1$H-NMR (300 MHz, DMSO-d$_6$) δ: 1.48-1.54 (m, 1H), 1.56-1.73 (m, 2H), 2.01-2.23 (m, 2H), 2.27-2.32 (m, 2H), 3.15 (t, J=9.6 Hz, 1 H), 3.24-3.38 (m, 2H), 3.48-3.56 (m, 1H), 7.24-7.26 (m, 2H), 7.33-7.38 (m, 1H), 12.07 (s, 1H).

Example 15

3-{3-[3,5-bis(trifluoromethyl)phenyl]-2-oxoimidazolidin-1-yl}propanoic acid

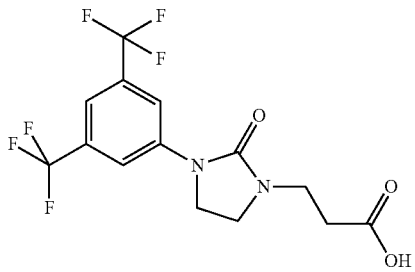

The title compound (108 mg, yield 79%) was obtained from ethyl 3-{3-[3,5-bis(trifluoromethyl)phenyl]-2-oxoimidazolidin-1-yl}propanoate obtained in Reference Example 17 by a method similar to that in Example 1.

$^1$H-NMR (300 MHz, CDCl$_3$) δ: 2.61-2.78 (m, 2H), 3.56-3.72 (m, 4H), 3.81-3.95 (m, 2H), 7.52 (s, 1H), 8.03 (s, 2H).

Example 16

({(3S)-1-[3,5-bis(trifluoromethyl)phenyl]pyrrolidin-3-yl}oxy)acetic acid

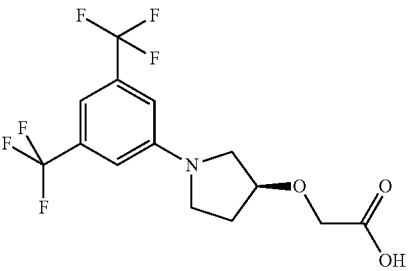

A solution of (3S)-1-[3,5-bis(trifluoromethyl)phenyl]pyrrolidin-3-ol (9.60 g) obtained in Reference Example 18 in N,N-dimethylformamide (20 mL) was added to a suspension of sodium hydride (60% in oil, 1.80 g) in N,N-dimethylformamide (200 ml) at 60° C. After stirring for 30 min, sodium chloroacetate (7.50 g) and tetrabutylammonium bromide (1.03 g) were added, and the mixture was stirred at 60° C. for 16 hr. The reaction mixture was allowed to cool to room temperature, and water was added. The mixture was adjusted to pH 2 with concentrated hydrochloric acid, and the mixture was extracted with ethyl acetate. The organic layer was dried over anhydrous sodium sulfate and filtered. The filtrate was concentrated, and the residue was purified by silica gel column chromatography (petroleum ether/ethyl acetate 1:10), and recrystallized from hexane-acetone to give the title compound (5.82 g, yield 51%) as a white solid.

$^1$H-NMR (300 MHz, DMSO-d$_6$) δ: 2.06-2.16 (m, 2H), 3.33-3.54 (m, 4H), 4.10 (s, 2H), 4.31-4.36 (m, 1H), 7.01 (s, 2H), 7.11 (s, 1H), 12.64 (s, 1H). 97.2% ee, [α]$_D$=+5.9° (c=0.54, MeOH, 22° C.).

Example 17

({(3R)-1-[3,5-bis(trifluoromethyl)phenyl]pyrrolidin-3-yl}oxy)acetic acid

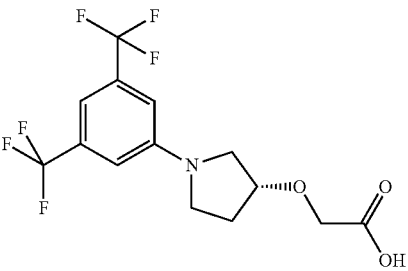

A solution of (3R)-1-[3,5-bis(trifluoromethyl)phenyl]pyrrolidin-3-ol (7.45 g) obtained in Reference Example 19 in N,N-dimethylformamide (20 mL) was added to a suspension of sodium hydride (60% in oil, 1.50 g) in N,N-dimethylformamide (200 mL) at 60° C. After stirring for 30 min, sodium chloroacetate (3.48 g) and tetrabutylammonium bromide (0.80 g) were added, and the mixture was stirred at 60° C. for 1 hr. The reaction mixture was allowed to cool to room temperature, and the reaction was quenched with cooled water. The reaction mixture was diluted with water and adjusted to pH 2 with concentrated hydrochloric acid, and the mixture was extracted with ethyl acetate. The organic layer was dried over anhydrous sodium sulfate and filtered. The filtrate was concentrated, and the residue was purified by silica gel column chromatography (ethyl acetate), and recrystallized from hexane-acetone to give the title compound (5.82 g, yield 64%) as a white solid.

$^1$H-NMR (300 MHz, DMSO-$d_6$) δ: 2.07-2.16 (m, 2H), 3.34-3.54 (m, 4 H), 4.10 (s, 2H), 4.33-4.35 (m, 1H), 7.01 (s, 2H), 7.11 (s, 1H), 12.65 (s, 1H). 99.1% ee, $[α]_D$=−5.9° (c=0.56, MeOH, 22° C.).

Example 18

({1-[3,5-bis(trifluoromethyl)phenyl]pyrrolidin-3-yl}sulfinyl)acetic acid

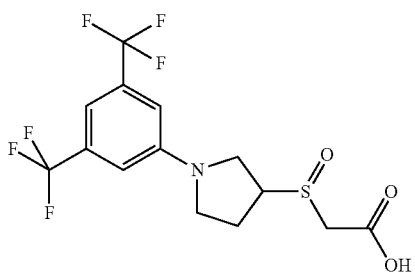

To a solution of optically resolved tR1 (AS, 300 mg) of ({1-[3,5-bis(trifluoromethyl)phenyl]pyrrolidin-3-yl}sulfanyl)acetic acid obtained in Example 10 in acetone (10 mL) was added aqueous solution (5 ml) of Oxone-persulfate compound (500 mg) at 0° C., and the mixture was stirred at 0° C. for 1 hr. The reaction mixture was extracted with ethyl acetate, and the organic layer was dried over anhydrous magnesium sulfate, and filtered. The filtrate was concentrated to give the title compound (291 mg, yield 93%) as a white solid.

$^1$H-NMR (300 MHz, DMSO-$d_6$) δ: 2.26-2.53 (m, 2H), 3.37-3.60 (m, 3H), 3.61-3.92 (m, 3H), 3.97-4.10 (m, 1H), 7.08 (s, 1H), 7.14 (s, 1H), 7.18 (s, 1H), 13.26 (br, 1H).

Example 19

({1-[3,5-bis(trifluoromethyl)phenyl]pyrrolidin-3-yl}sulfinyl)acetic acid

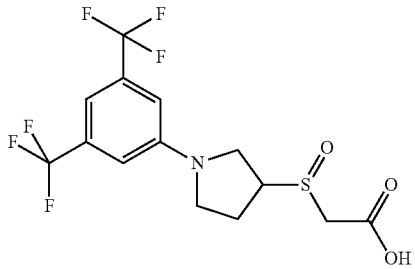

To a solution of optically resolved tR2 (AS, 300 mg) of ({1-[3,5-bis(trifluoromethyl)phenyl]pyrrolidin-3-yl}sulfanyl)acetic acid obtained in Example 11 in acetone (10 mL) was added aqueous solution (5 mL) of Oxone-persulfate compound (500 mg) at 0° C., and the mixture was stirred at 0° C. for 1 hr. The acetone was evaporated under reduced pressure, and the precipitate was collected by filtration. The precipitate was washed with water and hexane to give the title compound (311 mg, yield 99%) as a white solid.

$^1$H-NMR (300 MHz, DMSO-$d_6$) δ: 2.09-2.55 (m, 2H), 3.39-3.60 (m, 3 H), 3.60-3.90 (m, 3H), 3.98-4.11 (m, 1H), 7.08 (s, 1H), 7.14 (s, 1H), 7.18 (s, 1H), 13.24 (br, 1H).

Example 20

({1-[3,5-bis(trifluoromethyl)phenyl]pyrrolidin-3-yl}sulfonyl)acetic acid

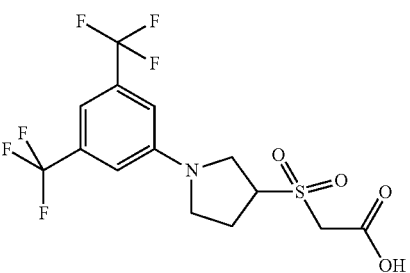

({1-[3,5-Bis(trifluoromethyl)phenyl]pyrrolidin-3-yl}sulfonyl)acetic acid (390 mg, two kinds of racemates) obtained in Example 3 was subjected to chiral preparative HPLC (column CHIRALCEL OJ 50 mm ID×500 mmL; solvent: hexane/ethanol/trifluoroacetic acid=800/200/1 (v/v/v); flow rate: 60 ml/min; detection method: UV 220 nm; temperature: 35° C.) to give a compound (tR1) having a shorter retention time, which was recrystallized from ethyl acetate-hexane to give the title compound (143.7 mg, yield 37%).

$^1$H-NMR (300 MHz, DMSO-$d_6$) δ: 2.36-2.48 (m, 2H), 3.40-3.61 (m, 2H), 3.66-3.92 (m, 2H), 4.27-4.54 (m, 3H), 7.11 (s, 2H), 7.20 (s, 1H), 13.60 (br, 1H).

Example 21

({1-[3,5-bis(trifluoromethyl)phenyl]pyrrolidin-3-yl}sulfonyl)acetic acid

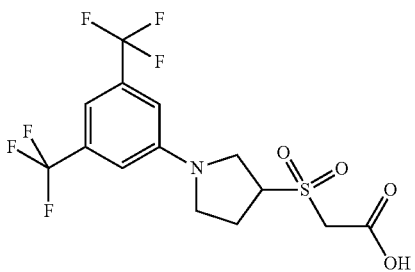

({1-[3,5-Bis(trifluoromethyl)phenyl]pyrrolidin-3-yl}sulfonyl)acetic acid (390 mg, two kinds of racemates) obtained in Example 3 was subjected to chiral preparative HPLC (column: CHIRALCEL OJ 50 mm ID×500 mmL;

solvent: hexane/ethanol/trifluoroacetic acid=800/200/1 (v/v/v); flow rate: 60 ml/min; detection method: UV 220 nm; temperature: 35° C.) to give a compound (tR2) having a longer retention time, which was recrystallized from ethyl acetate-hexane to give the title compound (136.6 mg, yield 35%).

$^1$H-NMR (300 MHz, DMSO-$d_6$) δ: 2.34-2.57 (m, 2H), 3.40-3.63 (m, 2 H), 3.67-3.89 (m, 2H), 4.28-4.60 (m, 3H), 7.11 (s, 2H), 7.20 (s, 1H), 13.57 (br, 1H).

Example 22

3-{4-[3,5-bis(trifluoromethyl)phenyl]tetrahydrofuran-2-yl}propanoic acid

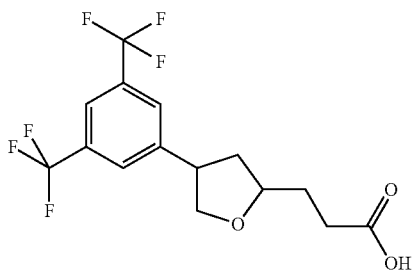

The title compound (239 mg, yield 79%) was obtained from ethyl 3-{4-[3,5-bis(trifluoromethyl)phenyl] tetrahydrofuran-2-yl}propanoate obtained in Reference Example 22 by a method similar to that in Example 1 as a stereo isomer mixture.

LC/MS ESI(+) m/z: 357 (M+H)$^+$, retention time 2.34 min.

Example 23

({1-[3,5-bis(trifluoromethyl)phenyl]pyrrolidin-3-yl}sulfinyl)acetic acid

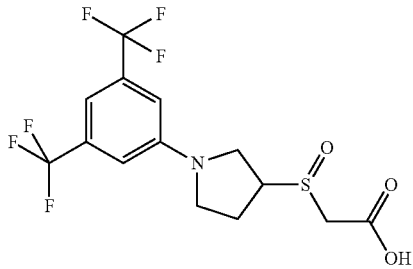

({1-[3,5-Bis(trifluoromethyl)phenyl]pyrrolidin-3-yl}sulfinyl)acetic acid (234 mg, mixture of two kinds of diastereomers) obtained in Example 19 was subjected to chiral preparative HPLC (column: CHIRALPAK AD-H 20 mm ID×250 mL; solvent: carbon dioxide/methanol/trifluoroacetic acid=800/200/0.2 (v/v/v); flow rate: 50 ml/min; detection method: UV 254 nm; temperature: 35° C.) to give a compound (tR1) having a shorter retention time as the title compound (128.4 mg, yield 55%).

$^1$H-NMR (300 MHz, DMSO-$d_6$) δ: 2.36-2.48 (m, 2H), 3.40-3.62 (m, 3 H), 3.63-3.75 (m, 2H), 3.75-3.92 (m, 1H), 4.05 (d, J=14.7 Hz, 1H), 7.08 (s, 2H), 7.18 (s, 1H).

Example 24

({1-[3,5-bis(trifluoromethyl)phenyl]pyrrolidin-3-yl}sulfinyl)acetic acid

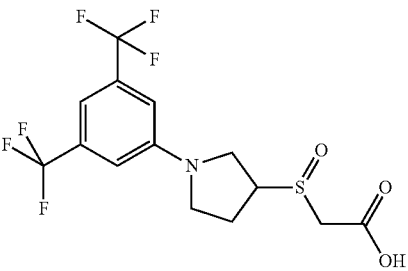

({1-[3,5-Bis(trifluoromethyl)phenyl]pyrrolidin-3-yl}sulfinyl)acetic acid (234 mg, mixture of two kinds of diastereomers) obtained in Example 19 was subjected to chiral preparative HPLC (column: CHIRALPAK AD-H 20 mm ID×250 mL; solvent: carbon dioxide/methanol/trifluoroacetic acid=800/200/0.2 (v/v/v); flow rate: 50 ml/min; detection method: UV 254 nm; temperature: 35° C.) to give a compound (tR2) having a longer retention time as the title compound (101.2 mg, yield 43%).

$^1$H-NMR (300 MHz, DMSO-$d_6$) δ: 2.07-2.26 (m, 1H), 2.31-2.47 (m, 1H), 3.37-3.58 (m, 2H), 3.58-3.72 (m, 1H), 3.72-3.83 (m, 3H), 4.03 (d, J=14.7 Hz, 1H), 7.14 (s, 2H), 7.17 (s, 1H), 13.25 (br, 1H).

Example 25

({1-[3,5-bis(trifluoromethyl)phenyl]pyrrolidin-3-yl}sulfinyl)acetic acid

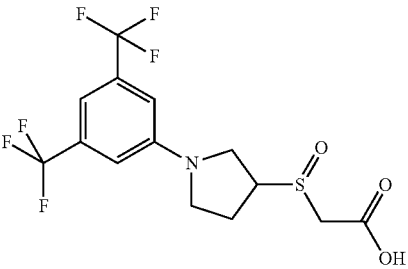

({1-[3,5-Bis(trifluoromethyl)phenyl]pyrrolidin-3-yl}sulfinyl)acetic acid (197 mg, mixture of two kinds of diastereomers) obtained in Example 18 was subjected to chiral preparative HPLC (column: CHIRALPAK AD-H 20 mm ID×250 mL; solvent: carbon dioxide/methanol/trifluoroacetic acid=850/150/0.15 (v/v/v); flow rate: 50 ml/min; detection method: UV 254 nm; temperature: 35° C.) to give a compound (tR1) having a shorter retention time as the title compound (83.5 mg, yield 42%).

$^1$H-NMR (300 MHz, DMSO-d$_6$) δ: 2.08-2.25 (m, 1H), 2.31-2.46 (m, 1H), 3.37-3.58 (m, 2H), 3.58-3.72 (m, 1H), 3.73-3.85 (m, 3H), 4.04 (d, J=14.4 Hz, 1H), 7.14 (s, 2H), 7.17 (s, 1H), 13.23 (br, 1H).

Example 26

({1-[3,5-bis(trifluoromethyl)phenyl]pyrrolidin-3-yl}sulfinyl)acetic acid

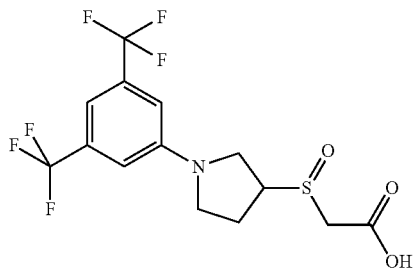

({1-[3,5-Bis(trifluoromethyl)phenyl]pyrrolidin-3-yl}sulfinyl)acetic acid (197 mg, mixture of two kinds of diastereomers) obtained in Example 18 was subjected to chiral preparative HPLC (column: CHIRALPAK AD-H 20 mm ID×250 mmL; solvent: carbon dioxide/methanol/trifluoroacetic acid=850/150/0.15 (v/v/v); flow rate: 50 ml/min; detection method: UV 254 nm; temperature: 35° C.) to give a compound (tR2) having a longer retention time as the title compound (102.9 mg, yield 52%).

$^1$H-NMR (300 MHz, DMSO-d$_6$) δ: 2.30-2.47 (m, 2H), 3.38-3.61 (m, 3H), 3.61-3.75 (m, 2H), 3.75-3.90 (m, 1H), 4.04 (d, J=14.8 Hz, 1H), 7.08 (s, 2H), 7.18 (s, 1H), 13.24 (br, 1H).

Example 27 calcium ({1-[4-chloro-3-(trifluoromethyl)phenyl]pyrrolidin-3-yl}oxy)acetate

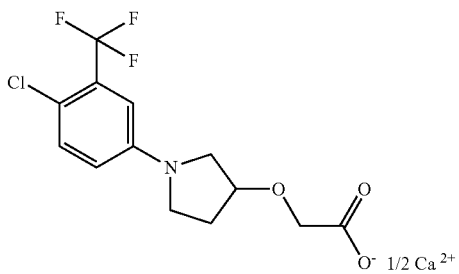

A yellow oil (0.42 g) was obtained from 1-[4-chloro-3-(trifluoromethyl)phenyl]pyrrolidin-3-ol obtained in Reference Example 23 by a method similar to that in Example 17. The yellow oil (0.18 g) was dissolved in methanol (5 ml), aqueous solution (5 ml) of potassium hydrogencarbonate (56.9 mg) was added, and the mixture was stirred at room temperature for 1 hr. The solvent was evaporated and the residue was dissolved in methanol (5 mL). Aqueous solution (5 ml) of calcium chloride (31.5 mg) was added, and the mixture was stirred at room temperature for 1 hr. The solvent was evaporated and the residue was dissolved in ethyl acetate (20 ml). The insoluble material was filtered, and the filtrate was concentrated to give the title compound (155 mg, yield 68%) as yellow crystals.

$^1$H-NMR (300 MHz, DMSO-d$_6$) δ: 1.93-2.16 (m, 2H), 3.21-3.35 (m, 2H), 3.35-3.46 (m, 2H), 3.70 (s, 2H), 4.25-4.48 (m, 1H), 6.69-6.82 (m, 2H), 7.29-7.47 (m, 1H).

Example 28

({1-[4-chloro-3-(trifluoromethyl)phenyl]pyrrolidin-3-yl}sulfanyl)acetic acid

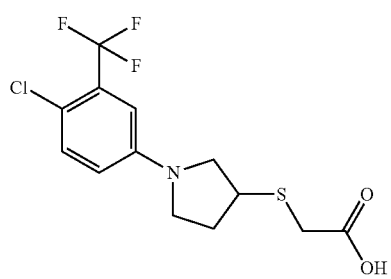

The title compound (2.30 g, yield 89%) was obtained from ethyl ({1-[4-chloro-3-(trifluoromethyl)phenyl]pyrrolidin-3-yl}sulfanyl)acetate obtained in Reference Example 25 by a method similar to that in Example 1.

$^1$H-NMR (300 MHz, CDCl$_3$) δ: 2.00-2.17 (m, 1H), 2.37-2.54 (m, 1H), 3.22-3.55 (m, 5H), 3.63-3.78 (m, 2H), 6.52-6.62 (m, 1H), 6.74-6.81 (m, 1H), 7.27-7.32 (m, 1H).

Example 29

({1-[4-chloro-3-(trifluoromethyl)phenyl]pyrrolidin-3-yl}sulfinyl)acetic acid

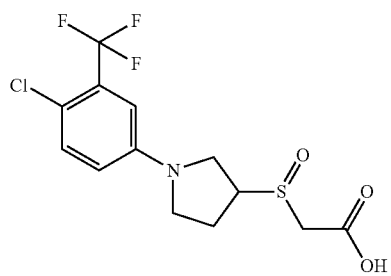

The title compound (32.0 mg, yield 10%) was obtained from ({1-[4-chloro-3-(trifluoromethyl)phenyl]pyrrolidin-3-yl}sulfanyl)acetic acid obtained in Example 28 by a method similar to that in Example 18.

$^1$H-NMR (300 MHz, DMSO-d$_6$) δ: 2.01-2.22 (m, 1H), 2.22-2.45 (m, 1H), 3.17-3.50 (m, 3H), 3.52-3.85 (m, 3H), 3.94-4.10 (m, 1H), 6.78-6.97 (m, 2H), 7.40-7.50 (m, 1H).

Example 30 calcium ({1-[4-chloro-3-(trifluoromethyl)phenyl]pyrrolidin-3-yl}sulfanyl)acetate

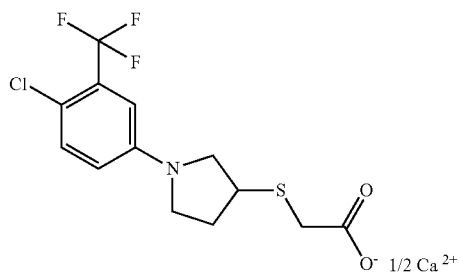

({1-[4-Chloro-3-(trifluoromethyl)phenyl]pyrrolidin-3-yl}sulfanyl)acetic acid (246 mg) obtained in Example 28 was dissolved in methanol (10 mL), aqueous solution (10 mL) of potassium hydrogencarbonate (72.4 mg) was added, and the mixture was stirred at room temperature for 1 hr. The solvent was evaporated and the residue was dissolved in methanol (10 mL). Aqueous solution (10 mL) of calcium chloride (40.1 mg) was added, and the mixture was stirred at room temperature for 1 hr. The solvent was evaporated and the residue was dissolved in ethyl acetate (20 mL). The insoluble material was filtered, and the filtrate was concentrated to give the title compound (172 mg, yield 66%) as yellow crystals.

$^1$H-NMR (300 MHz, DMSO-$d_6$) δ: 1.85-2.01 (m, 1H), 2.22-2.39 (m, 1H), 3.08 (s, 2H), 3.11-3.21 (m, 1H), 3.22-3.35 (m, 2H), 3.59-3.72 (m, 2H), 6.70-6.82 (m, 2H), 7.33-7.46 (m, 1H).

Example 31 potassium ({1-[2-chloro-3-(trifluoromethyl)phenyl]pyrrolidin-3-yl}sulfanyl)acetate

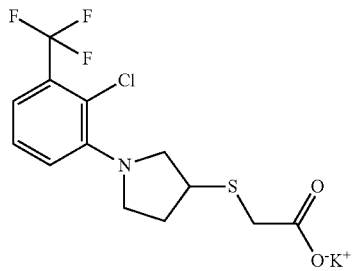

A solution of ethyl ({1-[2-chloro-3-(trifluoromethyl)phenyl]pyrrolidin-3-yl}sulfanyl)acetate (1.02 g) obtained in Reference Example 28 and 1N aqueous lithium hydroxide solution (20 ml) in tetrahydrofuran (20 ml) was stirred at room temperature for 3 hr. The reaction mixture was adjusted to pH 5 with 1N aqueous hydrochloric acid solution, and the mixture was extracted with ethyl acetate. The organic layer was washed with saturated brine, dried over magnesium sulfate and filtered, and the filtrate was concentrated to give a yellow oil (893 mg). The yellow oil (160 mg) was dissolved in methanol (5 ml), aqueous solution (10 ml) of potassium hydrogencarbonate (49.5 mg) was added, and the mixture was stirred at room temperature for 1 hr. The solvent was evaporated to give the title compound (136 mg, yield 68%) as yellow crystals.

$^1$H-NMR (300 MHz, DMSO-$d_6$) δ: 1.73-1.89 (m, 1H), 2.15-2.32 (m, 1H), 2.97 (s, 2H), 3.21-3.29 (m, 1H), 3.38-3.46 (m, 2H), 3.47-3.58 (m, 1H), 3.66-3.74 (m, 1H), 7.23-7.28 (m, 1H), 7.28-7.32 (m, 1H), 7.32-7.42 (m, 1H).

Example 32

({1-[3-(trifluoromethyl)phenyl]pyrrolidin-3-yl}sulfanyl)acetic acid

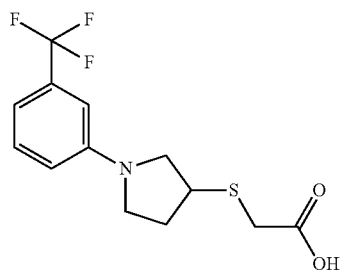

The title compound (104 mg, yield 54%) was obtained from ethyl ({1-[3-(trifluoromethyl)phenyl]pyrrolidin-3-yl}sulfanyl)acetate obtained in Reference Example 29 by a method similar to that in Example 1.

$^1$H-NMR (300 MHz, CDCl$_3$) δ: 2.01-2.15 (m, 1H), 2.39-2.54 (m, 1H), 3.21-3.33 (m, 1H), 3.33-3.45 (m, 1H), 3.38 (s, 2H), 3.45-3.59 (m, 1H), 3.61-3.83 (m, 2H), 6.60-6.71 (m, 1H), 6.72 (s, 1H), 6.87-6.98 (m, 1H), 7.27-7.36 (m, 1H).

Example 33

({1-[2,5-bis(trifluoromethyl)phenyl]pyrrolidin-3-yl}oxy)acetic acid

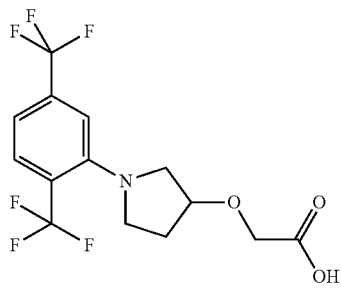

The title compound (110 mg, yield 28%) was obtained from 1-[2,5-bis(trifluoromethyl)phenyl]pyrrolidin-3-ol obtained in Reference Example 30 by a method similar to that in Example 17.

¹H-NMR (300 MHz, CDCl₃) δ: 2.16-2.23 (m, 2H), 3.29-3.48 (m, 2H), 3.58-3.76 (m, 2H), 4.08-4.25 (m, 2H), 4.29-4.38 (m, 1H), 7.07-7.15 (m, 1H), 7.18 (s, 1H), 7.63-7.78 (m, 1H).

Example 34

3-{5-[3,5-bis(trifluoromethyl)phenyl]tetrahydrofuran-2-yl}propanoic acid

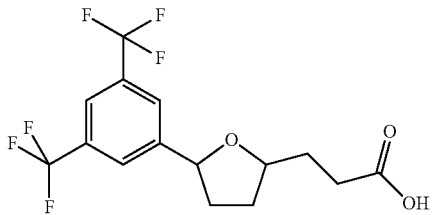

A solution of ethyl 3-{5-[3,5-bis(trifluoromethyl)phenyl]tetrahydrofuran-2-yl}propanoate (13.4 g) obtained in Reference Example 33 and 1M lithium hydroxide solution (103 mL) in ethanol (340 mL) was stirred at room temperature for 4 hr. The reaction mixture was adjusted to pH 3 with 1N hydrochloric acid, and concentrated under reduced pressure, and the residue was partitioned between ethyl acetate and water. The organic layer was washed with saturated brine, dried over anhydrous magnesium sulfate, and filtered. The filtrate was concentrated, and the obtained colorless solid was recrystallized from hexane to give the title compound (10.56 g, yield 86%, racemate of cis form) as colorless crystals.

¹H-NMR (300 MHz, CDCl₃) δ: 1.55-1.90 (m, 2H), 1.94-2.08 (m, 2H), 2.08-2.24 (m, 1H), 2.30-2.50 (m, 1H), 2.50-2.70 (m, 2H), 4.02-4.19 (m, 1H), 4.97 (t, J=7.3 Hz, 1H), 7.78 (s, 3H).

Example 35

3-{(2S,5R)-5-[3,5-bis(trifluoromethyl)phenyl]tetrahydrofuran-2-yl}propanoic acid

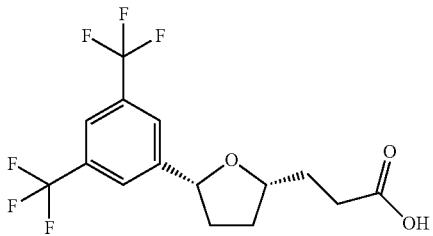

3-{5-[3,5-Bis(trifluoromethyl)phenyl]tetrahydrofuran-2-yl}propanoic acid (25.0 g, racemate of cis form) obtained in Example 34 was subjected to chiral preparative HPLC (column: CHIRALPAK AS 50 mm ID×500 mmL; solvent: hexane/ethanol/acetic acid=990/10/1 (v/v/v); flow rate: 80 ml/min; detection method: UV 220 nm; temperature: 30° C.) to give a compound (tR1) having a shorter retention time, which was recrystallized from hexane to give the title compound (12.25 g, recovery rate 98%).

¹H-NMR (300 MHz, CDCl₃) δ: 1.55-1.90 (m, 2H), 1.94-2.08 (m, 2H), 2.08-2.24 (m, 1H), 2.30-2.50 (m, 1H), 2.50-2.70 (m, 2H), 4.02-4.19 (m, 1H), 4.97 (t, J=7.3 Hz, 1H), 7.78 (s, 3H).

Example 36

3-{(2R,5S)-5-[3,5-bis(trifluoromethyl)phenyl]tetrahydrofuran-2-yl}propanoic acid

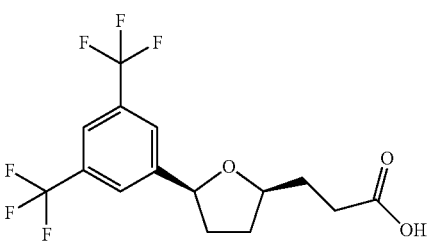

3-{5-[3,5-Bis(trifluoromethyl)phenyl]tetrahydrofuran-2-yl}propanoic acid (25.0 g, racemate of cis form) obtained in Example 34 was subjected to chiral preparative HPLC (column: CHIRALPAK AS 50 mm ID×500 mmL; solvent: hexane/ethanol/acetic acid=990/10/1 (v/v/v); flow rate: 80 ml/min; detection method: UV 220 nm; temperature: 30° C.) to give a compound (tR2) having a longer retention time, which was recrystallized from hexane to give the title compound (12.25 g, recovery rate 98%).

¹H-NMR (300 MHz, CDCl₃) δ: 1.55-1.90 (m, 2H), 1.94-2.08 (m, 2H), 2.08-2.24 (m, 1H), 2.30-2.50 (m, 1H), 2.50-2.70 (m, 2H), 4.02-4.19 (m, 1H), 4.97 (t, J=7.3 Hz, 1H), 7.78 (s, 3H).

Example 37

3-{1-[3,5-bis(trifluoromethyl)phenyl]pyrrolidin-3-yl}propanoic acid

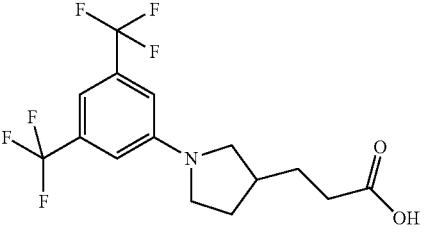

The title compound (0.13 g, yield 47%) was obtained from ethyl 3-{1-[3,5-bis(trifluoromethyl)phenyl]pyrrolidin-3-yl}propanoate obtained in Reference Example 36 by a method similar to that in Example 34.

¹H-NMR (300 MHz, DMSO-d₆) δ: 1.54-1.80 (m, 3H), 1.99-2.22 (m, 1H), 2.20-2.41 (m, 3H), 2.87-3.04 (m, 1H), 3.36-3.60 (m, 3H), 6.98 (s, 2H), 7.08 (s, 1H), 12.13 (br. s, 1H).

Example 38

3-{2-[3,5-bis(trifluoromethyl)phenyl]-1,1-dioxido-isothiazolidin-5-yl}propanoic acid

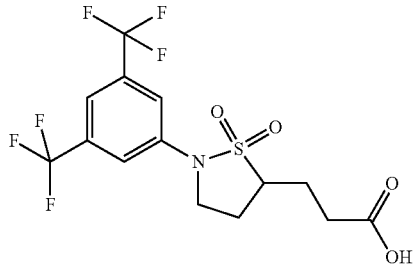

The title compound (0.23 g, yield 92%) was obtained from ethyl 3-{2-[3,5-bis(trifluoromethyl)phenyl]-1,1-dioxido-isothiazolidin-5-yl}propanoate obtained in Reference Example 41 by a method similar to that in Example 34.

$^1$H-NMR (300 MHz, DMSO-$d_6$) δ: 1.82-2.24 (m, 3H), 2.43-2.53 (m, 2H), 2.54-2.70 (m, 1H), 3.60-3.78 (m, 1H), 3.82-3.96 (m, 2H), 7.73 (s, 2H), 7.82 (s, 1H), 12.35 (s, 1H).

Example 39 calcium ({1-[2-(trifluoromethyl)phenyl]pyrrolidin-3-yl}oxy)acetate

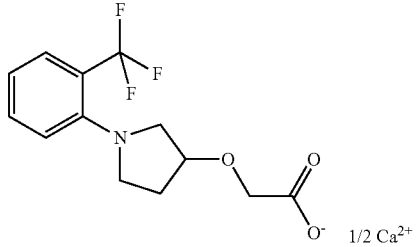

A brown oil (1.06 g, 60%) was obtained from 1-[2-(trifluoromethyl)phenyl]pyrrolidin-3-ol obtained in Reference Example 42 by a method similar to that in Example 17. The title compound (0.90 g, yield 90%) was obtained as a pale-brown solid from the brown oil (0.94 g) by a method similar to that in Example 27.

$^1$H-NMR (300 MHz, DMSO-$d_6$) δ: 1.78-2.11 (m, 2H), 3.19 (m, 2H), 3.29-3.61 (m, 2H), 3.72 (s, 2H), 4.30 (br. s, 1H), 6.76-6.96 (m, 1H), 6.98-7.16 (m, 1H), 7.32-7.49 (m, 1H), 7.47-7.68 (m, 1H).

Example 40 calcium ({1-[3-(trifluoromethyl)phenyl]pyrrolidin-3-yl}oxy)acetate

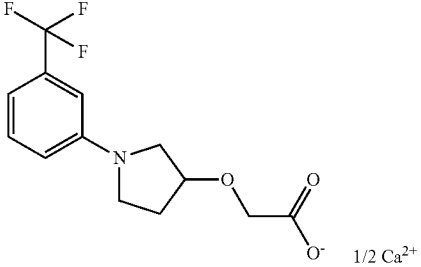

A brown oil (1.15 g, 66%) was obtained from 1-[3-(trifluoromethyl)phenyl]pyrrolidin-3-ol obtained in Reference Example 43 by a method similar to that in Example 17. The title compound (0.90 g, yield 90%) was obtained as a pale-brown solid from the brown oil by a method similar to that in Example 27.

$^1$H-NMR (300 MHz, DMSO-$d_6$) δ: 1.86-2.16 (m, 2H), 3.04-3.52 (m, 4H), 3.73 (s, 2H), 4.36 (br. s, 1H), 6.67 (s, 1H), 6.75 (d, J=8.7 Hz, 1H), 6.84 (d, J=7.6 Hz, 1H), 7.33 (t, J=7.8 Hz, 1H).

Example 41

({1-[4-(trifluoromethyl)phenyl]pyrrolidin-3-yl}oxy) acetic acid

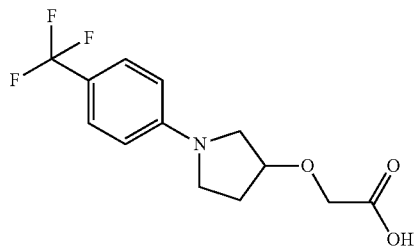

The title compound (1.10 g, 63%) as a pale-yellow solid was obtained from 1-[4-(trifluoromethyl)phenyl]pyrrolidin-3-ol obtained in Reference Example 44 by a method similar to that in Example 17.

$^1$H-NMR (300 MHz, CDCl$_3$) δ: 2.07-2.39 (m, 2H), 3.31-3.66 (m, 4H), 4.19 (s, 2H), 4.30-4.47 (m, 1H), 6.55 (d, J=8.7 Hz, 2H), 7.45 (d, J=8.7 Hz, 2H).

Example 42

3-{1-[4-(trifluoromethyl)phenyl]pyrrolidin-3-yl}propanoic acid

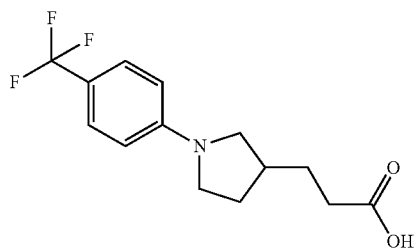

In a microwave reaction container were added ethyl 3-(pyrrolidin-3-yl)propanoate (0.15M dimethoxyethane solution, 800 μL; 120 μmol) obtained in Reference Example 12, 1-bromo-4-(trifluoromethyl)benzene (0.36M dimethoxyethane solution, 800 μL; 288 μmol), sodium tert-butoxide (16.9 mg; 168 μmol), (±)-2,2'-bis(diphenylphosphino)-1,1'-binaphthyl (4.0 mg; 6.0 μmol), and tris(dibenzylideneacetone)dipalladium(0) (2.8 mg; 3.0 μmol) at room temperature in this order, the container was filled with argon and sealed and irradiated in a microwave reaction apparatus at 120° C. for 6 min. After completion of the reaction, water (2 ml) was added to the reaction mixture, and the mixture was extracted with ethyl acetate (3 mL) to separate an organic layer. Ethyl acetate was evaporated under reduced pressure, and the residue was dissolved in dimethyl sulfoxide (1 ml) and purified by preparative HPLC to give a high purity fraction containing an ethyl ester form of the title compound. The solvent was evaporated, and the obtained residue was dissolved in ethanol (400 μL). 1M Aqueous sodium hydroxide solution (400 μL: 400 μmol) was added at room temperature, and the mixture was stirred for 16 hr. The mixture was neutralized with 1M hydrochloric acid (400 μL: 400 μmol), and purified by preparative HPLC (instrument: Gilson Inc., High throughput purification system; column: Combiprep Hydrosphere C18, 19×50 mm (YMC); solvent: SOLUTION A; 0.1% trifluoroacetic acid-containing water, SOLUTION B; 0.1% trifluoroacetic acid-containing acetonitrile; gradient cycle: 0.00 min (SOLUTION A/SOLUTION B=98/2), 1.00 min (SOLUTION A/SOLUTION B=98/2), 5.20 min (SOLUTION A/SOLUTION B=60/40), 5.40 min (SOLUTION A/SOLUTION B=5/95), 6.40 min (SOLUTION A/SOLUTION B=5/95), 6.50 min (SOLUTION A/SOLUTION B=98/2), and 6.60 min (SOLUTION A/SOLUTION B=98/2); flow rate: 20 mL/min, detection method: UV220 nm) to give the title compound.

yield: 2.0 mg
LC-MS analysis: purity>99.9%
LC/MS ESI(+) m/z: 288 (M+H)$^+$

Example 43

3-{1-[3-(trifluoromethyl)phenyl]pyrrolidin-3-yl}propanoic acid

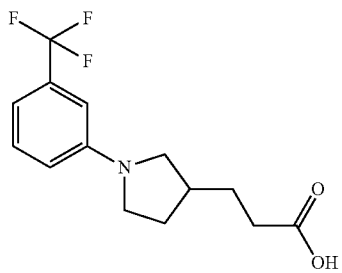

The title compound was obtained from ethyl 3-(pyrrolidin-3-yl)propanoate obtained in Reference Example 12 and 1-bromo-3-(trifluoromethyl)benzene by a method similar to that in Example 42.

yield: 0.6 mg
LC-MS analysis: purity>99.9%
LC/MS ESI(+) m/z: 288 (M+H)$^+$

Example 44

3-{1-[4-fluoro-3-(trifluoromethyl)phenyl]pyrrolidin-3-yl}propanoic acid

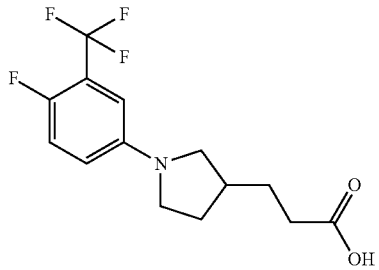

The title compound was obtained from ethyl 3-(pyrrolidin-3-yl)propanoate obtained in Reference Example 12 and 1-bromo-4-fluoro-3-(trifluoromethyl)benzene by a method similar to that in Example 42.

yield: 0.9 mg
LC-MS analysis: purity>99.9%
LC/MS ESI(+) m/z: 306 (M+H)$^+$

Example 45

3-{1-[2-fluoro-4-(trifluoromethyl)phenyl]pyrrolidin-3-yl}propanoic acid

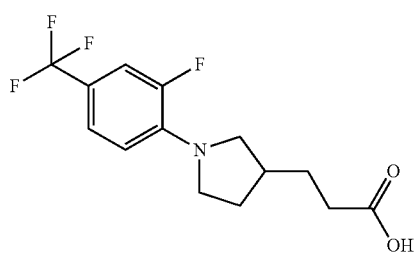

The title compound was obtained from ethyl 3-(pyrrolidin-3-yl)propanoate obtained in Reference Example 12 and 1-bromo-2-fluoro-4-(trifluoromethyl)benzene by a method similar to that in Example 42.

Yield: 0.8 mg
LC-MS analysis: purity>99.9%
LC/MS ESI(+) m/z: 306 (M+H)$^+$

Example 46

3-{1-[3-fluoro-4-(trifluoromethyl)phenyl]pyrrolidin-3-yl}propanoic acid

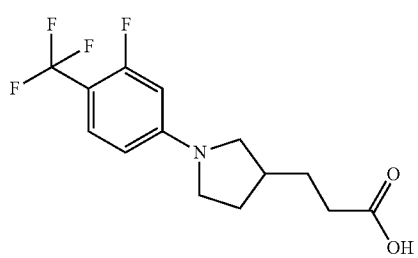

The title compound was obtained from ethyl 3-(pyrrolidin-3-yl)propanoate obtained in Reference Example 12 and 1-bromo-3-fluoro-4-(trifluoromethyl)benzene by a method similar to that in Example 42.

yield: 1.2 mg
LC-MS analysis: purity>99.9%
LC/MS ESI(+) m/z: 306 (M+H)$^+$

Example 47

3-{1-[3-fluoro-2-(trifluoromethyl)phenyl]pyrrolidin-3-yl}propanoic acid

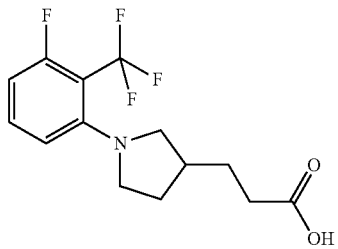

The title compound was obtained from ethyl 3-(pyrrolidin-3-yl)propanoate obtained in Reference Example 12 and 1-bromo-3-fluoro-2-(trifluoromethyl)benzene by a method similar to that in Example 42.
yield: 0.7 mg
LC-MS analysis: purity>99.9%
LC/MS ESI(+) m/z: 306 (M+H)$^+$

Example 48

{4-[3,5-bis(trifluoromethyl)phenyl]-2-oxopyrrolidin-1-yl}acetic acid

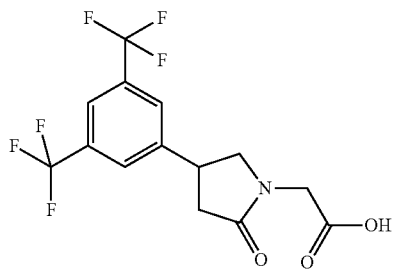

The title compound (0.41 g, 79%) was obtained as a white solid from methyl {4-[3,5-bis(trifluoromethyl)phenyl]-2-oxopyrrolidin-1-yl}acetate obtained in Reference Example 47 by a method similar to that in Example 34.
$^1$H-NMR (300 MHz, DMSO-d$_6$) δ: 2.39-2.49 (m, 1H), 2.75-2.93 (m, 1 H), 3.43-3.57 (m, 1H), 3.75-3.90 (m, 2H), 3.90-4.13 (m, 2H), 7.98 (s, 1H), 8.12 (s, 2H), 12.90 (br. s, 1H).

Example 49

{1-[3,5-bis(trifluoromethyl)phenyl]pyrrolidin-3-yl}acetic acid

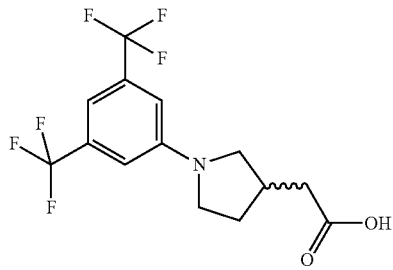

The title compound (0.33 g, 74%) was obtained as a pale-red solid from ethyl {1-[3,5-bis(trifluoromethyl)phenyl]pyrrolidin-3-yl}acetate obtained in Reference Example 50 by a method similar to that in Example 34.

$^1$H-NMR (300 MHz, DMSO-d$_6$) δ: 1.57-1.81 (m, 1H), 2.04-2.28 (m, 1H), 2.38-2.46 (m, 2H), 2.54-2.74 (m, 1H), 2.91-3.12 (m, 1H), 3.26-3.39 (m, 1H), 3.39-3.51 (m, 1H), 3.51-3.60 (m, 1H), 6.96 (s, 2H), 7.10 (s, 1H), 12.23 (s, 1H).

Example 50

3-({1-[3,5-bis(trifluoromethyl)phenyl]pyrrolidin-3-yl}sulfanyl)propanoic acid

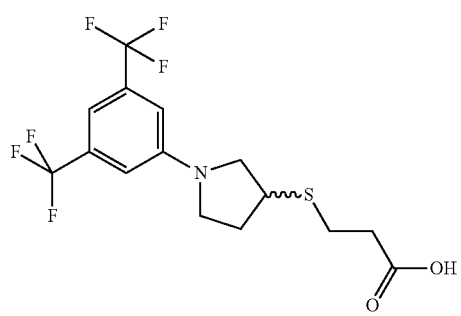

The title compound (0.32 g, 77%) was obtained as a pale-yellow solid from methyl 3-({1-[3,5-bis(trifluoromethyl)phenyl]pyrrolidin-3-yl}sulfanyl)propanoate obtained in Reference Example 51 by a method similar to that in Example 34.
$^1$H-NMR (300 MHz, DMSO-d$_6$) δ: 1.83-2.01 (m, 1H), 2.23-2.45 (m, 1H), 2.56 (t like, 2H), 2.75-2.84 (m, 2H), 3.17-3.30 (m, 1H), 3.34-3.54 (m, 2H), 3.55-3.67 (m, 1H), 3.73-3.84 (m, 1H), 7.03 (s, 2H), 7.12 (s, 1H), 12.30 (s, 1H).

Example 51

({1-[4-fluoro-2-(trifluoromethyl)phenyl]pyrrolidin-3-yl}oxy)acetic acid

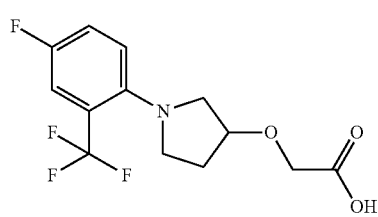

To a solution of 1-[4-fluoro-2-(trifluoromethyl)phenyl]pyrrolidin-3-ol (500 mg) obtained in Reference Example 52 in DMF (20 mL) was added sodium hydride (60% in oil, 120 mg) at 60° C. After stirring for 30 min, to the reaction mixture were added sodium chloroacetate (350 mg) and tetrabutylammonium bromide (97 mg), and the mixture was further stirred at 60° C. for 1 hr. The reaction mixture was allowed to cool to room temperature, water was added and the mixture was concentrated. The residue was diluted with ether, and the mixture was extracted with 1M sodium hydroxide. The aqueous layer was washed with ether, and acidified with 6M aqueous hydrochloric acid solution, and the mixture was extracted with ethyl acetate. The organic layer was washed with saturated brine, dried over anhydrous magnesium sulfate, and filtered. The filtrate was concentrated, and the residue was purified by silica gel column chromatography (hexane/ethyl acetate 80:20-0:100) to give the title compound (85 mg, yield 14%) as a gray-white solid.

$^1$H-NMR (300 MHz, CDCl$_3$) δ: 2.06-2.26 (m, 2H), 3.37-3.50 (m, 1H), 3.50-3.66 (m, 2H), 3.66-3.78 (m, 1H), 4.18 (s, 2H), 4.28-4.38 (m, 1H), 6.72-6.89 (m, 1H), 6.89-6.99 (m, 1H), 6.99-7.11 (m, 1H).

Example 52 potassium ({1-[4-fluoro-3-(trifluoromethyl)phenyl] pyrrolidin-3-yl}oxy)acetate

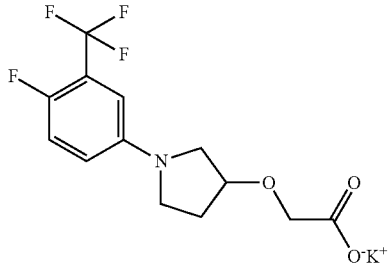

A solution of 1-[4-fluoro-3-(trifluoromethyl)phenyl]pyrrolidin-3-ol (6.0 g) obtained in Reference Example 53 in THF (45 mL) was added to a suspension of sodium hydride (60% in oil, 2.9 g) in THF (300 mL) at 60° C. After stirring for 30 min, to the reaction mixture were added sodium chloroacetate (4.21 g) and tetrabutylammonium bromide (776 mg), and the mixture was further stirred at 60° C. for 9 hr. The reaction mixture was allowed to cool to room temperature, water was added, and the mixture was concentrated. The mixture was acidified with 1M aqueous hydrochloric acid solution, and the mixture was extracted with ethyl acetate. The organic layer was washed with saturated brine, dried over anhydrous magnesium sulfate, and filtered. The filtrate was concentrated, and the residue was purified by silica gel column chromatography (hexane/ethyl acetate 90:10-0:100) to give a brown oil (6.27 g). The obtained oil (4.81 g) was diluted with methanol (100 ml), aqueous solution (100 mL) of potassium hydrogencarbonate (1.65 g) was added, and the mixture was concentrated. The residue was diluted with methanol (100 ml), aqueous solution (100 ml) of calcium chloride (956 mg) was added, and the mixture was concentrated. The residue was diluted with ethyl acetate, and filtered. The filtrate was concentrated to give the title compound (4.95 g, yield 77%) as a yellow amorphous form.

$^1$H-NMR (300 MHz, DMSO-d$_6$) δ: 1.93-2.16 (m, 2H), 2.99-3.33 (m, 3H), 3.33-3.44 (m, 1H), 3.76 (s, 2H), 4.22-4.42 (m, 1H), 6.62 (dd, J=5.7, 3.0 Hz, 1H), 6.74 (dt, J=9.0, 3.4 Hz, 1H), 7.24 (t, J=10.0 Hz, 1H).

Example 53 potassium ({1-[2-fluoro-4-(trifluoromethyl)phenyl] pyrrolidin-3-yl}oxy)acetate

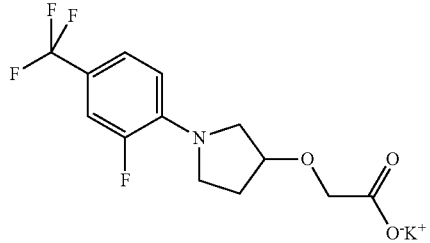

To a solution of 1-[2-fluoro-4-(trifluoromethyl)phenyl] pyrrolidin-3-ol (500 mg) obtained in Reference Example 54 in DMF (20 ml) was added sodium hydride (60% in oil, 120 mg) at 60° C. After stirring for 30 min, to the reaction mixture were added sodium chloroacetate (351 mg) and tetrabutylammonium bromide (97 mg), and the mixture was further stirred at 60° C. for 1 hr. The reaction mixture was allowed to cool to room temperature, water was added, and the mixture was concentrated. The residue was diluted with ether, and the mixture was extracted with 1M sodium hydroxide. The aqueous layer was washed with ether, and acidified with 6M aqueous hydrochloric acid solution, and the mixture was extracted with ethyl acetate. The organic layer was washed with saturated brine, dried over anhydrous magnesium sulfate, and filtered. The filtrate was concentrated, and the residue was purified by silica gel column chromatography (hexane/ethyl acetate 80:20-0:100) to give a yellow oil (311 mg). The obtained oil (310 mg) was diluted with methanol (20 ml), aqueous solution (20 ml) of potassium hydrogencarbonate (101 mg) was added, and the mixture was concentrated to give the title compound (352 mg, yield 51%) as a yellow amorphous form.

$^1$H-NMR (300 MHz, DMSO-d$_6$) δ: 1.82-2.13 (m, 2H), 3.40-3.46 (m, 2H), 3.49-3.81 (m, 4H), 4.20-4.48 (m, 1H), 6.60-6.93 (m, 1H), 7.20-7.53 (m, 2H).

Example 54 calcium ({1-[2-fluoro-5-(trifluoromethyl)phenyl] pyrrolidin-3-yl}oxy)acetate

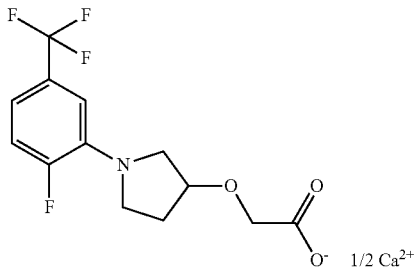

To a solution of 1-[2-fluoro-5-(trifluoromethyl)phenyl] pyrrolidin-3-ol (500 mg) obtained in Reference Example 55 in DMF (45 mL) was added sodium hydride (60% in oil, 120 mg) at 60° C. After stirring for 30 min, to the reaction mixture were added sodium chloroacetate (351 mg) and tetrabutylammonium bromide (97 mg), and the mixture was further stirred at 60° C. for 1 hr. The reaction mixture was allowed to cool to room temperature, water was added, and the mixture was concentrated. The residue was diluted with ether, and the mixture was extracted with 1M sodium hydroxide. The aqueous layer was washed with ether, and acidified with 6M aqueous hydrochloric acid solution, and the mixture was extracted with ethyl acetate. The organic layer was washed with saturated brine, dried over anhydrous magnesium sulfate, and filtered. The filtrate was concentrated, and the residue was purified by silica gel column chromatography (hexane/ethyl acetate 80:20-0:100) to give a yellow oil (105 mg). The obtained oil (100 mg) was diluted with methanol (10 mL), aqueous solution (10 mL) of potassium hydrogencarbonate (33 mg) was added, and the mixture was concentrated. The residue was diluted with methanol (10 ml), aqueous solution (10 ml) of calcium chloride (18 mg) was added, and the mixture was concentrated. The residue was diluted with ethyl acetate, and filtered. The filtrate was concentrated to give the title compound (69 mg, yield 11%) as a yellow amorphous form.

$^1$H-NMR (300 MHz, DMSO-d$_6$) δ: 1.81-2.11 (m, 2H), 3.06-3.19 (m, 2H), 3.25-3.37 (m, 1H), 3.37-3.50 (m, 1H), 3.66 (s, 2H), 4.23-4.37 (m, 1H), 7.00-7.31 (m, 1H), 7.31-7.54 (m, 2H).

Example 55 potassium ({1-[2-fluoro-3-(trifluoromethyl)phenyl] pyrrolidin-3-yl}oxy)acetate

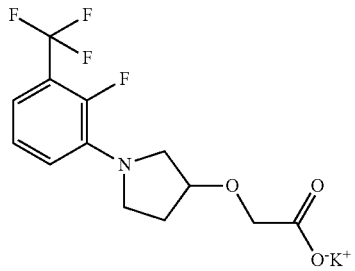

To a solution of 1-[2-fluoro-3-(trifluoromethyl)phenyl] pyrrolidin-3-ol (500 mg) obtained in Reference Example 56 in DMF (20 ml) was added sodium hydride (60% in oil, 120 mg) at 60° C. After stirring for 30 min, to the reaction mixture were added sodium chloroacetate (351 mg) and tetrabutylammonium bromide (97 mg), and the mixture was further stirred at 60° C. for 1 hr. The reaction mixture was allowed to cool to room temperature, water was added, and the mixture was concentrated. The residue was diluted with ether, and the mixture was extracted with 1M sodium hydroxide. The aqueous layer was washed with ether, and acidified with 6M aqueous hydrochloric acid solution, and the mixture was extracted with ethyl acetate. The organic layer was washed with saturated brine, dried over anhydrous magnesium sulfate, and filtered. The filtrate was concentrated, and the residue was purified by silica gel column chromatography (hexane/ethyl acetate 80:20-0:100) to give a yellow oil (130 mg). The obtained oil (80 mg) was diluted with methanol (10 ml), aqueous solution (10 mL) of potassium hydrogencarbonate (26 mg) was added, and the mixture was concentrated to give the title compound (100 mg, yield 14%) as a yellow amorphous form.

$^1$H-NMR (300 MHz, DMSO-d$_6$) δ: 1.80-2.08 (m, 2H), 3.35-3.39 (m, 2 H), 3.40-3.62 (m, 4H), 4.24-4.38 (m, 1H), 6.79-6.95 (m, 1H), 6.95-7.05 (m, 1H), 7.06-7.23 (m, 1H).

Example 56 calcium ({1-[2,4-bis(trifluoromethyl)phenyl]pyrrolidin-3-yl}oxy)acetate

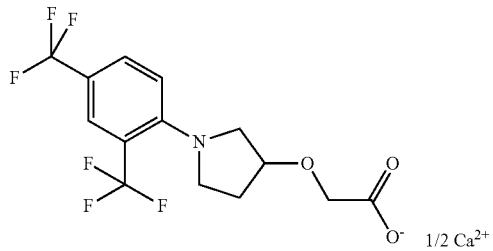

To a solution of 1-[2,4-bis(trifluoromethyl)phenyl]pyrrolidin-3-ol (500 mg) obtained in Reference Example 57 in DMF (20 mL) was added sodium hydride (60% in oil, 100 mg) at 60° C. After stirring for 30 min, to the reaction mixture were added sodium chloroacetate (292 mg) and tetrabutylammonium bromide (81 mg), and the mixture was further stirred at 60° C. for 1 hr. The reaction mixture was allowed to cool to room temperature, water was added, and the mixture was concentrated. The residue was diluted with ether, and the mixture was extracted with 1M sodium hydroxide. The aqueous layer was washed with ether, and acidified with 6M aqueous hydrochloric acid solution, and the mixture was extracted with ethyl acetate. The organic layer was washed with saturated brine, dried over anhydrous magnesium sulfate, and filtered. The filtrate was concentrated, and the residue was purified by silica gel column chromatography (hexane/ethyl acetate 80:20-0:100) to give a yellow oil (162 mg). The obtained oil (160 mg) was diluted with methanol (10 mL), aqueous solution (10 ml) of potassium hydrogencarbonate (45 mg) was added, and the mixture was concentrated. The residue was diluted with methanol (10 ml), aqueous solution (10 ml) of calcium chloride (25 mg) was added, and the mixture was concentrated. The residue was diluted with ethyl acetate, and filtered. The filtrate was concentrated to give the title compound (188 mg, yield 30%) as a yellow amorphous form.

$^1$H-NMR (300 MHz, DMSO-d$_6$) δ: 1.95-2.04 (m, 1H), 2.04-2.17 (m, 1H), 3.15-3.45 (m, 4H), 3.45-3.69 (m, 2H), 4.34 (br. s, 1H), 7.09 (d, J=9.0 Hz, 1H), 7.70 (d, J=8.7 Hz, 1H), 7.77 (s, 1H).

Example 57

({1-[3-(methylamino)-5-(trifluoromethyl)phenyl] pyrrolidin-3-yl}oxy)acetic acid

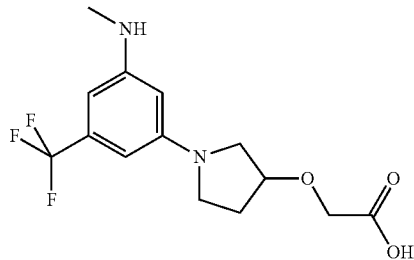

To a solution of N-[3-(3-hydroxypyrrolidin-1-yl)-5-(trifluoromethyl)phenyl]-N-methylacetamide (1.0 g) obtained in Reference Example 60 in DMF (33 ml) was added sodium hydride (60% in oil, 198 mg) at 60° C. After stirring for 30 min, to the reaction mixture were added sodium chloroacetate (578 mg) and tetrabutylammonium bromide (160 mg), and the mixture was further stirred at 60° C. for 1 hr. The reaction mixture was allowed to cool to room temperature, water was added, and the mixture was concentrated. The residue was diluted with ether, and the mixture was extracted with 1M sodium hydroxide. The aqueous layer was washed with ether, and acidified with 6M aqueous hydrochloric acid solution, and the mixture was extracted with ethyl acetate. The organic layer was washed with saturated brine, dried over anhydrous magnesium sulfate, and filtered. The filtrate was concentrated, and the residue was purified by silica gel column chromatography (hexane/ethyl acetate 80:20-0:100) to give a yellow oil (17 mg). The obtained oil was diluted with THF (1 mL), 1M aqueous lithium hydroxide solution (1 ml) was added, and the mixture was stirred at room temperature for 5 hr. The reaction mixture was acidified with 1M hydrochloric acid, and the mixture was extracted with ethyl acetate. The organic layer was washed with saturated brine, dried over anhydrous magnesium sulfate, and filtered. The filtrate was concentrated to give the title compound (7.7 mg, yield 0.7%) as a pale-yellow oil.

$^1$H-NMR (300 MHz, CDCl$_3$) δ: 2.13-2.27 (m, 2H), 2.85 (s, 3H), 3.31-3.62 (m, 5H), 4.16 (s, 2H), 4.31-4.41 (m, 1H), 5.87 (s, 1H), 6.16 (s, 1H), 6.22 (s, 1H).

Example 58

[(1-{3-[(1-oxidothiomorpholin-4-yl)carbonyl]-5-(trifluoromethyl)phenyl}pyrrolidin-3-yl)oxy]acetic acid

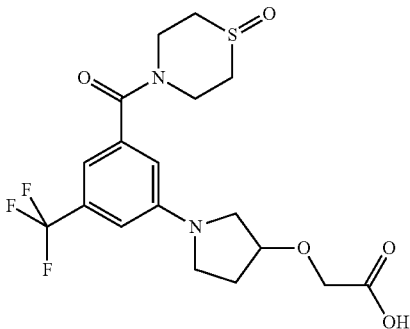

To a solution of 1-{3-[(1-oxidothiomorpholin-4-yl)carbonyl]-5-(trifluoromethyl)phenyl}pyrrolidin-3-ol (700 mg) obtained in Reference Example 64 in DMF (35 mL) was added sodium hydride (60% in oil, 112 mg) at 60° C. After stirring for 30 min, to the reaction mixture were added sodium chloroacetate (325 mg) and tetrabutylammonium bromide (90 mg), and the mixture was further stirred at 60° C. for 1 hr. The reaction mixture was allowed to cool to room temperature, water was added, and the mixture was concentrated. The residue was diluted with ether, and the mixture was extracted with 1M sodium hydroxide. The aqueous layer was washed with ether, and acidified with 6M aqueous hydrochloric acid solution, and the mixture was extracted with ethyl acetate. The organic layer was washed with saturated brine, dried over anhydrous magnesium sulfate, and filtered. The filtrate was concentrated, and the residue was purified by silica gel column chromatography (ethyl acetate/methanol 90:10-50:50) to give the title compound (67 mg, yield 8%) as a yellow amorphous form.

$^1$H-NMR (300 MHz, CDCl$_3$) δ: 2.08-2.22 (m, 1H), 2.22-2.37 (m, 1H), 2.97 (br. s, 4H), 3.32-3.61 (m, 4H), 3.78 (br. s, 1H), 4.11 (br. s, 2H), 4.16 (d, J=1.9 Hz, 2H), 4.32-4.40 (m, 1H), 4.56 (br. s, 1H), 6.68 (s, 1H), 6.78 (s, 1H), 6.87 (s, 1H).

Example 59 calcium [(1-{3-[methyl(methylsulfonyl)amino]-5-(trifluoromethyl)phenyl}pyrrolidin-3-yl)oxy]acetate

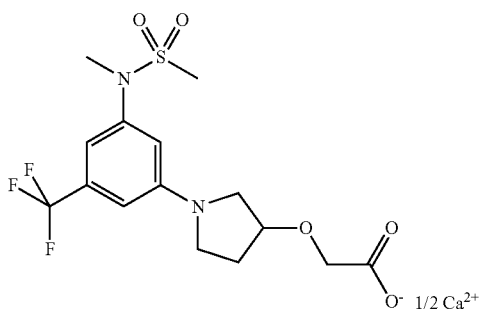

To a solution of N-[3-(3-hydroxypyrrolidin-1-yl)-5-(trifluoromethyl)phenyl]-N-methylmethanesulfonamide (1.0 g) obtained in Reference Example 67 in DMF (30 mL) was added sodium hydride (60% in oil, 177 mg) at 50° C. After stirring for 30 min, to the reaction mixture were added sodium chloroacetate (516 mg) and tetrabutylammonium bromide (143 mg), and the mixture was further stirred at 50° C. for 3 hr. The reaction mixture was allowed to cool to room temperature, water was added, and the mixture was concentrated. The residue was diluted with ether, and the mixture was extracted with 1M sodium hydroxide. The aqueous layer was washed with ether, and acidified with 6M aqueous hydrochloric acid solution, and the mixture was extracted with ethyl acetate. The organic layer was washed with saturated brine, dried over anhydrous magnesium sulfate, and filtered. The filtrate was concentrated, and the residue was purified by silica gel column chromatography (hexane/ethyl acetate 80:20-0:100). The residue was purified by preparative HPLC (instrument: Gilson Inc. High throughput purification system; column: YMC Combiprep ODS-A, S-5 μm, 50×20 mm; solvent: SOLUTION A; 0.1% trifluoroacetic acid-containing water, SOLUTION B; 0.1% trifluoroacetic acid-containing acetonitrile; gradient cycle: 0.00 min (SOLUTION A/SOLUTION B=90/10), 1.00 min (SOLUTION A/SOLUTION B=90/10), 4.20 min (SOLUTION A/SOLUTION B=10/90), 5.40 min (SOLUTION A/SOLUTION B=10/90), 5.50 min (SOLUTION A/SOLUTION B=90/10), 5.60 min (SOLUTION A/SOLUTION B=90/10); flow rate: 25 mL/min; detection method: UV 220 nm) to give a yellow oil (108 mg). The obtained oil (61 mg) was diluted with methanol (5 ml), aqueous solution (5 mL) of potassium hydrogencarbonate (16 mg) was added, and the mixture was concentrated. The residue was diluted with methanol (5 mL), aqueous solution (5 mL) of calcium chloride (9 mg) was added, and the mixture was concentrated. The residue was diluted with ethyl acetate, and filtered. The filtrate was concentrated to give the title compound (71 mg, yield 6%) as a yellow amorphous form.

$^1$H-NMR (300 MHz, DMSO-d$_6$) δ: 1.99-2.15 (m, 2H), 2.97 (s, 3H), 3.25 (s, 3H), 3.27-3.37 (m, 3H), 3.37-3.49 (m, 1H), 3.68 (s, 2H), 4.33-4.43 (m, 1H), 6.62-6.69 (m, 1H), 6.74 (s, 1H), 6.89 (s, 1H).

Example 60

({1-[3-bromo-5-(trifluoromethyl)phenyl]pyrrolidin-3-yl}oxy)acetic acid

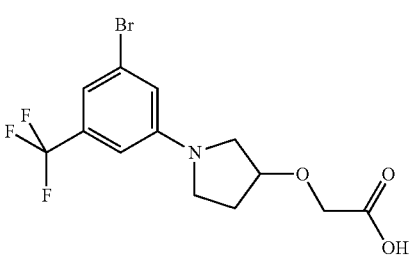

To a solution of 1-[3-bromo-5-(trifluoromethyl)phenyl]pyrrolidin-3-ol (500 mg) obtained in Reference Example 68 in DMF (16 mL) was added sodium hydride (60% in oil, 97 mg) at 60° C. After stirring for 30 min, to the reaction mixture were added sodium chloroacetate (282 mg) and tetrabutylammonium bromide (78 mg), and the mixture was stirred at 60° C. for 1 hr. The reaction mixture was allowed to cool to room temperature, water was added, and the mixture was concentrated. The residue was diluted with ether, and the mixture was extracted with 1M sodium hydroxide. The aqueous layer was washed with ether, and acidified with 6M aqueous hydrochloric acid solution, and the mixture was extracted with ethyl acetate. The organic layer was washed with saturated brine, dried over anhydrous magnesium sulfate, and filtered. The filtrate was concentrated, and the residue was purified by silica gel column chromatography (hexane/ethyl acetate 80:20-0:100). The residue was purified by preparative HPLC (instrument: Gilson Inc. High throughput purification system; column: YMC Combiprep ODS-A, S-5 µm, 50×20 mm; solvent: SOLUTION A; 0.1% trifluoroacetic acid-containing water, SOLUTION B; 0.1% trifluoroacetic acid-containing acetonitrile; gradient cycle: 0.00 min (SOLUTION A/SOLUTION B=90/10), 1.00 min (SOLUTION A/SOLUTION B=90/10), 4.20 min (SOLUTION A/SOLUTION B=10/90), 5.40 min (SOLUTION A/SOLUTION B=10/90), 5.50 min (SOLUTION A/SOLUTION B=90/10), and 5.60 min (SOLUTION A/SOLUTION B=90/10); flow rate: 25 mL/min; detection method: UV 220 nm) to give the title compound (27.6 mg, yield 5%) as a yellow oil.

$^1$H-NMR (300 MHz, CDCl$_3$) δ: 2.08-2.33 (m, 2H), 3.28-3.62 (m, 4H), 4.18 (s, 2H), 4.32-4.45 (m, 1H), 6.64 (s, 1H), 6.80 (s, 1H), 7.03 (s, 1H).

Example 61

({1-[3-methoxy-5-(trifluoromethyl)phenyl]pyrrolidin-3-yl}oxy)acetic acid

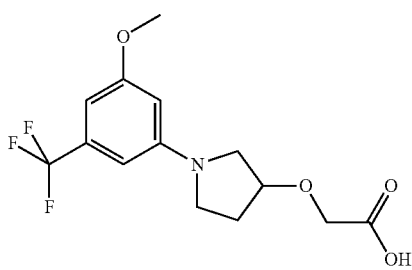

To a solution of 1-[3-methoxy-5-(trifluoromethyl)phenyl]pyrrolidin-3-ol (1.68 g) obtained in Reference Example 69 in DMF (129 mL) was added sodium hydride (60% in oil, 386 mg) at 60° C. After stirring for 30 min, to the reaction mixture were added sodium chloroacetate (1.12 g) and tetrabutylammonium bromide (311 mg), and the mixture was stirred at 60° C. for 3 hr. The reaction mixture was allowed to cool to room temperature, water was added, and the mixture was concentrated. The residue was diluted with ether, and the mixture was extracted with 1M sodium hydroxide. The aqueous layer was washed with ether, and acidified with 6M aqueous hydrochloric acid solution, and the mixture was extracted with ethyl acetate. The organic layer was washed with saturated brine, dried over anhydrous magnesium sulfate, and filtered. The filtrate was concentrated, and the residue was purified by silica gel column chromatography (hexane/ethyl acetate 50:50-0:100) to give the title compound (1.86 g, yield 91%) as a white solid.

$^1$H-NMR (300 MHz, CDCl$_3$) δ: 2.08-2.35 (m, 2H), 3.32-3.59 (m, 4H), 3.82 (s, 3H), 4.19 (s, 2H), 4.32-4.41 (m, 1H), 6.16-6.24 (m, 1H), 6.39 (s, 1H), 6.48 (s, 1H).

Example 62

({1-[3-(thiomorpholin-4-ylcarbonyl)-5-(trifluoromethyl)phenyl]pyrrolidin-3-yl}oxy)acetic acid

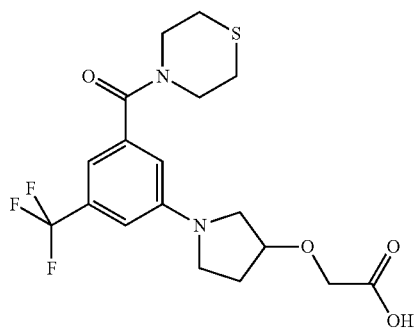

To a solution of 1-[3-(thiomorpholin-4-ylcarbonyl)-5-(trifluoromethyl)phenyl]pyrrolidin-3-ol (1.0 g) obtained in Reference Example 62 in DMF (37 µL) was added sodium hydride (60% in oil, 166 mg) at 60° C. After stirring for 30 min, to the reaction mixture were added sodium chloroacetate (484 mg) and tetrabutylammonium bromide (134 mg), and the mixture was stirred at 60° C. for 2 hr, and further at 80° C. for 1 hr. The reaction mixture was allowed to cool to room temperature, water was added, and the mixture was concentrated. The mixture was acidified with 1M aqueous hydrochloric acid solution, and the mixture was extracted with ethyl acetate. The organic layer was washed with saturated brine, dried over anhydrous magnesium sulfate, and filtered. The filtrate was concentrated, and the residue was purified by silica gel column chromatography (hexane/ethyl acetate 50:50-0:100) to give the title compound (519 mg, yield 45%) as a yellow amorphous form.

$^1$H-NMR (300 MHz, CDCl$_3$) δ: 2.08-2.39 (m, 2H), 2.58 (br. s, 2H), 2.74 (br. s, 2H), 3.34-3.59 (m, 4H), 3.70 (br. s, 1H), 4.09 (br. s, 2H), 4.16 (s, 2H), 4.30-4.41 (m, 1H), 4.66 (br. s, 1H), 6.68 (s, 1H), 6.75 (s, 1H), 6.84 (s, 1H).

Example 63

({1-[3-chloro-5-(trifluoromethyl)phenyl]pyrrolidin-3-yl}oxy)acetic acid

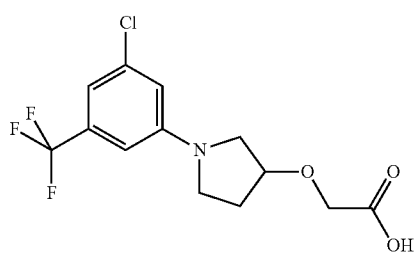

To a solution of 1-[3-chloro-5-(trifluoromethyl)phenyl]pyrrolidin-3-ol (1.0 g) obtained in Reference Example 70 in DMF (38 mL) was added sodium hydride (60% in oil, 226 mg) at 60° C. After stirring for 30 min, to the reaction mixture were added sodium chloroacetate (657 mg) and tetrabutylammonium bromide (123 mg), and the mixture was stirred at 60° C. for 2 hr, and then at 80° C. for 2 hr. The reaction mixture was allowed to cool to room temperature, water was added, and the mixture was concentrated. The residue was diluted with ether, and the mixture was extracted with 1M sodium hydroxide. The aqueous layer was washed with ether, and acidified with 6M aqueous hydrochloric acid solution, and the mixture was extracted with ethyl acetate. The organic layer was washed with saturated brine, dried over anhydrous magnesium sulfate, and filtered. The filtrate was concentrated, and the residue was purified by silica gel column chromatography (hexane/ethyl acetate 80:20-0:100) to give the title compound (77.2 mg, yield 6%) as a brown oil.

$^1$H-NMR (300 MHz, CDCl$_3$) δ: 2.06-2.38 (m, 2H), 3.26-3.64 (m, 4H), 4.18 (s, 2H), 4.30-4.42 (m, 1H), 6.60 (s, 1H), 6.64 (s, 1H). 6.89 (s, 1H).

Example 64

({1-[4-fluoro-3-(trifluoromethyl)phenyl]pyrrolidin-3-yl}oxy)acetic acid

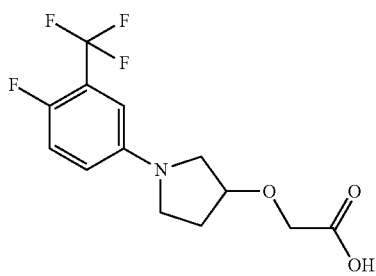

A solution of 1-[4-fluoro-3-(trifluoromethyl)phenyl]pyrrolidin-3-ol (3.29 g) obtained in Reference Example 53 in THF (30 mL) was added to a suspension of sodium hydride (60% in oil, 1.58 g) in THF (160 ml) at 60° C. After stirring for 30 min, to the reaction mixture were added sodium chloroacetate (2.31 g) and tetrabutylammonium bromide (427 mg), and the mixture was further stirred at 60° C. for 2 hr. The reaction mixture was allowed to cool to room temperature, water was added, and the mixture was concentrated. The mixture was acidified with 1M aqueous hydrochloric acid solution, and the mixture was extracted with ethyl acetate. The organic layer was washed with saturated brine, dried over anhydrous magnesium sulfate, and filtered. The filtrate was concentrated, and the residue was purified by silica gel column chromatography (hexane/ethyl acetate 90:10-0:100) to give the title compound (3.18 g, yield 78%) as a gray-white solid.

$^1$H-NMR (300 MHz, CDCl$_3$) δ: 2.08-2.33 (m, 2H), 3.26-3.60 (m, 4H), 4.19 (s, 2H), 4.32-4.43 (m, 1H), 6.55-6.71 (m, 2H), 7.05 (t, J=9.4 Hz, 1H).

Example 65

({1-[3-fluoro-5-(trifluoromethyl)phenyl]pyrrolidin-3-yl}oxy)acetic acid

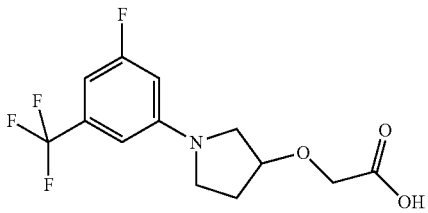

A solution of 1-[3-fluoro-5-(trifluoromethyl)phenyl]pyrrolidin-3-ol (2.46 g) obtained in Reference Example 71 in THF (30 ml) was added to a suspension of sodium hydride (60% in oil, 1.18 g) in THF (110 ml) at 60° C. After stirring for 30 min, to the reaction mixture were added sodium chloroacetate (1.72 g) and tetrabutylammonium bromide (320 mg), and the mixture was further stirred at 60° C. for 2 hr. The reaction mixture was allowed to cool to room temperature, water was added, and the mixture was concentrated. The mixture was acidified with 1M aqueous hydrochloric acid solution, and the mixture was extracted with ethyl acetate. The organic layer was washed with saturated brine, dried over anhydrous magnesium sulfate, and filtered. The filtrate was concentrated, and the residue was purified by silica gel column chromatography (hexane/ethyl acetate 80:20-0:100) to give the title compound (2.83 g, yield 93%) as a white solid.

$^1$H-NMR (300 MHz, CDCl$_3$) δ: 2.08-2.36 (m, 2H), 3.33-3.60 (m, 4H), 4.19 (s, 2H), 4.38 (tt, J=4.8, 2.4 Hz, 1H), 6.36 (dt, J=11.3, 2.3 Hz, 1H), 6.52 (s, 1H), 6.62 (d, J=8.7 Hz, 1H).

Example 66

({(3S)-1-[4-chloro-2-(trifluoromethyl)phenyl]pyrrolidin-3-yl}oxy)acetic acid

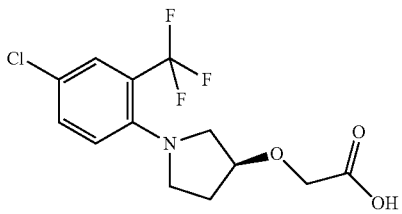

A solution of (3S)-1-[4-chloro-2-(trifluoromethyl)phenyl]pyrrolidin-3-ol (2.66 g) obtained in Reference Example 72 in THF (23 mL) was added to a suspension of sodium hydride (60% in oil, 1.2 g) in THF (120 ml) at 60° C. After stirring for 30 min, to the reaction mixture were added sodium chloroacetate (1.75 g) and tetrabutylammonium bromide (323 mg), and the mixture was further stirred at 60° C. for 7 hr. The reaction mixture was allowed to cool to room temperature, water was added, and the mixture was concentrated. The mixture was acidified with 1M aqueous hydrochloric acid solution, and the mixture was extracted with ethyl acetate. The organic layer was washed with saturated brine, dried over anhydrous magnesium sulfate, and filtered. The filtrate was concentrated, and the residue was purified by silica gel column chromatography (hexane/ethyl acetate 80:20-0:100) to give the title compound (1.38 g, yield 43%) as a yellow solid.

¹H-NMR (300 MHz, CDCl₃) δ: 2.05-2.24 (m, 2H), 3.18-3.40 (m, 2H), 3.44-3.65 (m, 2H), 4.05-4.25 (m, 2H), 4.27-4.37 (m, 1H), 6.97 (d, J=8.7 Hz, 1H), 7.35 (dd, J=8.9, 2.4 Hz, 1H), 7.56 (d, J=2.6 Hz, 1H).

Example 67

3-{5-[3-fluoro-5-(trifluoromethyl)phenyl]tetrahydrofuran-2-yl}propanoic acid

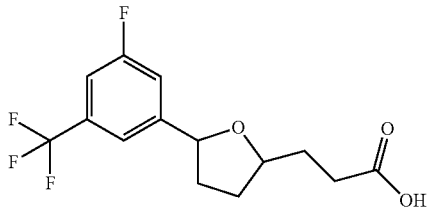

A solution of ethyl 3-{5-[3-fluoro-5-(trifluoromethyl)phenyl]tetrahydrofuran-2-yl}propanoate (0.55 g, 1.65 mmol) obtained in Reference Example 77 and lithium hydroxide (0.20 g, 8.23 mmol) in ethanol/water (20 mL/5 mL) was stirred at room temperature for 4 hr. The reaction solution was adjusted to pH 2 with 1M hydrochloric acid, and concentrated under reduced pressure, and the residue was partitioned between ethyl acetate and water. The organic layer was washed with water and saturated brine, dried over anhydrous sodium sulfate, filtered, and the filtrate was concentrated under reduced pressure. The obtained white solid was recrystallized from hexane to give the title compound (0.32 g, yield 63%) as a white solid.

¹H-NMR (300 MHz, CDCl₃) δ: 1.66-1.84 (m, 2H), 1.96-2.03 (m, 2H), 2.07-2.53 (m, 2H), 2.57 (q, J=7.2 Hz, 2H), 4.04-4.13 (m, 1H), 4.91 (t, J=7.2 Hz, 1H), 7.19-7.26 (m, 2H), 7.35 (s, 1H).

Example 68

3-{5-[3-methoxy-5-(trifluoromethyl)phenyl]tetrahydrofuran-2-yl}propanoic acid

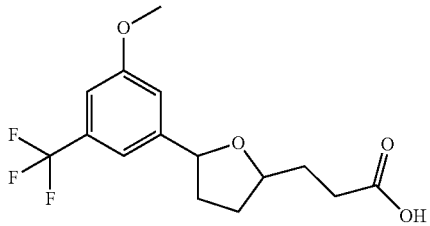

A solution of ethyl 3-{5-[3-methoxy-5-(trifluoromethyl)phenyl]tetrahydrofuran-2-yl}propanoate (0.47 g, 1.36 mmol) obtained in Reference Example 79 and lithium hydroxide (0.17 g, 4.08 mmol) in ethanol/water (20 mL/5 ml) was stirred at room temperature for 2 hr. The reaction solution was concentrated, and the residue was partitioned between ethyl acetate and water. The aqueous layer was adjusted to pH 2 with 2M hydrochloric acid, and the mixture was extracted with ethyl acetate. The organic layer was dried over anhydrous sodium sulfate, and filtered, and the filtrate was concentrated under reduced pressure to give the title compound (0.34 g, yield 79%) as a white solid.

¹H-NMR (300 MHz, CDCl₃) δ: 1.62-1.69 (m, 1H), 1.75-1.86 (m, 1H), 1.98 (t, J=8.7 Hz, 2H), 2.07-2.17 (m, 1H), 2.31-2.38 (m, 1H), 2.53-2.61 (m, 2H), 3.85 (s, 3H), 4.06-4.10 (m, 1H), 4.90 (t, J=7.2 Hz, 1H), 7.01 (s, 1H), 7.08 (s, 1H), 7.15 (s, 1H).

Example 69

3-{5-[4-methoxy-3-(trifluoromethyl)phenyl]tetrahydrofuran-2-yl}propanoic acid

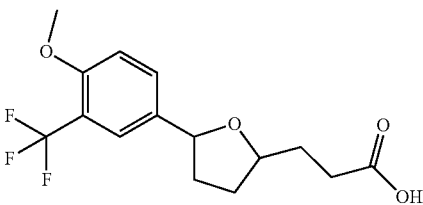

A solution of ethyl 3-{5-[4-methoxy-3-(trifluoromethyl)phenyl]tetrahydrofuran-2-yl}propanoate (0.40 g, 1.16 mmol) obtained in Reference Example 81 and lithium hydroxide (0.15 g, 3.47 mmol) in ethanol/water (20 mL/5 mL) was stirred at room temperature for 2 hr. The reaction solution was concentrated, and the residue was partitioned between ethyl acetate and water. The aqueous layer was adjusted to pH 2 with 2M hydrochloric acid, and the mixture was extracted with ethyl acetate. The organic layer was dried over anhydrous sodium sulfate, and filtered, and the filtrate was concentrated under reduced pressure to give the title compound (0.25 g, yield 88%) as a white solid.

¹H-NMR (300 MHz, CDCl₃) δ: 1.64-1.81 (m, 2H), 1.98 (q, J=7.2 Hz, 2H), 2.11-2.17 (m, 1H), 2.24-2.33 (m, 1H), 2.51-2.59 (m, 2H), 3.89 (s, 3H), 4.04-4.14 (m, 1H), 4.84 (t, J=7.2 Hz, 1H), 6.97 (d, J=8.4 Hz, 1H), 7.46-7.52 (m, 2H).

Example 70

3-{5-[2-fluoro-3-(trifluoromethyl)phenyl]tetrahydrofuran-2-yl}propanoic acid

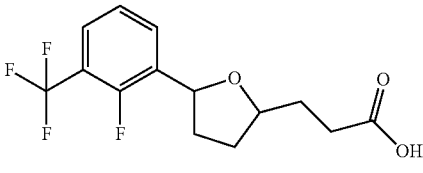

A solution of ethyl 3-{5-[2-fluoro-3-(trifluoromethyl)phenyl]tetrahydrofuran-2-yl}propanoate (0.55 g, 1.64 mmol) obtained in Reference Example 83 and lithium hydroxide (0.21 g, 4.93 mmol) in ethanol/water (20 mL/5 mL) was stirred at room temperature for 2 hr. The reaction solution was concentrated, and the residue was partitioned between ethyl acetate and water. The aqueous layer was adjusted to pH 2 with 2M hydrochloric acid, and the mixture was extracted with ethyl acetate. The organic layer was dried over anhydrous sodium sulfate, and filtered, and the filtrate was concentrated under reduced pressure to give the title compound (0.40 g, yield 79%) as a white solid.

$^1$H-NMR (300 MHz, CDCl$_3$) δ: 1.61-1.68 (m, 1H), 1.70-1.82 (m, 1H), 1.98-2.05 (m, 2H), 2.09-2.18 (m, 1H), 2.40-2.55 (m, 1H), 2.57-2.68 (m, 2H), 4.04-4.11 (m, 1H), 5.16 (t, J=7.8 Hz, 1H), 7.20-7.25 (m, 1H), 7.48-7.53 (m, 1H), 7.69-7.74 (m, 1H).

Example 71

3-{5-[3-(trifluoromethyl)phenyl]tetrahydrofuran-2-yl}propanoic acid

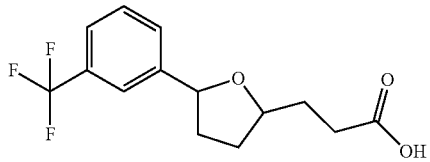

A solution of ethyl 3-{5-[3-(trifluoromethyl)phenyl]tetrahydrofuran-2-yl}propanoate (0.73 g, 2.33 mmol) obtained in Reference Example 85 and lithium hydroxide (0.29 g, 7.00 mmol) in ethanol/water (20 mL/5 mL) was stirred at room temperature for 2 hr. The reaction solution was concentrated, and the residue was partitioned between ethyl acetate and water. The aqueous layer was adjusted to pH 2 with 2M hydrochloric acid, and the mixture was extracted with ethyl acetate. The organic layer was dried over anhydrous sodium sulfate, and filtered, and the filtrate was concentrated under reduced pressure to give the title compound (0.66 g, yield 98%) as a white solid.

$^1$H-NMR (300 MHz, CDCl$_3$) δ: 1.62-1.74 (m, 1H), 1.80-1.86 (m, 1H), 1.96-2.03 (m, 2H), 2.13-2.19 (m, 1H), 2.30-2.41 (m, 1H), 2.53-2.61 (m, 2H), 4.07-4.14 (m, 1H), 4.92 (t, J=7.2 Hz, 1H), 7.44-7.54 (m, 3H), 7.58 (s, 1H).

Example 72

3-{5-[2-cyano-3-(trifluoromethyl)phenyl]tetrahydrofuran-2-yl}propanoic acid

A solution of ethyl 3-{5-[2-cyano-3-(trifluoromethyl)phenyl]tetrahydrofuran-2-yl}propanoate (0.34 g, 1.00 mmol) obtained in Reference Example 87 and lithium hydroxide (0.13 g, 3.00 mmol) in ethanol/water (15 mL/4 mL) was stirred at room temperature for 2 hr. The reaction solution was concentrated, and the residue was partitioned between ethyl acetate and water. The aqueous layer was adjusted to pH 2 with 2M hydrochloric acid, and the mixture was extracted with ethyl acetate. The organic layer was dried over anhydrous sodium sulfate, and filtered, and the filtrate was concentrated under reduced pressure to give the title compound (0.29 g, yield 91%) as a white solid.

$^1$H-NMR (300 MHz, CDCl$_3$) δ: 1.64-1.81 (m, 2H), 2.02-2.09 (m, 2H), 2.16-2.24 (m, 1H), 2.50-2.70 (m, 3H), 4.10-4.15 (m, 1H), 5.29 (t, J=7.2 Hz, 1H), 7.69-7.71 (m, 2H), 7.88-7.91 (m, 1H).

Example 73

3-{5-[4-fluoro-3-(trifluoromethyl)phenyl]tetrahydrofuran-2-yl}propanoic acid

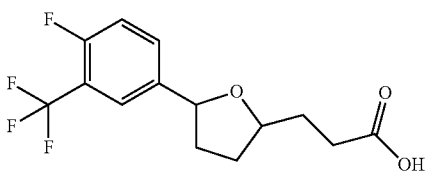

A solution of ethyl 3-{5-[4-fluoro-3-(trifluoromethyl)phenyl]tetrahydrofuran-2-yl}propanoate (0.52 g, 1.58 mmol) obtained in Reference Example 89 and lithium hydroxide (0.20 g, 4.76 mmol) in ethanol/water (20 mL/5 ml) was stirred at room temperature for 2 hr. The reaction solution was concentrated, and the residue was partitioned between ethyl acetate and water. The aqueous layer was adjusted to pH 2 with 2M hydrochloric acid, and the mixture was extracted with ethyl acetate. The organic layer was dried over anhydrous sodium sulfate, and filtered, and the filtrate was concentrated under reduced pressure to give the title compound (0.42 g, yield 88%) as a yellow oil.

$^1$H-NMR (300 MHz, CDCl$_3$) δ: 1.60-1.80 (m, 2H), 1.95-2.02 (m, 2H), 2.09-2.18 (m, 1H), 2.29-2.38 (m, 1H), 2.46-2.59 (m, 2H), 4.04-4.14 (m, 1H), 4.87 (t, J=7.2 Hz, 1H), 7.12-7.18 (m, 1H), 7.50-7.56 (m, 2H).

Example 74

3-{5-[2-methoxy-3-(trifluoromethyl)phenyl]tetrahydrofuran-2-yl}propanoic acid

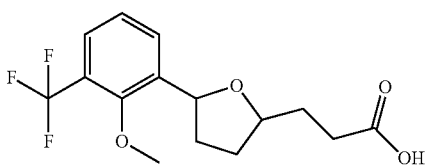

A solution of ethyl 3-{5-[2-methoxy-3-(trifluoromethyl)phenyl]tetrahydrofuran-2-yl}propanoate (0.34 g, 0.98 mmol) obtained in Reference Example 92 and lithium hydroxide (0.12 g, 2.94 mmol) in ethanol/water (20 ml/5 ml) was stirred at room temperature for 2 hr. The reaction solution was concentrated, and the residue was partitioned between ethyl acetate and water. The aqueous layer was adjusted to pH 2 with 2M hydrochloric acid, and the mixture was extracted with ethyl acetate. The organic layer was dried over anhydrous sodium sulfate, and filtered, and the filtrate was concentrated under reduced pressure to give the title compound (0.42 g, yield 88%) as a yellow oil.

¹H-NMR (300 MHz, CDCl₃) δ: 1.64-1.83 (m, 2H), 1.99-2.06 (m, 2H), 2.10-2.17 (m, 1H), 2.37-2.48 (m, 1H), 2.54-2.65 (m, 2H), 3.87 (s, 3H), 4.03-4.11 (m, 1H), 5.20 (t, J=7.2 Hz, 1H), 7.22 (t, J=7.8 Hz, 1H), 7.51 (dd, J=7.8, 1.5 Hz, 1H), 7.70 (dd, J=7.8, 1.5 Hz, 1H).

Example 75

3-{5-[3-methoxy-2-(trifluoromethyl)phenyl]tetrahydrofuran-2-yl}propanoic acid

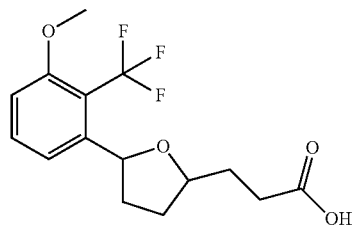

A solution of ethyl 3-{5-[3-methoxy-2-(trifluoromethyl)phenyl]tetrahydrofuran-2-yl}propanoate (0.21 g, 0.61 mmol) obtained in Reference Example 93 and lithium hydroxide (76 mg, 1.82 mmol) in ethanol/water (15 mL/5 mL) was stirred at room temperature for 2 hr. The reaction solution was concentrated, and the residue was partitioned between ethyl acetate and water. The aqueous layer was adjusted to pH 2 with 2M hydrochloric acid, and the mixture was extracted with ethyl acetate. The organic layer was dried over anhydrous sodium sulfate, and filtered, and the filtrate was concentrated under reduced pressure to give the title compound (0.19 g, yield 97%) as a yellow solid.

¹H NMR (300 MHz, CDCl₃): δ 1.52-1.60 (m, 1H), 1.66-1.77 (m, 1H), 2.02-2.11 (m, 3H), 2.41-2.53 (m, 1H), 2.56-2.65 (m, 2H), 3.88 (s, 3H), 3.98-4.07 (m, 1H), 5.30-5.36 (m, 1H), 6.92 (d, J=7.8 Hz, 1H), 7.39-7.49 (m, 2H).

Example 76

3-{(2R,5S)-5-[3,5-bis(trifluoromethyl)phenyl]tetrahydrofuran-2-yl}propanoate tromethamine salt

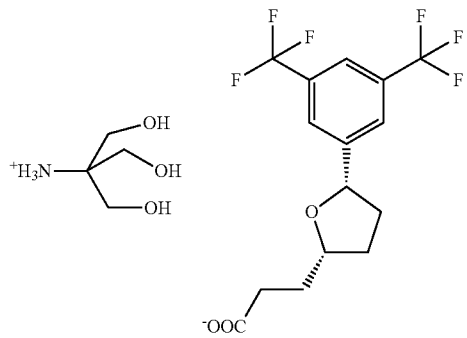

To a solution of 3-{(2R,5S)-5-[3,5-bis(trifluoromethyl)phenyl]tetrahydrofuran-2-yl}propanoic acid (3.00 g, 8.42 mmol) obtained in Example 36 in methanol (60 mL) was added a solution of tromethamine (1.02 g, 8.42 mmol) in water (5 mL), and the mixture was stirred at room temperature for 2 hr. The solution was concentrated under reduced pressure, and the obtained solid was dissolved in ethyl acetate/toluene (10:1, 50 mL), and concentrated under reduced pressure. The obtained solid was disrupted in diisopropyl ether to give the title compound (3.79 g, yield 94%) as a white solid. Mp 110° C. Anal. Calcd. for C₁₉H₂₅NO₆F₆: C, 47.80; H, 5.28; N, 2.93. Found: C, 47.61; H, 5.47; N, 2.99.

Example 77

({5-[3,5-bis(trifluoromethyl)phenyl]tetrahydrofuran-2-yl}methoxy)acetic acid

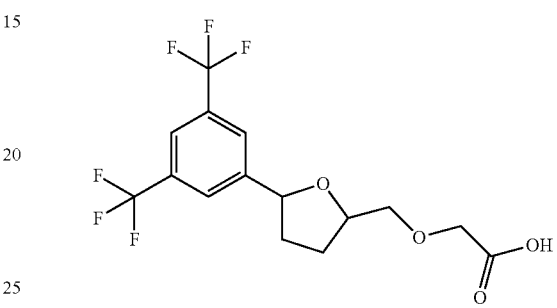

A solution of ethyl ({5-[3,5-bis(trifluoromethyl)phenyl]tetrahydrofuran-2-yl}methoxy)acetate (0.28 g, 0.70 mmol) obtained in Reference Example 97 and 1M lithium hydroxide solution (2.1 ml, 2.1 mmol) in ethanol (10 ml) was stirred at room temperature for 3 hr. The reaction solution was adjusted to pH 3 with 1M hydrochloric acid, and concentrated under reduced pressure. The residue was partitioned between ethyl acetate and water, and the organic layer was washed with saturated brine, dried over anhydrous magnesium sulfate, and filtered. The filtrate was concentrated under reduced pressure to give the title compound (0.23 g, yield 88%) as a white solid.

¹H-NMR (300 MHz, CDCl₃) δ: 1.77-2.01 (m, 2H), 2.08-2.22 (m, 1H), 2.31-2.57 (m, 1H), 3.64-3.78 (m, 1H), 3.78-3.89 (m, 1H), 4.24 (s, 2H), 4.28-4.43 (m, 1H), 5.04 (t, J=7.0 Hz, 1H), 7.78 (s, 1H), 7.84 (s, 2H).

Example 78

{5-[3,5-bis(trifluoromethyl)phenyl]tetrahydrofuran-2-yl}acetic acid

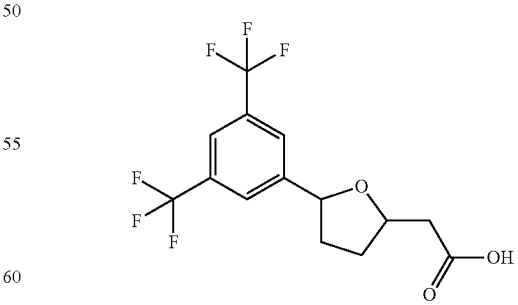

A solution of {5-[3,5-bis(trifluoromethyl)phenyl]furan-2-yl}acetic acid (1.23 g, 3.64 mmol) obtained in Reference Example 100 and palladium (10% on carbon, containing water (50%), 0.36 g) in ethanol (30 mL) was stirred under a hydrogen atmosphere at room temperature for 16 hr. After confirmation of the completion of the reaction by TLC, the reaction solution was filtered, and concentrated under reduced pressure. The residue was purified by silica gel column chromatography (hexane/ethyl acetate 50:50), and the obtained solid was washed with hexane to give the title compound (1.01 g, yield 81%) as a pale-yellow solid.

$^1$H-NMR (300 MHz, DMSO-d$_6$) δ: 1.60-1.85 (m, 2H), 2.05-2.25 (m, 1H), 2.34-2.48 (m, 1H), 2.53-2.63 (m, 2H), 4.30-4.48 (m, 1H), 5.04 (t, J=7.0 Hz, 1H), 7.99 (s, 1H), 8.03 (s, 2H), 12.27 (br. s, 1H).

Experimental Example 1

The action of the compound of the present invention to inhibit the binding between RBP4, and retinol and TTR was evaluated using the Retinol-RBP4-TTR ELISA (human type ELISA) system shown below.

1A: Cloning of Human RBP4 Gene and Human TTR Gene

Human RBP4 gene was cloned by a PCR reaction using human Universal cDNA (Clontech, QUICK-Clone cDNA) as a template and the following primer set.

```
RBPU:
                                    (SEQ ID NO: 1)
5'-ATATGGATCCACCATGAAGTGGGTGTGGGCGCTC-3'

RBPL:
                                    (SEQ ID NO: 2)
5'-ATATGCGGCCGCCTACAAAAGGTTTCTTTCTGATCTGC-3'
```

The PCR reaction was performed according to the protocol attached to Pyrobest polymerase (TAKARA SHUZO CO., LTD.). The obtained PCR product was subjected to agarose gel (1%) electrophoresis, and an about 0.6 kb DNA fragment containing RBP4 gene was recovered from the gel and digested with restriction enzymes BamHI and NotI. The DNA treated with the restriction enzymes was subjected to agarose gel (1%) electrophoresis, an about 0.6 kb DNA fragment was recovered and ligated to plasmid pcDNA3.1(+) (Invitrogen) digested with restriction enzymes BamHI and NotI to give an expression plasmid pcDNA3.1(+)/hRBP4. The base sequence of the fragment inserted into this plasmid was confirmed to have matched with the object sequence.

Human TTR gene was cloned by a PCR reaction using human small intestine cDNA (Clontech, QUICK-Clone cDNA) as a template and the following primer set.

```
TTRU:
                                    (SEQ ID NO: 3)
5'-ATATGGATCCACCATGGCTTCTCATCGTCTGCTCC-3'

TTRL:
                                    (SEQ ID NO: 4)
5'-ATATGCGGCCGCTCATTCCTTGGGATTGGTGACGA-3'
```

The PCR reaction was performed according to the protocol attached to Pyrobest polymerase (TAKARA SHUZO CO., LTD.). The obtained PCR product was subjected to agarose gel (1%) electrophoresis, a 0.5 kb DNA fragment containing TTR gene was recovered from the gel, and digested with restriction enzymes BamHI and NotI. The DNA treated with the restriction enzymes was subjected to agarose gel (1%) electrophoresis, an about 0.5 kb DNA fragment was recovered and ligated to plasmid pcDNA3.1(+) (Invitrogen) digested with restriction enzymes BamHI and NotI to give an expression plasmid pcDNA3.1(+)/hTTR. The base sequence of the fragment inserted into this plasmid was confirmed to have matched with the object sequence.

1B: Construction of Human RBP4-His Expression Plasmid

EcoRI site was introduced into the 3' end of hRBP4 gene by PCR reaction using the expression plasmid pcDNA3.1(+)/hRBP4 prepared in the above-mentioned 1A as a template and the following primer set.

```
CMVP:
5'-TGGGAGGTCTATATAAGCAGAGCTCG-3'    (SEQ ID NO: 5)

RBPECO:
5'-ATATGAATTCTTCCTTGGGATTGGTGAC-3'  (SEQ ID NO: 6)
```

The PCR reaction was performed according to the protocol attached to Z-Taq polymerase (TAKARA SHUZO CO., LTD.). The obtained PCR product was purified using QIAquick PCR purification Kit (QIAGEN), and digested with restriction enzymes BamHI and EcoRI. The DNA treated with the restriction enzymes was subjected to agarose gel (1%) electrophoresis, the obtained about 0.6 kb DNA was recovered and ligated to plasmid pcDNA3.1(+) (Invitrogen) digested with restriction enzymes BamHI and EcoRI to give pcDNA3.1(+)/hRBP4-Eco having EcoRI site at the 3' end of hRBP4 gene.

EcoRI site was introduced into the hTTR gene 3' end by PCR reaction using expression plasmid pcDNA3.1(+)/hTTR prepared in the above-mentioned 1A as a template and CMVP and TTRECO primer set.

```
                                    (SEQ ID NO: 7)
TTRECO:     5'-ATATGAATTCCAAAAGGTTTCTTTCTGATC-3'
```

PCR reaction was performed according to the protocol attached to Z-Taq polymerase (TAKARA SHUZO CO., LTD.). The obtained PCR product was purified using QIAquick PCR purification Kit (QIAGEN), and digested with restriction enzymes BamHI and EcoRI. The DNA treated with the restriction enzymes was subjected to agarose gel (1%) electrophoresis, the obtained about 0.6 kb DNA was recovered and ligated to plasmid pcDNA3.1(+) (Invitrogen) digested with restriction enzymes BamHI and EcoRI to give pcDNA3.1(+)/hTTR-Eco having EcoRI site at the 3' end of hTTR gene.

TTR-His expression plasmid pcDNA3.1(+)/hTTR-His having His tag added to the C-terminal of human TTR was prepared by inserting a synthetic gene fragment containing His tag sequence prepared by annealing the following oligo DNA to EcoRI and NotI sites of the above-mentioned pcDNA3.1(+)/hTTR-Eco.

```
HISENU:
5'-AATTCCATCATCATCATCATCACTAGGC-3'  (SEQ ID NO: 8)

HISENL:
5'-GGCCGCCTAGTGATGATGATGATGATGG-3'  (SEQ ID NO: 9)
```

HISENU and HISENL were each dissolved in TE buffer (50 μl) at a concentration of 25 pmole/μL, heated at 94° C. for 5 min and cooled gradually to room temperature to give a synthetic gene fragment containing His tag sequence. pcDNA3.1(+)/hTTR-Eco was digested with EcoRI and NotI, the DNA treated with the restriction enzyme was subjected to agarose gel (1%) electrophoresis, the obtained about 5.9 kb DNA was recovered, the synthetic gene segment containing the His tag sequence was ligated thereto to give TTR-His expression plasmid pcDNA3.1(+)/hTTR-His having His tag added to the C-terminal of human TTR.

RBP4-His expression plasmid pcDNA3.1(+)/hRBP4-His having His tag added to the C-terminal of human RBP4 was produced according to the following steps.

pcDNA3.1(+)/hRBP4-Eco was digested with restriction enzymes EcoRI and DraIII, subjected to agarose gel (1%) electrophoresis, and the obtained about 6.0 kb DNA was recovered. pcDNA3.1(+)/hTTR-His was digested with restriction enzymes EcoRI and DraIII, subjected to agarose gel (1%) electrophoresis, and the obtained about 0.6 kb DNA was recovered. The both DNA fragments were ligated to give RBP4-His expression plasmid pcDNA3.1(+)/hRBP4-His having His tag added to the C-terminal of human RBP4.

1C: Preparation of Human RBP4-His

Human RBP4-His was expressed using FreeStyle293 expression system (Invitrogen) and expression plasmid pcDNA3.1(+)/hRBP4-His prepared in the above-mentioned 1B. According to the protocol attached to the FreeStyle293 expression system, 600 mL of culture medium was used for the expression. After transfection and culture for 3 days, the culture supernatant containing secreted/expressed hRBP4-His was recovered. The culture supernatant was repeatedly concentrated using VIVACELL250 (molecular weight cut off 10K, VIVASCIENCE) and diluted with 20 mM Tris (pH 8), whereby the buffer was substituted. The liquid was passed through TOYOPEARL DEAE-650M column (1 cm ID×10 cm, Tosoh Corporation) equilibrated with 20 mM Tris buffer (pH 8) at a flow rate of 2.5 mL/min to allow adsorption and human RBP4-His fraction was obtained by elution with 0-0.35M NaCl gradient. The fractions were concentrated to about 5 mL using Vivaspin 20 (molecular weight cut off 10K, VIVASCIENCE). The concentrated solution was passed through HiLoad 26/60 Superdex 200 pg column (2.6 cm ID×60 cm, GE Healthcare) equilibrated with TBS (pH 7.4) and eluted with TBS (pH 7.4). The fractions containing human RBP4-His were collected and concentrated to about 8 ml using Vivaspin 20 (molecular weight cut off 10K, VIVASCIENCE). About 8 mg of human RBP4-His was obtained from 600 mL of the culture medium.

1D: Preparation of Human TTR

Human TTR was expressed using FreeStyle293 expression system (Invitrogen) and expression plasmid pcDNA3.1(+)/hTTR prepared in the above-mentioned 1A. According to the protocol attached to the FreeStyle293 expression system, 600 mL of culture medium was used for the expression. After transfection and culture for 3 days, the culture supernatant containing secreted/expressed human TTR was recovered. The culture supernatant was repeatedly concentrated using VIVACELL250 (molecular weight cut off 10K, VIVASCIENCE) and diluted with 20 mM Tris (pH 8), whereby the buffer was substituted. The liquid was passed through TOYOPEARL DEAE-650M column (1 cm ID×10 cm, Tosoh Corporation) equilibrated with 20 mM Tris buffer (pH 8) at a flow rate of 2.5 mL/min to allow adsorption and human TTR fraction was obtained by elution with 0-0.55M NaCl gradient. This fraction was repeatedly concentrated using Vivaspin 20 (molecular weight cut off 10K, VIVASCIENCE) and diluted with 20 mM Tris (pH 8), whereby the buffer was substituted. The liquid was passed through HiLoad Q Sepharose HP column (1.6 cm ID×10 cm, GE Healthcare) equilibrated with 20 mM Tris buffer (pH 8) at a flow rate of 1.0 mL/min to allow adsorption and human TTR fraction was obtained by elution with 0-0.4M NaCl gradient. The fractions were concentrated to about 5 mL using Vivaspin 20 (molecular weight cut off 10K, VIVASCIENCE). The concentrated solution was passed through HiLoad 26/60 Superdex 75 pg column (2.6 cm ID×60 cm, GE Healthcare) equilibrated with PBS (pH 7.4) and eluted with PBS (pH 7.4). The fractions containing human TTR were collected and concentrated to about 5 mL using Vivaspin 20 (molecular weight cut off 10K, VIVASCIENCE). About 6 mg of human TTR was obtained from 600 ml of the culture medium.

1E: Preparation of Human TTR-Biotin

Human TTR prepared in the above-mentioned 1D was labeled with biotin using Biotinylation Kit (Sulfo-Osu) (DOJINDO LABORATORIES) according to the protocol attached to the kit, whereby human TTR-biotin was prepared. Human TTR 5.0 mg was repeatedly concentrated using Vivaspin 6 (molecular weight cut off 10K, VIVASCIENCE) and diluted with 50 mM $NaHCO_3$, whereby the buffer was substituted. The liquid was diluted with 50 mM $NaHCO_3$ to human TTR concentration of 2.0 mg/mL, then aqueous Biotin-$(AC5)_2$ Sulfo-OSu solution (10 mg/mL) (9.9 μL) prepared when in use was added and the mixture was reacted at 25° C. for 2 hr. The solution after the reaction was passed through NAP-25 column (GE Healthcare) equilibrated with PBS (pH 7.4), eluted with PBS (pH 7.4), and an eluate (3.5 mL) containing human TTR-biotin was collected.

Experimental Example 2

Binding Assay by Retinol-RBP4-TTR ELISA

The binding assay was performed by an ELISA system (Retinol-RBP4-TTR ELISA) for detecting retinol-RBP4-TTR conjugate by streptavidin-biotin reaction.

His-tagged human RBP4 used was prepared in the above-mentioned 1C.

Biotinylated human TTR used was prepared in the above-mentioned 1E.

Streptavidin (20 μl) (10 μg/ml Streptavidin type II (Wako Pure Chemical Industries, Ltd.), 10 mM Tris-HCl (pH 7.5), 10 mM NaCl) was added to a 384 well black maxisorp plate (Nunc), and the plate was subjected to centrifugation (1000 rpm, 1 min) and coated overnight at 4° C. The plate was washed twice with PBST (PBS, 0.05% Tween 20, 100 μl/well) and blocked with 25% Block Ace (Snow Brand Milk Products Co., Ltd., PBS, 100 μl/well). The plate was subjected to centrifugation (1000 rpm, 1 min) and incubated at room temperature for 4 hr or overnight at 4° C. The plate was washed twice with PBST (PBS, 0.05% Tween 20, 100 μl/well), and biotinylated human TTR (stock solution concentration 1.3 mg/ml) diluted 1000-fold with PBST was added at 20 μl/well. The plate was subjected to centrifugation (1000 rpm, 1 min) and stood still at room temperature for 1.5 hr or overnight at 4° C. The plate was washed 3 times with PEST (100 μl/well), and His-tagged human RBP4 (stock solution concentration 0.96 mg/ml) diluted 4000-fold with a reaction buffer (50 mM Tris-HCl, 150 mM NaCl, 0.005% Tween 20, 1 mM DTT, 0.1% BSA) was added at 10 μl/well. The dilution series (8 doses from 10 mM, 200-fold concentration) of the compound was prepared with DMSO, and 1 μl of each was added to a reaction buffer (200 μl) containing retinol (0.5 μM) (Sigma-Aldrich Co.). A reaction buffer (200 μl) containing retinol and added with DMSO was used as a positive control, and reaction buffer (200 μl) free of retinol and added with DMSO was used as a negative control. Mixed solutions of retinol and the compound were added to the plate at 15 μl/well. The mixture was stirred in a platemixer, subjected to centrifugation (1000 rpm, 1 min) and reacted at room temperature for 2 hr. A 35% Block Ace solution diluted with the reaction buffer was added at 10 μl/well, centrifuged (1000 rpm, 1 min) and reacted at room temperature for 30 min. The plate was washed 3 times with PBST (100 μl/well) and SuperSignal ELISA Femto Maximum Sensitivity Substrate reagent (PIERCE) was added at 30 μl/well, and the luminescence was measured by a platereader (Wallac).

The binding activity rate of the compound was determined by 100×(test compound value−negative control value)/(positive control value−negative control value). The binding inhibitory activity ($IC_{50}$) was calculated from the binding activity rate at each compound concentration using a graph drawing software, Prism (GraphPad Software Inc.). The results are shown below.

TABLE 1

| Example No. | human RBP4 binding inhibitory activity ($IC_{50}$ nM) |
|---|---|
| 1 | 45 |
| 2 | 38 |
| 10 | 27 |
| 11 | 13 |
| 13 | 26 |
| 14 | 39 |
| 15 | 320 |
| 16 | 28 |
| 17 | 20 |
| 27 | 140 |
| 34 | 26 |
| 48 | 210 |
| 50 | 81 |

From the above results, it is clear that the compound of the present invention inhibits binding of RBP4 with retinol and TTR.

Experimental Example 3

A blood RBP4 lowering action of the compound of the present invention was evaluated using C57BL/6J mouse.

Male 7- to 15-week-old C57BL/6J mice (Charles River Laboratories Japan Inc.) were individually bred for acclimation for 4-6 days under conditions with free access to CE-2 solid food (CLEA Japan, Inc.), and grouped based on the body weight (5 per group). The next day of grouping, blood samples were collected from the orbital venous plexus, and plasma was separated (0 hr value). Thereafter, the test compounds (Examples 1, 13, 15, 16, 17, 27 and 34) were orally administered at a dose of 50 mg/kg (solvent: 0.5% methylcellulose solution (10 mL/kg)). At 4, 7 and 24 hr after administration of the compounds, blood samples were collected from the orbital venous plexus, and plasma was separated. A 0.5% methylcellulose solution (10 mL/kg) was orally administered to the control group.

The RBP4 level of the collected plasma was measured by ELISA. RBP4 was quantified by the following steps using a rabbit, anti-mouse RBP4 polyclonal antibody (Hokudo Co., Ltd). A 96 well ELISA plate was coated with 50 μg/ml of the antibody (100 μL) and stood at 4° C. overnight. After blocking with BlockAce (DAINIPPON PHARMACEUTICAL CO., LTD.), mouse RBP4 or a sample (100 μL) was added and the plate was stood at room temperature for 2 hr. After washing with PBS-0.5% Tween 20, HRP-labeled anti-RBP4 antibody (prepared by labeling RBP4 polyclonal antibody (Hokudo Co., Ltd) with HRP (DOJINDO LABORATORIES)) was added by 100 μL, and the plate was stood at room temperature for 1 hr. After washing, TMB (Dako Cytomations) was added, and the mixture was stood at room temperature for 20 min to allow color development, and the reaction was quenched with 2N sulfuric acid. Thereafter, the absorbance at A450 nm was measured on a platereader. The amount of change from the initial value of each animal was determined as a relative value from the control group (% of initial/Control) at each time point. The results are shown in the following in mean±standard deviation (n=5).

TABLE 2

| Example No. | RBP4 (% of initial/Control) | | | |
|---|---|---|---|---|
| | 0 hr later | 4 hr later | 7 hr later | 24 hr later |
| 1 | 100 ± 20.2 | 42.5 ± 3.3 | 36.0 ± 3.2 | 73.8 ± 19.3 |
| 13 | 100.0 ± 10.9 | 54.5 ± 1.2 | 56.5 ± 2.5 | 106.6 ± 3.9 |
| 15 | 100.0 ± 4.4 | 51.0 ± 1.4 | 49.0 ± 1.1 | 58.2 ± 2.7 |
| 16 | 100.0 ± 11.0 | 39.5 ± 0.6 | 39.6 ± 0.4 | 37.5 ± 0.4 |
| 17 | 100.0 ± 7.1 | 42.2 ± 0.6 | 40.5 ± 0.2 | 38.6 ± 0.8 |
| 27 | 100.0 ± 2.1 | 56.2 ± 1.7 | 56.0 ± 1.6 | 59.6 ± 2.1 |
| 34 | 100.0 ± 5.6 | 37.4 ± 2.4 | 34.8 ± 2.6 | 107.4 ± 15.3 |

All of the above-mentioned compounds showed lower levels than the control group at 4 hr and the lowest level at 7 hr after administration by single oral administration. These results show that the compound of the present invention has a blood RBP4-lowering action.

Experimental Example 4

A hypoglycemic action of the compound of the present invention was evaluated using Zucker fa/fa rats.

Experimental Example 4A

Male 19-week-old Zucker fa/fa rats (Takeda Pharmaceutical Company Limited) were bred in group on CE-2 solid food (CLEA Japan, Inc.) until 12-week-old, thereafter bred on high-fat diet D06110702 (LSG Corporation) for acclimation under conditions with free access to food. At 19-week-old, the rats were grouped based on the body weight, blood glucose level, glycated hemoglobin level and blood RBP4 level value (6 per group). Thereafter, the test compound (Example 34) was orally administered at a dose of 30 mg/kg (solvent: 0.5% methylcellulose solution (5 mL/kg)) for 2 weeks. After 24 hr of the final administration of the compound, blood samples were collected from the tail vein, and plasma was separated. Using the collected plasma, (1) RBP4 concentration, (2) glycated hemoglobin level and (3) blood glucose level were measured. (1) was quantified according to the protocol described in Experimental Example 3. (2) was measured using Tosoh Corporation automatic glycohemoglobin analyzer (HLC-723 GHbV A1c2.2 or HLC-723G7 GHbV A1c2.2), and (3) was measured using Hitachi full-automatic analyzer (7070 or 7080), respectively.

A 0.5% methylcellulose solution (5 mL/kg) was orally administered to the control group. As a result, the blood RBP4 concentration, glycated hemoglobin change and blood glucose level showed significant decrease by the oral administration (30 mg/kg) of the compound (Example 34) for 2 weeks. The results are shown in the following in mean±standard deviation (n=6). In the following Table, glycated hemoglobin change is obtained by subtracting the value before administration from that after administration.

TABLE 3

| | RBP4 (μg/mL) | glycated hemoglobin change (%) | blood glucose level (mg/dL) |
|---|---|---|---|
| control | 28.6 ± 10.2 | 0.00 ± 0.13 | 303.2 ± 95.6 |
| Example 34 | 5.2 ± 0.2 | −1.72 ± 0.52 | 157.2 ± 50.6 |

The compound of the present invention showed a significant decrease in the glycated hemoglobin and blood glucose level in correlation with a decrease in the blood RBP4 concentration.

Experimental Example 4B

Male 25-week-old Zucker fa/fa rats (Takeda Pharmaceutical Company Limited) were acclimation bred in groups on CE-2 solid food (CLEA Japan, Inc.) up to 12 weeks of age, thereafter on high-fat diet D06110702 (LSG Corporation), with free access to food. At 25 weeks of age, the rats were grouped based on the body weight, blood glucose level, glycated hemoglobin level and blood RBP4 level (5 per group). Then, test compounds (Examples 16 and 17) were orally administered at a dose of 10 mg/kg (solvent: 0.5% methylcellulose solution (3 mL/kg)) for 2 weeks. At 24 hr from the final administration of the compounds, blood samples were collected from the tail vein, and plasma was separated. Using the collected plasma, (1) RBP4 concentration, (2) glycated hemoglobin level and (3) blood glucose level were measured. (1) was quantified according to the protocol described in Experimental Example 3. (2) was measured using Tosoh Corporation automatic glycohamoglobin analyzer (HLC-723 GHbV A1c2.2 or HLC-723G7 GHbV A1c2.2), and (3) was measured using Hitachi full-automatic analyzer (7070 or 7080).

A 0.5% methylcellulose solution (3 ml/kg) was orally administered to the control group. The results are shown below in mean±standard deviation (n=5). In the following Table, glycated hemoglobin change is obtained by subtracting the value before administration from that after administration.

TABLE 4

|  | RBP4 (µg/mL) | glycated hemoglobin change (%) | blood glucose level (mg/dL) |
| --- | --- | --- | --- |
| control | 19.0 ± 5.4 | 0.78 ± 0.31 | 397.4 ± 38.2 |
| Example 16 | 5.7 ± 0.1 | −0.58 ± 0.59 | 275.9 ± 127.5 |
| Example 17 | 6.0 ± 0.1 | −0.60 ± 0.39 | 255.4 ± 106.7 |

The compound of the present invention showed a significant decrease in glycated hemoglobin and blood glucose level in correlation with a decrease in blood RBP4 concentration.

| Formulation Example 1 (production of capsules) | |
| --- | --- |
| 1) compound of Example 1 | 30 mg |
| 2) finely divided powder cellulose | 10 mg |
| 3) lactose | 19 mg |
| 4) magnesium stearate | 1 mg |
| total | 60 mg |

1), 2), 3) and 4) are mixed and filled in a gelatin capsule.

| Formulation Example 2 (production of tablets) | |
| --- | --- |
| 1) compound of Example 1 | 30 g |
| 2) lactose | 50 g |
| 3) cornstarch | 15 g |
| 4) calcium carboxymethylcellulose | 44 g |
| 5) magnesium stearate | 1 g |
| 1000 tablets total | 140 g |

The total amount of 1), 2) and 3) and 4) (30 g) is kneaded with water, vacuum dried, and sieved. The sieved powder is mixed with 4) (14 g) and 5) (1 g), and punched by a tableting machine, whereby 1000 tablets containing 30 mg of the compound of Example 1 per tablet are obtained.

INDUSTRIAL APPLICABILITY

The compound of the present invention has a superior RBP4-lowering action, and is useful as a medicament for the prophylaxis or treatment of the diseases and conditions mediated by increased RBP4, such as diabetes, hyperlipidemia and the like.

This application is based on a patent application No. 61/129,032 filed in the USA, the contents of which are all encompassed in the present specification.

The invention claimed is:
1. A compound represented by the formula

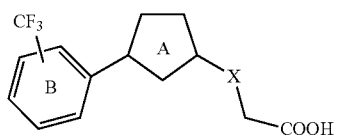

(I)

wherein
 ring A is a 5-membered non-aromatic heterocycle optionally further substituted by one oxo group;
 ring B is a benzene ring optionally further substituted by 1 to 4 substituents selected from Substituent A; and
 X is O, $CH_2O$, $OCH_2$, $CH_2$, $(CH_2)_2$, S, $CH_2S$, $SCH_2$, S(O), $CH_2S(O)$, $S(O)CH_2$, $S(O)_2$, $CH_2S(O)_2$ or $S(O)_2CH_2$,
or a salt thereof,
wherein Substituent A is a substituent selected from the group consisting of:
 (1) a $C_{3-10}$ cycloalkyl group;
 (2) a $C_{6-14}$ aryl group optionally substituted by 1 to 3 substituents selected from the group consisting of:
  (a) a $C_{1-6}$ alkyl group optionally substituted by 1 to 3 halogen atoms,
  (b) a hydroxy group,
  (c) a $C_{1-6}$ alkoxy group optionally substituted by 1 to 3 halogen atoms, and
  (d) a halogen atom,
 (3) an aromatic heterocyclic group optionally substituted by 1 to 3 substituents selected from the group consisting of:
  (a) a $C_{1-6}$ alkyl group optionally substituted by 1 to 3 halogen atoms,
  (b) a hydroxy group,
  (c) a $C_{1-6}$ alkoxy group optionally substituted by 1 to 3 halogen atoms, and
  (d) a halogen atom;
 (4) a non-aromatic heterocyclic group optionally substituted by 1 to 3 substituents selected from the group consisting of:
  (a) a $C_{1-6}$ alkyl group optionally substituted by 1 to 3 halogen atoms,
  (b) a hydroxy group,
  (c) a $C_{1-6}$ alkoxy group optionally substituted by 1 to 3 halogen atoms,
  (d) a halogen atom, and
  (e) an oxo group;
 (5) an amino group optionally mono- or di-substituted by substituent(s) selected from the group consisting of:
  (a) a $C_{1-6}$ alkyl group optionally substituted by 1 to 3 halogen atoms,
  (b) a $C_{1-6}$ alkyl-carbonyl group optionally substituted by 1 to 3 halogen atoms,
  (c) a $C_{6-14}$ aryl-carbonyl group optionally substituted by 1 to 3 halogen atoms,
  (d) a $C_{1-6}$ alkoxy-carbonyl group optionally substituted by 1 to 3 halogen atoms,
  (e) a $C_{1-6}$ alkylsulfonyl group optionally substituted by 1 to 3 halogen atoms,
  (f) a carbamoyl group optionally mono- or di-substituted by $C_{1-6}$ alkyl group(s) optionally substituted by 1 to 3 halogen atoms, and
  (g) an aromatic heterocyclic group;
 (6) a $C_{1-6}$ alkyl-carbonyl group optionally substituted by 1 to 3 halogen atoms;
 (7) a $C_{1-6}$ alkoxy-carbonyl group optionally substituted by 1 to 3 substituents selected from the group consisting of:
  (a) a halogen atom,
  (b) a $C_{1-6}$ alkoxy group, and
  (c) a $C_{6-14}$ aryl group;
 (8) a $C_{1-6}$ alkylsulfonyl group optionally substituted by 1 to 3 halogen atoms;
 (9) a carbamoyl group optionally mono- or di-substituted by substituent(s) selected from the group consisting of:
  (a) a $C_{1-6}$ alkyl group optionally substituted by 1 to 3 halogen atoms,
  (b) a $C_{1-6}$ alkylsulfonyl group optionally substituted by 1 to 3 halogen atoms,
  (c) a $C_{6-14}$ arylsulfonyl group optionally substituted by an aromatic heterocyclic group, and
  (d) an aromatic heterocyclic group;
 (10) a thiocarbamoyl group optionally mono- or di-substituted by $C_{1-6}$ alkyl group(s) optionally substituted by 1 to 3 halogen atoms;
 (11) a sulfamoyl group optionally mono- or di-substituted by $C_{1-6}$ alkyl group(s) optionally substituted by 1 to 3 halogen atoms;
 (12) a carboxy group;
 (13) a hydroxy group;
 (14) a $C_{1-6}$ alkoxy group optionally substituted by 1 to 3 substituents selected from the group consisting of:
  (a) a halogen atom,
  (b) a carboxy group,
  (c) a $C_{1-6}$ alkoxy group,
  (d) a $C_{1-6}$ alkoxy-carbonyl group optionally substituted by 1 to 3 $C_{6-14}$ aryl group, and
  (e) an amino group optionally mono- or di-substituted by substituent(s) selected from the group consisting of a $C_{1-6}$ alkyl group and a $C_{1-6}$ alkoxy-carbonyl group;
 (15) a $C_{2-6}$ alkenyloxy group optionally substituted by 1 to 3 halogen atoms;
 (16) a $C_{7-13}$ aralkyloxy group;
 (17) a $C_{6-14}$ aryloxy group;
 (18) a $C_{1-6}$ alkyl-carbonyloxy group;
 (19) a $C_{6-14}$ aryl-carbonyl group optionally substituted by 1 to 3 substituents selected from the group consisting of:

(a) a halogen atom, and
(b) a $C_{1-6}$ alkyl group optionally substituted by 1 to 3 halogen atoms;
(20) a non-aromatic heterocyclylcarbonyl group optionally substituted by 1 to 3 substituents selected from a $C_{1-6}$ alkyl group optionally substituted by 1 to 3 halogen atoms;
(21) a mercapto group;
(22) a $C_{1-6}$ alkylthio group optionally substituted by 1 to 3 substituents selected from the group consisting of:
(a) a halogen atom, and
(b) a $C_{1-6}$ alkoxy-carbonyl group;
(23) a $C_{7-13}$ aralkylthio group;
(24) a $C_{6-14}$ arylthio group;
(25) a cyano group;
(26) a nitro group;
(27) a halogen atom;
(28) a $C_{1-3}$ alkylenedioxy group;
(29) an aromatic heterocyclylcarbonyl group optionally substituted by 1 to 3 substituents selected from a $C_{1-6}$ alkyl group optionally substituted by 1 to 3 halogen atoms;
(30) a formyl group;
(31) a $C_{1-6}$ alkyl group optionally substituted by 1 to 3 substituents selected from the group consisting of:
(a) a halogen atom,
(b) a carboxy group,
(c) a hydroxy group,
(d) a $C_{1-6}$ alkoxy-carbonyl group,
(e) a $C_{1-6}$ alkoxy group, and
(f) an amino group optionally mono- or di-substituted by $C_{1-6}$ alkyl group(s);
(32) a $C_{2-10}$ alkenyl group optionally substituted by 1 to 3 substituents selected from the group consisting of:
(a) a halogen atom,
(b) a carboxy group,
(c) a hydroxy group,
(d) a $C_{1-6}$ alkoxy-carbonyl group,
(e) a $C_{1-6}$ alkoxy group,
(f) an amino group optionally mono- or di-substituted by $C_{1-6}$ alkyl group(s), and
(g) a non-aromatic heterocyclic group optionally substituted by 1 to 3 substituents selected from the group consisting of:
(i) a $C_{1-6}$ alkyl group optionally substituted by 1 to 3 halogen atoms,
(ii) a hydroxy group,
(iii) a $C_{1-6}$ alkoxy group optionally substituted by 1 to 3 halogen atoms,
(iv) a halogen atom, and
(v) an oxo group; and
(33) a $C_{7-13}$ aralkyl group optionally substituted by 1 to 3 substituents selected from the group consisting of:
(a) a $C_{1-6}$ alkyl group optionally substituted by 1 to 3 halogen atoms,
(b) a hydroxy group,
(c) a $C_{1-6}$ alkoxy group, and
(d) a halogen atom.

2. The compound or salt of claim 1, wherein X is O, $CH_2O$, $OCH_2$, $CH_2$, S, $CH_2S$, $SCH_2$, S(O) or $S(O)_2$.

3. The compound or salt of claim 1, wherein ring B is a benzene ring optionally further substituted by 1 to 3 substituents selected from the group consisting of:
(a) a halogen atom,
(b) a $C_{1-6}$ alkyl group optionally substituted by 1 to 3 halogen atoms, and
(c) a $C_{1-6}$ alkoxy group optionally substituted by 1 to 3 halogen atoms.

4. The compound or salt of claim 1, wherein ring A is a pyrrolidine ring or a tetrahydrofuran ring, each of which is optionally further substituted by one oxo group.

5. The compound or salt of claim 1, wherein
ring B is a benzene ring optionally further substituted by 1 to 3 substituents selected from the group consisting of:
(a) a halogen atom,
(b) a $C_{1-6}$ alkyl group optionally substituted by 1 to 3 halogen atoms, and
(c) a $C_{1-6}$ alkoxy group optionally substituted by 1 to 3 halogen atoms; and
X is O, $CH_2O$, $OCH_2$, $CH_2$, S, $CH_2S$, $SCH_2$, S(O) or $S(O)_2$.

6. The compound or salt of claim 1, wherein
ring A is a pyrrolidine ring or a tetrahydrofuran ring, each of which is optionally further substituted by one oxo group; and
ring B is a benzene ring further substituted by 1 to 3 substituents selected from the group consisting of:
(a) a halogen atom,
(b) a $C_{1-6}$ alkyl group optionally substituted by 1 to 3 halogen atoms, and
(c) a $C_{1-6}$ alkoxy group optionally substituted by 1 to 3 halogen atoms.

7. The compound or salt of claim 1, wherein
X is O, S or $CH_2$.

8. ({(3S)-1-[3,5-Bis(trifluoromethyl)phenyl]pyrrolidin-3-yl}oxy)acetic acid or a salt thereof.

9. ({1-[4-Chloro-3-(trifluoromethyl)phenyl]pyrrolidin-3-yl}sulfanyl)acetic acid or a salt thereof.

10. 3-{(2R,5S)-5-[3,5-Bis(trifluoromethyl)phenyl]tetrahydrofuran-2-yl}propanoic acid or a salt thereof.

11. A pharmaceutical composition comprising the compound or salt of claim 1 and a pharmaceutically acceptable carrier.

12. A method of lowering retinol binding protein 4 in a mammal, which comprises administering an effective amount of the compound or salt of claim 1 to the mammal.

13. A method for the treatment of diabetes in a mammal, which comprises administering an effective amount of the compound or salt of claim 1 to the mammal.

* * * * *

SEQUENCE LISTING

```
<160> NUMBER OF SEQ ID NOS: 9

<210> SEQ ID NO 1
<211> LENGTH: 34
<212> TYPE: DNA
<213> ORGANISM: Artificial sequence
<220> FEATURE:
<223> OTHER INFORMATION: Synthetic construct; primer

<400> SEQUENCE: 1
atatggatcc accatgaagt gggtgtgggc gctc                              34

<210> SEQ ID NO 2
<211> LENGTH: 38
<212> TYPE: DNA
<213> ORGANISM: Artificial sequence
<220> FEATURE:
<223> OTHER INFORMATION: Synthetic construct; primer
```

```
<400> SEQUENCE: 2
atatgcggcc gcctacaaaa ggtttctttc tgatctgc                                38

<210> SEQ ID NO 3
<211> LENGTH: 35
<212> TYPE: DNA
<213> ORGANISM: Artificial sequence
<220> FEATURE:
<223> OTHER INFORMATION: Synthetic construct; primer

<400> SEQUENCE: 3
atatggatcc accatggctt ctcatcgtct gctcc                                   35

<210> SEQ ID NO 4
<211> LENGTH: 35
<212> TYPE: DNA
<213> ORGANISM: Artificial sequence
<220> FEATURE:
<223> OTHER INFORMATION: Synthetic construct; primer

<400> SEQUENCE: 4
atatgcggcc gctcattcct tgggattggt gacga                                   35

<210> SEQ ID NO 5
<211> LENGTH: 26
<212> TYPE: DNA
<213> ORGANISM: Artificial sequence
<220> FEATURE:
<223> OTHER INFORMATION: Synthetic construct; primer

<400> SEQUENCE: 5
tgggaggtct atataagcag agctcg                                             26

<210> SEQ ID NO 6
<211> LENGTH: 28
<212> TYPE: DNA
<213> ORGANISM: Artificial sequence
<220> FEATURE:
<223> OTHER INFORMATION: Synthetic construct; primer

<400> SEQUENCE: 6
atatgaattc ttccttggga ttggtgac                                           28

<210> SEQ ID NO 7
<211> LENGTH: 30
<212> TYPE: DNA
<213> ORGANISM: Artificial sequence
<220> FEATURE:
<223> OTHER INFORMATION: Synthetic construct; primer

<400> SEQUENCE: 7
atatgaattc caaaggtttc ctttctgatc                                         30

<210> SEQ ID NO 8
<211> LENGTH: 28
<212> TYPE: DNA
<213> ORGANISM: Artificial sequence
<220> FEATURE:
<223> OTHER INFORMATION: Synthetic construct; synthesized
      oligonucleotide

<400> SEQUENCE: 8
aattccatca tcatcatcat cactaggc                                           28

<210> SEQ ID NO 9
<211> LENGTH: 28
```

```
<212> TYPE: DNA
<213> ORGANISM: Artificial sequence
<220> FEATURE:
<223> OTHER INFORMATION: Synthetic construct; synthesized
      oligonucleotide

<400> SEQUENCE: 9
ggccgcctag tgatgatgat gatgatgg                                          28
```